(12) United States Patent
Bhanot et al.

(10) Patent No.: US 8,895,529 B2
(45) Date of Patent: Nov. 25, 2014

(54) ANTISENSE MODULATION OF FIBROBLAST GROWTH FACTOR RECEPTOR 4 EXPRESSION

(71) Applicant: Isis Pharmaceuticals, Inc., Carlsbad, CA (US)

(72) Inventors: Sanjay Bhanot, Carlsbad, CA (US); Xing-Xian Yu, San Diego, CA (US); Susan M. Freier, San Diego, CA (US); Ravi Jain, Fremont, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/915,855

(22) Filed: Jun. 12, 2013

(65) Prior Publication Data
US 2014/0080892 A1 Mar. 20, 2014

Related U.S. Application Data

(63) Continuation of application No. 12/681,360, filed as application No. PCT/US2008/078497 on Oct. 1, 2008, now Pat. No. 8,486,904.

(60) Provisional application No. 60/976,782, filed on Oct. 1, 2007.

(51) Int. Cl.
*C12N 15/113* (2010.01)
*A61K 45/06* (2006.01)
*A61K 31/7105* (2006.01)

(52) U.S. Cl.
CPC ...... *C12N 15/1138* (2013.01); *C12N 2310/315* (2013.01); *C12N 2310/321* (2013.01); *C12N 2310/11* (2013.01); *C12N 2310/341* (2013.01); *C12N 2310/346* (2013.01); *C12N 2310/3341* (2013.01); *A61K 45/06* (2013.01); *A61K 31/7105* (2013.01)
USPC ........................................ 514/44 A; 536/24.5

(58) Field of Classification Search
None
See application file for complete search history.

(56) References Cited

U.S. PATENT DOCUMENTS

| | | | |
|---|---|---|---|
| 5,801,154 A | 9/1998 | Baracchini et al. | |
| 6,582,908 B2 | 6/2003 | Fodor et al. | |
| 2001/0053519 A1 | 12/2001 | Fodor et al. | |
| 2002/0001825 A1 | 1/2002 | Itoh | |
| 2003/0212024 A1 | 11/2003 | Keating et al. | |
| 2003/0228597 A1 | 12/2003 | Cowsert et al. | |
| 2004/0006005 A1 | 1/2004 | Bhanot et al. | |
| 2004/0009154 A1 | 1/2004 | Khan et al. | |
| 2005/0048494 A1 | 3/2005 | Wang | |
| 2005/0053976 A1 | 3/2005 | Baker et al. | |
| 2005/0246794 A1 | 11/2005 | Khvorova et al. | |
| 2006/0286102 A1* | 12/2006 | Jin et al. ..................... 424/143.1 | |
| 2007/0248605 A1 | 10/2007 | Hestir et al. | |
| 2010/0143386 A1 | 6/2010 | Ullrich et al. | |
| 2010/0292140 A1 | 11/2010 | Bhanot et al. | |
| 2014/0087959 A1* | 3/2014 | Ellis et al. ....................... 506/9 |

FOREIGN PATENT DOCUMENTS

| | | |
|---|---|---|
| EP | 0420081 | 4/1991 |
| EP | 1202065 | 1/2002 |
| WO | WO 94/15945 | 7/1994 |
| WO | WO 99/53927 | 10/1999 |
| WO | WO 00/44882 | 8/2000 |
| WO | WO 00/71129 | 11/2000 |
| WO | WO 01/18210 | 3/2001 |
| WO | WO 01/49849 | 7/2001 |
| WO | WO 01/70977 | 9/2001 |
| WO | WO 01/88103 | 11/2001 |
| WO | WO 03/004602 | 1/2003 |
| WO | WO 03/035065 | 5/2003 |
| WO | WO 03/035664 | 5/2003 |
| WO | WO 03/099796 | 12/2003 |
| WO | WO/2004/001059 | 12/2003 |
| WO | WO 2004/003179 | 1/2004 |
| WO | WO 2004/006005 | 1/2004 |
| WO | WO 2004/041277 | 5/2004 |
| WO | WO 2005/037235 | 4/2005 |
| WO | WO 2005/076998 | 8/2005 |
| WO | WO 2005/076999 | 8/2005 |
| WO | WO 2006/044531 | 4/2006 |
| WO | WO 2009/046141 | 4/2009 |

OTHER PUBLICATIONS

Armstrong et al., "Localization of the fibroblast growth factor receptor-4 gene to chromosome region 5q33-qter." Genes Chromosomes Cancer (1992) 4(1):94-98.

Avraham et al., "Mapping of murine fibroblast growth factor receptors refines regions of homology between mouse and human chromosomes." Genomics (1994) 21(3):656-658.

Bange et al., "Cancer progression and tumor cell motility are associated with the FGFR4 Arg(388) allele." Cancer Res. (2002) 62(3):840-847.

Bo et al., "AOBase: a dataase for antisense oligonucleotide selection and design" Nucleic Acids Res. (2006) 34:D664-D667.

(Continued)

*Primary Examiner* — Tracy Vivlemore

(74) *Attorney, Agent, or Firm* — Knobbe, Martens, Olson & Bear LLP

(57) ABSTRACT

Antisense compounds, compositions and methods are provided for modulating the expression of fibroblast growth factor receptor 4 (FGFR4). The compositions comprise antisense compounds, particularly antisense oligonucleotides, targeted to nucleic acids encoding fibroblast growth factor receptor 4. Methods of using these compounds for modulation of fibroblast growth factor receptor 4 expression and for treatment of diseases associated with expression of fibroblast growth factor receptor 4 are provided.

25 Claims, 4 Drawing Sheets

(56) References Cited

OTHER PUBLICATIONS

Figure 1:
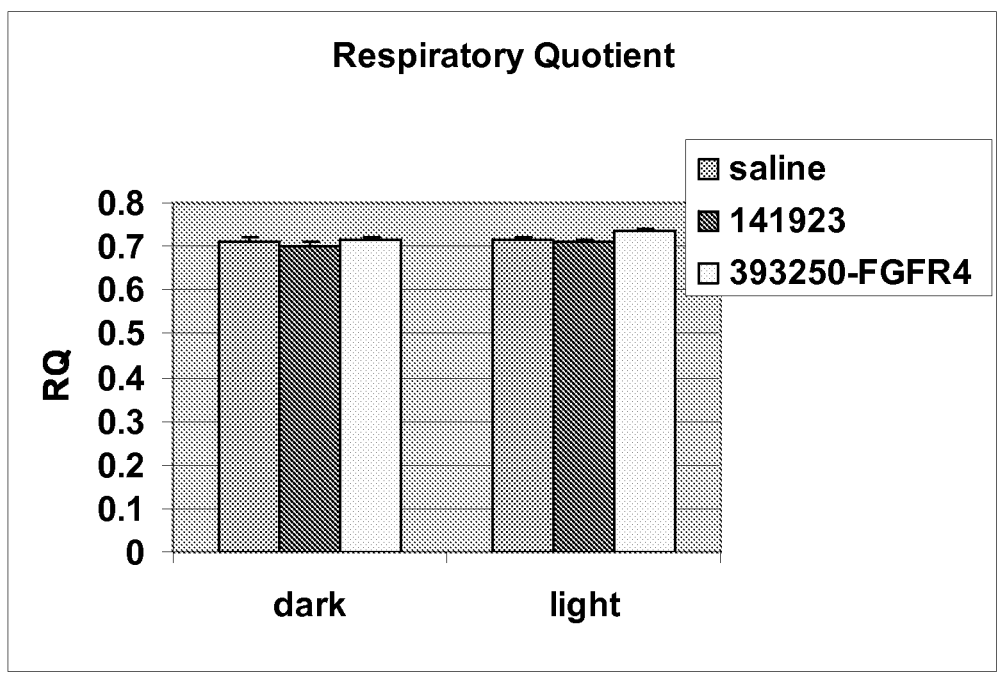

Branch et al., "A good antisense molecule is hard to find," TIBS (1998) 23:45-50.
Brysch et al., "Design and application of antisense oligonucleotides in cell culture, in vivo, and as therapeutic agents" Cell Mol. Neurobiol. (1994) 14(5):557-568.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Collins et al., "Mas musculus fibroblast growth factor receptor 4." NCBI GenBank Entry, Sep. 1, 2006 retrieved from the internet URL: <http://www.ncbi.nlm.nih.gov/entrez/viewer.fcgi?val=BC033313> see definition and sequence origin.
Cosic et al., "In vitro inhibition of the actions of basic FGF by a novel 16 amino acid peptide" Mol. Cell Biochem. (1994) 130:1-9.
Crooke et al., "Basic Principles of Antisense Therapeutics" Antisense Research and Application (1998) Chapter 1:1-50.
Dailey et al., "Mechanisms underlying differential responses to FGF signaling." Cytokine Growth Factor Rev. (2005) 16(2):233-247.
Eswarakumar et al., "Cellular signaling by fibroblast growth factor receptors." Cytokine Growth Factor Rev. (2005) 16(2):139-149.
Expert Panel on Detection, Evaluation, and Treatment of High Blood Cholesterol in Adults "Executive Summary of the Third Report of the National Cholesterol Education Program (NCEP) Expert Panel on Detection, Evaluation, and Treatment of High Blood Cholesterol in Adults (Adult Treatment Panel III)" JAMA (2001) 285:2486-2497.
Garcia et al., "Growth Factor Regulation of Uncoupling Protein-1 mRNA Expression in Brown Adipocytes" Am. J. Physiol. Cell Physiol. (2002) 282:C105-C112.
Gautschi et al., "Activity of a novel bc1-2/bc1-xL-bispecific antisense oligonucleotide against tumors of diverse histologic origins." J. Natl. Cancer Inst. (2001) 93(6):463-471.
Holtrich et al., "Two additional protein-tyrosine kinases expressed in human lung: fourth member of the fibroblast growth factor receptor family and an intracellular protein-tyrosine kinase." PNAS (1991) 88(23):10411-10415.
Huang et al., "FGFR4 prevents hyperlipidemia and insulin resistance but underlies high-fat diet induced fatty liver." Diabetes (2007) 56(10):2501-2510.
Hutley et al., "Human adipose tissue endothelial cells promote preadipocyte proliferation." Am. J. Physiol. Endocrinol. Metab. (2001) 281(5):E1037-1044.
Hutley et al., "Fibroblast growth factor 1: a key regulator of human adipogenesis." Diabetes (2004) 53(12):3097-3106.
Jaye et al., "Fibroblast growth factor receptor tyrosine kinases: molecular analysis and signal transduction." Biochim. Biophys. Acta (1992) 1135(2):185-199.
Kawaguchi et al., "De novo adipogenesis in mice at the site of injection of basement membrane and basic fibroblast growth factor" PNAS (1998) 95:1062-1066.
Klagsbrun et al., "A dual receptor system is required for basic fibroblast growth factor activity." Cell (1991) 67(2):229-231.
Kostrzewa et al., "Genomic structure and complete sequence of the human FGFR4 gene." Mammalian Genome (1998) 9(2):131-135.
Krieger-Brauer et al., "Antagonistic effects of different members of the fibroblast and platelet-derived growth factor families on adipose conversion and NADPG-dependent H2O2 generation in 3T2 L1-cells" Biochem. J. (1995) 307:549-556.
Maher et al., "Comparative hybrid arrest by tandem antisense oligodeoxyribonucleotides or oligodeoxyribonucleoside methylphosphonates in a cell-free system." Nuc. Acid. Res. (1988) 16(8):3341-3358.
Mamidipalli et al., "OligoMatcher: analysis and selection of specific oligonucleotide sequences for gene silencing by antisense or siRNA" Appl. Bioinformatics (2006) 5(2):121-124. (abstract only).
Mohammadi et al., "Structures of the tyrosine kinase domain of fibroblast growth factor receptor in complex with inhibitors." Science (1997) 276:955-960.
Nawano et al., "Hyperglycemia contributes insulin resistance in hepatic and adipose tissue but not skeletal muscle of ZDF rats." Am. J. Physiol. Endocrinol. Metab. (2000) 278(3):E535-543.
New England Biolabs 1998/99 Catalog (cover page and pp. 121 and 284).
Ozawa et al., "Growth factors and their receptors in pancreatic cancer." Teratog. Carcinog. Mutagen. (2001) 21(1):27-44.
Patel et al., "Essential role of fibroblast growth factor signaling in preadipocyte differentiation." J Clin Endocrinol Metab. (2005) 90(2):1226-1232.
Powers et al., "Fibroblast growth factors, their receptors and signaling." Endocr. Relat. Cancer (2000) 7(3):165-197.
Prusty et al., "Activation of MEK/ERK Signaling Promotes Adipogenesis by Enhancing Peroxisome Proliferator-activated Receptor y (PPARy) and C/EBPa Gene Expression during the Differentiation of 3T3-L1 Preadipocytes" J. Biol. Chem. (2002) 277(48):46226-46232.
Reynolds et al., "Rational siRNA design for RNA interference" Nature Biotechnology (2004) 22(31:326- 330.
Sakaue et al., "Requirement of Fibroblast Growth Factor 10 in Development of White Adipose Tissue" Genes & Development (2002) 16:908-912.
Sahadevan et al., "Selective over-expression of fibroblast growth factor receptors 1 and 4 in clinical prostate cancer" J. Pathol. (2007) 213(1):82-90.
Sanghvi et al., "Heterocyclic Base Modifications in Nucleic Acids and Their Applications in Antisense Oligonucleotides" Antisense Research and Applications (1993) pp. 273-288.
Sindelka et al., "Association of obesity, diabetes, serum lipids and blood pressure regulates insulin action." Physiol. Res. (2002) 51(1):85-91.
Sorisky, "From Preadipocyte to Adipocyte: Differentiation-Directed Signals of Insulin from the Cell Surface to the Nucleus" Critical Reviews in Clinical Laboratory Sciences (1999) 36(1):1-34.
Varzaneh et al., "Extracellular matrix components secreted by microvascular endothelial cells stimulate preadipocyte differentiation in vitro." Metabolism (1994) 43(7):906-912.
Woolf et al., "Specificity of antisense oligonucleotides in vivo." PNAS (1992) 89(16):7305-7309.
Yu et al., "Decreased adiposity and improved insulin selectivity in obese mice after suppression of hepatic and adipose tissue FGFR4 expression" 68th Annual Meeting of the American Diabetes Association (2008) Abstract 1708-P, Retrieved from the Internet: URL: http://professional.diabetes.org/Abstracts_Display.aspx?TYP=1&CID=70680.
European Search Report for application EP 08835484.0 dated Mar. 9, 2012.
Supplementary Partial European Search Report for application EP 03735152 dated Jul. 6, 2006.
International Search Report for application PCT/AU03/00826 dated Sep. 17, 2003.
International Search Report for application PCT/AU05/000008 dated Feb. 25, 2005.
International Search Report for application PCT/US08/78497 dated Mar. 16, 2009.
International Search Report for application PCT/US12/42813 dated Jan. 16, 2013.

\* cited by examiner

Respiratory Intake in both Light and dark conditions

ITT to determine Fasting Plasma Glucose levels (mg/dL) at Week 5.5 in DIO Mice

IPGTT to determine Fasting Plasma Glucose levels (mg/dL) at Week 6 in DIO mice

Treatment with ISIS 393250 reduced White Adipose (WAT) Tissue cell size

ANTISENSE MODULATION OF FIBROBLAST GROWTH FACTOR RECEPTOR 4 EXPRESSION

RELATED APPLICATIONS

This application is a continuation of U.S. application Ser. No. 12/681,360, filed Aug. 4, 2010, now U.S. Pat. No. 8,486,904, which is a U.S. National Phase application under 35 USC 371 of International Application No. PCT/US2008/078497, filed Oct. 1, 2008; which is the non-provisional claiming priority to U.S. Provisional Application No. 60/976,782, filed Oct. 1, 2007, each of the above applications is incorporated herein in its entirety.

SEQUENCE LISTING

The present application is being filed along with a Sequence Listing in electronic format. The Sequence Listing is provided as a file entitled BIOL0097USC1SEQ.txt, created on May 22, 2013 which is 120 Kb in size. The information in the electronic format of the sequence listing is incorporated herein by reference in its entirety.

FIELD OF THE INVENTION

The present invention provides compositions and methods for modulating the expression of fibroblast growth factor receptor 4. In particular, this invention relates to compounds, particularly oligonucleotides, specifically hybridizable with nucleic acids encoding fibroblast growth factor receptor 4. Such compounds have been shown to modulate the expression of fibroblast growth factor receptor 4 (FGFR4).

BACKGROUND OF THE INVENTION

Obesity is considered a long-term metabolic disease. There are several serious medical sequelae related to obesity. There are over 1 billion overweight individuals worldwide with 100 million clinically obese. The increasing health care costs of treating obesity related diseases in the US alone are estimated at over $100 billion annually. Current methods for treating obesity include behavioral modification, diet, surgery (gastroplasty), administering pharmaceutical agents that block appetite stimulating signals or absorption of nutrients (fat), and administering agents that increase thermogenesis or fat metabolism. Some of these methods have disadvantages in that they rely on patient resolve, are invasive, or have unwanted side effects. An understanding of the mechanisms by which obesity is regulated may provide important therapeutic information.

Obesity is frequently associated with insulin resistance and together constitutes risk factors for later development of type 2 diabetes and cardiovascular diseases. Insulin resistance occurs well before development of type 2 diabetes, and insulin is overproduced to compensate for the insulin resistance and to maintain normal glucose levels. Type 2 diabetes ensues, as the pancreas can no longer produce enough insulin to maintain normal glucose levels. Early stages of type 2 diabetes are associated with elevated levels of insulin but as the disease progresses the pancreas may fail to produce insulin, resulting in increased blood glucose levels. Diabetes is a significant risk factor for both heart disease and stroke and is the leading cause of blindness and end-stage renal failure.

Diabetes is a disorder characterized by hyperglycemia due to deficient insulin action that may result from reduced insulin production or insulin resistance or both. Diabetes mellitus is a polygenic disorder affecting a significant portion of the people in the world. It is divided into two types. In type I diabetes, or insulin-dependent diabetes mellitus (IDDM), patients produce little or no insulin, the hormone that regulates glucose utilization. In type 2 diabetes, or noninsulin-dependent diabetes mellitus (NIDDM), patients often have plasma insulin levels that are the same compared to nondiabetic humans; however, these patients have developed a resistance to the insulin stimulating effect of glucose and lipid metabolism in the main insulin-sensitive tissues, i.e., muscle, liver and adipose tissues, and the plasma insulin levels are insufficient to overcome the pronounced insulin resistance. Additionally, glucotoxicity, which results from long-term hyperglycemia, induces tissue-dependent insulin resistance (Nawano et al., *Am. J. Physiol. Endocrinol. Metab.*, 278, E535-543) exacerbating the disease.

Type 2 diabetes accounts for over 90% of all diabetes cases. It is a metabolic disorder characterized by hyperglycemia leading to secondary complications such as neuropathy, nephropathy, retinopathy, hypertriglyceridemia, obesity, and other cardiovascular diseases generally referred to as metabolic syndrome.

Metabolic syndrome is a combination of medical disorders that increase one's risk for cardiovascular disease and diabetes. The symptoms, including high blood pressure, high triglycerides, decreased HDL and obesity, tend to appear together in some individuals. Metabolic syndrome is known under various other names, such as (metabolic) syndrome X, insulin resistance syndrome or Reaven's syndrome.

Diabetes and obesity (sometimes now collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 51, 85-91). Additionally, several compounds on the market for the treatment of diabetes are known to induce weight gain, a very undesirable side effect to the treatment of this disease. Therefore, a compound that has the potential to treat both diabetes and obesity would provide a significant improvement over current treatments.

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independent state (Powers et al., *Endocr. Relat. Cancer*, 7, 165-197). FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., *Teratog. Carcinog. Mutagen.*, 21, 27-44).

Fibroblast growth factors (FGFs) and their receptors (FGFRs) are critical for the development of most cell types. The cellular response to FGFs is transmitted via four types of high affinity transmembrane tyrosine-kinase fibroblast growth factor receptors numbered 1 to 4 (FGFR1 to FGFR4). There are at least 22 distinct FGF ligands and, as indicated above, four receptors (FGFR1-4). Different ligand/receptor pairs regulate cell growth in either a positive or negative manner, depending on the cell type and stage of development (Dailey et al., *Cytokine Growth Factor Rev.* 16, 233-247; Eswarakumar et al. *Cytokine Growth Factor Rev.,* 16, 139-149) Upon ligand binding, the receptors dimerize and auto- or trans-phosphorylate specific cytoplasmic tyrosine residues to transmit an intracellular signal that ultimately reaches nuclear transcription factor effectors. Mitogenic signaling by these FGFRs is subsequently mediated via a number of pathways, including the ras/raf/MAP kinase cascade (Ozawa et al., *Teratog. Carcinog. Mutagen.,* 21, 27-44).

Alternative splicing of the mRNA for the FGFRs 1, 2, 3 and 4 results in a wide range of receptor isoforms with varying ligand-binding properties and specificities. (Klagsbrun et al., *Cell,* 67, 229-231; Jaye et al., *Biochim Biophys acta,* 1135, 185-199). With different receptor possibilities and at least 22 ligands in the FGF family, there is a great deal of diversity in the FGF signaling pathway (Powers et al., *Endocr. Relat. Cancer,* 7, 165-197). Furthermore, expression and localization of the receptor isoforms is regulated in a tissue specific manner. Thus, the various FGFs may exert different influences upon different cell types by interacting with different receptor splice variants to initiate unique intracellular signaling cascades, leading to a panoply of cellular responses (Ozawa et al., *Teratog. Carcinog. Mutagen.,* 21, 27-44).

Fibroblast growth factor receptor 4 (also known as FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2) has high affinity for the acidic and/or basic fibroblast growth factors. (Armstrong et al., *Genes Chromosomes Cancer,* 4, 94-98).

The FGFR4 gene was mapped to 5q35.1-qter, the long (q) arm of chromosome 5 between position 35.1 and the end (terminus) of the arm, an area involved in leukemias and lymphomas. (Armstrong et al., *Genes Chromosomes Cancer,* 4, 94-98). More precisely, the FGFR4 gene is located from base pair 176,446,526 to base pair 176,457,732 on chromosome 5. The mouse Fgfr4 gene was mapped to mouse chromosome 13 located from base pair 54,235,030 to base pair to 54,251,130, in a region of homology of synteny with distal human 5q. (Avraham et al., *Genomics,* 21, 656-658).

The FGFR4 gene spans approximately 11.3 kb and is composed of 18 exons ranging in size from 17 to 600 bp. Exon 1 is untranslated and preceded by structural elements characteristic of a TATA-free promoter. Short tandem repeat polymorphisms were identified in introns 2 and 16 of FGFR4. (Kostrzewa et al., *Mammalian Genome,* 9, 131-135)

Although FGFRs generally have been shown to have wide distribution throughout the body. To date, FGFR4 has only been found in a few tissues. Among a wide variety of cells and tissues tested, including human lymphocytes and macrophages, FGFR4 was found to be expressed in the lung and in some tumors of lung origin as well as in malignancies not derived from lung tissues. (Holtrich et al., *Proc. Nat. Acad. Sci.,* 88, 10411-10415). FGFR4 has also been found to be expressed in the liver and in adipose tissues. (Patel et al., *JCEM,* 90(2), 1226-1232).

FGFR4 has also been found to be expressed in certain carcinoma cell lines. In the FGFR4 gene transcript from a mammary carcinoma cell line, a G-to-A transition was discovered that resulted in the substitution of glycine by arginine at position 388 in the transmembrane domain of the receptor. The arg388 allele was also found in cell lines derived from a variety of other tumor types as well as in the germline of cancer patients and healthy individuals. Analysis of 3 geographically separated groups indicated that it occurs in approximately 50% of humans. Investigation of the clinical data of 84 breast cancer patients revealed that homo- or heterozygous carriers of the arg388 allele had a significantly reduced disease-free survival time (P=0.01) within a median follow-up of 62 months. Moreover, the FGFR4 arg388 allele was associated with early metastasis and advanced tumor-node metastasis stage in 82 colon cancer patients. Consistent with this finding, the mammary tumor cell line expressing FGFR4 arg388 exhibited increased motility relative to cells expressing the FGFR4 gly388 isotype. The results supported the conclusion that the FGFR4 arg388 allele represents a determinant that is innocuous in healthy individuals but predisposes cancer patients for significantly accelerated disease progression. (Bange et al., *Cancer Res.,* 62, 840-847).

Fibroblast growth factor 1 (FGF1) plays an important role in adipogenesis. (Hutley et al., *Diabetes,* 53, 3097-3106). Further, FGF1 has been shown to bind FGFR4 which is also expressed in adipose tissue, (Patel et al., *JCEM,* 90(2), 1226-1232).

Additionally, FGFR4 has been shown to play a role in systemic lipid and glucose homeostasis. FGFR4-deficient mice on a normal diet exhibited features of metabolic syndrome that include increase mass of insulin resistance, in addition to hypercholesterolemia. FGFR4 deficiency was shown to alleviate high-fat diet-induced fatty liver in a certain obese mouse model, which is also a correlate of metabolic syndrome. Restoration of FGFR4, specifically in hepatocytes of FGFR4 deficient mice, decrease plasma lipid level and restored the high fat diet-induced fatty liver but failed to restore glucose tolerance and sensitivity to insulin. (Huang et al., *Diabetes,* 56, 2501-2510).

Effective treatments are needed for diabetes, obesity, metabolic syndrome and other diseases and conditions thereof. Provided herein is data establishing a role for FGFR4 in both diabetes and obesity. The data supports targeting of FGFR4 for treatment of a range of metabolic conditions, including diabetes, obesity and metabolic syndrome. Therefore, among the objectives herein, it is an object to provide compounds, compositions and methods for the treatment of such diseases and conditions.

Antisense technology is emerging as an effective means for reducing the expression of specific gene products and therefore may prove to be uniquely useful in a number of therapeutic, diagnostic, and research applications for the modulation of FGFR4 expression.

The present invention provides compositions and methods for modulating FGFR4 expression, including modulation of the truncated mutants and alternatively spliced forms of FGFR4.

There remains a need for non-invasive therapies to promote weight loss in obese individuals with improved specificity to avoid side-effects and the present invention meets this need.

SUMMARY OF THE INVENTION

The present invention is directed to compounds, particularly antisense oligonucleotides, which are targeted to a nucleic acid encoding fibroblast growth factor receptor 4 (FGFR4), and which modulate the expression of FGFR4. Pharmaceutical and other compositions comprising the compounds of the invention are also provided. Further provided are methods of modulating the expression of FGFR4 in cells or tissues comprising contacting said cells or tissues with one or more of the antisense compounds or compositions of the invention. Further provided are methods of treating an animal, particularly a human, suspected of having or being prone to a disease or condition associated with expression of FGFR4 by administering a therapeutically or prophylactically effective amount of one or more of the antisense compounds or compositions of the invention.

Methods of reducing FGFR4 expression, activity and/or nucleic acid levels include administering to an individual a compound targeted to a nucleic acid encoding FGFR4. In certain embodiments, the compound is administered in a composition. Compounds targeted to a FGFR4 nucleic acid may be targeted to sequences as set forth in GENBANK® Accession Nos. AY493377.2, BC033313.1, BQ567109.1, NM_008011.1, nucleotides 790799 to 800614 of GENBANK® Accession No NT_039586.1, nucleotides 792000 to 811000 of GENBANK® Accession No. NT_039586.5, AF202063.1, AF359241.1, BF305431.1, BM803172.1, NM_002011.3, NM_022963.1, nucleotides 21323018 to 21335213 of GENBANK® Accession No. NT_023133.11; and nucleotides 8583892 to 8595932 of GENBANK® Accession No. NT_023132.9. All of the in GENBANK® Accession Nos. along with their associated sequence and structural data pertaining to such sequences including gene organization and structural elements that may be found in sequence databases such as the National Center for Biotechnology Information (NCBI) are incorporated herein by reference in their entirety.

In certain embodiments, the compounds are antisense compounds. In certain embodiments, the antisense compounds are oligomeric antisense compounds. In certain embodiment the oligomeric antisense compounds are or include modified or unmodified oligonucleotides. In certain embodiments, the antisense compounds are single stranded modified oligonucleotides.

Provided herein are methods, compounds and compositions for the treatment, prevention, slowed progression of and/or amelioration of diabetes, obesity, metabolic syndrome or related diseases or conditions thereof.

Provided herein are methods, compounds and compositions for lowering body fat content and improving blood glucose control or tolerance. In certain embodiments, the methods, compounds and compositions are for improving insulin sensitivity. Also provided are methods, compounds and compositions for the reduction of glucose levels. In certain embodiments, such glucose levels can be blood, plasma and/or serum glucose levels. In certain embodiments, such glucose levels can be fed or fasting glucose levels. In certain embodiments, such glucose levels are fed or fasting blood glucose levels. In certain embodiments, such methods include administering to a subject an antisense compound targeted to a nucleic acid encoding fibroblast growth factor receptor 4.

Further provided are methods for treating, preventing and/or ameliorating diabetes, obesity or metabolic syndrome, or another disease or condition thereof in an individual. Such method includes selecting an individual diagnosed with diabetes, obesity or metabolic syndrome or other disease or condition, administering to the individual a therapeutically effective amount of an antisense compound targeted to an fibroblast growth factor receptor 4 nucleic acid, and monitoring factors related to diabetes, obesity or metabolic syndrome or other related disease or condition.

Further provided are methods of increasing metabolic rate. Also provided are methods for lowering body weight gain. Also provided are methods for lowering abdominal fat. Abdominal fat can include perirenal and/or epididymal fat pad weight. Also provided are methods for lowering whole body fat content. Such methods include administering to a subject an antisense compound targeted to a nucleic acid encoding fibroblast growth factor receptor 4. In certain embodiments, such methods include the administration of a therapeutically effective amount of an antisense compound targeted to an fibroblast growth factor receptor 4 nucleic acid. In certain embodiments, the compound is administered in a composition. In certain embodiments the subject is an animal. In certain embodiments the animal is a human. In certain embodiments, the subject to which the antisense compound is administered and in which metabolic rate is increased and/or weight or fat content is lowered has one or more of the diseases or disorders listed above. In certain embodiments, the subject to which the antisense compound is administered and in which metabolic rate is increased and/or weight or fat content is lowered has obesity, diabetes or metabolic syndrome.

In certain embodiments, the methods, compounds and compositions are for the treatment, prevention and/or amelioration of diabetes, obesity and metabolic syndrome. In certain embodiments, the methods, compounds and compositions are for the treatment, prevention and/or amelioration of type 2 diabetes, and type 2 diabetes with dyslipidemia. In certain embodiments, such methods, compounds and compositions are used to treat, slow, prevent, delay or ameliorate the sequelae of diabetes including, but not limited to, retinopathy, neuropathy, cardiovascular complications and nephropathy.

It is understood that the terms individual and subject are used interchangeably herein and that any of the methods provided herein may be useful for a subject or an individual and that subject or individual can be an animal and particularly a human.

In any of the methods provided, an fibroblast growth factor receptor 4 nucleic acid may be the sequence set forth in SEQ ID NO: 1, 2, 3, 4, 5, 6, 7, 8, 9, 10, 11, 12, 13, or 14. Thus, the antisense compound may be targeted to an fibroblast growth factor receptor 4 nucleic acid as set forth in SEQ ID NO: 1, 2, 3, 4, 5, 6, 7, 8, 9, 10, 11, 12, 13, or 14.

In any of the aforementioned methods, administration of the antisense compound may comprise parenteral administration. The parenteral administration may further comprise subcutaneous or intravenous administration.

In any of the compounds, compositions or methods provided herein, the antisense compound may have least 80%, at least 90%, or at least 95% complementarity to 1, 2, 3, 4, 5, 6, 7, 8, 9, 10, 11, 12, 13, or 14. Alternatively, the antisense compound may have 100% complementarity to SEQ ID NO: 1, 2, 3, 4, 5, 6, 7, 8, 9, 10, 11, 12, 13, or 14.

The antisense compounds provided herein and employed in any of the described methods may be 8 to 80 subunits in length, 12 to 50 subunits in length, 12 to 30 subunits in length, 15 to 30 subunits in length, 18 to 24 subunits in length, 19 to 22 subunits in length, or 20 subunits in length. Further, the antisense compounds employed in any of the described methods may be antisense oligonucleotides 8 to 80 nucleotides in length, 12 to 50 nucleotides in length, 12 to 30 nucleotides in length 15 to 30 nucleotides in length, 18 to 24 nucleotides in length, 19 to 22 nucleotides in length, or 20 nucleotides in length.

In any of the compounds, compositions and methods provided, the antisense compound may be an antisense oligonucleotide. Moreover, the antisense oligonucleotide may be chimeric. The chimeric antisense oligonucleotide may be a gapmer antisense oligonucleotide. The gapmer antisense oligonucleotide may comprise a gap segment of ten 2'-deoxynucleotides positioned between wing segments of five 2'-MOE nucleotides.

In any of the compounds, compositions and methods provided, the antisense compounds may have at least one modified internucleoside linkage. Additionally, each internucleoside linkage may be a phosphorothioate internucleoside linkage. Each cytosine may be a 5-methyl cytosine.

A compound for treatment of obesity and metabolic syndrome may be an antisense compound 12 to 30 nucleobases targeted to an fibroblast growth factor receptor 4 nucleic acid. The compound may have at least 70% to 100% complementarity to any of SEQ ID NOSEQ ID NOs: 1, 2, 3, 4, 5, 6, 7, 8, 9, 10, 11, 12, 13, or 14. The antisense oligonucleotide may be a gapmer antisense oligonucleotide. The gapmer antisense oligonucleotide may comprise a gap segment of ten 2'-deoxynucleotides positioned between wing segments of five 2'-MOE nucleotides.

The antisense compounds may have at least one modified internucleoside linkage. Additionally, each internucleoside linkage may be a phosphorothioate internucleoside linkage. Each cytosine may be a 5-methyl cytosine.

LISTING OF FIGURES

FIG. 1: A bar graph showing the measurement of the respiratory quotient in the PBS control group; the control oligonucleotide, ISIS 141923-treated group; and the FGFR4 ASO, ISIS 393250-treated group. The measurements were taken in both light and dark conditions.

Figure 2:
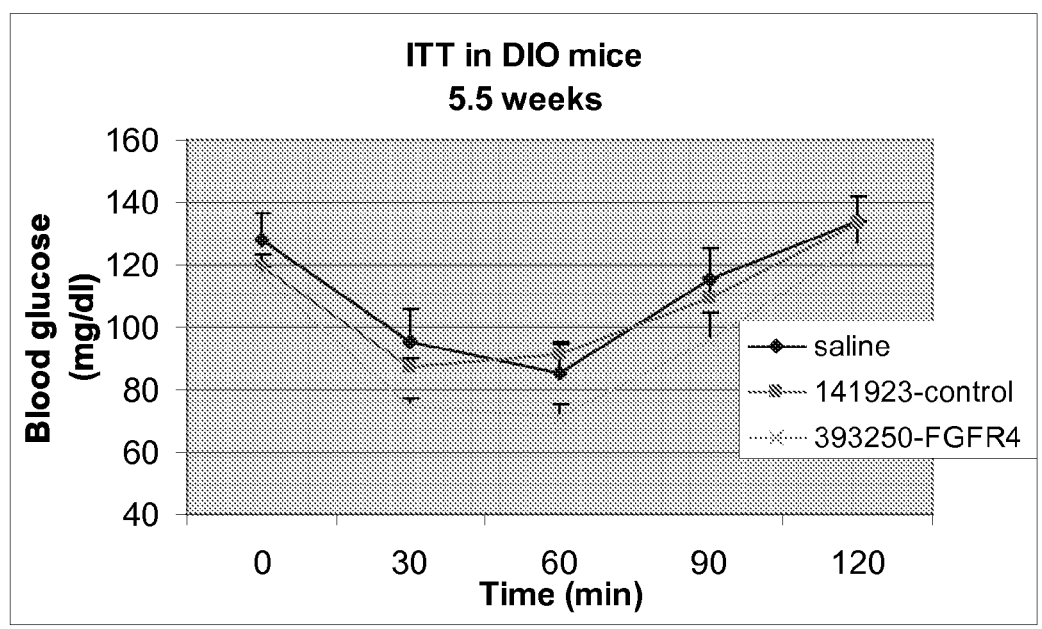

FIG. 2: A line graph showing the determination of insulin sensitivity by ITT at week 5.5 in the PBS control group; the control oligonucleotide, ISIS 141923-treated group; and the FGFR4 ASO, ISIS 393250-treated group in DIO mice.

Figure 3:
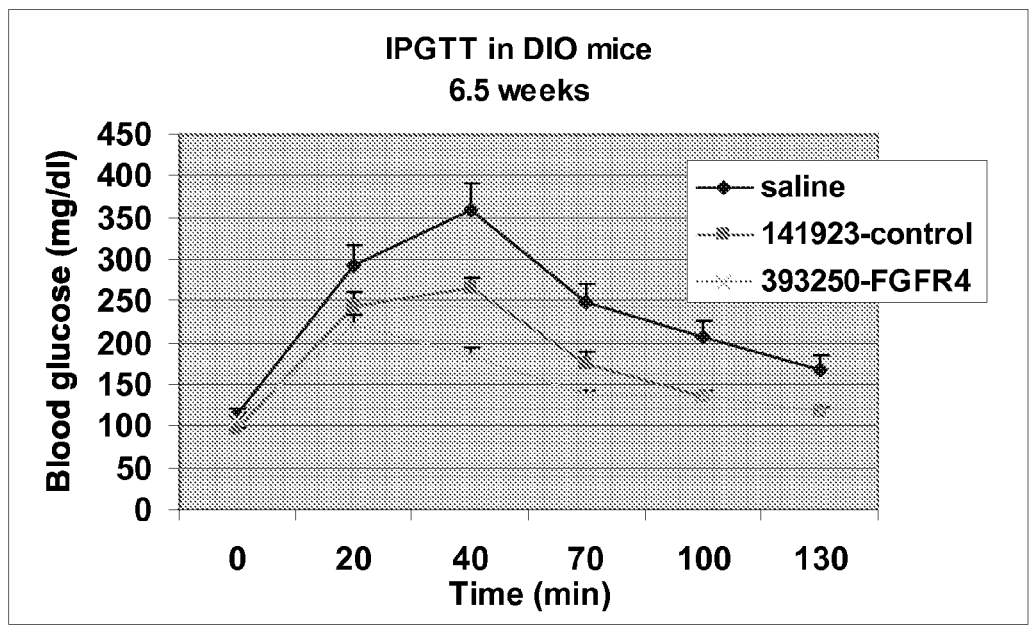

FIG. 3: A line graph showing the determination of glucose tolerance by IPGTT at week 6 in the PBS control group; the control oligonucleotide, ISIS 141923-treated group; and the FGFR4 ASO, ISIS 393250-treated group in DIO mice.

Figure 4:
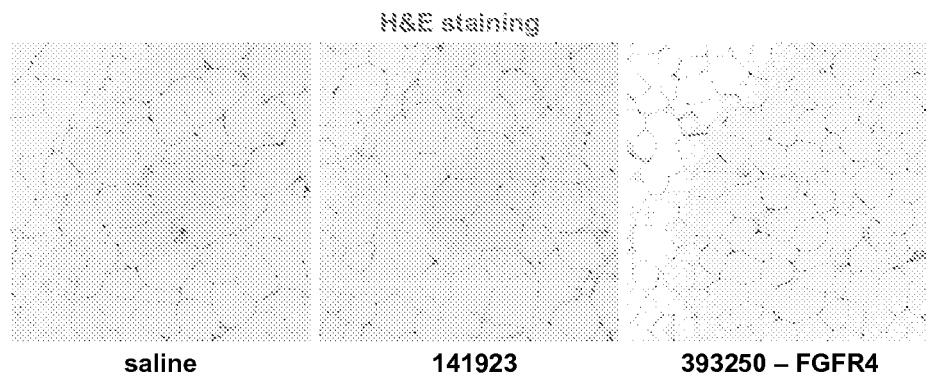

FIG. 4: Histological sections showing hematoxylin- and eosin-stained tissue sections of white adipose tissue in the PBS control group; the control oligonucleotide, ISIS 141923-treated group; and the FGFR4 ASO, ISIS 393250-treated group, demonstrating adipocyte cell size.

DETAILED DESCRIPTION OF THE INVENTION

Definitions

Unless defined otherwise, all technical and scientific terms used herein have the same meaning as is commonly understood by on of skill in the art to which the invention(s) belong. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, chemical analysis, pharmaceutical preparation, formulation and delivery, and treatment of subjects. Certain such techniques and procedures may be found for example in "Antisense Drug Technology: Principles, Strategies, and Applications." by Stanley Crooke, Boca Raton: Taylor & Francis Group, 2008; "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. All of the in GENBANK® Accession Nos. along with their associated sequence and structural data pertaining to such sequences including gene organization and structural elements that may be found in sequence databases such as the National Center for Biotechnology Information (NCBI) are incorporated herein by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

"FGFR4" means fibroblast growth factor receptor 4.

"Obesity" is defined as an excessively high amount of body fat or adipose tissue in relation to lean body mass. The amount of body fat (or adiposity) includes concern for both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Diabetes" is (also called diabetes mellitus), is a metabolic disorder typically characterized by high levels of blood glucose. Diabetes mellitus can take one of two forms: type I or type 2.

"Type I diabetes" (also known as insulin-dependent diabetes mellitus or IDDM—strikes people under age 35, typically appearing suddenly between the ages of 10 and 16. In this form of the illness, which affects 10 percent of diabetics, a virus or autoimmune reaction probably destroys the insulin-producing cells. Insulin normally enables sugar to pass from the blood into the body's cells. Since a person with type I diabetes has completely stopped producing insulin, lifelong treatment means taking insulin several times daily.

"Type 2 diabetes," (also known as diabetes mellitus type 2, and formerly called diabetes mellitus type 2, non-insulin-dependent diabetes (NIDDM), obesity related diabetes, or adult-onset diabetes) is a metabolic disorder that is primarily characterized by insulin resistance, relative insulin deficiency, and hyperglycemia.

"Diabetic dyslipidemia" or "Type 2 diabetes with dyslipidemia" means a condition characterized by Type 2 diabetes, reduced HDL-C, elevated serum triglycerides, and elevated small, dense LDL particles.

"Metabolic disorder" refers to a condition characterized by an alteration or disturbance in metabolic function. "Metabolic" and "metabolism" are terms well know in the art and generally include the whole range of biochemical processes that occur within a living organism. Metabolic disorders include, but are not limited to, hyperglycemia, prediabetes, diabetes (type I and type 2), obesity, insulin resistance and metabolic syndrome.

"Metabolic syndrome" means a condition characterized by a clustering of lipid and non-lipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"IPGTT" or "Intraperitoneal Glucose Tolerance Testing" in medical practice is defined as the administration of glucose through Intraperitoneal injection to determine how quickly it is cleared from the blood. The test is usually used to test for diabetes, insulin resistance, and sometimes reactive hypoglycemia.

"ITT" or "Insulin Tolerance Test" in medical practice is defined as a test to measure insulin sensitivity through the hormone response to the stress of a low blood sugar level. The test is usually used to test for diabetes, insulin resistance, and sometimes reactive hypoglycemia.

"Metabolic rate" means the rate of metabolism or the amount of energy expended in a give period. Metabolic rate also is the amount of energy expended while at rest in a neutrally temperate environment, in the post-absorptive state (meaning that the digestive system is inactive, which requires about twelve hours of fasting in humans). The release of energy in this state is sufficient only for the functioning of the vital organs, such as the heart, lungs, brain and the rest of the nervous system, liver, kidneys, sex organs, muscles and skin. Metabolic rate decreases with age and with the loss of lean body mass. Increased cardiovascular exercise and muscle mass can increase metabolic rate. Illness, previously consumed food and beverages, environmental temperature, and stress levels can affect one's overall energy expenditure, and can affect one's metabolic rate as revealed by gas analysis. It is measured when the person is at complete rest, but awake.

"Prevention" refers to delaying or forestalling the onset or development of a condition or disease for a period of time from hours to days, preferably weeks to months.

"Amelioration" refers to a lessening of at least one indicator of the severity of a condition or disease. The severity of indicators may be determined by subjective or objective measures which are known to those skilled in the art.

"Treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

"Slows progression" means decrease in the development of the said disease.

"Cures" means a method or course that restores health or a prescribed treatment for an illness.

"Expression" refers to all the functions and steps by which a gene's coded information is converted into structures present and operating in a cell. Such structures include, but are not limited to the products of transcription and translation.

"Modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

"Animal" refers to a human or non-human animal, including, but not limited to, mice, rats, rabbits, dogs, cats, pigs, and non-human primates, including, but not limited to, monkeys and chimpanzees.

"Subject" refers to an animal, including, but not limited to a human, to whom a pharmaceutical composition is administered.

"Oligonucleotide" means a polymer of linked nucleosides each of which can be modified or unmodified, independent one from another.

"Single-stranded modified oligonucleotide" means a modified oligonucleotide which is not hybridized to a complementary strand.

"Nucleoside" means a nucleobase linked to a sugar.

"Linked nucleosides" means adjacent nucleosides which are bonded together.

"Nucleobase" means a heterocyclic moiety capable of pairing with a base of another nucleic acid.

"Contiguous nucleobases" means nucleobases immediately adjacent to each other.

"Modified oligonucleotide" means an oligonucleotide comprising a modified internucleoside linkage, a modified sugar, and/or a modified nucleobase.

"Nucleobase sequence" means the order of contiguous nucleobases independent of any sugar, linkage, and/or nucleobase modification.

"Internucleoside linkage" refers to the chemical bond between nucleosides.

"5-methylcytosine" means a cytosine modified with a methyl group attached to the 5' position. A 5-methylcytosine is a modified nucleobase "Modified internucleoside linkage" refers to a substitution and/or any change from a naturally occurring internucleoside bond (i.e. a phosphodiester internucleoside bond).

"Modified nucleobase" refers to any nucleobase other than adenine, cytosine, guanine or thymidine.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"2'-O-methoxyethyl" refers to an O-methoxy-ethyl modification of the 2' position of a furosyl ring. A 2'-O-methoxyethyl modified sugar is a modified sugar.

"Modified sugar" refers to a substitution and/or any change from a natural sugar.

"Diluent" means an ingredient in a composition that lacks pharmacological activity, but is pharmaceutically necessary or desirable. For example, in drugs that are injected the diluent may be a liquid, e.g. saline solution.

"Salts" mean physiologically and pharmaceutically acceptable salts of antisense compounds, i.e., salts that retain the desired biological activity of the parent oligonucleotide and do not impart undesired toxicological effects thereto.

"Linked deoxynucleoside" means a nucleic acid base (A, G, C, T, U) substituted by deoxyribose linked by a phosphate ester to form a nucleotide.

"Pharmaceutically acceptable carrier" or "excipient" means a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition.

"Bicyclic sugar" means a furosyl ring modified by the bridging of two non-geminal ring atoms. A bicyclic sugar is a modified sugar.

"Pharmaceutical agent" refers to a substance provides a therapeutic benefit when administered to a subject.

"Therapeutically effective amount" refers to an amount of a pharmaceutical agent that provides a therapeutic benefit to an animal. In certain embodiments, a therapeutically effective amount of antisense compound targeted to an FGFR4 nucleic acid is an amount that improves adiposity in the individual.

"Prophylactically effective amount" refers to an amount of a pharmaceutical agent that provides a prophylactic or preventative benefit to an animal. In certain embodiments, a prophylactically effective amount of antisense compound targeted to an FGFR4 nucleic acid is an amount that improves adiposity in the individual.

A "Pharmaceutical composition" means a mixture of substances suitable for administering to an individual. For example, a pharmaceutical composition may comprise an antisense oligonucleotide and a sterile aqueous solution.

"Administering" means providing a pharmaceutical agent or composition to an individual, and includes, but is not limited to administering by a medical professional and self-administering.

"Co-administration" refers to administration of two or more pharmaceutical agents to an animal. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Administered concomitantly" refers to the administration of two agents at the same time in any manner in which the pharmacological effects of both are manifest in the patient at the same time. Concomitant administration does not require that both agents be administered in a single pharmaceutical composition, in the same dosage form, or by the same route of administration.

"Individual" means a human or non-human animal selected for treatment or therapy. "Individual", "subject", and "human" may be used interchangeably herein.

"Duration" means the period of time during which an activity or event continues. In certain embodiments, the duration of treatment is the period of time during which doses of a pharmaceutical agent are administered.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intraperitoneal administration" means administration through infusion or injection into the peritoneum.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized antisense oligonucleotide. In certain embodiments, a dosage unit is a vial containing reconstituted antisense oligonucleotide.

"Pharmaceutical agent" means a substance which provides a therapeutic benefit when administered to an individual. For example, in certain embodiments, an antisense oligonucleotide targeted to FGFR4 is a pharmaceutical agent.

"Active pharmaceutical ingredient" means the substance in a pharmaceutical composition that provides a desired effect.

"Major risk factors" refers to factors that contribute to a high risk for a particular disease or condition "Efficacy" means the ability to produce a desired effect.

"Acceptable safety profile" means a pattern of side effects that is within clinically acceptable limits.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Individual compliance" means adherence to a recommended or prescribed therapy by an individual.

"Therapeutic lifestyle change" means dietary and lifestyle changes intended to lower overall body weight and reduce the risk of developing diabetes and obesity, and includes recommendations for dietary intake of total daily calories, total fat, saturated fat, polyunsaturated fat, monounsaturated fat, carbohydrate, protein, cholesterol, insoluble fiber, as well as recommendations for physical activity.

Overview

Effective treatments are needed for diabetes, obesity, metabolic syndrome and other diseases and conditions thereof. Because of its role in both diabetes and obesity, FGFR4 has been developed as an antisense target. Antisense compounds have been developed which target nucleic acid encoding FGFR4 and which function to reduce FGFR4 levels in a subject.

The antisense compounds provided herein are therefore useful for treating a number of metabolic conditions, including diabetes, obesity and metabolic syndrome. Such treatments encompass a therapeutic regimen that results in a clinically desirable outcome. The clinically desired outcomes may be tied to glucose metabolism. For example, the antisense compounds and methods provided herein are useful for improving blood glucose control or tolerance and for improving insulin sensitivity in a subject in need thereof. The antisense compounds and methods provided herein are also useful for reducing glucose levels in a subject in need thereof. The compounds and methods are particularly useful for reducing blood, plasma and/or serum glucose levels. The compounds and methods are useful for reducing both fed and fasting glucose levels. Such clinical outcomes are desirable in disease and disorders related to glucose metabolism and insulin resistance including, for example, diabetes, particularly type 2 diabetes, obesity and metabolic syndrome. Therefore, the antisense compounds and methods provided herein are useful for the treatment of such diseases and disorders.

The compounds and methods are also particularly useful for increasing metabolic rate and, in turn, lowering body weight gain. The compounds and methods are also particularly useful for lowering epididymal and perirenal fat pad weight and whole body fat content. Such clinical outcomes are desirable in conditions such as metabolic syndrome, obesity, diabetes, in particular type 2 diabetes, type 2 diabetes with dyslipidemia. Therefore, the antisense compounds and methods provided herein are useful for the treatment of such diseases and disorders.

Metabolic syndrome is a condition characterized by a clustering of lipid and non-lipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497). Accordingly, the compounds and methods provided herein may be used to treat individuals exhibiting one or more risk factors for metabolic syndrome. Particularly, the compounds and methods provided herein may be used to reduce body weight, thereby likely reducing waist circumference, and fasting glucose levels.

As illustrated herein, administration of an antisense oligonucleotide targeted to FGFR4 to animals models of diabetes and obesity which exhibit insulin resistance, hyperglycemia and hyperlipidemia, resulted in antisense inhibition of FGFR4, a reduction in body fat weight, percentage body fat content and tissue weight of both epididymal and perirenal fat. Particularly, expression of FGFR4 was reduced. Thus, it is demonstrated that in an experimental model of obesity, antisense inhibition of FGFR4 results in reduced glucose levels and reduced lipogenesis. Accordingly, provided herein are methods of reducing lipogenesis and blood glucose through the administration of an antisense compound targeted to an FGFR4 nucleic acid. Blood glucose and triglyceride levels are considered a risk factor for development of diabetes, obesity and metabolic syndrome. Accordingly, also provided herein are methods for the treatment, prevention and/or amelioration of diabetes, obesity and metabolic syndrome, and for the treatment, prevention and/or amelioration of associated disorders.

Obesity is characterized by an excess of subcutaneous fat in proportion to lean body mass. In obesity, adipose tissue, as opposed to most tissues in the body, will continue to grow. Growth of the adipose tissue results from both the enlargement of mature adipocytes and the formation of new adipocytes from adipocyte precursor cells (preadipocytes). Thus, fat accumulation is associated with increase in the size (hypertrophy) as well as the number (hyperplasia) of adipose tissue cells.

The Examples provided herein show that reduction of FGFR4 by antisense oligonucleotides results in a reduction in body fat content. As indicated by the description of fat accumulation above, the lowered body fat content is partially due to a decrease in adipocyte size (see FIG. 4.) Additionally, due to the function of FGFR4 in cell differentiation and angiogenesis, the lowered body fat content is also achieved by a reduction adipocyte proliferation.

Certain Indications

In certain embodiments, the invention provides methods of treating an individual comprising administering one or more pharmaceutical compositions of the present invention. In certain embodiments, the individual has diabetes, obesity, metabolic syndrome and/or associated disorders including but not limited to type 2 diabetes, type 2 diabetes with dyslipidemia, dyslipidemia, hyperlipidemia, or non-alcoholic fatty liver disease.

In one embodiment are methods for methods for treating obesity or metabolic syndrome, or alternatively methods for decreasing blood glucose levels or triglyceride levels, by administering to an individual suffering from obesity or elevated glucose or triglyceride levels a therapeutically effective amount of an antisense compound targeted to an FGFR4 nucleic acid. In another embodiment, a method of decreasing body fat content comprises selecting an individual in need of a decrease in body fat content, and administering to the individual a therapeutically effective amount of an antisense compound targeted to an FGFR4 nucleic acid. In a further embodiment, a method of reducing risk of development of obesity and metabolic syndrome includes selecting an individual having elevated blood glucose or triglyceride levels and one or more additional indicators risk of development of obesity or metabolic syndrome, and administering to the individual a therapeutically effective amount of an antisense compound targeted to an FGFR4 nucleic acid.

In one embodiment, administration of a therapeutically effective amount of an antisense compound targeted an FGFR4 nucleic acid is accompanied by monitoring of glucose levels in the serum of an individual, to determine an individual's response to administration of the antisense compound. An individual's response to administration of the antisense compound is used by a physician to determine the amount and duration of therapeutic intervention.

A physician may determine the need for therapeutic intervention for individuals in cases where more or less aggressive blood glucose or adiposity therapy is needed. The practice of the methods herein may be applied to any altered guidelines provided by the NCEP, or other entities that establish guidelines for physicians used in treating any of the diseases or conditions listed herein, for determining and diagnosing metabolic syndrome.

In one embodiment, administration of an antisense compound targeted an FGFR4 nucleic acid is parenteral administration. Parenteral administration may be intravenous or subcutaneous administration. Accordingly, in another embodiment, administration of an antisense compound targeted to an FGFR4 nucleic acid is intravenous or subcutaneous administration. Administration may include multiple doses of an antisense compound targeted to an FGFR4 nucleic acid.

In certain embodiments a pharmaceutical composition comprising an antisense compound targeted to FGFR4 is for use in therapy. In certain embodiments, the therapy is the reduction of blood glucose, body fat content, or fat tissue weight in an individual. In certain embodiments, the therapy is the treatment of obesity, metabolic syndrome, mixed dyslipidemia, type 2 diabetes, type 2 diabetes with dyslipidemia, dyslipidemia, hypertriglyceridemia, hyperlipidemia, or non-alcoholic fatty liver disease.

In certain embodiments pharmaceutical composition comprising an antisense compound targeted to FGFR4 is used for the preparation of a medicament for reduction of blood glucose, blood glucose, body fat content, or fat tissue weight. In certain embodiments pharmaceutical composition comprising an antisense compound targeted to FGFR4 is used for the preparation of a medicament for reducing body fat content and obesity. In certain embodiments an antisense compound targeted to FGFR4 is used for the preparation of a medicament for the treatment of metabolic syndrome disorders. In certain embodiments an antisense compound targeted to FGFR4 is used for the preparation of a medicament of type 2 diabetes, type 2 diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition comprising an antisense compound targeted to a FGFR4 nucleic acid include glucose-lowering agents and therapies. In some embodiments, the glucose-lowering agent is a PPAR agonist (gamma, dual, or pan), a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain such embodiments, the glucose-lowering agent is administered prior to administration of a pharmaceutical composition of the present invention. In certain such embodiments, the glucose-lowering agent is administered following administration of a pharmaceutical composition of the present invention. In certain such embodiments the glucose-lowering agent is administered at the same time as a pharmaceutical composition of the present invention. In certain such embodiments the dose of a co-administered glucose-lowering agent is the same as the dose that would be administered if the glucose-lowering agent was administered alone. In certain such embodiments the dose of a co-administered glucose-lowering agent is lower than the dose that would be administered if the glucose-lowering agent was administered alone. In certain such embodiments the dose of a co-administered glucose-lowering agent is greater than the dose that would be administered if the glucose-lowering agent was administered alone.

In certain embodiments, pharmaceutical agents that may be co-administered with a pharmaceutical composition comprising an antisense compound targeted to a FGFR4 nucleic acid include anti-obesity agents. Such anti-obesity agents include but are not limited to Orlistat, Sibutramine, or Rimonabant, and may be administered as described above as adipose or body weight lowering agents.

In certain embodiments, pharmaceutical agents that may be co-administered with a pharmaceutical composition comprising an antisense compound targeted to a FGFR4 nucleic acid include antipsychotic agents. Such antipsychotic agents therapeutics may be administered as described above to reduce metabolic abnormalities associated with treatment with antipsychotic agents.

Due to the ability of FGFR4 antisense oligonucleotides to increase metabolic rate and insulin sensitivity and reduce adiposity and weight gain, these compounds can be administered to reduce metabolic abnormalities associated with treatment with antipsychotic agents. In certain embodiments the FGFR4 antisense oligonucleotide is delivered in a method of reducing metabolic abnormalities associated with the therapeutic use of psychotherapeutic agents. Such weight inducing antipsychotic agents include, but are not limited to clozapine, olanzapine, aripiprazole, risperidone and ziprasidone.

In certain embodiments the FGFR4 antisense oligonucleotide is delivered concomitant with delivery of the psychotherapeutic agent. Alternatively, delivery can be in the same formulation or can be administered separately. In certain embodiments, FGFR4 antisense oligonucleotide is administered prior to the treatment with antipsychotic agents. In a certain embodiment, the FGFR4 antisense oligonucleotide is administered after treatment with an obesity inducing drug or agent is ceased. In a particular embodiment administering of the FGFR4 antisense compound results in increased metabolic rate or decreasing adiposity or both without affecting the CNS effects of the psychotherapeutic agent In certain embodiments, FGFR4 antisense oligonucleotides are administered in combination either in the same formulation or separate formulations with other anti-obesity drugs or agents. In certain embodiment, the anti-obesity agents are CNS based such as, but not limited to, sibutramine or GLP-1 based such as, but not limited to, liraglutide.

Further provided is a method of administering an antisense compound targeted to a FGFR4 nucleic acid via injection and further including administering a topical steroid at the injection site.

Further examples of pharmaceutical agents that may be co-administered with a pharmaceutical composition of the present invention include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjunction with a lipid-lowering therapy. In certain such embodiments, a lipid-lowering therapy is therapeutic lifestyle change. In certain such embodiments, a lipid-lowering therapy is LDL apheresis.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, the present invention provides oligonucleotides of any of a variety of ranges of lengths. In certain embodiments, the invention provides oligonucleotides consisting of X—Y linked oligonucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligonucleotides comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 liked nucleosides.

In certain embodiments, an antisense compound targeted to an FGFR4 nucleic acid is 8 to 80, 12 to 50, 12 to 30 or 15 to 30 subunits in length. In other words, antisense compounds are from 8 to 80, 12 to 50, 12 to 30 or 15 to 30 linked subunits. In certain such embodiments, the antisense compounds are 12, 13, 14, 15, 16, 17, 18, 19, 20, 21, 22, 23, 24, 25, 26, 27, 28, 29, or 30 subunits in length.

In certain embodiments, an antisense oligonucleotide targeted to an FGFR4 nucleic acid is 12 to 30 nucleotides in length. In certain such embodiments, an antisense oligonucleotide targeted to an FGFR4 nucleic acid is 12, 13, 14, 15, 16, 17, 18, 19, 20, 21, 22, 23, 24, 25, 26, 27, 28, 29, or 30 nucleotides in length.

In certain embodiment, an antisense compound targeted to an FGFR4 nucleic acid is 15 to 30 subunits in length. In other words, antisense compounds are from 15 to 30 linked subunits. In certain such embodiments, the antisense compounds are 15, 16, 17, 18, 19, 20, 21, 22, 23, 24, 25, 26, 27, 28, 29, or 30 subunits in length.

In certain embodiments, an antisense oligonucleotide targeted to an FGFR4 nucleic acid is 15 to 30 nucleotides in length. In certain such embodiments, an antisense oligonucleotide targeted to an FGFR4 nucleic acid is 15, 16, 17, 18, 19, 20, 21, 22, 23, 24, 25, 26, 27, 28, 29, or 30 nucleotides in length.

In certain embodiments, an antisense compound targeted to an FGFR4 nucleic acid is 18 to 24 subunits in length. In other words, antisense compounds are from 18 to 24 linked subunits. In one embodiment, the antisense compounds are 18, 19, 20, 21, 22, 23, or 24 subunits in length.

In certain embodiments, an antisense oligonucleotide targeted to an FGFR4 nucleic acid is 18 to 24 nucleotides in length. In certain such embodiments, an antisense oligonucleotide targeted to an FGFR4 nucleic acid is 18, 19, 20, 21, 22, 23, or 24 nucleotides in length.

In certain embodiments, an antisense compound targeted to an FGFR4 nucleic acid is 19 to 22 subunits in length. In other words, antisense compounds are from 19 to 22 linked subunits. This embodies antisense compounds of 19, 20, 21, or 22 subunits in length.

In certain embodiments, an antisense oligonucleotide targeted to an FGFR4 nucleic acid is 19 to 22 nucleotides in length. In certain such embodiments, an antisense oligonucleotide targeted to an FGFR4 nucleic acid is 19, 20, 21, or 22 nucleotides in length.

In certain embodiments, an antisense compound targeted to an FGFR4 nucleic acid is 20 subunits in length. In certain such embodiments, antisense compounds are 20 linked subunits in length.

In certain embodiments, an antisense oligonucleotide targeted to an FGFR4 nucleic acid is 20 nucleotides in length. In certain such embodiments, an antisense oligonucleotide targeted to an FGFR4 nucleic acid is 20 linked nucleotides in length.

In certain embodiments, a shortened or truncated antisense compound targeted to an FGFR4 nucleic acid has a single subunit deleted from the 5' end (5' truncation), or alternatively from the 3' end (3' truncation). A shortened or truncated antisense compound targeted to an FGFR4 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two are more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

(Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense compounds targeted to an FGFR4 nucleic acid are synthesized in vitro and do not include genetic vector constructs designed to direct the in vivo synthesis of antisense molecules. In certain embodiments, the compounds provided herein targeted to an FGFR4 nucleic acid are specific for FGFR4 meaning they are not cross-reactive with other FGF receptor subtypes.

Antisense Compound Motifs

In certain embodiments, antisense compounds targeted to an FGFR4 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may serve as a substrate for the cellular endonuclease RNase H, which cleaves the RNA strand of an RNA:DNA duplex.

Antisense compounds having a gapmer motif are considered chimeric antisense compounds. In a gapmer an internal position having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. The regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). In general, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region.

In one embodiment, antisense compounds targeted to an FGFR4 nucleic acid possess a 5-10-5 gapmer motif.

Target Nucleic Acids, Target Regions and Nucleotide Sequences

Gene Targets

Nucleotide sequences that encode *Mus musculus* FGFR4 include, without limitation, the following: GENBANK® Accession No. AY493377.2, incorporated herein as SEQ ID NO: 9 GENBANK® Accession No. BC033313.1, incorporated herein as SEQ ID NO: 10; GENBANK® Accession No. BQ567109.1 incorporated herein as SEQ ID NO: 11; GENBANK® Accession No. NM_008011.1 incorporated herein as SEQ ID NO: 12; and nucleotides 790799 to 800614 of GENBANK® Accession No NT_039586. incorporated herein as SEQ ID NO: 13; and nucleotides 792000 to 811000 of GENBANK® Accession No. NT_039586.5 incorporated herein as SEQ ID NO: 14.

Nucleotide sequences that encode human FGFR4 include, without limitation, the following: GENBANK® Accession No. AF202063.1, incorporated herein as SEQ ID NO: 1; GENBANK® Accession No. AF359241.1, incorporated herein as SEQ ID NO: 2; GENBANK® Accession No. BF305431.1, incorporated herein as SEQ ID NO: 3; GENBANK® Accession No. BM803172.1, incorporated herein as SEQ ID NO: 4; GENBANK® Accession No. NM_002011.3, incorporated herein as SEQ ID NO: 5; GENBANK® Accession NM_022963.1 incorporated herein as SEQ ID NO: 6; nucleotides 21323018 to 21335213 of GENBANK® Accession No. NT_023133.11, incorporated herein as SEQ ID NO: 7; and nucleotides 8583892 to 8595932 of GENBANK® Accession No. NT_023132.9, incorporated herein as SEQ ID NO: 8.

TABLE 1

Gene Targets, Synonyms and Regions

| Target Name | Synonyms | Species | Genbank # | SEQ ID NO |
|---|---|---|---|---|
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | AF202063.1 | 1 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | AF359241.1 | 2 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | BF305431.1 | 3 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | BM803172.1 | 4 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | NM_002011.3 | 5 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | NM_022963.1 | 6 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | nucleotides 21323018 to 21335213 of NT_023133.11 | 7 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Human | nucleotides 8583892 to 8595932 of NT_023132.9 | 8 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | AY493377.2 | 9 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | BC033313.1 | 10 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | BQ567109.1 | 11 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | NM_008011.1 | 12 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | nucleotides 790799 to 800614 of NT_039586.2 | 13 |
| fibroblast growth factor receptor 4 | FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2 | Mouse | nucleotides 792000 to 811000 of NT_039586.5 | 14 |

*Mus musculus* Nucleotide Sequences Targeted to FGFR4

Nucleotide sequences that encode *Mus musculus* FGFR4 include, without limitation, the following: GENBANK® Accession No. AY493377.2, incorporated herein as SEQ ID NO: 9 GENBANK® Accession No. BC033313.1, incorporated herein as SEQ ID NO: 10; GENBANK® Accession No. BQ567109.1 incorporated herein as SEQ ID NO: 11; GENBANK® Accession No. NM_008011.1 incorporated herein as SEQ ID NO: 12; and nucleotides 790799 to 800614 of GENBANK® Accession No NT_039586. incorporated herein as SEQ ID NO: 13; and nucleotides 792000 to 811000 of GENBANK® Accession No. NT_039586.5 incorporated herein as SEQ ID NO: 14.

It is noted that some portions of these nucleotide sequences share identical sequence. Examples of such antisense compounds are shown in Table 2. In certain such embodiments, an antisense oligonucleotide targets SEQ ID NO: 9, 10, 11, 12, 13 or 14. In certain such embodiments, an antisense oligonucleotide that is targeted to any of SEQ ID NO: 9, 10, 11, 12, 13 or 14 is at least 90% complementary to the corresponding SEQ ID NO: 9, 10, 11, 12, 13 or 14. In certain such embodiments, an antisense oligonucleotide that is targeted to any of SEQ ID NO: 9, 10, 11, 12, 13 or 14 is at least 95% complementary to the corresponding SEQ ID NO: 9, 10, 11, 12, 13 or 14. In certain such embodiments, an antisense oligonucleotide that is targeted to any of SEQ ID NO: 9, 10, 11, 12, 13 or 14 is 100% complementary to the corresponding SEQ ID NO: 9, 10, 11, 12, 13 or 14. In certain embodiments, an antisense oligonucleotide targeted to any of SEQ ID NO: 9, 10, 11, 12, 13 or 14 comprises a nucleotide sequence selected from the nucleotide sequences set forth in Table 1.

In certain embodiments, gapmer antisense compounds are targeted to an FGFR4 nucleic acid of *Mus musculus*. In certain such embodiments, gapmer antisense compounds are targeted to SEQ ID NOs: 9, 10, 11, 12, 13 or 14. In certain such embodiments, the nucleotide sequences illustrated in Table 1 have a 5-10-5 gapmer motif. Table 2 illustrates gapmer antisense compounds targeted to SEQ ID NO: 10 and 14, having a 5-10-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 2

Nucleotide sequences targeted to Mouse (*Mus musculus*) FGFR4 Sequences of SEQ ID NOs: 10 and 14

| ISIS # | Target SEQ ID NO | 5' Target Site | 3' Target Site | Sequence (5' to 3') | SEQ ID NO | 2'MOE Gapmer Motif |
|---|---|---|---|---|---|---|
| 393247 | 10 | 228 | 247 | GGGCTGGCACACTCACCCGC | 15 | 5 10 5 |
| 393248 | 10 | 238 | 257 | GATCCCGGCAGGGCTGGCAC | 16 | 5 10 5 |
| 393249 | 10 | 244 | 263 | GGTCACGATCCCGGCAGGGC | 17 | 5 10 5 |
| 393250 | 10 | 337 | 356 | GCCACATTTCCTTCCAGCTG | 18 | 5 10 5 |
| 393251 | 10 | 346 | 365 | CCAAGAGCAGCCACATTTCC | 19 | 5 10 5 |
| 393252 | 10 | 355 | 374 | TCAACAGGGCCAAGAGCAGC | 20 | 5 10 5 |
| 393253 | 10 | 402 | 421 | TTCCTCAGAGGCCTCAAGGG | 21 | 5 10 5 |
| 393254 | 10 | 600 | 619 | AGGAAGGAAGCTGGCGATCT | 22 | 5 10 5 |
| 393255 | 10 | 610 | 629 | CAGCATCCTCAGGAAGGAAG | 23 | 5 10 5 |
| 393256 | 10 | 635 | 654 | CCACGGGCCAGGCAGAGGTA | 24 | 5 10 5 |
| 393257 | 10 | 644 | 663 | GTCATGGAGCCACGGGCCAG | 25 | 5 10 5 |
| 393258 | 10 | 682 | 701 | AGGAGTCATCCATAAGCAAC | 26 | 5 10 5 |
| 393259 | 10 | 687 | 706 | GGTTAAGGAGTCATCCATAA | 27 | 5 10 5 |
| 393260 | 10 | 694 | 713 | TGATGGAGGTTAAGGAGTCA | 28 | 5 10 5 |
| 393261 | 10 | 773 | 792 | TGTGTCCAGTAGGGTGCTTG | 29 | 5 10 5 |
| 393262 | 10 | 873 | 892 | CCAGTGGATGGTAGGCATGG | 30 | 5 10 5 |
| 393263 | 10 | 878 | 897 | TTGAGCCAGTGGATGGTAGG | 31 | 5 10 5 |
| 393264 | 10 | 996 | 1015 | AAGGCATGTGTATGTGCCAC | 32 | 5 10 5 |
| 393265 | 10 | 1001 | 1020 | TCCACAAGGCATGTGTATGT | 33 | 5 10 5 |
| 393266 | 10 | 1020 | 1039 | AATGCTACCCAGAGAGTTCT | 34 | 5 10 5 |
| 393267 | 10 | 1048 | 1067 | CCAGCACATCCAGGAGATAG | 35 | 5 10 5 |
| 299029 | 10 | 1200 | 1219 | GCTGCTGCCGTTGATGACGA | 36 | 5 10 5 |
| 393268 | 10 | 1245 | 1264 | TGTTGTCTTCAGGACTTGTA | 37 | 5 10 5 |
| 393269 | 10 | 1364 | 1383 | AGCCACGCTGACTGGTAGGA | 38 | 5 10 5 |
| 299036 | 10 | 1380 | 1399 | CTCTGGCAGCACCGTGAGCC | 39 | 5 10 5 |
| 393270 | 10 | 1446 | 1465 | TGATACATCAGGATGATAT | 40 | 5 10 5 |
| 393271 | 10 | 1466 | 1485 | ACAAGCAGAACCAGTGAGCC | 41 | 5 10 5 |
| 393272 | 10 | 1471 | 1490 | GGAGCACAAGCAGAACCAGT | 42 | 5 10 5 |
| 393273 | 10 | 1490 | 1509 | TACACCCCGGCCAGCAGCAG | 43 | 5 10 5 |
| 393274 | 10 | 1604 | 1623 | GACTTGCCAGAGGACCTCGA | 44 | 5 10 5 |

TABLE 2-continued

Nucleotide sequences targeted to Mouse (*Mus musculus*)
FGFR4 Sequences of SEQ ID NOs: 10 and 14

| ISIS # | Target SEQ ID NO | 5' Target Site | 3' Target Site | Sequence (5' to 3') | SEQ ID NO | 2'MOE Gapmer Motif |
|---|---|---|---|---|---|---|
| 393275 | 10 | 1615 | 1634 | GGGACAAACTTGACTTGCCA | 45 | 5 10 5 |
| 393276 | 10 | 1625 | 1644 | CCTCGCACCAGGGACAAACT | 46 | 5 10 5 |
| 393277 | 10 | 1670 | 1689 | ACAAGGCCCGTGAGCAAGGG | 47 | 5 10 5 |
| 393278 | 10 | 1756 | 1775 | CAAAGCAGCCCTCACCCAGG | 48 | 5 10 5 |
| 393279 | 10 | 1775 | 1794 | TCTGCACGAACCACTTGCCC | 49 | 5 10 5 |
| 393280 | 10 | 1796 | 1815 | GAGGGATCCATACCAAAGGC | 50 | 5 10 5 |
| 393281 | 10 | 1850 | 1869 | GAGGCATTGTCTTTCAGCAT | 51 | 5 10 5 |
| 393282 | 10 | 1870 | 1889 | GGTCTGCCAAATCCTTGTCG | 52 | 5 10 5 |
| 393283 | 10 | 1910 | 1929 | TGTCTTCCGATTAGCTTCAT | 53 | 5 10 5 |
| 393284 | 10 | 1939 | 1958 | AGACACCCAGCAGGTTGATG | 54 | 5 10 5 |
| 393285 | 10 | 1945 | 1964 | GAGTGCAGACACCCAGCAGG | 55 | 5 10 5 |
| 393286 | 10 | 1956 | 1975 | GGGCCCTTCCTGAGTGCAGA | 56 | 5 10 5 |
| 393287 | 10 | 2048 | 2067 | CCATCAGGGCTGAGATCAGG | 57 | 5 10 5 |
| 322160 | 10 | 2131 | 2150 | CCAGATACTGCATGCCTCGG | 58 | 5 10 5 |
| 393288 | 10 | 2150 | 2169 | TGGATGCACTTCCGAGACTC | 59 | 5 10 5 |
| 393289 | 10 | 2380 | 2399 | CCCCGAGGGTGAAGATTTCC | 60 | 5 10 5 |
| 393290 | 10 | 2440 | 2459 | TGTGCCCCTCTCGCAGCAGT | 61 | 5 10 5 |
| 393291 | 10 | 2490 | 2509 | CCTCATTAGCCCATACAGCT | 62 | 5 10 5 |
| 393292 | 10 | 2555 | 2574 | TTGTCCAGAGCTTCCACCAG | 63 | 5 10 5 |
| 299052 | 10 | 2567 | 2586 | GCCAGCAGGACCTTGTCCAG | 64 | 5 10 5 |
| 393293 | 10 | 2580 | 2599 | CTCTTCAGAGACAGCCAGCA | 65 | 5 10 5 |
| 393294 | 10 | 2600 | 2619 | GTCAGGCGGAGGTCAAGGTA | 66 | 5 10 5 |
| 393295 | 10 | 2616 | 2635 | AGAAAAGGGTCCAAAGGTCA | 67 | 5 10 5 |
| 393296 | 10 | 2628 | 2647 | CCCATTGGAGGGAGAAAAGG | 68 | 5 10 5 |
| 393297 | 10 | 2635 | 2654 | TGGCATCCCCATTGGAGGGA | 69 | 5 10 5 |
| 393298 | 10 | 2641 | 2660 | TGCTGCTGGCATCCCCATTG | 70 | 5 10 5 |
| 393299 | 10 | 2880 | 2899 | CAGGGCCAGAGAGAGGATCT | 71 | 5 10 5 |
| 393300 | 10 | 2935 | 2954 | TGGAACAGAAGGCCTCAACT | 72 | 5 10 5 |
| 393301 | 10 | 2994 | 3013 | CCAAGGGCAAGGCCATGATC | 73 | 5 10 5 |
| 393302 | 10 | 3000 | 3019 | ATGAGTCCAAGGGCAAGGCC | 74 | 5 10 5 |
| 393303 | 10 | 3005 | 3024 | TGAGGATGAGTCCAAGGGCA | 75 | 5 10 5 |
| 393304 | 10 | 3085 | 3104 | TAGAGCATAAGTTTTGCAGC | 76 | 5 10 5 |
| 393305 | 10 | 3090 | 3109 | ATGTTTAGAGCATAAGTTTT | 77 | 5 10 5 |
| 393306 | 10 | 3095 | 3114 | TAGAAATGTTTAGAGCATAA | 78 | 5 10 5 |
| 393307 | 10 | 3120 | 3139 | AGGCCTCTAGGTTGTTTGGG | 79 | 5 10 5 |
| 393308 | 10 | 3277 | 3296 | TTTATAAAAATGCCATGTTC | 80 | 5 10 5 |

TABLE 2-continued

Nucleotide sequences targeted to Mouse (Mus musculus) FGFR4 Sequences of SEQ ID NOs: 10 and 14

| ISIS # | Target SEQ ID NO | 5' Target Site | 3' Target Site | Sequence (5' to 3') | SEQ ID NO | 2'MOE Gapmer Motif |
|---|---|---|---|---|---|---|
| 393310 | 14 | 3566 | 3585 | TTCCATGCCCAGTTTGGGAC | 81 | 5 10 5 |
| 393311 | 14 | 4800 | 4819 | GGAGTCATTGATACCCATAG | 82 | 5 10 5 |
| 393312 | 14 | 6049 | 6068 | GTCAGAGTGGAGGCAGGTTA | 83 | 5 10 5 |
| 393313 | 14 | 7448 | 7467 | TTGATTCCCAGCAAATACAT | 84 | 5 10 5 |
| 393314 | 14 | 7805 | 7824 | ACCCAGCACATCCAGGAGAT | 85 | 5 10 5 |
| 393315 | 14 | 8295 | 8314 | CCCCACAAATGTTGCACCCA | 86 | 5 10 5 |
| 393316 | 14 | 10349 | 10368 | GCCCAGGTTGCCATGTGTAC | 87 | 5 10 5 |
| 393317 | 14 | 12504 | 12523 | GGTTTTGTTATGCATTAGAG | 88 | 5 10 5 |
| 393318 | 14 | 14115 | 14134 | GATCAGGAAGCATAGAAGGA | 89 | 5 10 5 |
| 393319 | 14 | 15655 | 15674 | GACAGTGGTGTGAGTAGTAT | 90 | 5 10 5 |
| 393320 | 14 | 16387 | 16406 | GAACAGGTCAAAGAGGTTTG | 91 | 5 10 5 |

Human Nucleotide Sequences Targeted to FGFR4

Nucleotide sequences that encode human FGFR4 include, without limitation, the following: GENBANK® Accession No. AF202063.1, incorporated herein as SEQ ID NO: 1; GENBANK® Accession No. AF359241.1, incorporated herein as SEQ ID NO: 2; GENBANK® Accession No. BF305431.1, incorporated herein as SEQ ID NO: 3; GENBANK® Accession No. BM803172.1, incorporated herein as SEQ ID NO: 4; GENBANK® Accession No. NM_002011.3, incorporated herein as SEQ ID NO: 5; GENBANK® Accession NM_022963.1 incorporated herein as SEQ ID NO: 6; nucleotides 21323018 to 21335213 of GENBANK® Accession No. NT_023133.11, incorporated herein as SEQ ID NO: 7; and nucleotides 8583892 to 8595932 of GENBANK® Accession No. NT_023132.9, incorporated herein as SEQ ID NO: 8.

Antisense oligonucleotides with a 5-10-5 2'-MOE gapmer motif were designed to target human FGFR4 (Table 3). All oligonucleotides of the two series are full phosphorothioate oligonucleotides. GENBANK® Accession No. NM_002011.3 represents the main mRNA which uses exons 1-18. GENBANK® Accession No. NM_022963.1 represents a variant that uses exons 1-8, splices to 10a, and 11-18. Exon 10a starts at the beginning of intron 9 and ends at the end of exon 10. GENBANK® Accession No. AF202063.1 uses exons 3-8, 10a, 10-17, and intron 9. Exon 10a starts 1 nucleotide residue after Exon 8 and ends 219 nucleotide residues after. GENBANK® Accession No. NT_023132.9 (nucleotide residues 8583892-8595932) represents a variant that starts with exon 1, splices to exon 1a, exons 2-4, splices to exon 4a, exons 5-9, splices to exon 10a, exons 10-18 and introns 1, splices to intron 1a, and introns 2-17. Exon 1a starts 10 nucleotide residues before Exon1 ends and ends 44 nucleotide residues after exon1 ends. Exon 4a starts at the beginning of there exon 4 starts and ends 271 nucleotide residues after exon 4. Exon 10a starts 1 nucleotide residue after exon 9 and ends 220 nucleotide residues after. Intron 1a, starts 44 nucleotide residues after the start of intron 1 and ends at the end of intron 1. GENBANK® Accession No. BM803172.1 represents a variant that uses exons 1-2, then splices to exons 4-6. GENBANK® Accession No. BF305431.1 represents a variant that uses and starts with exon 1a (ends in intron 1), splices to and uses exon 2, splices to and uses exons 4-6. GENBANK® Accession No. AF359241.1 represents a variant that begins with and uses exons 2-3, splices to and uses exon 4a (starts at the beginning of exon 4 and ends in exon 5). GENBANK® Accession No. NT_023133.11 (nucleotide residues 21323018-21335213) represents a gene that starts with exon 1, splices to exon 1a, exons 2-4, splices to exon 4a, exons 5-9, splices to exon 10a, exons 10-18 and introns 1, splices to intron 1a, and introns 2-17. Exon 1a starts 10 nucleotide residues before exon1 ends and ends 44 nucleotide residues after exon 1 ends. Exon 4a starts at the beginning of there exon 4 starts and ends 271 nucleotide residues after exon 4. Exon 10a starts 1 nucleotide residue after exon 9 and ends 220 nucleotide residues after. Intron 1a, starts 44 nucleotide residues after the start of intron 1 and ends at the end of intron 1.

GENBANK® Accession No. NM_002011.3 represents the genomic sequence that uses exons 2-18. The antisense oligonucleotides were selected to cover the full genomic human FGFR4 sequence.

In certain embodiments, an antisense oligonucleotide targets SEQ ID NO: 1, 2, 3, 4, 5, 6, 7, or 8. In certain such embodiments, an antisense oligonucleotide that is targeted to any of SEQ ID NO: 1, 2, 3, 4, 5, 6, 7, or 8 is at least 90% complementary to the corresponding SEQ ID NO: 1, 2, 3, 4, 5, 6, 7, or 8. In certain such embodiments, an antisense oligonucleotide that is targeted to any of SEQ ID NO: 1, 2, 3, 4, 5, 6, 7, or 8 is at least 95% complementary to the corresponding SEQ ID NO: 1, 2, 3, 4, 5, 6, 7, or 8. In certain such embodiments, an antisense oligonucleotide that is targeted to any of SEQ ID NO: 1, 2, 3, 4, 5, 6, 7, or 8 is 100% complementary to the corresponding SEQ ID NO: 1, 2, 3, 4, 5, 6, 7, or 8. In certain embodiments, an antisense oligonucleotide targeted to any of SEQ ID NOs: 1, 2, 3, 4, 5, 6, 7, or 8 comprises a nucleotide sequence selected from the nucleotide sequences set forth in Table 3.

In certain embodiments, gapmer antisense compounds are targeted to an FGFR4 nucleic acid. In certain such embodiments, gapmer antisense compounds are targeted to SEQ ID NOs: 1, 2, 3, 4, 5, 6, 7, or 8. In certain such embodiments, the nucleotide sequences illustrated in Table 3 have a 5-10-5 gapmer motif. Table 3 illustrates gapmer antisense compounds targeted to SEQ ID NOs: 1, 2, 3, 4, 5, 6, 7, or 8, having a 5-10-5 motif, where the gap segment comprises 2'-deoxynucleotides and each wing segment comprises nucleotides comprising a 2'-O-methoxyethyl sugar modification.

Internucleoside linkages are phosphorothioate, and cytidines are 5-methylcytidines. The following embodiments set forth target regions of *Mus musculus* and human FGFR4 nucleic acids. Also illustrated are examples of antisense compounds targeted to the target regions. It is understood that the sequence set forth in each SEQ ID NO is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Internucleoside linkages are phosphorothioate, and cytidines are 5-methylcytidines.

TABLE 3

Nucleotide sequences targeted to Human FGFR4 Sequences of SEQ ID NOs: 2, 3, 4, 5, 6 and 8

| ISIS # | Target SEQ ID NO | 5' Target Site | 3' Target Site | Sequence (5' to 3') | SEQ ID NO | 2'-MOE Gapmer Motif |
|---|---|---|---|---|---|---|
| 299069 | 2 | 455 | 474 | CAGCGGGACACAAGTCCTTG | 92 | 5 10 5 |
| 299067 | 3 | 46 | 65 | AACTGCCTTCCTCGAGCCTG | 93 | 5 10 5 |
| 299065 | 4 | 306 | 325 | GTCAAGGAGTCAAGCTCCAC | 94 | 5 10 5 |
| 299066 | 4 | 891 | 910 | GGTAGAGGGATGTCAACCAG | 95 | 5 10 5 |
| 299003 | 5 | 26 | 45 | GGCAGGGTCCGCAGACAGCC | 96 | 5 10 5 |
| 299004 | 5 | 160 | 179 | CAGCAGCCGCATCTCCTTCT | 97 | 5 10 5 |
| 299005 | 5 | 192 | 211 | GGCACACTCAGCAGGACCCC | 98 | 5 10 5 |
| 299006 | 5 | 208 | 227 | CAAGACTGGAGGCCCAGGCA | 99 | 5 10 5 |
| 299007 | 5 | 254 | 273 | GAGCCAGGCAGGGCTCAAGC | 100 | 5 10 5 |
| 299008 | 5 | 278 | 297 | CCTGCTCTTGCTGCTCCAGG | 101 | 5 10 5 |
| 299009 | 5 | 289 | 308 | TACTGTCAGCTCCTGCTCTT | 102 | 5 10 5 |
| 299010 | 5 | 304 | 323 | AGGCTGCCCAAGGGCTACTG | 103 | 5 10 5 |
| 299012 | 5 | 354 | 373 | TCCTTGTACCAGTGGCCACC | 104 | 5 10 5 |
| 299013 | 5 | 380 | 399 | GGCCAGCAGGTGCCAGGCGA | 105 | 5 10 5 |
| 299014 | 5 | 412 | 431 | AATCTCTAGGCGGCCCCTCC | 106 | 5 10 5 |
| 299015 | 5 | 475 | 494 | GACGATCATGGAGCCTCGTG | 107 | 5 10 5 |
| 299016 | 5 | 483 | 502 | TTCTGCAGGACGATCATGGA | 108 | 5 10 5 |
| 299017 | 5 | 529 | 548 | ATCATCGTTGCTGGAGGTCA | 109 | 5 10 5 |
| 299018 | 5 | 597 | 616 | GTCCAGTAGGGTGCTTGCTG | 110 | 5 10 5 |
| 299019 | 5 | 602 | 621 | GGTGTGTCCAGTAGGGTGCT | 111 | 5 10 5 |
| 299020 | 5 | 627 | 646 | TGCAGTTTCTTCTCCATGCG | 112 | 5 10 5 |
| 299021 | 5 | 711 | 730 | CCATCCTTAAGCCAGCGGAT | 113 | 5 10 5 |
| 299022 | 5 | 727 | 746 | CCCATGAAAGGCCTGTCCAT | 114 | 5 10 5 |
| 299023 | 5 | 739 | 758 | AATGCGGTTCTCCCCATGAA | 115 | 5 10 5 |
| 299024 | 5 | 757 | 776 | GCGCAGCCGAATGCCTCCAA | 116 | 5 10 5 |
| 299025 | 5 | 785 | 804 | TCTCCATCACGAGACTCCAG | 117 | 5 10 5 |
| 299026 | 5 | 833 | 852 | CGTTCTCTACCAGGCAGGTG | 118 | 5 10 5 |
| 299027 | 5 | 964 | 983 | CTTGCACAGCAGCTCCACGT | 119 | 5 10 5 |
| 299028 | 5 | 969 | 988 | TACACCTTGCACAGCAGCTC | 120 | 5 10 5 |

TABLE 3-continued

Nucleotide sequences targeted to Human FGFR4 Sequences of SEQ ID NOs: 2, 3, 4, 5, 6 and 8

| ISIS # | Target SEQ ID NO | 5' Target Site | 3' Target Site | Sequence (5' to 3') | SEQ ID NO | 2'-MOE Gapmer Motif |
|---|---|---|---|---|---|---|
| 299029 | 5 | 1027 | 1046 | GCTGCTGCCGTTGATGACGA | 36 | 5 10 5 |
| 299030 | 5 | 1032 | 1051 | CCGAAGCTGCTGCCGTTGAT | 121 | 5 10 5 |
| 299031 | 5 | 1076 | 1095 | TGTCTGCAGTCTTTAGGACT | 122 | 5 10 5 |
| 299032 | 5 | 1090 | 1109 | CTCTGAGCTATTGATGTCTG | 123 | 5 10 5 |
| 299033 | 5 | 1095 | 1114 | TCCACCTCTGAGCTATTGAT | 124 | 5 10 5 |
| 299034 | 5 | 1121 | 1140 | CTGACACGTTCCGCAGGTAC | 125 | 5 10 5 |
| 299035 | 5 | 1181 | 1200 | ACTGGTAGGAGAGGCCGATG | 126 | 5 10 5 |
| 299036 | 5 | 1207 | 1226 | CTCTGGCAGCACCGTGAGCC | 39 | 5 10 5 |
| 299037 | 5 | 1235 | 1254 | GCGCTGCTGCGGTCCATGTG | 127 | 5 10 5 |
| 299038 | 5 | 1326 | 1345 | TGCCCTCGATACAGCCCGGC | 128 | 5 10 5 |
| 299039 | 5 | 1428 | 1447 | TTGCCGGAAGAGCCTGACTC | 129 | 5 10 5 |
| 299040 | 5 | 1447 | 1466 | TACCAGGGATGAGCTTGACT | 130 | 5 10 5 |
| 299041 | 5 | 1452 | 1471 | CCTCGTACCAGGGATGAGCT | 131 | 5 10 5 |
| 299042 | 5 | 1555 | 1574 | AAGCACCAGCCTGTCCCGGG | 132 | 5 10 5 |
| 299043 | 5 | 1607 | 1626 | AGGCCTCTGCACGTACTACC | 133 | 5 10 5 |
| 299044 | 5 | 1656 | 1675 | TTGACGGCCACAGTGCTGGC | 134 | 5 10 5 |
| 299045 | 5 | 1741 | 1760 | CTTGTGTCGGCCGATCAGCT | 135 | 5 10 5 |
| 299046 | 5 | 1772 | 1791 | GGGTGCAGACACCAAGCAGG | 136 | 5 10 5 |
| 299047 | 5 | 1919 | 1938 | AGACCAGGACTGGGAAGGAG | 137 | 5 10 5 |
| 299048 | 5 | 1968 | 1987 | TTCCGGGACTCCAGATACTG | 138 | 5 10 5 |
| 299049 | 5 | 1979 | 1998 | GGTGGATACACTTCCGGGAC | 139 | 5 10 5 |
| 299050 | 5 | 2268 | 2287 | CGATGTCCCTCCCGCAGCAG | 140 | 5 10 5 |
| 299051 | 5 | 2313 | 2332 | ATCAGCCCGTACAGCTCTGG | 141 | 5 10 5 |
| 299052 | 5 | 2394 | 2413 | GCCAGCAGGACCTTGTCCAG | 64 | 5 10 5 |
| 299053 | 5 | 2416 | 2435 | GTCGAGGTACTCCTCAGAGA | 142 | 5 10 5 |
| 299054 | 5 | 2481 | 2500 | CTGGAGGAGCAGGTGCTGCT | 143 | 5 10 5 |
| 299055 | 5 | 2497 | 2516 | GCTGAAGACAGAATCGCTGG | 144 | 5 10 5 |
| 299056 | 5 | 2503 | 2522 | GTCGTGGCTGAAGACAGAAT | 145 | 5 10 5 |
| 299057 | 5 | 2557 | 2576 | TCATGTCTGCACCCCAGACC | 146 | 5 10 5 |
| 299058 | 5 | 2565 | 2584 | AGCCTTGCTCATGTCTGCAC | 147 | 5 10 5 |
| 299059 | 5 | 2629 | 2648 | TGTGTCAGGCTGTGGCTGAG | 148 | 5 10 5 |
| 299060 | 5 | 2698 | 2717 | AAGGGCACGGCCCTTGGACA | 149 | 5 10 5 |
| 299061 | 5 | 2738 | 2757 | ATTTGGGCCATCAGGACACA | 150 | 5 10 5 |
| 299062 | 5 | 2752 | 2771 | AGCAGAACCCTGACATTTGG | 151 | 5 10 5 |
| 299063 | 5 | 2851 | 2870 | CCTGCTGGTATTGGGAGGCA | 152 | 5 10 5 |
| 299011 | 6 | 308 | 327 | ACAGCACAGCCGCACAGGCT | 153 | 5 10 5 |

TABLE 3-continued

Nucleotide sequences targeted to Human FGFR4 Sequences of SEQ ID NOs: 2, 3, 4, 5, 6 and 8

| ISIS # | Target SEQ ID NO | 5' Target Site | 3' Target Site | Sequence (5' to 3') | SEQ ID NO | 2'-MOE Gapmer Motif |
|---|---|---|---|---|---|---|
| 298992 | 6 | 1204 | 1223 | CGCCCAGTACCTGGCAGCAC | 154 | 5 10 5 |
| 299064 | 8 | 423 | 442 | GGAGCGAGGAATGTACCCGC | 155 | 5 10 5 |
| 299003 | 8 | 460 | 479 | GGCAGGGTCCGCAGACAGCC | 96 | 5 10 5 |
| 298994 | 8 | 583 | 602 | TCCGGCTCACCTCGAGCCTG | 156 | 5 10 5 |
| 298995 | 8 | 1913 | 1932 | GGAAACATCCTCTCCCTCGG | 157 | 5 10 5 |
| 299004 | 8 | 3110 | 3129 | CAGCAGCCGCATCTCCTTCT | 97 | 5 10 5 |
| 299005 | 8 | 3142 | 3161 | GGCACACTCAGCAGGACCCC | 98 | 5 10 5 |
| 299006 | 8 | 3158 | 3177 | CAAGACTGGAGGCCCAGGCA | 99 | 5 10 5 |
| 298996 | 8 | 3199 | 3218 | GAAGCCATACCAAGCTCCAC | 158 | 5 10 5 |
| 299008 | 8 | 3924 | 3943 | CCTGCTCTTGCTGCTCCAGG | 101 | 5 10 5 |
| 299009 | 8 | 3935 | 3954 | TACTGTCAGCTCCTGCTCTT | 102 | 5 10 5 |
| 299010 | 8 | 3950 | 3969 | AGGCTGCCCAAGGGCTACTG | 103 | 5 10 5 |
| 299012 | 8 | 4000 | 4019 | TCCTTGTACCAGTGGCCACC | 104 | 5 10 5 |
| 299013 | 8 | 4026 | 4045 | GGCCAGCAGGTGCCAGGCGA | 105 | 5 10 5 |
| 299014 | 8 | 4058 | 4077 | AATCTCTAGGCGGCCCCTCC | 106 | 5 10 5 |
| 299015 | 8 | 4121 | 4140 | GACGATCATGGAGCCTCGTG | 107 | 5 10 5 |
| 299016 | 8 | 4129 | 4148 | TTCTGCAGGACGATCATGGA | 108 | 5 10 5 |
| 299068 | 8 | 4174 | 4193 | TTCACTCCCTGCTAGAGTCT | 159 | 5 10 5 |
| 298997 | 8 | 4250 | 4269 | GTCAAGGAGTCTACATCAGG | 160 | 5 10 5 |
| 299017 | 8 | 4266 | 4285 | ATCATCGTTGCTGGAGGTCA | 109 | 5 10 5 |
| 299019 | 8 | 4451 | 4470 | GGTGTGTCCAGTAGGGTGCT | 111 | 5 10 5 |
| 299020 | 8 | 4476 | 4495 | TGCAGTTTCTTCTCCATGCG | 112 | 5 10 5 |
| 299021 | 8 | 4560 | 4579 | CCATCCTTAAGCCAGCGGAT | 113 | 5 10 5 |
| 299022 | 8 | 4576 | 4595 | CCCATGAAAGGCCTGTCCAT | 114 | 5 10 5 |
| 299023 | 8 | 4588 | 4607 | AATGCGGTTCTCCCCATGAA | 115 | 5 10 5 |
| 299025 | 8 | 5214 | 5233 | TCTCCATCACGAGACTCCAG | 117 | 5 10 5 |
| 299026 | 8 | 5262 | 5281 | CGTTCTCTACCAGGCAGGTG | 118 | 5 10 5 |
| 299027 | 8 | 5905 | 5924 | CTTGCACAGCAGCTCCACGT | 119 | 5 10 5 |
| 299028 | 8 | 5910 | 5929 | TACACCTTGCACAGCAGCTC | 120 | 5 10 5 |
| 299029 | 8 | 5968 | 5987 | GCTGCTGCCGTTGATGACGA | 36 | 5 10 5 |
| 299030 | 8 | 5973 | 5992 | CCGAAGCTGCTGCCGTTGAT | 121 | 5 10 5 |
| 299032 | 8 | 6165 | 6184 | CTCTGAGCTATTGATGTCTG | 123 | 5 10 5 |
| 299033 | 8 | 6170 | 6189 | TCCACCTCTGAGCTATTGAT | 124 | 5 10 5 |
| 299034 | 8 | 6196 | 6215 | CTGACACGTTCCGCAGGTAC | 125 | 5 10 5 |
| 299035 | 8 | 6256 | 6275 | ACTGGTAGGAGAGGCCGATG | 126 | 5 10 5 |
| 299037 | 8 | 6663 | 6682 | GCGCTGCTGCGGTCCATGTG | 127 | 5 10 5 |
| 299038 | 8 | 6754 | 6773 | TGCCCTCGATACAGCCCGGC | 128 | 5 10 5 |

TABLE 3-continued

Nucleotide sequences targeted to Human FGFR4 Sequences of SEQ ID NOs: 2, 3, 4, 5, 6 and 8

| ISIS # | Target SEQ ID NO | 5' Target Site | 3' Target Site | Sequence (5' to 3') | SEQ ID NO | 2'-MOE Gapmer Motif |
|---|---|---|---|---|---|---|
| 298993 | 8 | 6868 | 6887 | AGTCAGGCTGTCACATGTGA | 161 | 5 10 5 |
| 299039 | 8 | 6930 | 6949 | TTGCCGGAAGAGCCTGACTC | 129 | 5 10 5 |
| 299040 | 8 | 6949 | 6968 | TACCAGGGATGAGCTTGACT | 130 | 5 10 5 |
| 299041 | 8 | 6954 | 6973 | CCTCGTACCAGGGATGAGCT | 131 | 5 10 5 |
| 299043 | 8 | 7211 | 7230 | AGGCCTCTGCACGTACTACC | 133 | 5 10 5 |
| 299044 | 8 | 7260 | 7279 | TTGACGGCCACAGTGCTGGC | 134 | 5 10 5 |
| 298998 | 8 | 7654 | 7673 | GTGAGCCCCTTCTATTAGTC | 162 | 5 10 5 |
| 298999 | 8 | 8267 | 8286 | AATGTGCATTTCTCAATCCC | 163 | 5 10 5 |
| 299045 | 8 | 8899 | 8918 | CTTGTGTCGGCCGATCAGCT | 135 | 5 10 5 |
| 299046 | 8 | 8930 | 8949 | GGGTGCAGACACCAAGCAGG | 136 | 5 10 5 |
| 299000 | 8 | 8971 | 8990 | AACGGCCCGTGCAGCCAGCC | 164 | 5 10 5 |
| 299047 | 8 | 9169 | 9188 | AGACCAGGACTGGGAAGGAG | 137 | 5 10 5 |
| 299048 | 8 | 9218 | 9237 | TTCCGGGACTCCAGATACTG | 138 | 5 10 5 |
| 299001 | 8 | 9863 | 9882 | CAGGACTCACACGTCACTCT | 165 | 5 10 5 |
| 299050 | 8 | 10204 | 10223 | CGATGTCCCTCCCGCAGCAG | 140 | 5 10 5 |
| 299002 | 8 | 10797 | 10816 | CAGCCCGTACCTGCGAGAGG | 166 | 5 10 5 |
| 299052 | 8 | 10880 | 10899 | GCCAGCAGGACCTTGTCCAG | 64 | 5 10 5 |
| 299054 | 8 | 11096 | 11115 | CTGGAGGAGCAGGTGCTGCT | 143 | 5 10 5 |
| 299055 | 8 | 11112 | 11131 | GCTGAAGACAGAATCGCTGG | 144 | 5 10 5 |
| 299056 | 8 | 11118 | 11137 | GTCGTGGCTGAAGACAGAAT | 145 | 5 10 5 |
| 299057 | 8 | 11172 | 11191 | TCATGTCTGCACCCCAGACC | 146 | 5 10 5 |
| 299058 | 8 | 11180 | 11199 | AGCCTTGCTCATGTCTGCAC | 147 | 5 10 5 |
| 299059 | 8 | 11244 | 11263 | TGTGTCAGGCTGTGGCTGAG | 148 | 5 10 5 |
| 299060 | 8 | 11313 | 11332 | AAGGGCACGGCCCTTGGACA | 149 | 5 10 5 |
| 299061 | 8 | 11353 | 11372 | ATTTGGGCCATCAGGACACA | 150 | 5 10 5 |
| 299062 | 8 | 11367 | 11386 | AGCAGAACCCTGACATTTGG | 151 | 5 10 5 |
| 299063 | 8 | 11466 | 11485 | CCTGCTGGTATTGGGAGGCA | 152 | 5 10 5 |

The following embodiments set forth target regions of human FGFR4 nucleic acids. Also illustrated are examples of antisense compounds targeted to the target regions. It is understood that the sequence set forth in each SEQ ID NO is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Target Regions of Human FGFR4

In certain embodiments, a target region is nucleotides 455-474 of SEQ ID NO: 2. In certain embodiments, an antisense compound is targeted to nucleotides 455-474 of SEQ ID NO: 2. In certain such embodiments, an antisense compound targeted to nucleotides 455-474 of SEQ ID NO: 2 is Isis No: 299069. In certain embodiments, an antisense compound targeted to nucleotides 455-474 of SEQ ID NO: 2 has the sequence of SEQ ID NO: 92.

In certain embodiments, a target region is nucleotides 46-65 of SEQ ID NO: 3. In certain embodiments, an antisense compound is targeted to nucleotides 46-65 of SEQ ID NO: 3. In certain such embodiments, an antisense compound targeted to nucleotides 46-65 of SEQ ID NO: 3 is Isis No: 299067. In certain embodiments, an antisense compound targeted to nucleotides 46-65 of SEQ ID NO: 3 has the sequence of SEQ ID NO: 93.

In certain embodiments, a target region is nucleotides 306-325 of SEQ ID NO: 4. In certain embodiments, an antisense compound is targeted to nucleotides 306-325 of SEQ ID NO: 4. In certain such embodiments, an antisense compound targeted to nucleotides 306-325 of SEQ ID NO: 4 is Isis No: 299065. In certain embodiments, an antisense compound targeted to nucleotides 306-325 of SEQ ID NO: 4 has the sequence of SEQ ID NO: 94.

In certain embodiments, a target region is nucleotides 891-910 of SEQ ID NO: 4. In certain embodiments, an antisense compound is targeted to nucleotides 891-910 of SEQ ID NO: 4. In certain such embodiments, an antisense compound targeted to nucleotides 891-910 of SEQ ID NO: 4 is Isis No: 299066. In certain embodiments, an antisense compound targeted to nucleotides 891-910 of SEQ ID NO: 4 has the sequence of SEQ ID NO: 95.

In certain embodiments, a target region is nucleotides 26-45 of SEQ ID NO: 5. In certain embodiments, an antisense compound is targeted to nucleotides 26-45 of SEQ ID NO: 5. In certain such embodiments, an antisense compound targeted to nucleotides 26-45 of SEQ ID NO: 5 is Isis No: 299003. In certain embodiments, an antisense compound targeted to nucleotides 26-45 of SEQ ID NO: 5 has the sequence of SEQ ID NO: 96.

In certain embodiments, a target region is nucleotides 160-179 of SEQ ID NO: 5. In certain embodiments, an antisense compound is targeted to nucleotides 160-179 of SEQ ID NO: 5. In certain such embodiments, an antisense compound targeted to nucleotides 160-179 of SEQ ID NO: 5 is Isis No: 299004. In certain embodiments, an antisense compound targeted to nucleotides 160-179 of SEQ ID NO: 5 has the sequence of SEQ ID NO: 97.

In certain embodiments, a target region is nucleotides 192-211 of SEQ ID NO: 5. In certain embodiments, an antisense compound is targeted to nucleotides 192-211 of SEQ ID NO: 5. In certain such embodiments, an antisense compound targeted to nucleotides 192-211 of SEQ ID NO: 5 is Isis No: 299005. In certain embodiments, an antisense compound targeted to nucleotides 192-211 of SEQ ID NO: 5 has the sequence of SEQ ID NO: 98.

In certain embodiments, a target region is nucleotides 208-227 of SEQ ID NO: 5. In certain embodiments, an antisense compound is targeted to nucleotides 208-227 of SEQ ID NO: 5. In certain such embodiments, an antisense compound targeted to nucleotides 208-227 of SEQ ID NO: 5 is Isis No: 299006. In certain embodiments, an antisense compound targeted to nucleotides 208-227 of SEQ ID NO: 5 has the sequence of SEQ ID NO: 99.

In certain embodiments, a target region is nucleotides 160-211 of SEQ ID NO: 5. In certain such embodiments, an antisense compound targeted to nucleotides 160-211 of SEQ ID NO: 5 is selected from Isis Nos: 299004 and 299005. In certain embodiments, an antisense compound targeted to nucleotides 160-211 of SEQ ID NO: 5 has the sequence of SEQ ID NOs: 97 or 98.

In certain embodiments, a target region is nucleotides 192-227 of SEQ ID NO: 5. In certain such embodiments, an antisense compound targeted to nucleotides 192-227 of SEQ ID NO: 5 is selected from Isis Nos: 299005 and 299006. In certain embodiments, an antisense compound targeted to nucleotides 192-227 of SEQ ID NO: 5 has the sequence of SEQ ID NOs: 98 or 99.

In certain embodiments, a target region is nucleotides 160-227 of SEQ ID NO: 5. In certain such embodiments, an antisense compound targeted to nucleotides 160-227 of SEQ ID NO: 5 is selected from Isis Nos: 299004, 299005 and 299006. In certain embodiments, an antisense compound targeted to nucleotides 160-227 of SEQ ID NO: 5 has the sequence of SEQ ID NOs: 97, 98 or 99.

In certain embodiments, a target region is nucleotides 254-273 of SEQ ID NO: 5. In certain embodiments, an antisense compound is targeted to nucleotides 254-273 of SEQ ID NO: 5. In certain such embodiments, an antisense compound targeted to nucleotides 254-273 of SEQ ID NO: 5 is Isis No: 299007. In certain embodiments, an antisense compound targeted to nucleotides 254-273 of SEQ ID NO: 5 has the sequence of SEQ ID NO: 100.

In certain embodiments, a target region is nucleotides 278-297 of SEQ ID NO: 5. In certain embodiments, an antisense compound is targeted to nucleotides 278-297 of SEQ ID NO: 5. In certain such embodiments, an antisense compound targeted to nucleotides 278-297 of SEQ ID NO: 5 Isis No: 299008. In certain embodiments, an antisense compound targeted to nucleotides 278-297 of SEQ ID NO: 5 has the sequence of SEQ ID NO: 101.

In certain embodiments, a target region is nucleotides 289-308 of SEQ ID NO: 5. In certain embodiments, an antisense compound is targeted to nucleotides 289-308 of SEQ ID NO: 5. In certain such embodiments, an antisense compound targeted to nucleotides 289-308 of SEQ ID NO: 5 is Isis No: 299009. In certain embodiments, an antisense compound targeted to nucleotides 289-308 of SEQ ID NO: 5 has the sequence of SEQ ID NO: 102.

In certain embodiments, a target region is nucleotides 304-323 of SEQ ID NO: 5. In certain embodiments, an antisense compound is targeted to nucleotides 304-323 of SEQ ID NO: 5. In certain such embodiments, an antisense compound targeted to nucleotides 304-323 of SEQ ID NO: 5 is Isis No: 299010. In certain embodiments, an antisense compound targeted to nucleotides 304-323 of SEQ ID NO: 5 has the sequence of SEQ ID NO: 103.

In certain embodiments, a target region is nucleotides 354-373 of SEQ ID NO: 5. In certain embodiments, an antisense compound is targeted to nucleotides 354-373 of SEQ ID NO: 5. In certain such embodiments, an antisense compound targeted to nucleotides 354-373 of SEQ ID NO: 5 is Isis No: 299012. In certain embodiments, an antisense compound targeted to nucleotides 354-373 of SEQ ID NO: 5 has the sequence of SEQ ID NO: 104.

In certain embodiments, a target region is nucleotides 278-308 of SEQ ID NO: 5. In certain such embodiments, an antisense compound targeted to nucleotides 278-308 of SEQ ID NO: 5 is selected from Isis Nos: 299008 and 299009. In certain embodiments, an antisense compound targeted to nucleotides 278-308 of SEQ ID NO: 5 has the sequence of SEQ ID NOs: 101 or 102.

In certain embodiments, a target region is nucleotides 289-323 of SEQ ID NO: 5. In certain such embodiments, an antisense compound targeted to nucleotides 289-323 of SEQ ID NO: 5 is selected from Isis Nos: 299009 and 299010. In certain embodiments, an antisense compound targeted to nucleotides 289-323 of SEQ ID NO: 5 has the sequence of SEQ ID NOs: 102 or 103.

In certain embodiments, a target region is nucleotides 304-373 of SEQ ID NO: 5. In certain such embodiments, an antisense compound targeted to nucleotides 304-373 of SEQ ID NO: 5 is selected from Isis Nos: 299010 and 299012. In certain embodiments, an antisense compound targeted to nucleotides 304-373 of SEQ ID NO: 5 has the sequence of SEQ ID NOs: 103 or 104.

In certain embodiments, a target region is nucleotides 278-323 of SEQ ID NO: 5. In certain such embodiments, an antisense compound targeted to nucleotides 278-323 of SEQ ID NO: 5 is selected from Isis Nos: 299008, 299009 and 299010. In certain embodiments, an antisense compound targeted to nucleotides 278-323 of SEQ ID NO: 5 has the sequence of SEQ ID NOs: 101, 102, or 103.

In certain embodiments, a target region is nucleotides 289-373 of SEQ ID NO: 5. In certain such embodiments, an antisense compound targeted to nucleotides 289-373 of SEQ ID NO: 5 is selected from Isis Nos: 299009, 299010 and 299012. In certain embodiments, an antisense compound targeted to nucleotides 289-373 of SEQ ID NO: 5 has the sequence of SEQ ID NOs: 102, 103, or 104.

In certain embodiments, a target region is nucleotides 278-373 of SEQ ID NO: 5. In certain such embodiments, an antisense compound targeted to nucleotides 278-373 of SEQ ID NO: 5 is selected from Isis Nos: 299008, 299009, 299010 and 299012. In certain embodiments, an antisense compound targeted to nucleotides 278-373 of SEQ ID NO: 5 has the sequence of SEQ ID NOs: 101, 102, 103, or 104.

In certain embodiments, a target region is nucleotides 380-399 of SEQ ID NO: 5. In certain embodiments, an antisense compound is targeted to nucleotides 380-399 of SEQ ID NO: 5. In certain such embodiments, an antisense compound targeted to nucleotides 380-399 of SEQ ID NO: 5 is Isis No: 299013. In certain embodiments, an antisense compound targeted to nucleotides 380-399 of SEQ ID NO: 5 has the sequence of SEQ ID NO: 105.

In certain embodiments, a target region is nucleotides 412-431 of SEQ ID NO: 5. In certain embodiments, an antisense compound is targeted to nucleotides 412-431 of SEQ ID NO: 5. In certain such embodiments, an antisense compound targeted to nucleotides 412-431 of SEQ ID NO: 5 is Isis No: 299014. In certain embodiments, an antisense compound targeted to nucleotides 412-431 of SEQ ID NO: 5 has the sequence of SEQ ID NO: 106.

In certain embodiments, a target region is nucleotides 475-494 of SEQ ID NO: 5. In certain embodiments, an antisense compound is targeted to nucleotides 475-494 of SEQ ID NO: 5. In certain such embodiments, an antisense compound targeted to nucleotides 475-494 of SEQ ID NO: 5 is Isis No: 299015. In certain embodiments, an antisense compound targeted to nucleotides 475-494 of SEQ ID NO: 5 has the sequence of SEQ ID NO: 107.

In certain embodiments, a target region is nucleotides 412-494 of SEQ ID NO: 5. In certain embodiments, an antisense compound is targeted to nucleotides 412-494 of SEQ ID NO: 5. In certain such embodiments, an antisense compound targeted to nucleotides 412-494 of SEQ ID NO: 5 is selected from Isis Nos: 299014 or 299015. In certain embodiments, an antisense compound targeted to nucleotides 412-494 of SEQ ID NO: 5 has the sequence of SEQ ID NO: 106 or 107.

In certain embodiments, a target region is nucleotides 483-502 of SEQ ID NO: 5. In certain embodiments, an antisense compound is targeted to nucleotides 483-502 of SEQ ID NO: 5. In certain such embodiments, an antisense compound targeted to nucleotides 483-502 of SEQ ID NO: 5 is Isis No: 299016. In certain embodiments, an antisense compound targeted to nucleotides 483-502 of SEQ ID NO: 5 has the sequence of SEQ ID NO: 108.

In certain embodiments, a target region is nucleotides 475-502 of SEQ ID NO: 5. In certain such embodiments, an antisense compound targeted to nucleotides 475-502 of SEQ ID NO: 5 is selected from Isis Nos: 299015 or 299016. In certain embodiments, an antisense compound targeted to nucleotides 475-502 of SEQ ID NO: 5 has the sequence of SEQ ID NO: 107 or 108.

In certain embodiments, a target region is nucleotides 529-548 of SEQ ID NO: 5. In certain embodiments, an antisense compound is targeted to nucleotides 529-548 of SEQ ID NO: 5. In certain such embodiments, an antisense compound targeted to nucleotides 529-548 of SEQ ID NO: 5 is Isis No: 299017. In certain embodiments, an antisense compound targeted to nucleotides 529-548 of SEQ ID NO: 5 has the sequence of SEQ ID NO: 109.

In certain embodiments, a target region is nucleotides 597-616 of SEQ ID NO: 5. In certain embodiments, an antisense compound is targeted to nucleotides 597-616 of SEQ ID NO: 5. In certain such embodiments, an antisense compound targeted to nucleotides 597-616 of SEQ ID NO: 5 is Isis No: 299018. In certain embodiments, an antisense compound targeted to nucleotides 597-616 of SEQ ID NO: 5 has the sequence of SEQ ID NO: 110.

In certain embodiments, a target region is nucleotides 602-621 of SEQ ID NO: 5. In certain embodiments, an antisense compound is targeted to nucleotides 602-621 of SEQ ID NO: 5. In certain such embodiments, an antisense compound targeted to nucleotides 602-621 of SEQ ID NO: 5 is Isis No: 299019. In certain embodiments, an antisense compound targeted to nucleotides 602-621 of SEQ ID NO: 5 has the sequence of SEQ ID NO: 111.

In certain embodiments, a target region is nucleotides 597-621 of SEQ ID NO: 5. In certain such embodiments, an antisense compound targeted to nucleotides 597-621 of SEQ ID NO: 5 is selected from Isis Nos: 299018 or 299019. In certain embodiments, an antisense compound targeted to nucleotides 597-621 of SEQ ID NO: 5 has the sequence of SEQ ID NO: 110 or 111.

In certain embodiments, a target region is nucleotides 627-646 of SEQ ID NO: 5. In certain embodiments, an antisense compound is targeted to nucleotides 627-646 of SEQ ID NO: 5. In certain such embodiments, an antisense compound targeted to nucleotides 627-646 of SEQ ID NO: 5 is Isis No: 299020. In certain embodiments, an antisense compound targeted to nucleotides 627-646 of SEQ ID NO: 5 has the sequence of SEQ ID NO: 112.

In certain embodiments, a target region is nucleotides 602-646 of SEQ ID NO: 5. In certain such embodiments, an antisense compound targeted to nucleotides 602-646 of SEQ ID NO: 5 is selected from Isis Nos: 299019 or 299020. In certain embodiments, an antisense compound targeted to nucleotides 602-646 of SEQ ID NO: 5 has the sequence of SEQ ID NO: 111 or 112.

In certain embodiments, a target region is nucleotides 597-646 of SEQ ID NO: 5. In certain such embodiments, an antisense compound targeted to nucleotides 597-646 of SEQ ID NO: 5 is selected from Isis Nos: 299018, 299019, or 299020. In certain embodiments, an antisense compound targeted to nucleotides 597-646 of SEQ ID NO: 5 has the sequence of SEQ ID NO: 110, 111 or 112.

In certain embodiments, a target region is nucleotides 711-730 of SEQ ID NO: 5. In certain embodiments, an antisense compound is targeted to nucleotides 711-730 of SEQ ID NO: 5. In certain such embodiments, an antisense compound targeted to nucleotides 711-730 of SEQ ID NO: 5 is Isis No: 299021. In certain embodiments, an antisense compound targeted to nucleotides 711-730 of SEQ ID NO: 5 has the sequence of SEQ ID NO: 113.

In certain embodiments, a target region is nucleotides 727-746 of SEQ ID NO: 5. In certain embodiments, an antisense compound is targeted to nucleotides 727-746 of SEQ ID NO: 5. In certain such embodiments, an antisense compound targeted to nucleotides 727-746 of SEQ ID NO: 5 is Isis No: 299022. In certain embodiments, an antisense compound targeted to nucleotides 727-746 of SEQ ID NO: 5 has the sequence of SEQ ID NO: 114.

In certain embodiments, a target region is nucleotides 739-758 of SEQ ID NO: 5. In certain embodiments, an antisense compound is targeted to nucleotides 739-758 of SEQ ID NO: 5. In certain such embodiments, an antisense compound targeted to nucleotides 739-758 of SEQ ID NO: 5 is Isis No: 299023. In certain embodiments, an antisense compound targeted to nucleotides 739-758 of SEQ ID NO: 5 has the sequence of SEQ ID NO: 115.

In certain embodiments, a target region is nucleotides 757-776 of SEQ ID NO: 5. In certain embodiments, an antisense compound is targeted to nucleotides 757-776 of SEQ ID NO: 5. In certain such embodiments, an antisense compound targeted to nucleotides 757-776 of SEQ ID NO: 5 is Isis No: 299024. In certain embodiments, an antisense compound targeted to nucleotides 757-776 of SEQ ID NO: 5 has the sequence of SEQ ID NO: 116.

In certain embodiments, a target region is nucleotides 711-746 of SEQ ID NO: 5. In certain such embodiments, an antisense compound targeted to nucleotides 711-746 of SEQ ID NO: 5 is selected from Isis Nos: 299021 and 299022. In certain embodiments, an antisense compound targeted to nucleotides 711-746 of SEQ ID NO: 5 has the sequence of SEQ ID NOs: 113 or 114.

In certain embodiments, a target region is nucleotides 727-758 of SEQ ID NO: 5. In certain such embodiments, an antisense compound targeted to nucleotides 727-758 of SEQ ID NO: 5 is selected from Isis Nos: 299022 and 299023. In certain embodiments, an antisense compound targeted to nucleotides 727-758 of SEQ ID NO: 5 has the sequence of SEQ ID NOs: 114 or 115.

In certain embodiments, a target region is nucleotides 739-776 of SEQ ID NO: 5. In certain such embodiments, an antisense compound targeted to nucleotides 739-776 of SEQ ID NO: 5 is selected from Isis Nos: 299023 and 299024. In certain embodiments, an antisense compound targeted to nucleotides 739-776 of SEQ ID NO: 5 has the sequence of SEQ ID NOs: 115 or 116.

In certain embodiments, a target region is nucleotides 711-758 of SEQ ID NO: 5. In certain such embodiments, an antisense compound targeted to nucleotides 711-758 of SEQ ID NO: 5 is selected from Isis Nos: 299021, 299022 and 299023. In certain embodiments, an antisense compound targeted to nucleotides 711-758 of SEQ ID NO: 5 has the sequence of SEQ ID NOs: 113, 114, or 115.

In certain embodiments, a target region is nucleotides 727-776 of SEQ ID NO: 5. In certain such embodiments, an antisense compound targeted to nucleotides 727-776 of SEQ ID NO: 5 is selected from Isis Nos: 299022, 299023 and 299024. In certain embodiments, an antisense compound targeted to nucleotides 727-776 of SEQ ID NO: 5 has the sequence of SEQ ID NOs: 114, 115, or 116.

In certain embodiments, a target region is nucleotides 711-776 of SEQ ID NO: 5. In certain such embodiments, an antisense compound targeted to nucleotides 711-776 of SEQ ID NO: 5 is selected from Isis Nos: 299021, 299022, 299023 and 299024. In certain embodiments, an antisense compound targeted to nucleotides 711-776 of SEQ ID NO: 5 has the sequence of SEQ ID NOs: 113, 114, 115, or 116.

In certain embodiments, a target region is nucleotides 785-804 of SEQ ID NO: 5. In certain embodiments, an antisense compound is targeted to nucleotides 785-804 of SEQ ID NO: 5. In certain such embodiments, an antisense compound targeted to nucleotides 785-804 of SEQ ID NO: 5 is Isis No: 299025. In certain embodiments, an antisense compound targeted to nucleotides 785-804 of SEQ ID NO: 5 has the sequence of SEQ ID NO: 117.

In certain embodiments, a target region is nucleotides 833-852 of SEQ ID NO: 5. In certain embodiments, an antisense compound is targeted to nucleotides 833-852 of SEQ ID NO: 5. In certain such embodiments, an antisense compound targeted to nucleotides 833-852 of SEQ ID NO: 5 is Isis No: 299026. In certain embodiments, an antisense compound targeted to nucleotides 833-852 of SEQ ID NO: 5 has the sequence of SEQ ID NO: 118.

In certain embodiments, a target region is nucleotides 964-983 of SEQ ID NO: 5. In certain embodiments, an antisense compound is targeted to nucleotides 964-983 of SEQ ID NO: 5. In certain such embodiments, an antisense compound targeted to nucleotides 964-983 of SEQ ID NO: 5 is Isis No: 299027. In certain embodiments, an antisense compound targeted to nucleotides 964-983 of SEQ ID NO: 5 has the sequence of SEQ ID NO: 119.

In certain embodiments, a target region is nucleotides 969-988 of SEQ ID NO: 5. In certain embodiments, an antisense compound is targeted to nucleotides 969-988 of SEQ ID NO: 5. In certain such embodiments, an antisense compound targeted to nucleotides 969-988 of SEQ ID NO: 5 is Isis No: 299028. In certain embodiments, an antisense compound targeted to nucleotides 969-988 of SEQ ID NO: 5 has the sequence of SEQ ID NO: 120.

In certain embodiments, a target region is nucleotides 785-852 of SEQ ID NO: 5. In certain such embodiments, an antisense compound targeted to nucleotides 785-852 of SEQ ID NO: 5 is selected from Isis Nos: 299025 and 299026. In certain embodiments, an antisense compound targeted to nucleotides 785-852 of SEQ ID NO: 5 has the sequence of SEQ ID NOs: 117 or 118.

In certain embodiments, a target region is nucleotides 833-983 of SEQ ID NO: 5. In certain such embodiments, an antisense compound targeted to nucleotides 833-983 of SEQ ID NO: 5 is selected from Isis Nos: 299026 and 299027. In certain embodiments, an antisense compound targeted to nucleotides 833-983 of SEQ ID NO: 5 has the sequence of SEQ ID NOs: 118 or 119.

In certain embodiments, a target region is nucleotides 964-988 of SEQ ID NO: 5. In certain such embodiments, an antisense compound targeted to nucleotides 964-988 of SEQ ID NO: 5 is selected from Isis Nos: 299027 and 299028. In certain embodiments, an antisense compound targeted to nucleotides 964-988 of SEQ ID NO: 5 has the sequence of SEQ ID NOs: 119 or 120.

In certain embodiments, a target region is nucleotides 785-983 of SEQ ID NO: 5. In certain such embodiments, an antisense compound targeted to nucleotides 785-983 of SEQ ID NO: 5 is selected from Isis Nos: 299025, 299026 and 299027. In certain embodiments, an antisense compound targeted to nucleotides 785-983 of SEQ ID NO: 5 has the sequence of SEQ ID NOs: 117, 118, or 119.

In certain embodiments, a target region is nucleotides 833-988 of SEQ ID NO: 5. In certain such embodiments, an antisense compound targeted to nucleotides 833-988 of SEQ ID NO: 5 is selected from Isis Nos: 299026, 299027 and 299028. In certain embodiments, an antisense compound targeted to nucleotides 833-988 of SEQ ID NO: 5 has the sequence of SEQ ID NOs: 118, 119, or 120.

In certain embodiments, a target region is nucleotides 785-988 of SEQ ID NO: 5. In certain such embodiments, an antisense compound targeted to nucleotides 785-988 of SEQ ID NO: 5 is selected from Isis Nos: 299025, 299026, 299027 and 299028. In certain embodiments, an antisense compound targeted to nucleotides 785-988 of SEQ ID NO: 5 has the sequence of SEQ ID NOs: 117, 118, 119, or 120.

In certain embodiments, a target region is nucleotides 1027-1046 of SEQ ID NO: 5. In certain embodiments, an antisense compound is targeted to nucleotides 1027-1046 of SEQ ID NO: 5. In certain such embodiments, an antisense compound targeted to nucleotides 1027-1046 of SEQ ID NO: 5 is Isis No: 299029. In certain embodiments, an antisense compound targeted to nucleotides 1027-1046 of SEQ ID NO: 5 has the sequence of SEQ ID NO: 36.

In certain embodiments, a target region is nucleotides 1032-1051 of SEQ ID NO: 5. In certain embodiments, an antisense compound is targeted to nucleotides 1032-1051 of SEQ ID NO: 5. In certain such embodiments, an antisense compound targeted to nucleotides 1032-1051 of SEQ ID NO: 5 is Isis No: 299030. In certain embodiments, an antisense compound targeted to nucleotides 1032-1051 of SEQ ID NO: 5 has the sequence of SEQ ID NO: 121.

In certain embodiments, a target region is nucleotides 1027-1051 of SEQ ID NO: 5. In certain such embodiments, an antisense compound targeted to nucleotides 1027-1051 of SEQ ID NO: 5 is selected from Isis Nos: 299029 or 299030. In certain embodiments, an antisense compound targeted to nucleotides 1027-1051 of SEQ ID NO: 5 has the sequence of SEQ ID NO: 36 or 121.

In certain embodiments, a target region is nucleotides 1076-1095 of SEQ ID NO: 5. In certain embodiments, an antisense compound is targeted to nucleotides 1076-1095 of SEQ ID NO: 5. In certain such embodiments, an antisense compound targeted to nucleotides 1076-1095 of SEQ ID NO: 5 is Isis No: 299031. In certain embodiments, an antisense compound targeted to nucleotides 1076-1095 of SEQ ID NO: 5 has the sequence of SEQ ID NO: 122.

In certain embodiments, a target region is nucleotides 1090-1109 of SEQ ID NO: 5. In certain embodiments, an antisense compound is targeted to nucleotides 1090-1109 of SEQ ID NO: 5. In certain such embodiments, an antisense compound targeted to nucleotides 1090-1109 of SEQ ID NO: 5 is Isis No: 299032. In certain embodiments, an antisense compound targeted to nucleotides 1090-1109 of SEQ ID NO: 5 has the sequence of SEQ ID NO: 123.

In certain embodiments, a target region is nucleotides 1076-1109 of SEQ ID NO: 5. In certain embodiments, an antisense compound is targeted to nucleotides 1076-1109 of SEQ ID NO: 5. In certain such embodiments, an antisense compound targeted to nucleotides 1076-1109 of SEQ ID NO: 5 is selected from Isis Nos: 299031 or 299032. In certain embodiments, an antisense compound targeted to nucleotides 1076-1109 of SEQ ID NO: 5 has the sequence of SEQ ID NO: 122 or 123

In certain embodiments, a target region is nucleotides 1095-1114 of SEQ ID NO: 5. In certain embodiments, an antisense compound is targeted to nucleotides 1095-1114 of SEQ ID NO: 5. In certain such embodiments, an antisense compound targeted to nucleotides 1095-1114 of SEQ ID NO: 5 is Isis No: 299033. In certain embodiments, an antisense compound targeted to nucleotides 1095-1114 of SEQ ID NO: 5 has the sequence of SEQ ID NO: 124.

In certain embodiments, a target region is nucleotides 1121-1140 of SEQ ID NO: 5. In certain embodiments, an antisense compound is targeted to nucleotides 1121-1140 of SEQ ID NO: 5. In certain such embodiments, an antisense compound targeted to nucleotides 1121-1140 of SEQ ID NO: 5 is Isis No: 299034. In certain embodiments, an antisense compound targeted to nucleotides 1121-1140 of SEQ ID NO: 5 has the sequence of SEQ ID NO: 125.

In certain embodiments, a target region is nucleotides 1181-1200 of SEQ ID NO: 5. In certain embodiments, an antisense compound is targeted to nucleotides 1181-1200 of SEQ ID NO: 5. In certain such embodiments, an antisense compound targeted to nucleotides 1181-1200 of SEQ ID NO: 5 is Isis No: 299035. In certain embodiments, an antisense compound targeted to nucleotides 1181-1200 of SEQ ID NO: 5 has the sequence of SEQ ID NO: 126.

In certain embodiments, a target region is nucleotides 1207-1226 of SEQ ID NO: 5. In certain embodiments, an antisense compound is targeted to nucleotides 1207-1226 of SEQ ID NO: 5. In certain such embodiments, an antisense compound targeted to nucleotides 1207-1226 of SEQ ID NO: 5 is Isis No: 299036. In certain embodiments, an antisense compound targeted to nucleotides 1207-1226 of SEQ ID NO: 5 has the sequence of SEQ ID NO: 39.

In certain embodiments, a target region is nucleotides 1121-1200 of SEQ ID NO: 5. In certain embodiments, an antisense compound is targeted to nucleotides 1121-1200 of SEQ ID NO: 5. In certain such embodiments, an antisense compound targeted to nucleotides 1121-1200 of SEQ ID NO: 5 is selected from Isis Nos: 299034 or 299035. In certain embodiments, an antisense compound targeted to nucleotides 1121-1200 of SEQ ID NO: 5 has the sequence of SEQ ID NO: 125 or 126.

In certain embodiments, a target region is nucleotides 1181-1226 of SEQ ID NO: 5. In certain embodiments, an antisense compound is targeted to nucleotides 1181-1226 of SEQ ID NO: 5. In certain such embodiments, an antisense compound targeted to nucleotides 1181-1226 of SEQ ID NO: 5 is selected from Isis Nos: 299035 or 299036. In certain embodiments, an antisense compound targeted to nucleotides 1181-1226 of SEQ ID NO: 5 has the sequence of SEQ ID NO: 126 or 39.

In certain embodiments, a target region is nucleotides 1121-1226 of SEQ ID NO: 5. In certain embodiments, an antisense compound is targeted to nucleotides 1121-1226 of SEQ ID NO: 5. In certain such embodiments, an antisense compound targeted to nucleotides 1121-1226 of SEQ ID NO: 5 is selected from Isis Nos: 299034, 299035 or 299036. In certain embodiments, an antisense compound targeted to nucleotides 1121-1226 of SEQ ID NO: 5 has the sequence of SEQ ID NO: 125, 126 or 39.

In certain embodiments, a target region is nucleotides 1235-1254 of SEQ ID NO: 5. In certain embodiments, an antisense compound is targeted to nucleotides 1235-1254 of SEQ ID NO: 5. In certain such embodiments, an antisense compound targeted to nucleotides 1235-1254 of SEQ ID NO: 5 is Isis No: 299037. In certain embodiments, an antisense compound targeted to nucleotides 1235-1254 of SEQ ID NO: 5 has the sequence of SEQ ID NO: 127.

In certain embodiments, a target region is nucleotides 1326-1345 of SEQ ID NO: 5. In certain embodiments, an antisense compound is targeted to nucleotides 1326-1345 of SEQ ID NO: 5. In certain such embodiments, an antisense compound targeted to nucleotides 1326-1345 of SEQ ID NO: 5 is Isis No: 299038. In certain embodiments, an antisense compound targeted to nucleotides 1326-1345 of SEQ ID NO: 5 has the sequence of SEQ ID NO: 128.

In certain embodiments, a target region is nucleotides 1235-1345 of SEQ ID NO: 5. In certain embodiments, an antisense compound is targeted to nucleotides 1235-1345 of SEQ ID NO: 5. In certain such embodiments, an antisense compound targeted to nucleotides 1235-1345 of SEQ ID NO: 5 is selected from Isis Nos: 299037 or 299038. In certain embodiments, an antisense compound targeted to nucleotides 1235-1345 of SEQ ID NO: 5 has the sequence of SEQ ID NO: 127 or 128.

In certain embodiments, a target region is nucleotides 1428-1447 of SEQ ID NO: 5. In certain embodiments, an antisense compound is targeted to nucleotides 1428-1447 of SEQ ID NO: 5. In certain such embodiments, an antisense compound targeted to nucleotides 1428-1447 of SEQ ID NO: 5 is Isis No: 299039. In certain embodiments, an antisense compound targeted to nucleotides 1428-1447 of SEQ ID NO: 5 has the sequence of SEQ ID NO: 129.

In certain embodiments, a target region is nucleotides 1447-1466 of SEQ ID NO: 5. In certain embodiments, an antisense compound is targeted to nucleotides 1447-1466 of SEQ ID NO: 5. In certain such embodiments, an antisense compound targeted to nucleotides 1447-1466 of SEQ ID NO: 5 is Isis No: 299040. In certain embodiments, an antisense compound targeted to nucleotides 1447-1466 of SEQ ID NO: 5 has the sequence of SEQ ID NO: 130.

In certain embodiments, a target region is nucleotides 1452-1471 of SEQ ID NO: 5. In certain embodiments, an antisense compound is targeted to nucleotides 1452-1471 of SEQ ID NO: 5. In certain such embodiments, an antisense compound targeted to nucleotides 1452-1471 of SEQ ID NO: 5 is Isis No: 299041. In certain embodiments, an antisense compound targeted to nucleotides 1452-1471 of SEQ ID NO: 5 has the sequence of SEQ ID NO: 131.

In certain embodiments, a target region is nucleotides 1428-1466 of SEQ ID NO: 5. In certain embodiments, an antisense compound is targeted to nucleotides 1428-1466 of SEQ ID NO: 5. In certain such embodiments, an antisense compound targeted to nucleotides 1428-1466 of SEQ ID NO: 5 is selected from Isis Nos: 299039 or 299040. In certain embodiments, an antisense compound targeted to nucleotides 1428-1466 of SEQ ID NO: 5 has the sequence of SEQ ID NO: 129 or 130.

In certain embodiments, a target region is nucleotides 1447-1471 of SEQ ID NO: 5. In certain embodiments, an antisense compound is targeted to nucleotides 1447-1471 of SEQ ID NO: 5. In certain such embodiments, an antisense compound targeted to nucleotides 1447-1471 of SEQ ID NO: 5 is selected from Isis Nos: 299040 or 299041. In certain embodiments, an antisense compound targeted to nucleotides 1447-1471 of SEQ ID NO: 5 has the sequence of SEQ ID NO: 130 or 131.

In certain embodiments, a target region is nucleotides 1428-1471 of SEQ ID NO: 5. In certain embodiments, an antisense compound is targeted to nucleotides 1428-1471 of SEQ ID NO: 5. In certain such embodiments, an antisense compound targeted to nucleotides 1428-1471 of SEQ ID NO: 5 is selected from Isis Nos: 299039, 299040 or 299041. In certain embodiments, an antisense compound targeted to nucleotides 1428-1471 of SEQ ID NO: 5 has the sequence of SEQ ID NO: 129, 130 or 131.

In certain embodiments, a target region is nucleotides 1555-1574 of SEQ ID NO: 5. In certain embodiments, an antisense compound is targeted to nucleotides 1555-1574 of SEQ ID NO: 5. In certain such embodiments, an antisense compound targeted to nucleotides 1555-1574 of SEQ ID NO: 5 is Isis No: 299042. In certain embodiments, an antisense compound targeted to nucleotides 1555-1574 of SEQ ID NO: 5 has the sequence of SEQ ID NO: 132.

In certain embodiments, a target region is nucleotides 1607-1626 of SEQ ID NO: 5. In certain embodiments, an antisense compound is targeted to nucleotides 1607-1626 of SEQ ID NO: 5. In certain such embodiments, an antisense compound targeted to nucleotides 1607-1626 of SEQ ID NO: 5 is Isis No: 299043. In certain embodiments, an antisense compound targeted to nucleotides 1607-1626 of SEQ ID NO: 5 has the sequence of SEQ ID NO: 133.

In certain embodiments, a target region is nucleotides 1656-1675 of SEQ ID NO: 5. In certain embodiments, an antisense compound is targeted to nucleotides 1656-1675 of SEQ ID NO: 5. In certain such embodiments, an antisense compound targeted to nucleotides 1656-1675 of SEQ ID NO: 5 is Isis No: 299044. In certain embodiments, an antisense compound targeted to nucleotides 1656-1675 of SEQ ID NO: 5 has the sequence of SEQ ID NO: 134.

In certain embodiments, a target region is nucleotides 1555-1626 of SEQ ID NO: 5. In certain embodiments, an antisense compound is targeted to nucleotides 1555-1626 of SEQ ID NO: 5. In certain such embodiments, an antisense compound targeted to nucleotides 1555-1626 of SEQ ID NO: 5 is selected from Isis Nos: 299042 or 299043. In certain embodiments, an antisense compound targeted to nucleotides 1555-1626 of SEQ ID NO: 5 has the sequence of SEQ ID NO: 132 or 133.

In certain embodiments, a target region is nucleotides 1607-1675 of SEQ ID NO: 5. In certain embodiments, an antisense compound is targeted to nucleotides 1607-1675 of SEQ ID NO: 5. In certain such embodiments, an antisense compound targeted to nucleotides 1607-1675 of SEQ ID NO: 5 is selected from Isis Nos: 299043 or 299044. In certain embodiments, an antisense compound targeted to nucleotides 1607-1675 of SEQ ID NO: 5 has the sequence of SEQ ID NO: 133 or 134.

In certain embodiments, a target region is nucleotides 1555-1675 of SEQ ID NO: 5. In certain embodiments, an antisense compound is targeted to nucleotides 1555-1675 of SEQ ID NO: 5. In certain such embodiments, an antisense compound targeted to nucleotides 1555-1675 of SEQ ID NO: 5 is selected from Isis Nos: 299042, 299043 or 299044. In certain embodiments, an antisense compound targeted to nucleotides 1555-1675 of SEQ ID NO: 5 has the sequence of SEQ ID NO: 132, 133 or 134.

In certain embodiments, a target region is nucleotides 1326-1675 of SEQ ID NO: 5. In certain embodiments, an antisense compound is targeted to nucleotides 1326-1675 of SEQ ID NO: 5. In certain such embodiments, an antisense compound targeted to nucleotides 1326-1675 of SEQ ID NO: 5 is selected from Isis Nos: 299038, 299039, 299040, 299041, 299042, 299043 or 299044. In certain embodiments, an antisense compound targeted to nucleotides 1326-1675 of SEQ ID NO: 5 has the sequence of SEQ ID NO: 128, 129, 130, 131, 132, 133 or 134.

In certain embodiments, a target region is nucleotides 1741-1760 of SEQ ID NO: 5. In certain embodiments, an antisense compound is targeted to nucleotides 1741-1760 of SEQ ID NO: 5. In certain such embodiments, an antisense compound targeted to nucleotides 1741-1760 of SEQ ID NO: 5 is Isis No: 299045. In certain embodiments, an antisense compound targeted to nucleotides 1741-1760 of SEQ ID NO: 5 has the sequence of SEQ ID NO: 135.

In certain embodiments, a target region is nucleotides 1772-1791 of SEQ ID NO: 5. In certain embodiments, an antisense compound is targeted to nucleotides 1772-1791 of SEQ ID NO: 5. In certain such embodiments, an antisense compound targeted to nucleotides 1772-1791 of SEQ ID NO: 5 is Isis No: 299046. In certain embodiments, an antisense compound targeted to nucleotides 1772-1791 of SEQ ID NO: 5 has the sequence of SEQ ID NO: 136.

In certain embodiments, a target region is nucleotides 1919-1938 of SEQ ID NO: 5. In certain embodiments, an antisense compound is targeted to nucleotides 1919-1938 of SEQ ID NO: 5. In certain such embodiments, an antisense compound targeted to nucleotides 1919-1938 of SEQ ID NO: 5 is Isis No: 299047. In certain embodiments, an antisense compound targeted to nucleotides 1919-1938 of SEQ ID NO: 5 has the sequence of SEQ ID NO: 137.

In certain embodiments, a target region is nucleotides 1968-1987 of SEQ ID NO: 5. In certain embodiments, an antisense compound is targeted to nucleotides 1968-1987 of SEQ ID NO: 5. In certain such embodiments, an antisense compound targeted to nucleotides 1968-1987 of SEQ ID NO: 5 is Isis No: 299048. In certain embodiments, an antisense compound targeted to nucleotides 1968-1987 of SEQ ID NO: 5 has the sequence of SEQ ID NO: 138.

In certain embodiments, a target region is nucleotides 1979-1998 of SEQ ID NO: 5. In certain embodiments, an antisense compound is targeted to nucleotides 1979-1998 of SEQ ID NO: 5. In certain such embodiments, an antisense compound targeted to nucleotides 1979-1998 of SEQ ID NO: 5 is Isis No: 299049. In certain embodiments, an antisense compound targeted to nucleotides 1979-1998 of SEQ ID NO: 5 has the sequence of SEQ ID NO: 139.

In certain embodiments, a target region is nucleotides 1968-1998 of SEQ ID NO: 5. In certain embodiments, an antisense compound is targeted to nucleotides 1968-1998 of SEQ ID NO: 5. In certain such embodiments, an antisense compound targeted to nucleotides 1968-1998 of SEQ ID NO: 5 is Isis No: 299048 or 299049. In certain embodiments, an antisense compound targeted to nucleotides 1968-1998 of SEQ ID NO: 5 has the sequence of SEQ ID NO: 138 or 139.

In certain embodiments, a target region is nucleotides 2268-2287 of SEQ ID NO: 5. In certain embodiments, an antisense compound is targeted to nucleotides 2268-2287 of SEQ ID NO: 5. In certain such embodiments, an antisense compound targeted to nucleotides 2268-2287 of SEQ ID NO: 5 is Isis No: 299050. In certain embodiments, an antisense compound targeted to nucleotides 2268-2287 of SEQ ID NO: 5 has the sequence of SEQ ID NO: 140.

In certain embodiments, a target region is nucleotides 2313-2332 of SEQ ID NO: 5. In certain embodiments, an antisense compound is targeted to nucleotides 2313-2332 of SEQ ID NO: 5. In certain such embodiments, an antisense compound targeted to nucleotides 2313-2332 of SEQ ID NO: 5 is Isis No: 299051. In certain embodiments, an antisense compound targeted to nucleotides 2313-2332 of SEQ ID NO: 5 has the sequence of SEQ ID NO: 141.

In certain embodiments, a target region is nucleotides 2394-2413 of SEQ ID NO: 5. In certain embodiments, an antisense compound is targeted to nucleotides 2394-2413 of SEQ ID NO: 5. In certain such embodiments, an antisense compound targeted to nucleotides 2394-2413 of SEQ ID NO: 5 is Isis No: 299052. In certain embodiments, an antisense compound targeted to nucleotides 2394-2413 of SEQ ID NO: 5 has the sequence of SEQ ID NO: 64.

In certain embodiments, a target region is nucleotides 2416-2435 of SEQ ID NO: 5. In certain embodiments, an antisense compound is targeted to nucleotides 2416-2435 of SEQ ID NO: 5. In certain such embodiments, an antisense compound targeted to nucleotides 2416-2435 of SEQ ID NO: 5 is Isis No: 299053. In certain embodiments, an antisense compound targeted to nucleotides 2416-2435 of SEQ ID NO: 5 has the sequence of SEQ ID NO: 142.

In certain embodiments, a target region is nucleotides 2481-2500 of SEQ ID NO: 5. In certain embodiments, an antisense compound is targeted to nucleotides 2481-2500 of SEQ ID NO: 5. In certain such embodiments, an antisense compound targeted to nucleotides 2481-2500 of SEQ ID NO: 5 is Isis No: 299054. In certain embodiments, an antisense compound targeted to nucleotides 2481-2500 of SEQ ID NO: 5 has the sequence of SEQ ID NO: 143.

In certain embodiments, a target region is nucleotides 2497-2516 of SEQ ID NO: 5. In certain embodiments, an antisense compound is targeted to nucleotides 2497-2516 of SEQ ID NO: 5. In certain such embodiments, an antisense compound targeted to nucleotides 2497-2516 of SEQ ID NO: 5 is Isis No: 299055. In certain embodiments, an antisense compound targeted to nucleotides 2497-2516 of SEQ ID NO: 5 has the sequence of SEQ ID NO: 144.

In certain embodiments, a target region is nucleotides 2503-2522 of SEQ ID NO: 5. In certain embodiments, an antisense compound is targeted to nucleotides 2503-2522 of SEQ ID NO: 5. In certain such embodiments, an antisense compound targeted to nucleotides 2503-2522 of SEQ ID NO: 5 is Isis No: 299056. In certain embodiments, an antisense compound targeted to nucleotides 2503-2522 of SEQ ID NO: 5 has the sequence of SEQ ID NO: 145.

In certain embodiments, a target region is nucleotides 2557-2576 of SEQ ID NO: 5. In certain embodiments, an antisense compound is targeted to nucleotides 2557-2576 of SEQ ID NO: 5. In certain such embodiments, an antisense compound targeted to nucleotides 2557-2576 of SEQ ID NO: 5 is Isis No: 299057. In certain embodiments, an antisense compound targeted to nucleotides 2557-2576 of SEQ ID NO: 5 has the sequence of SEQ ID NO: 146.

In certain embodiments, a target region is nucleotides 2565-2584 of SEQ ID NO: 5. In certain embodiments, an antisense compound is targeted to nucleotides 2565-2584 of SEQ ID NO: 5. In certain such embodiments, an antisense compound targeted to nucleotides 2565-2584 of SEQ ID NO: 5 is Isis No: 299058. In certain embodiments, an antisense compound targeted to nucleotides 2565-2584 of SEQ ID NO: 5 has the sequence of SEQ ID NO: 147.

In certain embodiments, a target region is nucleotides 2629-2648 of SEQ ID NO: 5. In certain embodiments, an antisense compound is targeted to nucleotides 2629-2648 of SEQ ID NO: 5. In certain such embodiments, an antisense compound targeted to nucleotides 2629-2648 of SEQ ID NO: 5 is Isis No: 299059. In certain embodiments, an antisense compound targeted to nucleotides 2629-2648 of SEQ ID NO: 5 has the sequence of SEQ ID NO: 148.

In certain embodiments, a target region is nucleotides 2698-2717 of SEQ ID NO: 5. In certain embodiments, an antisense compound is targeted to nucleotides 2698-2717 of SEQ ID NO: 5. In certain such embodiments, an antisense compound targeted to nucleotides 2698-2717 of SEQ ID NO: 5 is Isis No: 299060. In certain embodiments, an antisense compound targeted to nucleotides 2698-2717 of SEQ ID NO: 5 has the sequence of SEQ ID NO: 149.

In certain embodiments, a target region is nucleotides 2738-2757 of SEQ ID NO: 5. In certain embodiments, an antisense compound is targeted to nucleotides 2738-2757 of SEQ ID NO: 5. In certain such embodiments, an antisense compound targeted to nucleotides 2738-2757 of SEQ ID NO: 5 is Isis No: 299061. In certain embodiments, an antisense compound targeted to nucleotides 2738-2757 of SEQ ID NO: 5 has the sequence of SEQ ID NO: 150.

In certain embodiments, a target region is nucleotides 2752-2771 of SEQ ID NO: 5. In certain embodiments, an antisense compound is targeted to nucleotides 2752-2771 of SEQ ID NO: 5. In certain such embodiments, an antisense compound targeted to nucleotides 2752-2771 of SEQ ID NO: 5 is Isis No: 299062. In certain embodiments, an antisense compound targeted to nucleotides 2752-2771 of SEQ ID NO: 5 has the sequence of SEQ ID NO: 151.

In certain embodiments, a target region is nucleotides 2851-2870 of SEQ ID NO: 5. In certain embodiments, an antisense compound is targeted to nucleotides 2851-2870 of SEQ ID NO: 5. In certain such embodiments, an antisense compound targeted to nucleotides 2851-2870 of SEQ ID NO: 5 is Isis No: 299063. In certain embodiments, an antisense compound targeted to nucleotides 2851-2870 of SEQ ID NO: 5 has the sequence of SEQ ID NO: 152.

In certain embodiments, a target region is nucleotides 2497-2584 of SEQ ID NO: 5. In certain embodiments, an antisense compound is targeted to nucleotides 2497-2584 of SEQ ID NO: 5. In certain such embodiments, an antisense compound targeted to nucleotides 2497-2584 of SEQ ID NO: 5 is selected from Isis Nos: 299055, 299056, 299057, or 299058. In certain embodiments, an antisense compound targeted to nucleotides 2497-2584 of SEQ ID NO: 5 has the sequence of SEQ ID NO: 144, 145, 146, or 147.

In certain embodiments, a target region is nucleotides 2738-2870 of SEQ ID NO: 5. In certain embodiments, an antisense compound is targeted to nucleotides 2738-2870 of SEQ ID NO: 5. In certain such embodiments, an antisense compound targeted to nucleotides 2738-2870 of SEQ ID NO: 5 is selected from Isis Nos: 299061, 299062, or 299063. In certain embodiments, an antisense compound targeted to nucleotides 2738-2870 of SEQ ID NO: 5 has the sequence of SEQ ID NO: 150, 151, or 152.

In certain embodiments, a target region is nucleotides 2497-2870 of SEQ ID NO: 5. In certain embodiments, an antisense compound is targeted to nucleotides 2497-2870 of SEQ ID NO: 5. In certain such embodiments, an antisense compound targeted to nucleotides 2497-2870 of SEQ ID NO: 5 is selected from Isis Nos: 299055, 299056, 299057, 299058, 299059, 299060, 299061, 299062, or 299063. In certain embodiments, an antisense compound targeted to nucleotides 2497-2870 of SEQ ID NO: 5 has the sequence of SEQ ID NO: 144, 145, 146, 147, 148, 149, 150, 151, or 152.

In certain embodiments, a target region is nucleotides 308-327 of SEQ ID NO: 6. In certain embodiments, an antisense compound is targeted to nucleotides 308-327 of SEQ ID NO: 6. In certain such embodiments, an antisense compound targeted to nucleotides 308-327 of SEQ ID NO: 6 is Isis No: 299011. In certain embodiments, an antisense compound targeted to nucleotides 308-327 of SEQ ID NO: 6 has the sequence of SEQ ID NO: 153.

In certain embodiments, a target region is nucleotides 1204-1223 of SEQ ID NO: 6. In certain embodiments, an antisense compound is targeted to nucleotides 1204-1223 of SEQ ID NO: 6. In certain such embodiments, an antisense compound targeted to nucleotides 1204-1223 of SEQ ID NO: 6 is Isis No: 298992. In certain embodiments, an antisense compound targeted to nucleotides 1204-1223 of SEQ ID NO: 6 has the sequence of SEQ ID NO: 154.

In certain embodiments, a target region is nucleotides 423-442 of SEQ ID NO: 8. In certain embodiments, an antisense compound is targeted to nucleotides 423-442 of SEQ ID NO: 8. In certain such embodiments, an antisense compound targeted to nucleotides 423-442 of SEQ ID NO: 8 is Isis No: 299064. In certain embodiments, an antisense compound targeted to nucleotides 423-442 of SEQ ID NO: 8 has the sequence of SEQ ID NO: 155.

In certain embodiments, a target region is nucleotides 460-479 of SEQ ID NO: 8. In certain embodiments, an antisense compound is targeted to nucleotides 460-479 of SEQ ID NO: 8. In certain such embodiments, an antisense compound targeted to nucleotides 460-479 of SEQ ID NO: 8 is Isis No: 299003. In certain embodiments, an antisense compound targeted to nucleotides 460-479 of SEQ ID NO: 8 has the sequence of SEQ ID NO: 96.

In certain embodiments, a target region is nucleotides 583-602 of SEQ ID NO: 8. In certain embodiments, an antisense compound is targeted to nucleotides 583-602 of SEQ ID NO: 8. In certain such embodiments, an antisense compound targeted to nucleotides 583-602 of SEQ ID NO: 8 is Isis No: 298994. In certain embodiments, an antisense compound targeted to nucleotides 583-602 of SEQ ID NO: 8 has the sequence of SEQ ID NO: 156.

In certain embodiments, a target region is nucleotides 1913-1932 of SEQ ID NO: 8. In certain embodiments, an antisense compound is targeted to nucleotides 1913-1932 of SEQ ID NO: 8. In certain such embodiments, an antisense compound targeted to nucleotides 1913-1932 of SEQ ID NO: 8 is Isis No: 298995. In certain embodiments, an antisense compound targeted to nucleotides 1913-1932 of SEQ ID NO: 8 has the sequence of SEQ ID NO: 157.

In certain embodiments, a target region is nucleotides 3110-3129 of SEQ ID NO: 8. In certain embodiments, an antisense compound is targeted to nucleotides 3110-3129 of SEQ ID NO: 8. In certain such embodiments, an antisense compound targeted to nucleotides 3110-3129 of SEQ ID NO: 8 is Isis No: 299004. In certain embodiments, an antisense compound targeted to nucleotides 3110-3129 of SEQ ID NO: 8 has the sequence of SEQ ID NO: 97.

In certain embodiments, a target region is nucleotides 3142-3161 of SEQ ID NO: 8. In certain embodiments, an antisense compound is targeted to nucleotides 3142-3161 of SEQ ID NO: 8. In certain such embodiments, an antisense compound targeted to nucleotides 3142-3161 of SEQ ID NO: 8 is Isis No: 299005. In certain embodiments, an antisense compound targeted to nucleotides 3142-3161 of SEQ ID NO: 8 has the sequence of SEQ ID NO: 98.

In certain embodiments, a target region is nucleotides 3158-3177 of SEQ ID NO: 8. In certain embodiments, an antisense compound is targeted to nucleotides 3158-3177 of SEQ ID NO: 8. In certain such embodiments, an antisense compound targeted to nucleotides 3158-3177 of SEQ ID NO: 8 is Isis No: 299006. In certain embodiments, an antisense compound targeted to nucleotides 3158-3177 of SEQ ID NO: 8 has the sequence of SEQ ID NO: 99.

In certain embodiments, a target region is nucleotides 3199-3218 of SEQ ID NO: 8. In certain embodiments, an antisense compound is targeted to nucleotides 3199-3218 of SEQ ID NO: 8. In certain such embodiments, an antisense compound targeted to nucleotides 3199-3218 of SEQ ID NO: 8 is Isis No: 298996. In certain embodiments, an antisense compound targeted to nucleotides 3199-3218 of SEQ ID NO: 8 has the sequence of SEQ ID NO: 158.

In certain embodiments, a target region is nucleotides 3924-3943 of SEQ ID NO: 8. In certain embodiments, an antisense compound is targeted to nucleotides 3924-3943 of SEQ ID NO: 8. In certain such embodiments, an antisense compound targeted to nucleotides 3924-3943 of SEQ ID NO: 8 is Isis No: 299008. In certain embodiments, an antisense compound targeted to nucleotides 3924-3943 of SEQ ID NO: 8 has the sequence of SEQ ID NO: 101.

In certain embodiments, a target region is nucleotides 3935-3954 of SEQ ID NO: 8. In certain embodiments, an antisense compound is targeted to nucleotides 3935-3954 of SEQ ID NO: 8. In certain such embodiments, an antisense compound targeted to nucleotides 3935-3954 of SEQ ID NO: 8 is Isis No: 299009. In certain embodiments, an antisense compound targeted to nucleotides 3935-3954 of SEQ ID NO: 8 has the sequence of SEQ ID NO: 102.

In certain embodiments, a target region is nucleotides 3950-3969 of SEQ ID NO: 8. In certain embodiments, an antisense compound is targeted to nucleotides 3950-3969 of SEQ ID NO: 8. In certain such embodiments, an antisense compound targeted to nucleotides 3950-3969 of SEQ ID NO: 8 is Isis No: 2990010. In certain embodiments, an antisense compound targeted to nucleotides 3950-3969 of SEQ ID NO: 8 has the sequence of SEQ ID NO: 103.

In certain embodiments, a target region is nucleotides 3924-3954 of SEQ ID NO: 8. In certain embodiments, an antisense compound is targeted to nucleotides 3924-3954 of SEQ ID NO: 8. In certain such embodiments, an antisense compound targeted to nucleotides 3924-3954 of SEQ ID NO: 8 is selected from Isis Nos: 299008 or 299009. In certain embodiments, an antisense compound targeted to nucleotides 3924-3954 of SEQ ID NO: 8 has the sequence of SEQ ID NO: 101 or 102.

In certain embodiments, a target region is nucleotides 3935-3969 of SEQ ID NO: 8. In certain embodiments, an antisense compound is targeted to nucleotides 3935-3969 of SEQ ID NO: 8. In certain such embodiments, an antisense compound targeted to nucleotides 3935-3969 of SEQ ID NO: 8 is selected from Isis Nos: 299009 or 299010. In certain embodiments, an antisense compound targeted to nucleotides 3935-3969 of SEQ ID NO: 8 has the sequence of SEQ ID NO: 102 or 103.

In certain embodiments, a target region is nucleotides 3924-3969 of SEQ ID NO: 8. In certain embodiments, an antisense compound is targeted to nucleotides 3924-3969 of SEQ ID NO: 8. In certain such embodiments, an antisense compound targeted to nucleotides 3924-3969 of SEQ ID NO: 8 is selected from Isis Nos: 299008, 299009 or 299010. In certain embodiments, an antisense compound targeted to nucleotides 3924-3969 of SEQ ID NO: 8 has the sequence of SEQ ID NO: 101, 102 or 103.

In certain embodiments, a target region is nucleotides 4000-4019 of SEQ ID NO: 8. In certain embodiments, an antisense compound is targeted to nucleotides 4000-4019 of SEQ ID NO: 8. In certain such embodiments, an antisense compound targeted to nucleotides 4000-4019 of SEQ ID NO: 8 is Isis No: 299012. In certain embodiments, an antisense compound targeted to nucleotides 4000-4019 of SEQ ID NO: 8 has the sequence of SEQ ID NO: 104.

In certain embodiments, a target region is nucleotides 4026-4045 of SEQ ID NO: 8. In certain embodiments, an antisense compound is targeted to nucleotides 4026-4045 of SEQ ID NO: 8. In certain such embodiments, an antisense compound targeted to nucleotides 4026-4045 of SEQ ID NO: 8 is Isis No: 299013. In certain embodiments, an antisense compound targeted to nucleotides 4026-4045 of SEQ ID NO: 8 has the sequence of SEQ ID NO: 105.

In certain embodiments, a target region is nucleotides 4058-4077 of SEQ ID NO: 8. In certain embodiments, an antisense compound is targeted to nucleotides 4058-4077 of SEQ ID NO: 8. In certain such embodiments, an antisense compound targeted to nucleotides 4058-4077 of SEQ ID NO: 8 is Isis No: 299014. In certain embodiments, an antisense compound targeted to nucleotides 4058-4077 of SEQ ID NO: 8 has the sequence of SEQ ID NO: 106.

In certain embodiments, a target region is nucleotides 4121-4140 of SEQ ID NO: 8. In certain embodiments, an antisense compound is targeted to nucleotides 4121-4140 of SEQ ID NO: 8. In certain such embodiments, an antisense compound targeted to nucleotides 4121-4140 of SEQ ID NO: 8 is Isis No: 299015. In certain embodiments, an antisense compound targeted to nucleotides 4121-4140 of SEQ ID NO: 8 has the sequence of SEQ ID NO: 107.

In certain embodiments, a target region is nucleotides 4129-4148 of SEQ ID NO: 8. In certain embodiments, an antisense compound is targeted to nucleotides 4129-4148 of SEQ ID NO: 8. In certain such embodiments, an antisense compound targeted to nucleotides 4129-4148 of SEQ ID NO: 8 is Isis No: 299016. In certain embodiments, an antisense compound targeted to nucleotides 4129-4148 of SEQ ID NO: 8 has the sequence of SEQ ID NO: 108.

In certain embodiments, a target region is nucleotides 4121-4148 of SEQ ID NO: 8. In certain embodiments, an antisense compound is targeted to nucleotides 4121-4148 of SEQ ID NO: 8. In certain such embodiments, an antisense compound targeted to nucleotides 4121-4148 of SEQ ID NO: 8 is selected from Isis Nos: 299015 or 299016. In certain embodiments, an antisense compound targeted to nucleotides 4121-4148 of SEQ ID NO: 8 has the sequence of SEQ ID NO: 107 or 108.

In certain embodiments, a target region is nucleotides 4058-4148 of SEQ ID NO: 8. In certain embodiments, an antisense compound is targeted to nucleotides 4058-4148 of SEQ ID NO: 8. In certain such embodiments, an antisense compound targeted to nucleotides 4058-4148 of SEQ ID NO: 8 is selected from Isis Nos: 299014, 299015 or 299016. In certain embodiments, an antisense compound targeted to nucleotides 4058-4148 of SEQ ID NO: 8 has the sequence of SEQ ID NO: 106, 107 or 108.

In certain embodiments, a target region is nucleotides 4174-4193 of SEQ ID NO: 8. In certain embodiments, an antisense compound is targeted to nucleotides 4174-4193 of SEQ ID NO: 8. In certain such embodiments, an antisense compound targeted to nucleotides 4174-4193 of SEQ ID NO: 8 is Isis No: 299068. In certain embodiments, an antisense compound targeted to nucleotides 4174-4193 of SEQ ID NO: 8 has the sequence of SEQ ID NO: 159.

In certain embodiments, a target region is nucleotides 4250-4269 of SEQ ID NO: 8. In certain embodiments, an antisense compound is targeted to nucleotides 4250-4269 of SEQ ID NO: 8. In certain such embodiments, an antisense compound targeted to nucleotides 4250-4269 of SEQ ID NO: 8 is Isis No: 298997. In certain embodiments, an antisense compound targeted to nucleotides 4250-4269 of SEQ ID NO: 8 has the sequence of SEQ ID NO: 160.

In certain embodiments, a target region is nucleotides 4266-4285 of SEQ ID NO: 8. In certain embodiments, an antisense compound is targeted to nucleotides 4266-4285 of SEQ ID NO: 8. In certain such embodiments, an antisense compound targeted to nucleotides 4266-4285 of SEQ ID NO: 8 is Isis No: 299017. In certain embodiments, an antisense compound targeted to nucleotides 4266-4285 of SEQ ID NO: 8 has the sequence of SEQ ID NO: 109.

In certain embodiments, a target region is nucleotides 4174-4285 of SEQ ID NO: 8. In certain embodiments, an antisense compound is targeted to nucleotides 4174-4285 of SEQ ID NO: 8. In certain such embodiments, an antisense compound targeted to nucleotides 4174-4285 of SEQ ID NO: 8 is selected from Isis Nos: 299068, 298997, or 299017. In certain embodiments, an antisense compound targeted to nucleotides 4174-4285 of SEQ ID NO: 8 has the sequence of SEQ ID NO: 159, 160, or 109.

In certain embodiments, a target region is nucleotides 4058-4285 of SEQ ID NO: 8. In certain embodiments, an antisense compound is targeted to nucleotides 4058-4285 of SEQ ID NO: 8. In certain such embodiments, an antisense compound targeted to nucleotides 4058-4285 of SEQ ID NO: 8 is selected from Isis Nos: 2999014, 299015, 299016, 299068, 298997, or 299017. In certain embodiments, an antisense compound targeted to nucleotides 4058-4285 of SEQ ID NO: 8 has the sequence of SEQ ID NO: 106, 107, 108, 159, 160, or 109.

In certain embodiments, a target region is nucleotides 4451-4470 of SEQ ID NO: 8. In certain embodiments, an antisense compound is targeted to nucleotides 4451-4470 of SEQ ID NO: 8. In certain such embodiments, an antisense compound targeted to nucleotides 4451-4470 of SEQ ID NO: 8 is Isis No: 299019. In certain embodiments, an antisense compound targeted to nucleotides 4451-4470 of SEQ ID NO: 8 has the sequence of SEQ ID NO: 111.

In certain embodiments, a target region is nucleotides 4476-4495 of SEQ ID NO: 8. In certain embodiments, an antisense compound is targeted to nucleotides 4476-4495 of SEQ ID NO: 8. In certain such embodiments, an antisense compound targeted to nucleotides 4476-4495 of SEQ ID NO: 8 is Isis No: 299020. In certain embodiments, an antisense compound targeted to nucleotides 4476-4495 of SEQ ID NO: 8 has the sequence of SEQ ID NO: 112.

In certain embodiments, a target region is nucleotides 4560-4579 of SEQ ID NO: 8. In certain embodiments, an antisense compound is targeted to nucleotides 4560-4579 of SEQ ID NO: 8. In certain such embodiments, an antisense compound targeted to nucleotides 4560-4579 of SEQ ID NO: 8 is Isis No: 299021. In certain embodiments, an antisense compound targeted to nucleotides 4560-4579 of SEQ ID NO: 8 has the sequence of SEQ ID NO: 113.

In certain embodiments, a target region is nucleotides 4576-4595 of SEQ ID NO: 8. In certain embodiments, an antisense compound is targeted to nucleotides 4576-4595 of SEQ ID NO: 8. In certain such embodiments, an antisense compound targeted to nucleotides 4576-4595 of SEQ ID NO: 8 is Isis No: 299022. In certain embodiments, an antisense compound targeted to nucleotides 4576-4595 of SEQ ID NO: 8 has the sequence of SEQ ID NO: 114.

In certain embodiments, a target region is nucleotides 4588-4607 of SEQ ID NO: 8. In certain embodiments, an antisense compound is targeted to nucleotides 4588-4607 of SEQ ID NO: 8. In certain such embodiments, an antisense compound targeted to nucleotides 4588-4607 of SEQ ID NO: 8 is Isis No: 299023. In certain embodiments, an antisense compound targeted to nucleotides 4588-4607 of SEQ ID NO: 8 has the sequence of SEQ ID NO: 115.

In certain embodiments, a target region is nucleotides 4560-4595 of SEQ ID NO: 8. In certain embodiments, an antisense compound is targeted to nucleotides 4560-4595 of SEQ ID NO: 8. In certain such embodiments, an antisense compound targeted to nucleotides 4560-4595 of SEQ ID NO: 8 is selected from Isis Nos: 299021 or 299022. In certain embodiments, an antisense compound targeted to nucleotides 4560-4595 of SEQ ID NO: 8 has the sequence of SEQ ID NO: 113 or 114.

In certain embodiments, a target region is nucleotides 4576-4607 of SEQ ID NO: 8. In certain embodiments, an antisense compound is targeted to nucleotides 4576-4607 of SEQ ID NO: 8. In certain such embodiments, an antisense compound targeted to nucleotides 4576-4607 of SEQ ID NO: 8 is selected from Isis Nos: 299022 or 299023. In certain embodiments, an antisense compound targeted to nucleotides 4576-4607 of SEQ ID NO: 8 has the sequence of SEQ ID NO: 114 or 115.

In certain embodiments, a target region is nucleotides 4560-4607 of SEQ ID NO: 8. In certain embodiments, an antisense compound is targeted to nucleotides 4560-4607 of SEQ ID NO: 8. In certain such embodiments, an antisense compound targeted to nucleotides 4560-4607 of SEQ ID NO: 8 is selected from Isis Nos: 299021, 299022, or 299023. In certain embodiments, an antisense compound targeted to nucleotides 4560-4607 of SEQ ID NO: 8 has the sequence of SEQ ID NO: 113, 114, or 115.

In certain embodiments, a target region is nucleotides 5214-5233 of SEQ ID NO: 8. In certain embodiments, an antisense compound is targeted to nucleotides 5214-5233 of SEQ ID NO: 8. In certain such embodiments, an antisense compound targeted to nucleotides 5214-5233 of SEQ ID NO: 8 is Isis No: 299025. In certain embodiments, an antisense compound targeted to nucleotides 5214-5233 of SEQ ID NO: 8 has the sequence of SEQ ID NO: 117.

In certain embodiments, a target region is nucleotides 5262-5281 of SEQ ID NO: 8. In certain embodiments, an antisense compound is targeted to nucleotides 5262-5281 of SEQ ID NO: 8. In certain such embodiments, an antisense compound targeted to nucleotides 5262-5281 of SEQ ID NO: 8 is Isis No: 299026. In certain embodiments, an antisense compound targeted to nucleotides 5262-5281 of SEQ ID NO: 8 has the sequence of SEQ ID NO: 118.

In certain embodiments, a target region is nucleotides 5214-5281 of SEQ ID NO: 8. In certain embodiments, an antisense compound is targeted to nucleotides 5214-5281 of SEQ ID NO: 8. In certain such embodiments, an antisense compound targeted to nucleotides 5214-5281 of SEQ ID NO: 8 is selected from Isis Nos: 299025 or 299026. In certain embodiments, an antisense compound targeted to nucleotides 5214-5281 of SEQ ID NO: 8 has the sequence of SEQ ID NO: 117 or 118.

In certain embodiments, a target region is nucleotides 5905-5924 of SEQ ID NO: 8. In certain embodiments, an antisense compound is targeted to nucleotides 5905-5924 of SEQ ID NO: 8. In certain such embodiments, an antisense compound targeted to nucleotides 5905-5924 of SEQ ID NO: 8 is Isis No: 299027. In certain embodiments, an antisense compound targeted to nucleotides 5905-5924 of SEQ ID NO: has the sequence of SEQ ID NO: 119.

In certain embodiments, a target region is nucleotides 5910-5929 of SEQ ID NO: 8. In certain embodiments, an antisense compound is targeted to nucleotides 5910-5929 of SEQ ID NO: 8. In certain such embodiments, an antisense compound targeted to nucleotides 5910-5929 of SEQ ID NO: 8 is Isis No: 299028. In certain embodiments, an antisense compound targeted to nucleotides 5910-5929 of SEQ ID NO: 8 has the sequence of SEQ ID NO: 120.

In certain embodiments, a target region is nucleotides 5905-5929 of SEQ ID NO: 8. In certain embodiments, an antisense compound is targeted to nucleotides 5905-5929 of SEQ ID NO: 8. In certain such embodiments, an antisense compound targeted to nucleotides 5905-5929 of SEQ ID NO: 8 is Isis Nos 299027 or 299028. In certain embodiments, an antisense compound targeted to nucleotides 5905-5929 of SEQ ID NO: 8 has the sequence of SEQ ID NO: 119 or 120.

In certain embodiments, a target region is nucleotides 5968-5987 of SEQ ID NO: 8. In certain embodiments, an antisense compound is targeted to nucleotides 5968-5987 of SEQ ID NO: 8. In certain such embodiments, an antisense compound targeted to nucleotides 5968-5987 of SEQ ID NO: 8 is Isis No: 299029. In certain embodiments, an antisense compound targeted to nucleotides 5968-5987 of SEQ ID NO: 8 has the sequence of SEQ ID NO: 36.

In certain embodiments, a target region is nucleotides 5910-5987 of SEQ ID NO: 8. In certain embodiments, an antisense compound is targeted to nucleotides 5910-5987 of SEQ ID NO: 8. In certain such embodiments, an antisense compound targeted to nucleotides 5910-5987 of SEQ ID NO: 8 is Isis Nos 299028 or 299029. In certain embodiments, an antisense compound targeted to nucleotides 5910-5987 of SEQ ID NO: 8 has the sequence of SEQ ID NO: 120 or 36.

In certain embodiments, a target region is nucleotides 5905-5987 of SEQ ID NO: 8. In certain embodiments, an antisense compound is targeted to nucleotides 5905-5987 of SEQ ID NO: 8. In certain such embodiments, an antisense compound targeted to nucleotides 5905-5987 of SEQ ID NO: 8 is Isis Nos 299027, 299028 or 299029. In certain embodiments, an antisense compound targeted to nucleotides 5905-5987 of SEQ ID NO: 8 has the sequence of SEQ ID NO: 119, 120 or 36.

In certain embodiments, a target region is nucleotides 5973-5992 of SEQ ID NO: 8. In certain embodiments, an antisense compound is targeted to nucleotides 5973-5992 of SEQ ID NO: 8. In certain such embodiments, an antisense compound targeted to nucleotides 5973-5992 of SEQ ID NO: 8 is Isis No: 299030. In certain embodiments, an antisense compound targeted to nucleotides 5973-5992 of SEQ ID NO: 8 has the sequence of SEQ ID NO: 121.

In certain embodiments, a target region is nucleotides 5968-5992 of SEQ ID NO: 8. In certain embodiments, an antisense compound is targeted to nucleotides 5968-5992 of SEQ ID NO: 8. In certain such embodiments, an antisense compound targeted to nucleotides 5968-5992 SEQ ID NO: 8 is Isis Nos 299029 or 299030. In certain embodiments, an antisense compound targeted to nucleotides 5968-5992 of SEQ ID NO: 8 has the sequence of SEQ ID NO: 36 or 121.

In certain embodiments, a target region is nucleotides 5910-5992 of SEQ ID NO: 8. In certain embodiments, an antisense compound is targeted to nucleotides 5910-5992 of SEQ ID NO: 8. In certain such embodiments, an antisense compound targeted to nucleotides 5910-5992 of SEQ ID NO: 8 is Isis Nos 299028, 299029 or 299030. In certain embodiments, an antisense compound targeted to nucleotides 5910-5992 of SEQ ID NO: 8 has the sequence of SEQ ID NO: 120, 36 or 121.

In certain embodiments, a target region is nucleotides 5905-5992 of SEQ ID NO: 8. In certain embodiments, an antisense compound is targeted to nucleotides 5905-5992 of SEQ ID NO: 8. In certain such embodiments, an antisense compound targeted to nucleotides 5905-5992 of SEQ ID NO: 8 is Isis Nos 299027, 299028, 299029 or 299030. In certain embodiments, an antisense compound targeted to nucleotides 5905-5992 of SEQ ID NO: 8 has the sequence of SEQ ID NO: 119, 120, 36 or 121.

In certain embodiments, a target region is nucleotides 6165-6184 of SEQ ID NO: 8. In certain embodiments, an antisense compound is targeted to nucleotides 6165-6184 of SEQ ID NO: 8. In certain such embodiments, an antisense compound targeted to nucleotides 6165-6184 of SEQ ID NO: 8 is Isis No: 299032. In certain embodiments, an antisense compound targeted to nucleotides 6165-6184 of SEQ ID NO: 8 has the sequence of SEQ ID NO: 123.

In certain embodiments, a target region is nucleotides 6170-6189 of SEQ ID NO: 8. In certain embodiments, an antisense compound is targeted to nucleotides 6170-6189 of SEQ ID NO: 8. In certain such embodiments, an antisense compound targeted to nucleotides 6170-6189 of SEQ ID NO: 8 is Isis No: 299033. In certain embodiments, an antisense compound targeted to nucleotides 6170-6189 of SEQ ID NO: 8 has the sequence of SEQ ID NO: 124.

In certain embodiments, a target region is nucleotides 6165-6189 of SEQ ID NO: 8. In certain embodiments, an antisense compound is targeted to nucleotides 6165-6189 of SEQ ID NO: 8. In certain such embodiments, an antisense compound targeted to nucleotides 6165-6189 of SEQ ID NO: 8 is Isis Nos: 299032 or 299033. In certain embodiments, an antisense compound targeted to nucleotides 6165-6189 of SEQ ID NO: 8 has the sequence of SEQ ID NO: 123 or 124.

In certain embodiments, a target region is nucleotides 6196-6215 of SEQ ID NO: 8. In certain embodiments, an antisense compound is targeted to nucleotides 6196-6215 of SEQ ID NO: 8. In certain such embodiments, an antisense compound targeted to nucleotides 6196-6215 of SEQ ID NO: 8 is Isis No: 299034. In certain embodiments, an antisense compound targeted to nucleotides 6196-6215 of SEQ ID NO: 8 has the sequence of SEQ ID NO: 125.

In certain embodiments, a target region is nucleotides 6170-6215 of SEQ ID NO: 8. In certain embodiments, an antisense compound is targeted to nucleotides 6170-6215 of SEQ ID NO: 8. In certain such embodiments, an antisense compound targeted to nucleotides 6170-6215 of SEQ ID NO: 8 is selected from Isis Nos: 299033 or 299034. In certain embodiments, an antisense compound targeted to nucleotides 6170-6215 of SEQ ID NO: 8 has the sequence of SEQ ID NO: 124 or 125.

In certain embodiments, a target region is nucleotides 6165-6215 of SEQ ID NO: 8. In certain embodiments, an antisense compound is targeted to nucleotides 6165-6215 of SEQ ID NO: 8. In certain such embodiments, an antisense compound targeted to nucleotides 6165-6215 of SEQ ID NO: 8 is selected from Isis Nos: 299032, 299033, or 299034. In certain embodiments, an antisense compound targeted to nucleotides 6165-6215 of SEQ ID NO: 8 has the sequence of SEQ ID NO: 123, 124, or 125.

In certain embodiments, a target region is nucleotides 6256-6275 of SEQ ID NO: 8. In certain embodiments, an antisense compound is targeted to nucleotides 6256-6275 of SEQ ID NO: 8. In certain such embodiments, an antisense compound targeted to nucleotides 6256-6275 of SEQ ID NO: 8 is Isis No: 299035. In certain embodiments, an antisense compound targeted to nucleotides 6256-6275 of SEQ ID NO: 8 has the sequence of SEQ ID NO: 126.

In certain embodiments, a target region is nucleotides 6663-6682 of SEQ ID NO: 8. In certain embodiments, an antisense compound is targeted to nucleotides 6663-6682 of SEQ ID NO: 8. In certain such embodiments, an antisense compound targeted to nucleotides 6663-6682 of SEQ ID NO: 8 is Isis No: 299037. In certain embodiments, an antisense compound targeted to nucleotides 6663-6682 of SEQ ID NO: 8 has the sequence of SEQ ID NO: 127.

In certain embodiments, a target region is nucleotides 6754-6773 of SEQ ID NO: 8. In certain embodiments, an antisense compound is targeted to nucleotides 6754-6773 of SEQ ID NO: 8. In certain such embodiments, an antisense compound targeted to nucleotides 6754-6773 of SEQ ID NO: 8 is Isis No: 299038. In certain embodiments, an antisense compound targeted to nucleotides 6754-6773 of SEQ ID NO: 8 has the sequence of SEQ ID NO: 128.

In certain embodiments, a target region is nucleotides 6868-6887 of SEQ ID NO: 8. In certain embodiments, an antisense compound is targeted to nucleotides 6868-6887 of SEQ ID NO: 8. In certain such embodiments, an antisense compound targeted to nucleotides 6868-6887 of SEQ ID NO: 8 is Isis No: 298993. In certain embodiments, an antisense compound targeted to nucleotides 6868-6887 of SEQ ID NO: 8 has the sequence of SEQ ID NO: 161.

In certain embodiments, a target region is nucleotides 6930-6949 of SEQ ID NO: 8. In certain embodiments, an antisense compound is targeted to nucleotides 6930-6949 of SEQ ID NO: 8. In certain such embodiments, an antisense compound targeted to nucleotides 6930-6949 of SEQ ID NO: 8 is Isis No: 299039. In certain embodiments, an antisense compound targeted to nucleotides 6930-6949 of SEQ ID NO: 8 has the sequence of SEQ ID NO: 129.

In certain embodiments, a target region is nucleotides 6949-6968 of SEQ ID NO: 8. In certain embodiments, an antisense compound is targeted to nucleotides 6949-6968 of SEQ ID NO: 8. In certain such embodiments, an antisense compound targeted to nucleotides 6949-6968 of SEQ ID NO: 8 is Isis No: 299040. In certain embodiments, an antisense compound targeted to nucleotides 6949-6968 of SEQ ID NO: 8 has the sequence of SEQ ID NO: 130.

In certain embodiments, a target region is nucleotides 6930-6968 of SEQ ID NO: 8. In certain embodiments, an antisense compound is targeted to nucleotides 6930-6968 of SEQ ID NO: 8. In certain such embodiments, an antisense compound targeted to nucleotides 6930-6968 of SEQ ID NO: 8 is selected from Isis Nos: 299039 or 299040. In certain embodiments, an antisense compound targeted to nucleotides 6930-6968 of SEQ ID NO: 8 has the sequence of SEQ ID NO: 129 or 130.

In certain embodiments, a target region is nucleotides 6954-6973 of SEQ ID NO: 8. In certain embodiments, an antisense compound is targeted to nucleotides 6954-6973 of SEQ ID NO: 8. In certain such embodiments, an antisense compound targeted to nucleotides 6954-6973 of SEQ ID NO: 8 is Isis No: 299041. In certain embodiments, an antisense compound targeted to nucleotides 6954-6973 of SEQ ID NO: 8 has the sequence of SEQ ID NO: 131.

In certain embodiments, a target region is nucleotides 6949-6973 of SEQ ID NO: 8. In certain embodiments, an antisense compound is targeted to nucleotides 6949-6973 of SEQ ID NO: 8. In certain such embodiments, an antisense compound targeted to nucleotides 6949-6973 of SEQ ID NO: 8 is selected from Isis Nos: 299040 or 299041. In certain embodiments, an antisense compound targeted to nucleotides 6949-6973 of SEQ ID NO: 8 has the sequence of SEQ ID NO: 130 or 131.

In certain embodiments, a target region is nucleotides 6930-6973 of SEQ ID NO: 8. In certain embodiments, an antisense compound is targeted to nucleotides 6930-6973 of SEQ ID NO: 8. In certain such embodiments, an antisense compound targeted to nucleotides 6930-6973 of SEQ ID NO: 8 is selected from Isis Nos: 299039, 299040 or 299041. In certain embodiments, an antisense compound targeted to nucleotides 6930-6973 of SEQ ID NO: 8 has the sequence of SEQ ID NO: 129, 130 or 131.

In certain embodiments, a target region is nucleotides 7211-7230 of SEQ ID NO: 8. In certain embodiments, an antisense compound is targeted to nucleotides 7211-7230 of SEQ ID NO: 8. In certain such embodiments, an antisense compound targeted to nucleotides 7211-7230 of SEQ ID NO: 8 is Isis No: 299043. In certain embodiments, an antisense compound targeted to nucleotides 7211-7230 of SEQ ID NO: 8 has the sequence of SEQ ID NO: 133.

In certain embodiments, a target region is nucleotides 7260-7279 of SEQ ID NO: 8. In certain embodiments, an antisense compound is targeted to nucleotides 7260-7279 of SEQ ID NO: 8. In certain such embodiments, an antisense compound targeted to nucleotides 7260-7279 of SEQ ID NO: 8 is Isis No: 299044. In certain embodiments, an antisense compound targeted to nucleotides 7260-7279 of SEQ ID NO: 8 has the sequence of SEQ ID NO: 134.

In certain embodiments, a target region is nucleotides 7211-7279 of SEQ ID NO: 8. In certain embodiments, an antisense compound is targeted to nucleotides 7211-7279 of SEQ ID NO: 8. In certain such embodiments, an antisense compound targeted to nucleotides 7211-7279 of SEQ ID NO: 8 is selected from Isis Nos: 299043 or 299044. In certain embodiments, an antisense compound targeted to nucleotides 7211-7279 of SEQ ID NO: 8 has the sequence of SEQ ID NO: 133 or 134.

In certain embodiments, a target region is nucleotides 7654-7673 of SEQ ID NO: 8. In certain embodiments, an antisense compound is targeted to nucleotides 7654-7673 of SEQ ID NO: 8. In certain such embodiments, an antisense compound targeted to nucleotides 7654-7673 of SEQ ID NO: 8 is Isis No: 298998. In certain embodiments, an antisense compound targeted to nucleotides 7654-7673 of SEQ ID NO: 8 has the sequence of SEQ ID NO: 162.

In certain embodiments, a target region is nucleotides 8267-8286 of SEQ ID NO: 8. In certain embodiments, an antisense compound is targeted to nucleotides 8267-8286 of SEQ ID NO: 8. In certain such embodiments, an antisense compound targeted to nucleotides 8267-8286 of SEQ ID NO: 8 is Isis No: 298999. In certain embodiments, an antisense compound targeted to nucleotides 8267-8286 of SEQ ID NO: 8 has the sequence of SEQ ID NO: 163.

In certain embodiments, a target region is nucleotides 8899-8918 of SEQ ID NO: 8. In certain embodiments, an antisense compound is targeted to nucleotides 8899-8918 of SEQ ID NO: 8. In certain such embodiments, an antisense compound targeted to nucleotides 8899-8918 of SEQ ID NO: 8 is Isis No: 299045. In certain embodiments, an antisense compound targeted to nucleotides 8899-8918 of SEQ ID NO: 8 has the sequence of SEQ ID NO: 135.

In certain embodiments, a target region is nucleotides 8930-8949 of SEQ ID NO: 8. In certain embodiments, an antisense compound is targeted to nucleotides 8930-8949 of SEQ ID NO: 8. In certain such embodiments, an antisense compound targeted to nucleotides 8930-8949 of SEQ ID NO: 8 is Isis No: 299046. In certain embodiments, an antisense compound targeted to nucleotides 8930-8949 of SEQ ID NO: 8 has the sequence of SEQ ID NO: 136.

In certain embodiments, a target region is nucleotides 8899-8949 of SEQ ID NO: 8. In certain embodiments, an antisense compound is targeted to nucleotides 8899-8949 of SEQ ID NO: 8. In certain such embodiments, an antisense compound targeted to nucleotides 8899-8949 of SEQ ID NO: 8 is selected from Isis Nos: 299045 or 299046. In certain embodiments, an antisense compound targeted to nucleotides 8899-8949 of SEQ ID NO: 8 has the sequence of SEQ ID NO: 135 or 136.

In certain embodiments, a target region is nucleotides 8971-8990 of SEQ ID NO: 8. In certain embodiments, an antisense compound is targeted to nucleotides 8971-8990 of SEQ ID NO: 8. In certain such embodiments, an antisense compound targeted to nucleotides 8971-8990 of SEQ ID NO: 8 is Isis No: 299000. In certain embodiments, an antisense compound targeted to nucleotides 8971-8990 of SEQ ID NO: 8 has the sequence of SEQ ID NO: 164.

In certain embodiments, a target region is nucleotides 8930-8990 of SEQ ID NO: 8. In certain embodiments, an antisense compound is targeted to nucleotides 8930-8990 of SEQ ID NO: 8. In certain such embodiments, an antisense compound targeted to nucleotides 8930-8990 of SEQ ID NO: 8 is selected from Isis Nos: 299046 or 299000. In certain embodiments, an antisense compound targeted to nucleotides 8930-8990 of SEQ ID NO: 8 has the sequence of SEQ ID NO: 136 or 164.

In certain embodiments, a target region is nucleotides 8899-8990 of SEQ ID NO: 8. In certain embodiments, an antisense compound is targeted to nucleotides 8899-8990 of SEQ ID NO: 8. In certain such embodiments, an antisense compound targeted to nucleotides 8899-8990 of SEQ ID NO: 8 is selected from Isis Nos: 299045, 299046 or 299000. In certain embodiments, an antisense compound targeted to nucleotides 8899-8990 of SEQ ID NO: 8 has the sequence of SEQ ID NO: 135, 136 or 164.

In certain embodiments, a target region is nucleotides 9169-9188 of SEQ ID NO: 8. In certain embodiments, an antisense compound is targeted to nucleotides 9169-9188 of SEQ ID NO: 8. In certain such embodiments, an antisense compound targeted to nucleotides 9169-9188 of SEQ ID NO:

8 is selected from Isis Nos: 299047. In certain embodiments, an antisense compound targeted to nucleotides 9169-9188 of SEQ ID NO: 8 has the sequence of SEQ ID NO: 137.

In certain embodiments, a target region is nucleotides 8899-9188 of SEQ ID NO: 8. In certain embodiments, an antisense compound is targeted to nucleotides 8899-9188 of SEQ ID NO: 8. In certain such embodiments, an antisense compound targeted to nucleotides 8899-9188 of SEQ ID NO: 8 is selected from Isis Nos: 299045, 299046, 299000 or 299047. In certain embodiments, an antisense compound targeted to nucleotides 8899-9188 of SEQ ID NO: 8 has the sequence of SEQ ID NO: 135, 136, 164 or 137.

In certain embodiments, a target region is nucleotides 9218-9237 of SEQ ID NO: 8. In certain embodiments, an antisense compound is targeted to nucleotides 9218-9237 of SEQ ID NO: 8. In certain such embodiments, an antisense compound targeted to nucleotides 9218-9237 of SEQ ID NO: 8 is Isis No: 299048. In certain embodiments, an antisense compound targeted to nucleotides 9218-9237 of SEQ ID NO: 8 has the sequence of SEQ ID NO: 138.

In certain embodiments, a target region is nucleotides 9169-9237 of SEQ ID NO: 8. In certain embodiments, an antisense compound is targeted to nucleotides 9169-9237 of SEQ ID NO: 8. In certain such embodiments, an antisense compound targeted to nucleotides 9169-9237 of SEQ ID NO: 8 is selected from Isis Nos: 299047 or 299048. In certain embodiments, an antisense compound targeted to nucleotides 9169-9237 of SEQ ID NO: 8 has the sequence of SEQ ID NO: 137 or 138.

In certain embodiments, a target region is nucleotides 9863-9882 of SEQ ID NO: 8. In certain embodiments, an antisense compound is targeted to nucleotides 9863-9882 of SEQ ID NO: 8. In certain such embodiments, an antisense compound targeted to nucleotides 9863-9882 of SEQ ID NO: 8 is Isis No: 299001. In certain embodiments, an antisense compound targeted to nucleotides 9863-9882 of SEQ ID NO: 8 has the sequence of SEQ ID NO: 165.

In certain embodiments, a target region is nucleotides 10204-10233 of SEQ ID NO: 8. In certain embodiments, an antisense compound is targeted to nucleotides 10204-10233 of SEQ ID NO: 8. In certain such embodiments, an antisense compound targeted to nucleotides 10204-10233 of SEQ ID NO: 8 is Isis No: 299050. In certain embodiments, an antisense compound targeted to nucleotides 10204-10233 of SEQ ID NO: 8 has the sequence of SEQ ID NO: 140.

In certain embodiments, a target region is nucleotides 10797-10816 of SEQ ID NO: 8. In certain embodiments, an antisense compound is targeted to nucleotides 10797-10816 of SEQ ID NO: 8. In certain such embodiments, an antisense compound targeted to nucleotides 10797-10816 of SEQ ID NO: 8 is Isis No: 299002. In certain embodiments, an antisense compound targeted to nucleotides 10797-10816 of SEQ ID NO: 8 has the sequence of SEQ ID NO: 166.

In certain embodiments, a target region is nucleotides 10880-10899 of SEQ ID NO: 8. In certain embodiments, an antisense compound is targeted to nucleotides 10880-10899 of SEQ ID NO: 8. In certain such embodiments, an antisense compound targeted to nucleotides 10880-10899 of SEQ ID NO: 8 is Isis No: 299052. In certain embodiments, an antisense compound targeted to nucleotides 10880-10899 of SEQ ID NO: 8 has the sequence of SEQ ID NO: 64.

In certain embodiments, a target region is nucleotides 10797-10899 of SEQ ID NO: 8. In certain embodiments, an antisense compound is targeted to nucleotides 10880-10899 of SEQ ID NO: 8. In certain such embodiments, an antisense compound targeted to nucleotides 10797-10899 of SEQ ID NO: 8 is selected from Isis Nos: 299002 or 299052. In certain embodiments, an antisense compound targeted to nucleotides 10797-10899 of SEQ ID NO: 8 has the sequence of SEQ ID NO: 166 or 64.

In certain embodiments, a target region is nucleotides 11096-11115 of SEQ ID NO: 8. In certain embodiments, an antisense compound is targeted to nucleotides 11096-11115 of SEQ ID NO: 8. In certain such embodiments, an antisense compound targeted to 11096-11115 of SEQ ID NO: 8 is Isis No: 299054. In certain embodiments, an antisense compound targeted to nucleotides 11096-11115 of SEQ ID NO: 8 has the sequence of SEQ ID NO: 143.

In certain embodiments, a target region is nucleotides 11112-11131 of SEQ ID NO: 8. In certain embodiments, an antisense compound is targeted to nucleotides 11112-11131 of SEQ ID NO: 8. In certain such embodiments, an antisense compound targeted to 11112-11131 of SEQ ID NO: 8 is Isis No: 299055. In certain embodiments, an antisense compound targeted to nucleotides 11112-11131 of SEQ ID NO: 8 has the sequence of SEQ ID NO: 144.

In certain embodiments, a target region is nucleotides 11096-11131 of SEQ ID NO: 8. In certain embodiments, an antisense compound is targeted to nucleotides 11096-11131 of SEQ ID NO: 8. In certain such embodiments, an antisense compound targeted to 11096-11131 of SEQ ID NO: 8 is selected from Isis Nos: 299054 or 299055. In certain embodiments, an antisense compound targeted to nucleotides 11096-11131 of SEQ ID NO: 8 has the sequence of SEQ ID NO: 143 or 144.

In certain embodiments, a target region is nucleotides 11118-11137 of SEQ ID NO: 8. In certain embodiments, an antisense compound is targeted to nucleotides 11118-11137 of SEQ ID NO: 8. In certain such embodiments, an antisense compound targeted to 11118-11137 of SEQ ID NO: 8 is Isis No: 299056. In certain embodiments, an antisense compound targeted to nucleotides 11118-11137 of SEQ ID NO: 8 has the sequence of SEQ ID NO: 145.

In certain embodiments, a target region is nucleotides 11112-11137 of SEQ ID NO: 8. In certain embodiments, an antisense compound is targeted to nucleotides 11112-11137 of SEQ ID NO: 8. In certain such embodiments, an antisense compound targeted to 11112-11137 of SEQ ID NO: 8 is selected from Isis Nos: 299055 or 299056. In certain embodiments, an antisense compound targeted to nucleotides 11112-11137 of SEQ ID NO: 8 has the sequence of SEQ ID NO: 144 or 145.

In certain embodiments, a target region is nucleotides 11096-11137 of SEQ ID NO: 8. In certain embodiments, an antisense compound is targeted to nucleotides 11096-11137 of SEQ ID NO: 8. In certain such embodiments, an antisense compound targeted to nucleotides 11096-11137 of SEQ ID NO: 8 is selected from Isis Nos: 299054, 299055, or 299056. In certain embodiments, an antisense compound targeted to nucleotides 11096-11137 of SEQ ID NO: 8 has the sequence of SEQ ID NO: 143, 144, or 145.

In certain embodiments, a target region is nucleotides 11172-11191 of SEQ ID NO: 8. In certain embodiments, an antisense compound is targeted to nucleotides 11172-11191 of SEQ ID NO: 8. In certain such embodiments, an antisense compound targeted to nucleotides 11172-11191 of SEQ ID NO: 8 is Isis No: 299057. In certain embodiments, an antisense compound targeted to nucleotides 11172-11191 of SEQ ID NO: 8 has the sequence of SEQ ID NO: 146.

In certain embodiments, a target region is nucleotides 11118-11191 of SEQ ID NO: 8. In certain embodiments, an antisense compound is targeted to nucleotides 11172-11191 of SEQ ID NO: 8. In certain such embodiments, an antisense compound targeted to nucleotides 11118-11191 of SEQ ID NO: 8 is selected from Isis Nos: 299056 or 299057. In certain embodiments, an antisense compound targeted to nucleotides 11118-11191 of SEQ ID NO: 8 has the sequence of SEQ ID NO: 145 or 146.

In certain embodiments, a target region is nucleotides 11112-11191 of SEQ ID NO: 8. In certain embodiments, an antisense compound is targeted to nucleotides 11112-11191 of SEQ ID NO: 8. In certain such embodiments, an antisense compound targeted to nucleotides 11112-11191 of SEQ ID NO: 8 is selected from Isis Nos: 299055, 299056, or 299057. In certain embodiments, an antisense compound targeted to nucleotides 11112-11191 of SEQ ID NO: 8 has the sequence of SEQ ID NO: 144, 145, or 146.

In certain embodiments, a target region is nucleotides 11096-11191 of SEQ ID NO: 8. In certain embodiments, an antisense compound is targeted to nucleotides 11096 11191 of SEQ ID NO: 8. In certain such embodiments, an antisense compound targeted to nucleotides 11096-11191 of SEQ ID NO: 8 is selected from Isis Nos: 299054, 299055, 299056, or 299057. In certain embodiments, an antisense compound targeted to nucleotides 11096-11191 of SEQ ID NO: 8 has the sequence of SEQ ID NO: 143, 144, 145, or 146.

In certain embodiments, a target region is nucleotides 11180-11199 of SEQ ID NO: 8. In certain embodiments, an antisense compound is targeted to nucleotides 11180-11199 of SEQ ID NO: 8. In certain such embodiments, an antisense compound targeted to nucleotides 11180-11199 of SEQ ID NO: 8 is Isis No: 299058. In certain embodiments, an antisense compound targeted to nucleotides 11180-11199 of SEQ ID NO: 8 has the sequence of SEQ ID NO: 147.

In certain embodiments, a target region is nucleotides 11172-11199 of SEQ ID NO: 8. In certain embodiments, an antisense compound is targeted to nucleotides 11172-11199 of SEQ ID NO: 8. In certain such embodiments, an antisense compound targeted to nucleotides 11172-11199 of SEQ ID NO: 8 is selected from Isis Nos: 299057 or 299058. In certain embodiments, an antisense compound targeted to nucleotides 111172-11199 of SEQ ID NO: 8 has the sequence of SEQ ID NO: 146 or 147.

In certain embodiments, a target region is nucleotides 11118-11199 of SEQ ID NO: 8. In certain embodiments, an antisense compound is targeted to nucleotides 11118-11199 of SEQ ID NO: 8. In certain such embodiments, an antisense compound targeted to nucleotides 11118-11199 of SEQ ID NO: 8 is selected from Isis Nos: 299056, 299057 or 299058. In certain embodiments, an antisense compound targeted to nucleotides 11118-11199 of SEQ ID NO: 8 has the sequence of SEQ ID NO: 145, 146 or 147.

In certain embodiments, a target region is nucleotides 11112-11199 of SEQ ID NO: 8. In certain embodiments, an antisense compound is targeted to nucleotides 11112-11199 of SEQ ID NO: 8. In certain such embodiments, an antisense compound targeted to nucleotides 11112-11199 of SEQ ID NO: 8 is selected from Isis Nos: 299055, 299056, 299057 or 299058. In certain embodiments, an antisense compound targeted to nucleotides 11112-11199 of SEQ ID NO: 8 has the sequence of SEQ ID NO: 144, 145, 146 or 147.

In certain embodiments, a target region is nucleotides 11096-11199 of SEQ ID NO: 8. In certain embodiments, an antisense compound is targeted to nucleotides 11096-11199 of SEQ ID NO: 8. In certain such embodiments, an antisense compound targeted to nucleotides 11096-11199 of SEQ ID NO: 8 is selected from Isis Nos: 299054, 299055, 299056, 299057 or 299058. In certain embodiments, an antisense compound targeted to nucleotides 11096-11199 of SEQ ID NO: 8 has the sequence of SEQ ID NO: 143, 144, 145, 146 or 147.

In certain embodiments, a target region is nucleotides 11244-11263 of SEQ ID NO: 8. In certain embodiments, an antisense compound is targeted to nucleotides 11244-11263 of SEQ ID NO: 8. In certain such embodiments, an antisense compound targeted to nucleotides 11244-11263 of SEQ ID NO: 8. is Isis No: 299059. In certain embodiments, an antisense compound targeted to nucleotides 11244-11263 of SEQ ID NO: 8. has the sequence of SEQ ID NO: 148.

In certain embodiments, a target region is nucleotides 11313-11332 of SEQ ID NO: 8. In certain embodiments, an antisense compound is targeted to nucleotides 11313-11332 of SEQ ID NO: 8. In certain such embodiments, an antisense compound targeted to nucleotides 11313-11332 of SEQ ID NO: 8 is Isis No: 299060. In certain embodiments, an antisense compound targeted to nucleotides 11313-11332 of SEQ ID NO: 8 has the sequence of SEQ ID NO: 149.

In certain embodiments, a target region is nucleotides 11353-11372 of SEQ ID NO: 8. In certain embodiments, an antisense compound is targeted to nucleotides 11353-11372 of SEQ ID NO: 8. In certain such embodiments, an antisense compound targeted to nucleotides 11353-11372 of SEQ ID NO: 8 is Isis No: 299061. In certain embodiments, an antisense compound targeted to nucleotides 11353-11372 of SEQ ID NO: 8 has the sequence of SEQ ID NO: 150.

In certain embodiments, a target region is nucleotides 11367-11386 of SEQ ID NO: 8. In certain embodiments, an antisense compound is targeted to nucleotides 11367-11386 of SEQ ID NO: 8. In certain such embodiments, an antisense compound targeted to nucleotides 11367-11386 of SEQ ID NO: 8 is Isis No: 299062. In certain embodiments, an antisense compound targeted to nucleotides 11367-11386 of SEQ ID NO: 8 has the sequence of SEQ ID NO: 151

In certain embodiments, a target region is nucleotides 11353-11386 of SEQ ID NO: 8. In certain embodiments, an antisense compound is targeted to nucleotides 11353-11386 of SEQ ID NO: 8. In certain such embodiments, an antisense compound targeted to nucleotides 11353-11386 of SEQ ID NO: 8 is selected from Isis Nos: 299061 or 299062. In certain embodiments, an antisense compound targeted to nucleotides 11353-11386 of SEQ ID NO: 8 has the sequence of SEQ ID NO: 150 or 151.

In certain embodiments, a target region is nucleotides 11466-11485 of SEQ ID NO: 8. In certain embodiments, an antisense compound is targeted to nucleotides 11466-11485 of SEQ ID NO: 8. In certain such embodiments, an antisense compound targeted to nucleotides 11466-11485 of SEQ ID NO: 8 is Isis No: 299063. In certain embodiments, an antisense compound targeted to nucleotides 11466-11485 of SEQ ID NO: 8 has the sequence of SEQ ID NO: 152.

In certain embodiments, a target region is nucleotides 11367-11485 of SEQ ID NO: 8. In certain embodiments, an antisense compound is targeted to nucleotides 11367-11485 of SEQ ID NO: 8. In certain such embodiments, an antisense compound targeted to nucleotides 11367-11485 of SEQ ID NO: 8 is selected from Isis Nos: 299062 or 299063. In certain embodiments, an antisense compound targeted to nucleotides 11367-11485 of SEQ ID NO: 8 has the sequence of SEQ ID NO: 151 or 152.

In certain embodiments, a target region is nucleotides 11353-11485 of SEQ ID NO: 8. In certain embodiments, an antisense compound is targeted to nucleotides 11353-11485 of SEQ ID NO: 8. In certain such embodiments, an antisense compound targeted to nucleotides 11353-11485 of SEQ ID NO: 8 is selected from Isis Nos: 299061, 299062 or 299063. In certain embodiments, an antisense compound targeted to nucleotides 11353-11485 of SEQ ID NO: 8 has the sequence of SEQ ID NO: 150, 151 or 152.

In certain embodiments, the desired effect is a reduction in mRNA target nucleic acid levels. In other embodiments, the desired effect is reduction of levels of protein encoded by the target nucleic acid or a phenotypic change associated with the target nucleic acid.

In one embodiment, a target region is a structurally defined region of the nucleic acid. For example, a target region may encompass a 3' UTR, a 5' UTR, an exon, an intron, a coding region, a translation initiation region, translation termination region, or other defined nucleic acid region. In other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. A target region may contain one or more target segments. Multiple target segments within a target region may be overlapping. Alternatively, they may be non-overlapping. In one embodiment, target segments within a target region are separated by no more than about 10 nucleotides on the target nucleic acid. In another embodiment, target segments within a target region are separated by no more than about 5 nucleotides on the target nucleic acid. In additional embodiments, target segments are contiguous.

Suitable target segments may be found within a 5' UTR, a coding region, a 3' UTR, an intron, or an exon. Target segments containing a start codon or a stop codon are also suitable target segments.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In one embodiment, reductions in FGFR4 mRNA levels are indicative of inhibition of FGFR4 expression. Reductions in levels of an FGFR4 protein are also indicative of inhibition of target FGFR4 expression. Further, phenotypic changes are indicative of inhibition of FGFR4 expression. For example, a decrease in body fat content is indicative of inhibition of FGFR4 expression.

In certain embodiments, the compound comprises an antisense nucleic acid molecule that is specifically hybridizable with a region of a nucleic acid molecule encoding FGFR4 selected from a 5'-untranslated region (5'UTR), a start region, a coding region, a stop region, or a 3'-untranslated region (3'UTR).

In certain other embodiments, the antisense compound is targeted to nucleotides 26-45 in the (5'UTR), nucleotides 160-179, 192-227, 254-323, 354-399, 412-431, 475-502, 529-548, 597-646, 711-776, 785-804, 833-852, 964-988, 1027-1051, 1076-1140, 1181-1226, 1235-1254, 1326-1345, 1428-1471, 1555-1574, 1607-1626, 1656-1675, 1742-1760, 1772-1791, 1919-1938, 1968-1998, 2268-2287, 2313-2332, 2394-2435, 2481-2522 in the coding region of SEQ ID NO: 5; nucleotides 2557-2584, 2629-2648, 2698-2717, 2738-2757, 2752-2771, 2851-2870 in the 3' UTR, all of SEQ ID NO: 5; (exon2) nucleotides 115-258, (exon3) nucleotides 259-522, (exon4) nucleotides 523-603, (exon5) nucleotides 604-770, (exon6) nucleotides 771-894, (exon7) nucleotides 895-1085, (exon8) nucleotides 1086-1224, (exon9) nucleotides 1225-1418, (exon10) nucleotides 1419-1564, (exon11) nucleotides 1565-1696, (exon12) nucleotides 1687-1797, (exon13) nucleotides 1798-1988, (exon14) nucleotides 1989-2111, (exon15) nucleotides 2112-2182, (exon16) nucleotides 2183-2320, (exon17) nucleotides 2321-2426, (exon18) nucleotides 2427-3026, and nucleotides 26-45, 160-179, 192-211, 160-211, 208-227, 160-227, 192-227, 254-273, 278-297, 289-308, 289-323, 278-308, 304-323, 278-323, 289-373, 278-373, 354-373, 380-399, 412-431, 475-494, 412-494, 483-502, 475-502, 529-548, 597-616, 602-621, 597-621, 627-646, 711-730, 727-746, 739-758, 757-776, 711-746, 711-758, 711-776, 727-746, 727-758, 739-758, 727-776, 739-776, 757-776, 785-804, 833-852, 785-852, 833-983, 964-983, 785-983, 833-988, 785-988, 969-988, 964-988, 1027-1046, 1032-1051, 1027-1051, 1076-1096, 1090-1109, 1095-1114, 1076-1109, 1076-1114, 1090-1114, 1121-1040, 1181-1200, 1121-1200, 1121-1226, 1181-1226, 1235-1345, 1428-1447, 1447-1466, 1428-1466, 1452-1471, 1428-1471, 1555-1574, 1607-1626, 1656-1675, 155-1626, 1607-1675, 1555-1675, 1326-1675, 1741-1760, 1772-1791, 1919-1938, 1968-1987, 1979-1998, 1968-1998, 2268-2287, 2313-2332, 2394-2413, 2481-2500, 2497-2516, 2503-2522, 2557-2576, 2565-2584, 2629-2648, 2738-2757, 2752-2771, 2497-2584, 2738-2870, 2497-2870, or 2313-2413 of SEQ ID NO: 5.

In certain other embodiments, the antisense compound is targeted to nucleotides 26-45 in the (5'UTR), nucleotides 3118-3120 of the start codon, nucleotides 11192-111642 of the 3' UTR, (exon1) nucleotides 379-548, (exon1a) nucleotides 538-592, (exon2) nucleotides 3065-3208, (exon3) nucleotides 3905-4168, (exon4) nucleotides 4260-4340, (exon4a) nucleotides 4260-4611, (exon5) nucleotides 4453-4619, (exon6) nucleotides 5200-5323, (exon7) nucleotides 5836-6026, (exon8) nucleotides 6161-6299, (exon9) nucleotides 6653-6846, (exon10a) nucleotides 6847-7066, (exon10) nucleotides 6291-7066, (exon11) nucleotides 7169-7290, (exon12) nucleotides 8845-8955, (exon13) nucleotides 9048-9238, (exon14) nucleotides 9572-9694, (exon15) nucleotides 9802-9872, (exon16) nucleotides 10119-10256, (exon17) nucleotides 10807-10912, (exon18) nucleotides 11042-11641, (intron1) nucleotides 549-3064, (intron1a) nucleotides 593-3064, (intron2) nucleotides 3209-3904, (intron3) nucleotides 4169-4259, (intron4) nucleotides 4941-4452, (intron5) nucleotides 4620-5199, (intron6) nucleotides 5324-5835, (intron7) nucleotides 6027-6160, (intron8) nucleotides 6300-6652, (intron9) nucleotides 6847-6920, (intron10) nucleotides 7067-7168, (intron11) nucleotides 7291-8844, (intron12) nucleotides 8956-9047, (intron13) nucleotides 9239-9571, (intron14) nucleotides 9695-9801, (intron15) nucleotides 9873-10118, (intron16) nucleotides 10257-10806, and (intron17) nucleotides 10913-11041, nucleotides 432-442, 460-479, 538-602, 1913-1932, 3110-3129, 3142-3161, 3158-3177, 3199-3218, 3924-3943, 3935-3954, 3950-3969, 3924-3954, 3935-3969, 3924-3969, 4000-4019, 4026-4045, 4058-4077, 4121-4140, 4129-4148, 4121-4148, 4058-4148, 4174-4193, 4250-4269, 4266-4285, 4174-4285, 4058-4285, 4451-4470, 4476-4495, 4560-4579, 4576-4595, 4588-4607, 4560-4595, 4576-4607, 4560-4607, 5214-5233, 5262-5281, 5214-5281, 5905-5924, 5910-5929, 5905-5929, 5968-5987, 5910-5987, 5905-5987, 5973-5992, 5968-5992, 5910-5992, 6165-6184, 6170-6189, 6165-6189, 6196-6215, 6170-6215, 6256-6275, 6663-6682, 6754-6773, 6868-6887, 6930-6949, 6949-6968, 6930-6968, 6954-6973, 6949-6973, 6930-6973, 7211-7230, 7260-7279, 7211-7279, 7654-7673, 8267-8286, 8899-8918, 8930-8948, 8899-8948, 8971-8990, 8930-8990, 8899-8990, 9169-9188, 8899-9188, 9218-9237, 9169-9237, 9863-9882, 10204-10233, 10797-10816, 10880-10899, 10797-10899, 10880-10899, 11096-11115, 11112-11131, 11096-11131, 11118-11137, 11112-11137, 11096-11137, 11172-11191, 11118-11191, 11112-11191, 11096-11191, 11172-11199, 11180-11199, 11118-11199, 11112-11199, 11096-11199, 11244-11265, 11313-11332, 11353-11372, 11369-11386, 11466-11485, 11367-11485, or 11353-11485 of SEQ ID NO: 8.

Hybridization

For example, hybridization may occur between an antisense compound disclosed herein and a FGFR4 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In one embodiment, the antisense compounds provided herein are specifically hybridizable with an FGFR4 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an FGFR4 nucleic acid).

Non-complementary nucleobases between an antisense compound and an FGFR4 nucleic acid may be tolerated provided that the antisense compound remains able to specifically hybridize to a target nucleic acid. Moreover, an antisense compound may hybridize over one or more segments of an FGFR4 nucleic acid such that intervening or adjacent segments are not involved in the hybridization event (e.g., a loop structure, mismatch or hairpin structure).

In some embodiments, the antisense compounds provided herein are at least 70%, at least 75%, at least 80%, at least 85%, at least 90%, at least 95%, at least 96%, at least 97%, at least 98% or at least 99% complementary to an FGFR4 nucleic acid. Percent complementarity of an antisense compound with a target nucleic acid can be determined using routine methods.

In other embodiments, the antisense compounds provided herein are fully complementary (i.e., 100% complementary) to a target nucleic acid. For example, antisense compound may be fully complementary to an FGFR4 nucleic acid. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In one embodiment, antisense compounds up to 20 nucleobases in length comprise no more than 4, no more than 3, no more than 2 or no more than 1 non-complementary nucleobase(s) relative to a target nucleic acid, such as an FGFR4 nucleic acid.

In another embodiment, antisense compounds up to 30 nucleobases in length comprise no more than 6, no more than 5, no more than 4, no more than 3, no more than 2 or no more than 1 non-complementary nucleobase(s) relative to a target nucleic acid, such as an FGFR4 nucleic acid.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In one embodiment, the antisense compounds are complementary to at least an 8 nucleobase portion of a target segment. In another embodiment, the antisense compounds are complementary to at least a 12 nucleobase portion of a target segment. In yet another embodiment, the antisense compounds are complementary to at least a 15 nucleobase portion of a target segment.

Identity

The antisense compounds provided herein may also have a defined percent identity to a particular nucleotide sequence, SEQ ID NO, or compound represented by a specific Isis number. As used herein, an antisense compound is identical to the sequence disclosed herein if it has the same nucleobase pairing ability. For example, an RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, at least 75%, at least 80%, at least 85%, at least 90%, at least 95% or 100% identical to one or more of the antisense compounds disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, antisense compounds targeted to an FGFR4 nucleic acid comprise one or more modified internucleoside linkages. In some embodiments, the modified internucleoside linkages are phosphorothioate linkages. In other embodiments, each internucleoside linkage of an antisense compound is a phosphorothioate internucleoside linkage.

Modified Sugar Moieties

Antisense compounds targeted to an FGFR4 nucleic acid may contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C($R_1$)($R_2$) for the ring oxygen at the 4'-position. Modified sugars include, but are not limited to: substituted sugars, especially 2'-substituted sugars having a 2'-F, 2'-OCH$_2$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=2. Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In one embodiment, antisense compounds targeted to an FGFR4 nucleic acid comprise one or more nucleotides having modified sugar moieties. In a suitable embodiment, the modified sugar moiety is 2'-MOE. In other embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In one embodiment, antisense compounds targeted to an FGFR4 nucleic acid comprise one or more modified nucleobases. In an additional embodiment, gapmer antisense oligonucleotides targeted to an FGFR4 nucleic acid comprise one or more modified nucleobases. In some embodiments, the modified nucleobase is 5-methylcytosine. In further embodiments, each cytosine is a 5-methylcytosine.

Compositions and Methods for Formulating Pharmaceutical Compositions

Antisense oligonucleotides may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an FGFR4 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an FGFR4 nucleic acid and a pharmaceutically acceptable diluent. In one embodiment, the pharmaceutically acceptable diluent is PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, pharmaceutical compositions of the present invention comprise one or more oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulosem and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, a pharmaceutical composition of the present invention comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more oligonucleotides of the present invention is formulated as a prodrug. In certain embodiments, upon in vivo administration, a prodrug is chemically converted to the biologically, pharmaceutically or therapeutically more active form of the oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In certain embodiments, a pharmaceutical composition comprising one or more pharmaceutical agents of the present invention is useful for treating a conditions or disorders in a mammalian, and particularly in a human, subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition of the present invention is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain embodiments, a pharmaceutical composition is comprises a dose of oligonucleotide selected from 50 mg, 100 mg, 150 mg, 200 mg, 250 mg, 300 mg, and 400 mg. In certain embodiments the dose is administered at intervals ranging from more than once per day, once per day, once per week, twice per week, three times per week, four times per week, five times per week, 6 times per week, once per month to once per three months, for as long as needed to sustain the desired effect.

In a further aspect, a pharmaceutical agent is sterile lyophilized oligonucleotide that is reconstituted with a suitable diluent, e.g., sterile water for injection. The reconstituted product is administered as a subcutaneous injection or as an intravenous infusion after dilution into saline. The lyophilized drug product consists of the oligonucleotide which has been prepared in water for injection, adjusted to pH 7.0-9.0 with acid or base during preparation, and then lyophilized. The lyophilized oligonucleotide may be 25-800 mg of the oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal. In one embodiment, the lyophilized pharmaceutical agent comprises ISIS 301012.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of mDICT nucleic acids can be tested in vitro in a variety of cell types. Cell types used for such analyses are available from commerical vendors (e.g. American Type Culture Collection, Manassas, Va.; Zen-Bio, Inc., Research Triangle Park, NC; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when they cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an FGFR4 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH, or by quantifying total RNA using RIBOGREEN® (Invetrogen, Inc. Carlsbad, Calif.). GAPDH expression is quantified by real time PCR, by being run simultaneously with the target, multiplexing, or separately. Total RNA is quantified using RIBOGREEN® RNA quantification reagent (Invetrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to an mDICT nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of FGFR4 nucleic acids can be assessed by measuring FGFR4 protein levels. Protein levels of FGFR4 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat FGFR4 are commercially available.

In Vivo Testing of Antisense Compounds

Antisense compounds, for example, antisense oligonucleotides, are tested in animals to assess their ability to inhibit expression of FGFR4 and produce phenotypic changes, such as decreases in body weight. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from various tissues and changes in FGFR4 nucleic acid expression are measured. Changes in FGFR4 protein levels may also be measured.

Animal Models of Obesity

Non-Limiting Disclosure and Incorporation by Reference

The following examples serve only to illustrate the methods, antisense oligonucleotides, and compositions provided and are not intended to limit the same. Each of the references, GENBANK® accession numbers, and the like recited in the present application is incorporated herein by reference in its entirety. By incorporation of GENBANK® Accession Nos., associated sequence and structural data pertaining to such sequences including gene organization and structural elements that may be found in sequence databases such as the National Center for Biotechnology Information (NCBI) by searching such GENBANK® Accession Nos. are incorporated herein by reference in their entirety.

EXAMPLES

Example 1

Antisense Inhibition of *Mus musculus* FGFR4: Primary Hepatocytes

Antisense oligonucleotides targeted to a FGFR4 nucleic acid were tested for their effects on FGFR4 mRNA expression in vitro. Cultured primary hepatocytes plated in a 96-well plate were treated with 60 nM of antisense oligonucleotide. Transfection was carried out using Cytofectin™ (Genlantis, San Diego, Calif.). After a treatment period of approximately 24 hours, RNA was isolated from the cells and FGFR4 mRNA levels were measured by quantitative real-time PCR, as described herein using the primer/probe set shown in Table 4. Probes and primers to mouse FGFR4 were designed to hybridize to a mouse FGFR4 sequence, using published sequence information (GenBank® accession number BC033313.1 incorporated herein as SEQ ID NO: 10).

TABLE 4

Gene Target-specific mouse Primers and Probes for Use in Real-Time PCR

| Target Name | Species | Target Seq ID No | Sequence Description | Sequence (5' to 3') | Length | SEQ ID NO |
|---|---|---|---|---|---|---|
| mFGFR4 | Mouse | 10 | Forward Primer | CCTTATGCCCCCATCTCAG | 19 | 167 |
| mFGFR4 | Mouse | 10 | Reverse Primer | TCCCAAGGCCTCTAGGTTG | 19 | 168 |
| mFGFR4 | Mouse | 10 | Probe | CTCTCCGGGACTAGCTGCAA AACTTATGCTCTAAACATTT CTAGTTCCCC | 50 | 169 |

The FGFR4 mRNA levels were adjusted according to total RNA content as measured by RIBOGREEN®. Results are presented as percent inhibition of FGFR4, relative to untreated control cells. Antisense oligonucleotides that exhibited at least 30% inhibition of FGFR4 expression are shown in Table 5.

The oligonucleotides of Table 5, have a 5-10-5 2'-MOE gapmer motif. The heading "5' target site" indicates the 5'-most nucleotide corresponding to the first base to which the antisense oligonucleotide is targeted on the indicated GEN-BANK® Accession No.

All antisense compounds in Table 5 are gapmers having 20 linked nucleobases and composed of a central "gap" segment consisting of 2'-deoxynucleotides, which are flanked on both sides (5' and 3' directions) by wing segments having 2'-modifications. The wings are composed of 2'-methoxyethyl (2'-MOE) nucleotides. The internucleoside (backbone) linkages are phosphorothioate (P=S) throughout the oligonucleotide. All cytosine nucleobases are 5-methylcytosines.

TABLE 5

Inhibition of Gene Target mRNA Levels by Chimeric Oligonucleotides with 2'-MOE Wings and Deoxy Gap (mus musculus)

| ISIS # | Target SEQ ID NO | 5' Target Site | 3' Target Site | Sequence (5' to 3') | % Inhibition | SEQ ID NO |
|---|---|---|---|---|---|---|
| 393247 | 10 | 228 | 247 | GGGCTGGCACACTCACCCGC | 91 | 15 |
| 393248 | 10 | 238 | 257 | GATCCCGGCAGGGCTGGCAC | 87 | 16 |
| 393249 | 10 | 244 | 263 | GGTCACGATCCCGGCAGGGC | 83 | 17 |
| 393250 | 10 | 337 | 356 | GCCACATTTCCTTCCAGCTG | 95 | 18 |
| 393251 | 10 | 346 | 365 | CCAAGAGCAGCCACATTTCC | 68 | 19 |
| 393252 | 10 | 355 | 374 | TCAACAGGGCCAAGAGCAGC | 71 | 20 |
| 393253 | 10 | 402 | 421 | TTCCTCAGAGGCCTCAAGGG | 88 | 21 |
| 393254 | 10 | 600 | 619 | AGGAAGGAAGCTGGCGATCT | 59 | 22 |
| 393255 | 10 | 610 | 629 | CAGCATCCTCAGGAAGGAAG | 52 | 23 |
| 393256 | 10 | 635 | 654 | CCACGGGCCAGGCAGAGGTA | 93 | 24 |
| 393257 | 10 | 644 | 663 | GTCATGGAGCCACGGGCCAG | 87 | 25 |
| 393258 | 10 | 682 | 701 | AGGAGTCATCCATAAGCAAC | 79 | 26 |
| 393259 | 10 | 687 | 706 | GGTTAAGGAGTCATCCATAA | 85 | 27 |
| 393260 | 10 | 694 | 713 | TGATGGAGGTTAAGGAGTCA | 75 | 28 |
| 393261 | 10 | 773 | 792 | TGTGTCCAGTAGGGTGCTTG | 72 | 29 |
| 393262 | 10 | 873 | 892 | CCAGTGGATGGTAGGCATGG | 97 | 30 |
| 393263 | 10 | 878 | 897 | TTGAGCCAGTGGATGGTAGG | 87 | 31 |
| 393264 | 10 | 996 | 1015 | AAGGCATGTGTATGTGCCAC | 57 | 32 |
| 393265 | 10 | 1001 | 1020 | TCCACAAGGCATGTGTATGT | 79 | 33 |
| 393266 | 10 | 1020 | 1039 | AATGCTACCCAGAGAGTTCT | 80 | 34 |

TABLE 5-continued

Inhibition of Gene Target mRNA Levels by Chimeric Oligonucleotides with 2'-MOE Wings and Deoxy Gap (*mus musculus*)

| ISIS # | Target SEQ ID NO | 5' Target Site | 3' Target Site | Sequence (5' to 3') | % Inhibition | SEQ ID NO |
|---|---|---|---|---|---|---|
| 393267 | 10 | 1048 | 1067 | CCAGCACATCCAGGAGATAG | 61 | 35 |
| 299029 | 10 | 1200 | 1219 | GCTGCTGCCGTTGATGACGA | 95 | 36 |
| 393268 | 10 | 1245 | 1264 | TGTTGTCTTCAGGACTTGTA | 74 | 37 |
| 393269 | 10 | 1364 | 1383 | AGCCACGCTGACTGGTAGGA | 85 | 38 |
| 299036 | 10 | 1380 | 1399 | CTCTGGCAGCACCGTGAGCC | 90 | 39 |
| 393270 | 10 | 1446 | 1465 | TGATACATACAGGATGATAT | 37 | 40 |
| 393271 | 10 | 1466 | 1485 | ACAAGCAGAACCAGTGAGCC | 64 | 41 |
| 393272 | 10 | 1471 | 1490 | GGAGCACAAGCAGAACCAGT | 74 | 42 |
| 393273 | 10 | 1490 | 1509 | TACACCCCGGCCAGCAGCAG | 74 | 43 |
| 393274 | 10 | 1604 | 1623 | GACTTGCCAGAGGACCTCGA | 88 | 44 |
| 393275 | 10 | 1615 | 1634 | GGGACAAACTTGACTTGCCA | 79 | 45 |
| 393276 | 10 | 1625 | 1644 | CCTCGCACCAGGGACAAACT | 62 | 46 |
| 393277 | 10 | 1670 | 1689 | ACAAGGCCCGTGAGCAAGGG | 64 | 47 |
| 393278 | 10 | 1756 | 1775 | CAAAGCAGCCCTCACCCAGG | 50 | 48 |
| 393279 | 10 | 1775 | 1794 | TCTGCACGAACCACTTGCCC | 79 | 49 |
| 393280 | 10 | 1796 | 1815 | GAGGGATCCATACCAAAGGC | 93 | 50 |
| 393281 | 10 | 1850 | 1869 | GAGGCATTGTCTTTCAGCAT | 77 | 51 |
| 393282 | 10 | 1870 | 1889 | GGTCTGCCAAATCCTTGTCG | 86 | 52 |
| 393283 | 10 | 1910 | 1929 | TGTCTTCCGATTAGCTTCAT | 61 | 53 |
| 393284 | 10 | 1939 | 1958 | AGACACCCAGCAGGTTGATG | 56 | 54 |
| 393285 | 10 | 1945 | 1964 | GAGTGCAGACACCCAGCAGG | 76 | 55 |
| 393286 | 10 | 1956 | 1975 | GGGCCCTTCCTGAGTGCAGA | 72 | 56 |
| 393287 | 10 | 2048 | 2067 | CCATCAGGGCTGAGATCAGG | 70 | 57 |
| 322160 | 10 | 2131 | 2150 | CCAGATACTGCATGCCTCGG | 88 | 58 |
| 393288 | 10 | 2150 | 2169 | TGGATGCACTTCCGAGACTC | 61 | 59 |
| 393289 | 10 | 2380 | 2399 | CCCCGAGGGTGAAGATTTCC | 73 | 60 |
| 393290 | 10 | 2440 | 2459 | TGTGCCCCTCTCGCAGCAGT | 81 | 61 |
| 393291 | 10 | 2490 | 2509 | CCTCATTAGCCCATACAGCT | 44 | 62 |
| 393292 | 10 | 2555 | 2574 | TTGTCCAGAGCTTCCACCAG | 65 | 63 |
| 299052 | 10 | 2567 | 2586 | GCCAGCAGGACCTTGTCCAG | 85 | 64 |
| 393293 | 10 | 2580 | 2599 | CTCTTCAGAGACAGCCAGCA | 54 | 65 |
| 393294 | 10 | 2600 | 2619 | GTCAGGCGGAGGTCAAGGTA | 75 | 66 |
| 393295 | 10 | 2616 | 2635 | AGAAAAGGGTCCAAAGGTCA | 75 | 67 |
| 393296 | 10 | 2628 | 2647 | CCCATTGGAGGGAGAAAAGG | 65 | 68 |
| 393297 | 10 | 2635 | 2654 | TGGCATCCCCATTGGAGGGA | 83 | 69 |
| 393298 | 10 | 2641 | 2660 | TGCTGCTGGCATCCCCATTG | 87 | 70 |

TABLE 5-continued

Inhibition of Gene Target mRNA Levels by Chimeric Oligonucleotides with 2'-MOE Wings and Deoxy Gap (mus musculus)

| ISIS # | Target SEQ ID NO | 5' Target Site | 3' Target Site | Sequence (5' to 3') | % Inhibition | SEQ ID NO |
|---|---|---|---|---|---|---|
| 393299 | 10 | 2880 | 2899 | CAGGGCCAGAGAGAGGATCT | 90 | 71 |
| 393300 | 10 | 2935 | 2954 | TGGAACAGAAGGCCTCAACT | 80 | 72 |
| 393301 | 10 | 2994 | 3013 | CCAAGGGCAAGGCCATGATC | 76 | 73 |
| 393302 | 10 | 3000 | 3019 | ATGAGTCCAAGGGCAAGGCC | 80 | 74 |
| 393303 | 10 | 3005 | 3024 | TGAGGATGAGTCCAAGGGCA | 83 | 75 |
| 393304 | 10 | 3085 | 3104 | TAGAGCATAAGTTTTGCAGC | 79 | 76 |
| 393305 | 10 | 3090 | 3109 | ATGTTTAGAGCATAAGTTTT | 51 | 77 |
| 393306 | 10 | 3095 | 3114 | TAGAAATGTTTAGAGCATAA | 72 | 78 |
| 393307 | 10 | 3120 | 3139 | AGGCCTCTAGGTTGTTTGGG | 79 | 79 |
| 393308 | 10 | 3277 | 3296 | TTTATAAAAATGCCATGTTC | 61 | 80 |
| 393310 | 14 | 3566 | 3585 | TTCCATGCCCAGTTTGGGAC | 74 | 81 |
| 393311 | 14 | 4800 | 4819 | GGAGTCATTGATACCCATAG | 80 | 82 |
| 393312 | 14 | 6049 | 6068 | GTCAGAGTGGAGGCAGGTTA | 77 | 83 |
| 393313 | 14 | 7448 | 7467 | TTGATTCCCAGCAAATACAT | 49 | 84 |
| 393314 | 14 | 7805 | 7824 | ACCCAGCACATCCAGGAGAT | 68 | 85 |
| 393315 | 14 | 8295 | 8314 | CCCCACAAATGTTGCACCCA | 73 | 86 |
| 393316 | 14 | 10349 | 10368 | GCCCAGGTTGCCATGTGTAC | 84 | 87 |
| 393317 | 14 | 12504 | 12523 | GGTTTTGTTATGCATTAGAG | 80 | 88 |
| 393318 | 14 | 14115 | 14134 | GATCAGGAAGCATAGAAGGA | 66 | 89 |
| 393319 | 14 | 15655 | 15674 | GACAGTGGTGTGAGTAGTAT | 50 | 90 |
| 393320 | 14 | 16387 | 16406 | GAACAGGTCAAAGAGGTTTG | 54 | 91 |

Antisense oligonucleotides with the following Isis Nos. exhibited at least 75% inhibition of FGFR4 mRNA levels: 299029, 299036, 299052, 322160, 393247, 393248, 393249, 393250, 393253, 393256, 393257, 393258, 393259, 393260, 393262, 393263, 393265, 393266, 393269, 393274, 393275, 393279, 393280, 393281, 393282, 393285, 393290, 393294, 393295, 393297, 393298, 393299, 393300, 393301, 393302, 393303, 393304, 393307, 393311, 393312, 393316, and 393317. The target segments to which these antisense oligonucleotides are targeted are active target segments. The target regions to which these antisense oligonucleotides are targeted are active target regions.

Antisense oligonucleotides with the following Isis Nos. exhibited at least 80% inhibition of FGFR4 mRNA levels: 299029, 299036, 299052, 322160, 393247, 393248, 393249, 393250, 393253, 393256, 393257, 393259, 393262, 393263, 393266, 393269, 393274, 393280, 393282, 393290, 393297, 393298, 393299, 393300, 393302, 393303, 393311, 393316, and 393317. The target segments to which these antisense oligonucleotides are targeted are active target segments. The target regions to which these antisense oligonucleotides are targeted are active target regions.

Antisense oligonucleotides with the following Isis Nos. exhibited at least 85% inhibition of FGFR4 mRNA levels: 299029, 299036, 299052, 322160, 393247, 393248, 393250, 393253, 393256, 393257, 393259, 393262, 393263, 393269, 393274, 393280, 393282, 393298, and 393299. The target segments to which these antisense oligonucleotides are targeted are active target segments. The target regions to which these antisense oligonucleotides are targeted are active target regions.

Antisense oligonucleotides with the following Isis Nos. exhibited at least 90% inhibition of FGFR4 mRNA levels: 299036, 299029, 393247, 393250, 393256, 393262, 393280, and 393299. The target segments to which these antisense oligonucleotides are targeted are active target segments. The target regions to which these antisense oligonucleotides are targeted are active target regions Antisense oligonucleotides with the following Isis Nos. exhibited at least 95% inhibition of FGFR4 mRNA levels: 299029, 393250, and 393262. The target segments to which these antisense oligonucleotides are targeted are active target segments. The target regions to which these antisense oligonucleotides are targeted are active target regions.

Example 2

Antisense Inhibition of Human FGFR4: A459 Cells

Antisense oligonucleotides targeted to a FGFR4 nucleic acid were tested for their effects on FGFR4 mRNA expression in vitro. Cultured A459 Cells in a 96-well plate were treated with 160 nM of antisense oligonucleotide. Transfection was carried out using Cytofectin™ (Genlantis, San Diego, Calif.). After a treatment period of approximately 24 hours, RNA was isolated from the cells and FGFR4 mRNA levels were measured by quantitative real-time PCR, as described herein using the primer/probe set shown in Table 6. Probes and primers to human FGFR4 were designed to hybridize to a human FGFR4 sequence, using published sequence information (GenBank® accession number NM_002011.3, incorporated herein as SEQ ID NO: 5).

TABLE 6

Gene Target-specific human Primers and Probes for Use in Real-Time PCR

| Target Name | Species | Target Seq ID No | Sequence Description | Sequence (5' to 3') | Length | SEQ ID NO |
|---|---|---|---|---|---|---|
| FGFR4 | Human | 5 | Forward Primer | GTTCTGCTCGGCTTCTTGG | 19 | 170 |
| FGFR4 | Human | 5 | Reverse Primer | AGGCTTCCAGCTTCTCTGG | 19 | 171 |
| FGFR4 | Human | 5 | Probe | GGCTGAGCCTGGCTGGAGAGCTGCTATGCTAAACCTCCTGCCTCCCAATA | 50 | 172 |

The FGFR4 mRNA levels were adjusted according to total RNA content as measured by RIBOGREEN®. Results are presented as percent inhibition of FGFR4, relative to untreated control cells. Antisense oligonucleotides that exhibited inhibition of human FGFR4 expression are shown in Table 7.

The oligonucleotides of Table 7, have a 5-10-5 2'-MOE gapmer motif. The heading "5' target site" indicates the 5'-most nucleotide corresponding to the first base to which the antisense oligonucleotide is targeted on the indicated GENBANK® Accession No.

All antisense compounds in Table 7 are gapmers having 20 linked nucleobases and composed of a central "gap" segment consisting of 2'-deoxynucleotides, which are flanked on both sides (5' and 3' directions) by wing segments having 2'-modifications. The wings are composed of 2'-methoxyethyl (2'-MOE) nucleotides. The internucleoside (backbone) linkages are phosphorothioate (P=S) throughout the oligonucleotide. All cytosine nucleobases are 5-methylcytosines.

TABLE 7

Inhibition of Gene Target mRNA Levels by Chimeric Oligonucleotides with 2'-MOE Wings and Deoxy Gap (human)

| ISIS # | Target SEQ ID NO | 5' Target Site | 3' Target Site | Sequence (5' to 3') | % Inhibition | SEQ ID NO |
|---|---|---|---|---|---|---|
| 299069 | 2 | 455 | 474 | CAGCGGGACACAAGTCCTTG | 52 | 92 |
| 299067 | 3 | 46 | 65 | AACTGCCTTCCTCGAGCCTG | 59 | 93 |
| 299065 | 4 | 306 | 325 | GTCAAGGAGTCAAGCTCCAC | 2 | 94 |
| 299066 | 4 | 891 | 910 | GGTAGAGGGATGTCAACCAG | 5 | 95 |
| 299003 | 5 | 26 | 45 | GGCAGGGTCCGCAGACAGCC | 60 | 96 |
| 299004 | 5 | 160 | 179 | CAGCAGCCGCATCTCCTTCT | 86 | 97 |
| 299005 | 5 | 192 | 211 | GGCACACTCAGCAGGACCCC | 80 | 98 |
| 299006 | 5 | 208 | 227 | CAAGACTGGAGGCCCAGGCA | 82 | 99 |
| 299007 | 5 | 254 | 273 | GAGCCAGGCAGGGCTCAAGC | 47 | 100 |

TABLE 7-continued

Inhibition of Gene Target mRNA Levels by Chimeric Oligonucleotides with 2'-MOE Wings and Deoxy Gap (human)

| ISIS # | Target SEQ ID NO | 5' Target Site | 3' Target Site | Sequence (5' to 3') | % Inhibition | SEQ ID NO |
|---|---|---|---|---|---|---|
| 299008 | 5 | 278 | 297 | CCTGCTCTTGCTGCTCCAGG | 76 | 101 |
| 299009 | 5 | 289 | 308 | TACTGTCAGCTCCTGCTCTT | 75 | 102 |
| 299010 | 5 | 304 | 323 | AGGCTGCCCAAGGGCTACTG | 73 | 103 |
| 299012 | 5 | 354 | 373 | TCCTTGTACCAGTGGCCACC | 83 | 104 |
| 299013 | 5 | 380 | 399 | GGCCAGCAGGTGCCAGGCGA | 64 | 105 |
| 299014 | 5 | 412 | 431 | AATCTCTAGGCGGCCCCTCC | 79 | 106 |
| 299015 | 5 | 475 | 494 | GACGATCATGGAGCCTCGTG | 80 | 107 |
| 299016 | 5 | 483 | 502 | TTCTGCAGGACGATCATGGA | 63 | 108 |
| 299017 | 5 | 529 | 548 | ATCATCGTTGCTGGAGGTCA | 84 | 109 |
| 299018 | 5 | 597 | 616 | GTCCAGTAGGGTGCTTGCTG | 69 | 110 |
| 299019 | 5 | 602 | 621 | GGTGTGTCCAGTAGGGTGCT | 67 | 111 |
| 299020 | 5 | 627 | 646 | TGCAGTTTCTTCTCCATGCG | 69 | 112 |
| 299021 | 5 | 711 | 730 | CCATCCTTAAGCCAGCGGAT | 37 | 113 |
| 299022 | 5 | 727 | 746 | CCCATGAAAGGCCTGTCCAT | 82 | 114 |
| 299023 | 5 | 739 | 758 | AATGCGGTTCTCCCCATGAA | 55 | 115 |
| 299024 | 5 | 757 | 776 | GCGCAGCCGAATGCCTCCAA | 81 | 116 |
| 299025 | 5 | 785 | 804 | TCTCCATCACGAGACTCCAG | 76 | 117 |
| 299026 | 5 | 833 | 852 | CGTTCTCTACCAGGCAGGTG | 79 | 118 |
| 299027 | 5 | 964 | 983 | CTTGCACAGCAGCTCCACGT | 84 | 119 |
| 299028 | 5 | 969 | 988 | TACACCTTGCACAGCAGCTC | 79 | 120 |
| 299029 | 5 | 1027 | 1046 | GCTGCTGCCGTTGATGACGA | 69 | 36 |
| 299030 | 5 | 1032 | 1051 | CCGAAGCTGCTGCCGTTGAT | 81 | 121 |
| 299031 | 5 | 1076 | 1095 | TGTCTGCAGTCTTTAGGACT | 65 | 122 |
| 299032 | 5 | 1090 | 1109 | CTCTGAGCTATTGATGTCTG | 69 | 123 |
| 299033 | 5 | 1095 | 1114 | TCCACCTCTGAGCTATTGAT | 65 | 124 |
| 299034 | 5 | 1121 | 1140 | CTGACACGTTCCGCAGGTAC | 71 | 125 |
| 299035 | 5 | 1181 | 1200 | ACTGGTAGGAGAGGCCGATG | 57 | 126 |
| 299036 | 5 | 1207 | 1226 | CTCTGGCAGCACCGTGAGCC | 81 | 39 |
| 299037 | 5 | 1235 | 1254 | GCGCTGCTGCGGTCCATGTG | 61 | 127 |
| 299038 | 5 | 1326 | 1345 | TGCCCTCGATACAGCCCGGC | 86 | 128 |
| 299039 | 5 | 1428 | 1447 | TTGCCGGAAGAGCCTGACTC | 72 | 129 |
| 299040 | 5 | 1447 | 1466 | TACCAGGGATGAGCTTGACT | 84 | 130 |
| 299041 | 5 | 1452 | 1471 | CCTCGTACCAGGGATGAGCT | 85 | 131 |
| 299042 | 5 | 1555 | 1574 | AAGCACCAGCCTGTCCCGGG | 76 | 132 |
| 299043 | 5 | 1607 | 1626 | AGGCCTCTGCACGTACTACC | 89 | 133 |
| 299044 | 5 | 1656 | 1675 | TTGACGGCCACAGTGCTGGC | 78 | 134 |
| 299045 | 5 | 1741 | 1760 | CTTGTGTCGGCCGATCAGCT | 53 | 135 |

TABLE 7-continued

Inhibition of Gene Target mRNA Levels by Chimeric Oligonucleotides with 2'-MOE Wings and Deoxy Gap (human)

| ISIS # | Target SEQ ID NO | 5' Target Site | 3' Target Site | Sequence (5' to 3') | % Inhibition | SEQ ID NO |
|---|---|---|---|---|---|---|
| 299046 | 5 | 1772 | 1791 | GGGTGCAGACACCAAGCAGG | 86 | 136 |
| 299047 | 5 | 1919 | 1938 | AGACCAGGACTGGGAAGGAG | 86 | 137 |
| 299048 | 5 | 1968 | 1987 | TTCCGGGACTCCAGATACTG | 61 | 138 |
| 299049 | 5 | 1979 | 1998 | GGTGGATACACTTCCGGGAC | 48 | 139 |
| 299050 | 5 | 2268 | 2287 | CGATGTCCCTCCCGCAGCAG | 66 | 140 |
| 299051 | 5 | 2313 | 2332 | ATCAGCCCGTACAGCTCTGG | 77 | 141 |
| 299052 | 5 | 2394 | 2413 | GCCAGCAGGACCTTGTCCAG | 74 | 64 |
| 299053 | 5 | 2416 | 2435 | GTCGAGGTACTCCTCAGAGA | 62 | 142 |
| 299054 | 5 | 2481 | 2500 | CTGGAGGAGCAGGTGCTGCT | 5 | 143 |
| 299055 | 5 | 2497 | 2516 | GCTGAAGACAGAATCGCTGG | 86 | 144 |
| 299056 | 5 | 2503 | 2522 | GTCGTGGCTGAAGACAGAAT | 71 | 145 |
| 299057 | 5 | 2557 | 2576 | TCATGTCTGCACCCCAGACC | 83 | 146 |
| 299058 | 5 | 2565 | 2584 | AGCCTTGCTCATGTCTGCAC | 81 | 147 |
| 299059 | 5 | 2629 | 2648 | TGTGTCAGGCTGTGGCTGAG | 64 | 148 |
| 299060 | 5 | 2698 | 2717 | AAGGGCACGGCCCTTGGACA | 57 | 149 |
| 299061 | 5 | 2738 | 2757 | ATTTGGGCCATCAGGACACA | 81 | 150 |
| 299062 | 5 | 2752 | 2771 | AGCAGAACCCTGACATTTGG | 88 | 151 |
| 299063 | 5 | 2851 | 2870 | CCTGCTGGTATTGGGAGGCA | 78 | 152 |
| 299011 | 6 | 308 | 327 | ACAGCACAGCCGCACAGGCT | 66 | 153 |
| 298992 | 6 | 1204 | 1223 | CGCCCAGTACCTGGCAGCAC | 11 | 154 |
| 299064 | 8 | 423 | 442 | GGAGCGAGGAATGTACCCGC | 52 | 155 |
| 299003 | 8 | 460 | 479 | GGCAGGGTCCGCAGACAGCC | 60 | 96 |
| 298994 | 8 | 583 | 602 | TCCGGCTCACCTCGAGCCTG | 17 | 156 |
| 298995 | 8 | 1913 | 1932 | GGAAACATCCTCTCCCTCGG | 55 | 157 |
| 299004 | 8 | 3110 | 3129 | CAGCAGCCGCATCTCCTTCT | 86 | 97 |
| 299005 | 8 | 3142 | 3161 | GGCACACTCAGCAGGACCCC | 80 | 98 |
| 299006 | 8 | 3158 | 3177 | CAAGACTGGAGGCCCAGGCA | 82 | 99 |
| 298996 | 8 | 3199 | 3218 | GAAGCCATACCAAGCTCCAC | 47 | 158 |
| 299008 | 8 | 3924 | 3943 | CCTGCTCTTGCTGCTCCAGG | 76 | 101 |
| 299009 | 8 | 3935 | 3954 | TACTGTCAGCTCCTGCTCTT | 75 | 102 |
| 299010 | 8 | 3950 | 3969 | AGGCTGCCCAAGGGCTACTG | 73 | 103 |
| 299012 | 8 | 4000 | 4019 | TCCTTGTACCAGTGGCCACC | 83 | 104 |
| 299013 | 8 | 4026 | 4045 | GGCCAGCAGGTGCCAGGCGA | 64 | 105 |
| 299014 | 8 | 4058 | 4077 | AATCTCTAGGCGGCCCCTCC | 79 | 106 |
| 299015 | 8 | 4121 | 4140 | GACGATCATGGAGCCTCGTG | 80 | 107 |
| 299016 | 8 | 4129 | 4148 | TTCTGCAGGACGATCATGGA | 63 | 108 |

TABLE 7-continued

Inhibition of Gene Target mRNA Levels by Chimeric Oligonucleotides with 2'-MOE Wings and Deoxy Gap (human)

| ISIS # | Target SEQ ID NO | 5' Target Site | 3' Target Site | Sequence (5' to 3') | % Inhibition | SEQ ID NO |
|---|---|---|---|---|---|---|
| 299068 | 8 | 4174 | 4193 | TTCACTCCCTGCTAGAGTCT | 80 | 159 |
| 298997 | 8 | 4250 | 4269 | GTCAAGGAGTCTACATCAGG | 67 | 160 |
| 299017 | 8 | 4266 | 4285 | ATCATCGTTGCTGGAGGTCA | 84 | 109 |
| 299019 | 8 | 4451 | 4470 | GGTGTGTCCAGTAGGGTGCT | 67 | 111 |
| 299020 | 8 | 4476 | 4495 | TGCAGTTTCTTCTCCATGCG | 69 | 112 |
| 299021 | 8 | 4560 | 4579 | CCATCCTTAAGCCAGCGGAT | 37 | 113 |
| 299022 | 8 | 4576 | 4595 | CCCATGAAAGGCCTGTCCAT | 82 | 114 |
| 299023 | 8 | 4588 | 4607 | AATGCGGTTCTCCCCATGAA | 55 | 115 |
| 299025 | 8 | 5214 | 5233 | TCTCCATCACGAGACTCCAG | 76 | 117 |
| 299026 | 8 | 5262 | 5281 | CGTTCTCTACCAGGCAGGTG | 79 | 118 |
| 299027 | 8 | 5905 | 5924 | CTTGCACAGCAGCTCCACGT | 84 | 119 |
| 299028 | 8 | 5910 | 5929 | TACACCTTGCACAGCAGCTC | 79 | 120 |
| 299029 | 8 | 5968 | 5987 | GCTGCTGCCGTTGATGACGA | 69 | 36 |
| 299030 | 8 | 5973 | 5992 | CCGAAGCTGCTGCCGTTGAT | 81 | 121 |
| 299032 | 8 | 6165 | 6184 | CTCTGAGCTATTGATGTCTG | 69 | 123 |
| 299033 | 8 | 6170 | 6189 | TCCACCTCTGAGCTATTGAT | 65 | 124 |
| 299034 | 8 | 6196 | 6215 | CTGACACGTTCCGCAGGTAC | 71 | 125 |
| 299035 | 8 | 6256 | 6275 | ACTGGTAGGAGAGGCCGATG | 57 | 126 |
| 299037 | 8 | 6663 | 6682 | GCGCTGCTGCGGTCCATGTG | 61 | 127 |
| 299038 | 8 | 6754 | 6773 | TGCCCTCGATACAGCCCGGC | 86 | 128 |
| 298993 | 8 | 6868 | 6887 | AGTCAGGCTGTCACATGTGA | 48 | 161 |
| 299039 | 8 | 6930 | 6949 | TTGCCGGAAGAGCCTGACTC | 72 | 129 |
| 299040 | 8 | 6949 | 6968 | TACCAGGGATGAGCTTGACT | 84 | 130 |
| 299041 | 8 | 6954 | 6973 | CCTCGTACCAGGGATGAGCT | 85 | 131 |
| 299043 | 8 | 7211 | 7230 | AGGCCTCTGCACGTACTACC | 89 | 133 |
| 299044 | 8 | 7260 | 7279 | TTGACGGCCACAGTGCTGGC | 78 | 134 |
| 298998 | 8 | 7654 | 7673 | GTGAGCCCTTCTATTAGTC | 34 | 162 |
| 298999 | 8 | 8267 | 8286 | AATGTGCATTTCTCAATCCC | 70 | 163 |
| 299045 | 8 | 8899 | 8918 | CTTGTGTCGGCCGATCAGCT | 53 | 135 |
| 299046 | 8 | 8930 | 8949 | GGGTGCAGACACCAAGCAGG | 86 | 136 |
| 299000 | 8 | 8971 | 8990 | AACGGCCCGTGCAGCCAGCC | 71 | 164 |
| 299047 | 8 | 9169 | 9188 | AGACCAGGACTGGGAAGGAG | 86 | 137 |
| 299048 | 8 | 9218 | 9237 | TTCCGGGACTCCAGATACTG | 61 | 138 |
| 299001 | 8 | 9863 | 9882 | CAGGACTCACACGTCACTCT | 0 | 165 |
| 299050 | 8 | 10204 | 10223 | CGATGTCCCTCCCGCAGCAG | 66 | 140 |
| 299002 | 8 | 10797 | 10816 | CAGCCCGTACCTGCGAGAGG | 55 | 166 |
| 299052 | 8 | 10880 | 10899 | GCCAGCAGGACCTTGTCCAG | 74 | 64 |

TABLE 7-continued

Inhibition of Gene Target mRNA Levels by Chimeric Oligonucleotides with 2'-MOE Wings and Deoxy Gap (human)

| ISIS # | Target SEQ ID NO | 5' Target Site | 3' Target Site | Sequence (5' to 3') | % Inhibition | SEQ ID NO |
|---|---|---|---|---|---|---|
| 299054 | 8 | 11096 | 11115 | CTGGAGGAGCAGGTGCTGCT | 5 | 143 |
| 299055 | 8 | 11112 | 11131 | GCTGAAGACAGAATCGCTGG | 86 | 144 |
| 299056 | 8 | 11118 | 11137 | GTCGTGGCTGAAGACAGAAT | 71 | 145 |
| 299057 | 8 | 11172 | 11191 | TCATGTCTGCACCCCAGACC | 83 | 146 |
| 299058 | 8 | 11180 | 11199 | AGCCTTGCTCATGTCTGCAC | 81 | 147 |
| 299059 | 8 | 11244 | 11263 | TGTGTCAGGCTGTGGCTGAG | 64 | 148 |
| 299060 | 8 | 11313 | 11332 | AAGGGCACGGCCCTTGGACA | 57 | 149 |
| 299061 | 8 | 11353 | 11372 | ATTTGGGCCATCAGGACACA | 81 | 150 |
| 299062 | 8 | 11367 | 11386 | AGCAGAACCCTGACATTTGG | 88 | 151 |
| 299063 | 8 | 11466 | 11485 | CCTGCTGGTATTGGGAGGCA | 78 | 152 |

Antisense oligonucleotides with the following Isis Nos. exhibited at least 75% inhibition of FGFR4 mRNA levels: 299004, 299005, 299006, 299008, 299009, 299012, 299014, 299015, 299017, 299022, 299024, 299025, 299026, 299027, 299028, 299030, 299036, 299038, 299040, 299041, 299042, 299043, 299044, 299046, 299047, 299051, 299055, 299057, 299058, 299061, 299062, 299063, and 299068. The target segments to which these antisense oligonucleotides are targeted are active target segments. The target regions to which these antisense oligonucleotides are targeted are active target regions.

Antisense oligonucleotides with the following Isis Nos. exhibited at least 80% inhibition of FGFR4 mRNA levels: 299004, 299005, 299006, 299012, 299015, 299017, 299022, 299024, 299027, 299030, 299036, 299038, 299040, 299041, 299043, 299046, 299047, 299055, 299057, 299058, 299061, 299062, and 299068. The target segments to which these antisense oligonucleotides are targeted are active target segments. The target regions to which these antisense oligonucleotides are targeted are active target regions.

Antisense oligonucleotides with the following Isis Nos. exhibited at least 85% inhibition of FGFR4 mRNA levels: 299004, 299038, 299041, 299043, 299046, 299047, 299055, and 299062. The target segments to which these antisense oligonucleotides are targeted are active target segments. The target regions to which these antisense oligonucleotides are targeted are active target regions.

Example 3

Mus Musculus FGFR4 Cross-Species Reactivity

The antisense compounds in Table 5 were designed to target different regions of the mouse FGFR4 RNA but have complementarity across species. Specifically, certain of the antisense compounds in table 5 are cross-reactive with rat mRNA. These include ISIS No's 299052, 322160, 393247, 393248, 393249, 393250, 393253, 393254, 393255, 393256, 393257, 393266, 393268, 393269, 393273, 393274, 393275, 393276, 393277, 393278, 393279, 393281, 393282, 393283, 393285, 393286, 393287, 393288, 393289, 393290, 393291, 393292, 393293, 393294, 393298, 393299, 393300, 393303, and 393307. Certain of the antisense compounds in Table 5 are cross-reactive with human FGFR4 sequences. Mouse FGFR4 antisense compounds that are cross reactive with human FGFR4 sequences are listed in Table 8.

TABLE 8

Mus Musculus Cross-species reactivity

| Isis # | Target SEQ ID NO | 5' Target Site | Mismatches | Sequence (5' to 3') | SEQ ID NO |
|---|---|---|---|---|---|
| 393253 | 5 | 229 | 1 | TTCCTCAGAGGCCTCAAGGG | 21 |
| 393254 | 5 | 427 | 2 | AGGAAGGAAGCTGGCGATCT | 22 |
| 393255 | 5 | 437 | 1 | CAGCATCCTCAGGAAGGAAG | 23 |
| 393256 | 5 | 462 | 2 | CCACGGGCCAGGCAGAGGTA | 24 |
| 393260 | 5 | 521 | 2 | TGATGGAGGTTAAGGAGTCA | 28 |
| 393261 | 5 | 600 | 0 | TGTGTCCAGTAGGGTGCTTG | 29 |
| 393269 | 5 | 1191 | 2 | AGCCACGCTGACTGGTAGGA | 38 |

TABLE 8-continued

Mus Musculus Cross-species reactivity

| Isis # | Target SEQ ID NO | 5' Target Site | Mismatches | Sequence (5' to 3') | SEQ ID NO |
|---|---|---|---|---|---|
| 393273 | 5 | 1317 | 1 | TACACCCCGGCCAGCAGCAG | 43 |
| 393278 | 5 | 1583 | 2 | CAAAGCAGCCCTCACCCAGG | 48 |
| 393281 | 5 | 1677 | 2 | GAGGCATTGTCTTTCAGCAT | 51 |
| 393284 | 5 | 1766 | 1 | AGACACCCAGCAGGTTGATG | 54 |
| 393285 | 5 | 1772 | 2 | GAGTGCAGACACCCAGCAGG | 55 |
| 393286 | 5 | 1783 | 1 | GGGCCCTTCCTGAGTGCAGA | 56 |
| 322160 | 5 | 1958 | 0 | CCAGATACTGCATGCCTCGG | 58 |
| 393288 | 5 | 1977 | 2 | TGGATGCACTTCCGAGACTC | 59 |
| 393289 | 5 | 2207 | 1 | CCCCGAGGGTGAAGATTTCC | 60 |
| 393292 | 5 | 2382 | 2 | TTGTCCAGAGCTTCCACCAG | 63 |
| 393293 | 5 | 2407 | 2 | CTCTTCAGAGACAGCCAGCA | 65 |
| 393294 | 5 | 2427 | 1 | GTCAGGCGGAGGTCAAGGTA | 66 |
| 393253 | 8 | 3179 | 1 | TTCCTCAGAGGCCTCAAGGG | 21 |
| 393254 | 8 | 4073 | 2 | AGGAAGGAAGCTGGCGATCT | 22 |
| 393255 | 8 | 4083 | 1 | CAGCATCCTCAGGAAGGAAG | 23 |
| 393256 | 8 | 4108 | 2 | CCACGGGCCAGGCAGAGGTA | 24 |
| 393261 | 8 | 4449 | 1 | TGTGTCCAGTAGGGTGCTTG | 29 |
| 393269 | 8 | 6266 | 2 | AGCCACGCTGACTGGTAGGA | 38 |
| 393273 | 8 | 6745 | 1 | TACACCCCGGCCAGCAGCAG | 43 |
| 393278 | 8 | 7187 | 2 | CAAAGCAGCCCTCACCCAGG | 48 |
| 393284 | 8 | 8924 | 1 | AGACACCCAGCAGGTTGATG | 54 |
| 393285 | 8 | 8930 | 2 | GAGTGCAGACACCCAGCAGG | 55 |
| 322160 | 8 | 9208 | 0 | CCAGATACTGCATGCCTCGG | 58 |
| 393289 | 8 | 10143 | 1 | CCCCGAGGGTGAAGATTTCC | 60 |
| 393292 | 8 | 10868 | 2 | TTGTCCAGAGCTTCCACCAG | 63 |
| 393293 | 8 | 10893 | 2 | CTCTTCAGAGACAGCCAGCA | 65 |
| 393294 | 8 | 11042 | 1 | GTCAGGCGGAGGTCAAGGTA | 66 |

In Vivo Pharmacology

Prevention Study

Example 4

Antisense Inhibition of FGFR4 Levels In Vivo Studies in a Diet-Induced Model of Obesity (Prevention Study)

The C57BL/6 mouse strain is reported to be susceptible to weight gain when fed a high-fat diet. Accordingly, these mice (8 weeks old) were fed a high-fat diet for 14 days prior to administration of FGFR4 antisense oligonucleotides. They were then used in the following studies to evaluate the effects of FGFR4 antisense oligonucleotides on mRNA expression in liver and fat tissues in a diet-induced model of obesity.

Male C57BL/6 mice at 8 weeks of age were placed on a high-fat diet containing 58% calories from fat (Research Diet D12492, Research Diets Inc., New Brunswick, N.J.) 14 days prior to the initial dosing administration. The mice were divided into three treatment groups. One group received subcutaneous injections of ISIS 393250 (SEQ ID NO: 18) at a dose of 25 mg/kg twice per week for 12 weeks. The second group received subcutaneous injections of ISIS 141923, CCTTCCCTGAAGGTTCCTCC (SEQ ID NO: 173), at a dose of 25 mg/kg twice per week for 12 weeks. Oligonucleotides were dissolved in 0.9% saline for injection. A group of mice fed normal chow also received subcutaneous injections of saline twice weekly for 12 weeks. The saline-injected group fed the high-fat diet served as the control group to which the oligonucleotide-treated groups were compared.

After the 12 week treatment period, the mice were sacrificed and FGFR4 mRNA levels were evaluated in liver, brown adipose tissue (BAT) and white adipose tissue (WAT). mRNA levels were quantitated by real-time PCR as described in other examples herein. The results are presented in Table 9 and are expressed as percent inhibition relative to saline-treated mice receiving a high fat diet.

TABLE 9

Antisense inhibition of FGFR4 mRNA expression in liver and fat tissues (Prevention study)
% Inhibition of FGFR4 mRNAs

| ISIS # | Liver | Brown Fat tissue | White Fat tissue |
|---|---|---|---|
| Saline- 58% HF | 0 | 0 | 0 |
| FGFR4 393250 | −68.9 | −56.65 | −69.57 |

FGFR4 antisense oligonucleotide treatment, but not control antisense oligonucleotide treatment, reduced FGFR4 mRNA levels by ~69%, 57% and 70% in liver, brown adipose tissue and white adipose tissue, respectively. The data demonstrate that FGFR4 antisense oligonucleotide treatment can effectively reduce target mRNA levels in liver, brown adipose tissue and white adipose tissue.

Example 5

Effects of Antisense Inhibition of FGFR4 with ISIS 393250 on Body Weight (Prevention Study)

Male C57BL/6J mice (age 10 weeks at time 0) were fed 58% high-fat diet for 14 days and were then divided into matched groups (n=6) based on body weight and body composition, and treated by subcutaneous injections twice a week with saline, ISIS 141923 (SEQ ID NO: 173, a control oligonucleotide) or ISIS 393250 (SEQ ID NO: 18, FGFR4 antisense oligonucleotide). The mice were treated at a dose of 25 mg/kg twice a week of ISIS 141923 or ISIS 393250, or saline, twice a week. A group of mice fed normal chow also received subcutaneous injections of saline twice weekly as normal controls. Treatment was continued for 12 weeks. At the end of the study, mice were sacrificed and tissues where collected and weighed. The results are presented in Table 10.

TABLE 10

Antisense inhibition of FGFR4 on total body weight in Diet-induced Obese mice
(Prevention study)
Body Weight (g)

| | Mean | | | | | | | | | | | | |
|---|---|---|---|---|---|---|---|---|---|---|---|---|---|
| Weeks: | 0 | 1 | 2 | 3 | 4 | 5 | 6 | 7 | 8 | 9 | 10 | 11 | 12 |
| Saline | 26.1 | 27.8 | 29.0 | 30.0 | 31.2 | 32.1 | 32.4 | 33.2 | 34.2 | 35.5 | 35.5 | 36.6 | 36.5 |
| 141923- Control | 26.1 | 27.7 | 29.9 | 30.2 | 31.3 | 32.3 | 32.1 | 32.3 | 33.1 | 33.2 | 32.9 | 33.6 | 34.0 |
| 393250 - FGFR4 | 26.3 | 27.7 | 28.6 | 29.3 | 30.0 | 30.1 | 30.2 | 29.9 | 30.3 | 30.4 | 29.9 | 30.4 | 30.4 |
| Chow-saline | 23.9 | 24.2 | 24.8 | 25.3 | 25.7 | 25.9 | 25.7 | 26.0 | 26.8 | 26.8 | 26.5 | 27.3 | 27.5 |

Treatment of C57BL/6J mice with ISIS 393250 (SEQ ID NO: 18) resulted in a decrease in body weight gain, with animals gaining an average of 4.1 grams while saline treated controls gained 10.4 grams. Animals treated with the control oligonucleotide gained an average of 7.9 grams of body weight.

Saline-chow littermate animals gained 3.6 grams of body weight compared to a gain of 10.4 grams for the saline high-fat fed controls.

There was no appreciable change in food intake among the treatment groups.

Example 6

Effects of Antisense Inhibition of FGFR4 with ISIS 393250 on Body Fat Content (Prevention Study)

Male C57BL/6J mice (age 10 weeks at time 0) were divided into matched groups (n=6) based on body weight and body composition, and treated by subcutaneous injections twice a week with saline, ISIS 141923, (SEQ ID NO: 173, a control oligonucleotide) or ISIS 393250 (SEQ ID NO: 18, FGFR4 antisense oligonucleotide). The mice were treated at a dose of 25 mg/kg twice a week of ISIS 141923 or 25 mg/kg ISIS 393250, or with volume of saline. A group of mice fed normal chow also received subcutaneous injections of saline twice weekly. Treatment was continued for 12 weeks. Body fat content was measured at weeks 0, 6, 9.5 and 11. The results are presented in Table 11 and 12.

TABLE 11

Antisense inhibition of FGFR4 on total body fat content (g) (Prevention study)
Body fat content (g)

| | mean | | | |
|---|---|---|---|---|
| weeks: | 0 | 6 | 9.5 | 11 |
| saline | 4.66 | 8.93 | 11.20 | 11.93 |
| 141923 - Control | 4.55 | 7.69 | 8.15 | 8.21 |
| 393250 - FGFR4 | 4.28 | 5.25 | 4.91 | 4.67 |
| chow-saline | | 3.16 | 3.35 | 3.54 |

The mice on the high fat diet treated with ISIS 393250 (SEQ ID NO: 18) showed no increase in body fat content (maintained body fat at a constant level), starting at 4.28 g at week 0 and ending at 4.67 g at week 11. Saline treated animals on the high fat diet showed a significant increase in body fat content starting at 4.66 g at week 0 and ending at 11.93 g at week 11. The mice on the high fat diet treated with the control antisense oligonucleotide, ISIS 141923, demonstrated a similar increase in body fat content to that in the saline treated mice, starting at 4.55 g at week 0 and ending at 8.21 g at week 11. The lean body mass remained relatively unchanged. The mice on the chow diet showed no significant change in body fat content starting at 3.16 g at week 6 and ending at 3.54 g at week 11.

TABLE 12

Antisense inhibition of FGFR4 on total body fat content (%)
Percentage body fat content (%)

| weeks: | mean 0 | 6 | 9.5 | 11 |
|---|---|---|---|---|
| saline | 17.7 | 27.1 | 31.0 | 32.0 |
| 141923 - Control | 17.3 | 23.6 | 24.0 | 23.8 |
| 393250 - FGFR4 | 16.1 | 17.3 | 16.1 | 15.3 |
| chow-saline | | 12.2 | 12.6 | 12.9 |

Mice on the high fat diet treated with ISIS 393250 showed a decrease in percent body fat content starting at 16.1% at week 0 and ending at 15.3% at week 11. Saline treated animals on the high fat diet showed a significant increase in percent body fat content starting at 17.7% at week 0 and ending at 32.0% at week 11. Mice on the high fat diets treated with the control ASO, ISIS 141923, demonstrated an increase in percent body fat content starting at 17.3% at week 0 and ending at 23.8% at week 11. Mice on the chow diet showed no significant change body fat content starting at 12.2% at week 6 and ending at 12.9% at week 11.

In Vivo Pharmacology

Reversal Study

Example 7

Antisense Inhibition of FGFR4 Levels: In Vivo Studies in a Diet-Induced Model of Obesity (Reversal Study)

The C57BL/6 mouse strain is reported to be susceptible to weight gain when fed a high-fat diet. Accordingly, these mice were fed a high-fat diet for 3 months and then used in the following studies to evaluate the effects of FGFR4 antisense oligonucleotides on mRNA expression in liver and fat tissues in a diet-induced model of obesity.

Male C57BL/6 mice at 4 weeks of age were placed on a high-fat diet containing 58% calories from fat (Research Diet D12492, Research Diets Inc., New Brunswick, N.J.) for 3 months. The mice were divided into three treatment groups. One group received subcutaneous injections of ISIS 393250 (SEQ ID NO: 18) at a dose of 25 mg/kg twice per week for 9.5 weeks. The second group received subcutaneous injections of ISIS 141923 (SEQ ID NO: 173) at a dose of 25 mg/kg twice per week for 9.5 weeks. Oligonucleotides were dissolved in 0.9% saline for injection. The third group of mice received subcutaneous injections of saline twice weekly for 9.5 weeks. The saline-injected group served as the control group to which the oligonucleotide-treated groups were compared.

After the 9.5 week treatment period, the mice were sacrificed and FGFR4 mRNA levels were evaluated in liver, brown adipose tissue (BAT) and white adipose tissue (WAT). mRNA expression levels were quantitated by real-time PCR as described in other examples herein. The results are presented in Table 13 and are expressed as percent inhibition relative to saline-treated mice receiving a high fat diet.

TABLE 13

Antisense inhibition of FGFR4 mRNA expression in liver and fat tissues (Reversal study)
% Inhibition of FGFR4 mRNA

| ISIS # | Liver | Brown Fat tissue | White Fat tissue |
|---|---|---|---|
| Saline- 58% HF | 0 | 0 | 0 |
| FGFR4 393250 | −77.6 | −69.2 | −44.5 |
| Control 141923 | −7.7 | −18.2 | −11.2 |

FGFR4 antisense oligonucleotide treatment, but not control antisense oligonucleotide treatment, reduced FGFR4 mRNA levels by ~80%, 70% and 45% in liver, brown adipose tissue and white adipose tissue, respectively. The data demonstrate that FGFR4 antisense oligonucleotide treatment can effectively inhibit target mRNA expression in liver, brown adipose tissue and white adipose tissue.

Example 8

Effects of Antisense Inhibition of FGFR4 with ISIS 393250 on Body Weight (Reversal Study)

Male C57BL/6J mice, 4 weeks of age, were placed on a high-fat diet containing 58% calories from fat (Research Diet D12492, Research Diets Inc., New Brunswick, N.J.) for 3 months. The mice were divided into three groups (n=6) with the same starting average blood glucose levels, body weight, and body composition and treated by subcutaneous injection twice a week with saline, ISIS 141923 (the control oligonucleotide) or ISIS 393250. The mice were treated at a dose of 25 mg/kg of ISIS 141923 or ISIS 393250, or similar volume of saline. Treatment was continued for 9.5 weeks. At day 84 mice were sacrificed and the tissues were collected and weighed. The results are presented in Table 14.

TABLE 14

Effect of Antisense inhibition of FGFR4 gene expression on total body weight in Diet-induced Obese mice (Reversal study)
Body weight (g)

| | mean | | | | | | | | | |
|---|---|---|---|---|---|---|---|---|---|---|
| Weeks: | 0 | 1 | 2 | 3 | 4 | 5 | 6 | 7 | 8 | 9 |
| saline | 39.7 | 40.7 | 41.1 | 40.9 | 39.7 | 39.9 | 40.4 | 40.2 | 40.4 | 40.1 |
| 141923-control | 41.3 | 43.2 | 43.8 | 43.4 | 41.7 | 41.7 | 41.2 | 40.4 | 39.9 | 38.8 |
| 393250-FGFR4 | 40.8 | 42.6 | 42.9 | 42.5 | 40.7 | 40.1 | 39.3 | 37.4 | 36.6 | 35.2 |

Treatment of C57BL/6J mice with ISIS 393250 resulted in a decrease in body weight, with animals losing an average of 5.6 grams while saline treated controls remained relatively unchanged (gained 0.4 grams). Animals treated with the control oligonucleotide lost an average of 2.5 grams of body weight.

Therefore, FGFR4 antisense oligonucleotide treatment lowered body weight by ~10% (35.2±0.7 vs. 40.1±1.8 g in saline group; P<0.05), but it did not change lean body mass.

Example 9

Effects of Antisense Inhibition of FGFR4 with ISIS 393250 on Body Fat Content (Reversal Study)

Male C57BL/6J mice (4 weeks of age weeks at time 0) were fed a 58% high-fat diet for 3 months and then divided into matched groups (n=6) with the same average blood glucose levels, body weight, and body composition, and treated by subcutaneous injections twice a week with saline, or 25 mg/kg twice a week of ISIS 141923 or ISIS 393250. Treatment was continued for 9.5 weeks. Body fat content was measured at weeks 0, 3.5, 7.5 and 9.5. The results are presented in Table 15 and 16.

TABLE 15

Antisense inhibition of FGFR4 on total body fat content (g) (Reversal study)
Whole body fat content (g)

| Weeks: | mean 0 | 3.5 | 7.5 | 9.5 |
|---|---|---|---|---|
| saline | 14.63 | 15.74 | 15.60 | 15.26 |
| 141923-control | 14.94 | 16.38 | 14.14 | 12.15 |
| 393250-FGFR4 | 14.81 | 14.86 | 10.88 | 8.21 |

The mice on the high fat diet treated with ISIS 393250 showed a significant decrease in body fat content, starting at 14.81 g at week 0 and ending at 8.21 g at week 9.5. Saline treated animals on the high fat diet showed no decrease in body fat content starting at 14.63 g at week 0 and ending at 15.26 g at week 9.5. The mice on the high fat diet treated with the control ASO, ISIS 141923, demonstrated a slight decrease in body fat content, starting at 14.94 g at week 0 and ending at 12.15 at week 9.5.

FGFR4 antisense oligonucleotide treatment lowered epididymal fat pad weight by ~40% (1.41±0.06 vs. 2.37±0.15 g in saline group; P<0.001), peri-renal fat pad weight by ~62% (0.40±0.03 vs. 1.06±0.09 g in saline group; P<0.001) and whole body fat content by ~44% (8.21±0.55 vs. 15.25±1.12 g in saline group; P<0.001), but did not change lean body mass.

TABLE 16

Effect of Antisense inhibition of FGFR4 on total body fat content (%) (Reversal study)
fat/BW (%)

| Weeks: | mean 0 | 3.5 | 7.5 | 9.5 |
|---|---|---|---|---|
| saline | 36.5 | 37.7 | 37.9 | 37.0 |
| 141923-control | 36.1 | 37.1 | 34.5 | 30.9 |
| 393250-FGFR4 | 36.1 | 34.6 | 29.1 | 23.0 |

Mice on the high fat diet treated with ISIS 393250 showed a decrease in body fat content starting at 36.1% at week 0 and ending at 23% at week 9.5. Saline treated animals showed no decrease in body fat content starting at 36.5% at week 0 and ending at 37.0% at week 9.5. Mice on the high fat diet treated with the control antisense oligonucleotide, ISIS 141923, demonstrated a slight decrease in body fat content starting at 36.1% at week 0 and ending at 30.9% at week 9.5. FGFR4 antisense oligonucleotide treated animals demonstrated a significant decrease in body fat content after 9.5 weeks showing almost a 13% reduction.

Example 10

Effects of Antisense Inhibition of FGFR4 with ISIS 393250 on Blood Glucose Levels (Reversal Study)

A glucose tolerance test in medical practice is the administration of glucose to determine how quickly it is cleared from the blood and is used to test for diabetes. Blood was obtained from the Diet Induced Obese (DIO) C57BL/6J mice and analyzed for glucose concentration. The results are shown in Table 17, illustrating changes in fasting plasma glucose levels at Week 6. For the Insulin Tolerance Test (ITT), food was withdrawn at 9:15 am and ITT was started from 1:30 pm. The Insulin dose was 0.5 U/kg. For the Intraperitoneal Glucose Treatment test (IPGTT), mice were fasted overnight and IPGTT was started from 8:30 am. The Glucose dose was 1.00 g/kg. The results are shown in Tables 18.

TABLE 17

IPGTT to determine glucose tolerance at Week 6 in DIO mice (Reversal study)
Glucose mg/dL

| ISIS # | 0 mins | 20 mins | 40 mins | 70 mins | 100 mins | 130 mins |
|---|---|---|---|---|---|---|
| saline | 112.5 | 292.4 | 359.8 | 249.1 | 205.8 | 166.3 |
| 141923-control | 96.0 | 244.4 | 265.0 | 173.5 | 136.3 | 117.3 |
| 393250-FGFR4 | 109.3 | 222.0 | 184.6 | 138.3 | 135.3 | 119.1 |

In response to glucose challenge, animals treated with ISIS 393250 show improved glucose tolerance. Peak plasma glucose level at the 30 minute time point was decreased by over 50% from the saline treated control and the subsequent drop in glucose was enhanced compared to controls, indicating that inhibition of FGFR4 by antisense improved glucose tolerance. The results indicated that glucose was cleared much more quickly from the blood of mice treated with ISIS 393250 relative to the control groups. This indicates that inhibition of FGFR4 by antisense may increase glucose tolerance and, therefore, may be useful for treating, preventing and/or ameliorating disorders of or associated with glucose intolerance and/or insulin resistance, such as, obesity, metabolic syndrome, diabetes, and hyperglycemia. See also FIG. 3.

TABLE 18

ITT to determine insulin sensitivity at Week 5.5 in DIO Mice (Reversal study)
Glucose mg/dL

| ISIS # | mean 0 mins | 30 mins | 60 mins | 90 mins | 120 mins |
|---|---|---|---|---|---|
| saline | 128.1 | 95.3 | 85.1 | 115.6 | 134.1 |
| 141923-control | 119.6 | 87.4 | 91.4 | 109.4 | 133.3 |

TABLE 18-continued

ITT to determine insulin sensitivity at
Week 5.5 in DIO Mice (Reversal study)
Glucose mg/dL

| ISIS # | mean 0 mins | 30 mins | 60 mins | 90 mins | 120 mins |
|---|---|---|---|---|---|
| 393250-FGFR4 | 116.9 | 74.8 | 71.1 | 96.3 | 126.3 |

An insulin tolerance test was also completed. There was an increase in rate and magnitude of glucose lowering after injecting insulin in the animals treated with ISIS 393250. Glucose levels are reduced during ITT in mice treated with ISIS 393250 compared to saline treated control, indicating an increase in insulin sensitivity. See also FIG. 2.

Example 11

Effects of Antisense Inhibition of FGFR4 with ISIS 393250 on Metabolic Rate (Reversal Study)

Male C57BL/6J mice were subjected to measurements of metabolic rates at the 8 week time point by known methods. The metabolic rate (as measured by oxygen consumption rate, VO2-ml/hr/kg) was measured in both light and dark phases as shown in Table 19.

TABLE 19

Metabolic rates VO2 (ml/hr/kg) at Week 8
Metabolic rate- (VO2-ml/hr/kg) at week 8

|  | mean dark | light |
|---|---|---|
| Saline | 3082.8 | 2686.0 |
| 141923-control | 3090.4 | 2709.7 |
| 393250-FGFR4 | 3459.3 | 2865.0 |

As shown in Table 19, treatment with ISIS 393250 caused an increase in the metabolic rate in both light and dark phases compared to either the saline treated or ISIS 141923 treated controls. The data indicate that the mice treated with ISIS 393250 had a higher metabolic rate than the mice of the control groups. Specifically, ISIS 393250 increased metabolic rate by about 11% (dark) and 7% (Light) at 8 weeks compared to saline treated controls, while the respiratory quotient remained relatively unchanged (See FIG. 1). This indicates that ISIS 393250 may be useful for increasing metabolic rates and, in turn, reducing body weight and body fat. For the animals treated with ISIS 393250 in this example, a reduction in body weight and body fat (data shown in Examples 7 and 8) can be seen at 7.5 weeks of treatment. The compounds provided herein are therefore useful in the treatment, prevent and/or amelioration of obesity, metabolic syndrome and related disorders.

Example 12

Effects of Antisense Inhibition of FGFR4 with ISIS 393250 on Adipose Tissue Weight (Reversal Study)

Male C57BL/6J mice were subjected to measurement of tissue weight by known methods. The tissue weight of epididymal white adipose tissue (epiWAT), perirenal white adipose tissue (periWAT), and brown adipose tissue (BAT) were measured, as shown in Table 20.

TABLE 20

Tissue weight (g)
Tissue wt (g):

|  | Mean epididymal WAT | peri-renal WAT | BAT |
|---|---|---|---|
| saline | 2.37 | 1.06 | 0.22 |
| 141923-control | 1.93 | 0.74 | 0.20 |
| 393250-FGFR4 | 1.41 | 0.40 | 0.17 |

The data indicate that the antisense oligonucleotides are effective at reducing adipose tissue weight. The tissue weight of epididymal white adipose tissue (epiWAT), perirenal white adipose tissue (periWAT), and brown adipose tissue (BAT) were all lowered with the treatment of Isis 393250-FGFR4 antisense oligonucleotide compared to the saline counterpart within each adipose tissue type. The epididymal white adipose tissue (epiWAT) weight treated with Isis 393250-FGFR4 antisense oligonucleotide was decreased by ~40% compared to the saline treated control group. The peri-renal white adipose tissue (periWAT) weight treated with Isis 393250-FGFR4 antisense oligonucleotide was decreased by ~62% compared to the saline treated control group. The brown adipose tissue (BAT) weight treated with Isis 393250-FGFR4 antisense oligonucleotide was decreased by ~23% compared to the saline treated control group.

Example 13

Effects of Antisense Inhibition of FGFR4 with ISIS 393250 on Differentiation and Proliferation and Cell Size in White Adipose Tissue (Reversal Study)

Obesity is characterized by an excess of subcutaneous fat in proportion to lean body mass. In obesity, adipose tissue, as opposed to most tissues in the body, will continue to grow. Growth of the adipose tissue results from both the enlargement of mature adipocytes and the formation of new adipocytes from adipocyte precursor cells (preadipocytes). Thus, fat accumulation is associated with increase in the size (hypertrophy) as well as the number (hyperplasia) of adipose tissue cells.

As indicated by the description of fat accumulation above, the lowered body fat content is partially due to a decrease in adipocyte size (see FIG. 4). ISIS 393250 caused a reduction in white adipose tissue cell size compared to the saline and ISIS 141923 treated white adipose tissue, indicating a potential effect on adipocyte proliferation or differentiation.

Example 14

Dose Response Antisense Inhibition of Human FGFR4 in A549 Cells, Primer Probe Set RTS1325

Several antisense oligonucleotides exhibiting at least 80% in vitro inhibition of FGFR4 were tested at various doses in A549 cells. Cells were plated at densities of 5500 cells per well and treated with nM concentrations of antisense oligonucleotide as indicated in Table 21. After a treatment period of approximately 24 hours, RNA was isolated from the cells and FGFR4 mRNA levels were measured by quantitative real-time PCR, as described herein. Human FGFR4 primer probe set RTS1325 was used to measure mRNA levels. FGFR4 mRNA levels were adjusted according to total RNA content as measured by RIBOGREEN®. Results are presented as percent inhibition of FGFR4, relative to untreated control cells. As illustrated in Table 21, FGFR4 mRNA levels were reduced in a dose-dependent manner.

TABLE 21

Antisense Inhibition of human FGFR4 in A549 cells, Primer Probe Set RTS1325

| ISIS No | 2.4 nM | 4.7 nM | 9.4 nM | 18.8 nM | 37.5 nM | 75.0 nM | 150.0 nM | 300.0 nM |
|---|---|---|---|---|---|---|---|---|
| 299043 | 6 | 5 | 28 | 28 | 48 | 63 | 68 | 76 |
| 299062 | 8 | 40 | 44 | 53 | 78 | 84 | 94 | 97 |
| 299004 | 8 | 33 | 48 | 71 | 84 | 95 | 96 | 95 |
| 299038 | 6 | 35 | 34 | 42 | 73 | 84 | 87 | 85 |
| 299046 | 13 | 34 | 35 | 40 | 60 | 79 | 81 | 78 |
| 299055 | 11 | 19 | 37 | 52 | 71 | 88 | 91 | 92 |
| 299047 | 20 | 31 | 42 | 56 | 62 | 81 | 86 | 83 |
| 141923 (control) | 33 | 14 | 8 | 5 | 0 | 3 | 8 | 18 |

What is claimed is:

1. A compound comprising a modified oligonucleotide consisting of 12 to 30 linked nucleosides and having a nucleobase sequence comprising a portion which consists of at least 12 contiguous nucleobases complementary to an equal-length portion of nucleotides 254-273, 278-297, 289-308, 289-323, 278-308, 304-323, 278-323, 289-373, 278-373, 354-373, 380-399, 412-431, 475-494, 412-494, 483-502, 475-502, 529-548, 597-616, 602-621, 597-621, 627-646, 711-730, 727-746, 739-758, 757-776, 711-746, 711-758, 711-776, 727-746, 727-758, 739-758, 727-776, 739-776, 757-776, 785-804, 833-852, 785-852, 833-983, 964-983, 785-983, 833-988, 785-988, 969-988, 964-988, 1027-1046, 1032-1051, 1027-1051, 1076-1096, 1090-1109, 1095-1114, 1076-1109, 1076-1114, 1090-1114, 1121-1040, 1181-1200, 1121-1200, 1121-1226, 1181-1226, 1235-1345, 1428-1447, 1447-1466, 1428-1466, 1452-1471, 1428-1471, 1555-1574, 1607-1626, 1656-1675, 155-1626, 1607-1675, 1555-1675, 1326-1675, 1741-1760, 1772-1791, 1919-1938, 1968-1987, 1979-1998, 1968-1998, 2268-2287, 2313-2332, 2394-2413, 2481-2500, 2497-2516, 2503-2522, 2557-2576, 2565-2584, 2629-2648, 2738-2757, 2752-2771, 2497-2584, 2738-2870, 2497-2870, or 2313-2413 of SEQ ID NO: 5, and wherein the nucleobase sequence of the modified oligonucleotide is at least 95% complementary to SEQ ID NO: 5.

2. The compound of claim 1, consisting of a single-stranded modified oligonucleotide.

3. The compound of claim 2, wherein at least one internucleoside linkage of the oligonucleotide is a phosphorothioate internucleoside linkage.

4. The compound of claim 2, wherein at least one nucleoside of the oligonucleotide comprises a modified sugar.

5. The compound of claim 4, wherein at least one modified sugar is a bicyclic sugar.

6. The compound of claim 5, wherein at least one modified sugar comprises a 2'-O-methoxyethyl.

7. The compound of claim 2, wherein at least one nucleoside of the oligonucleotide comprises a modified nucleobase.

8. The compound of claim 7, wherein the modified nucleobase is a 5-methylcytosine.

9. The compound of claim 1 wherein the modified oligonucleotide is a chimeric oligonucleotide.

10. The compound of claim 2, wherein the modified oligonucleotide consists of 20 linked nucleosides.

11. A composition comprising the compound of claim 1 or a salt thereof and a pharmaceutically acceptable carrier or diluent.

12. The composition of claim 11, wherein the modified oligonucleotide is a single-stranded oligonucleotide.

13. The composition of claim 12, wherein the modified oligonucleotide consists of 20 linked nucleosides.

14. A method comprising administering to an animal the compound of claim 1.

15. The method of claim 14, wherein the animal is a human.

16. The method of claim 14 wherein administering the compound slows progression and/or ameliorates diabetes, obesity or metabolic syndrome.

17. The method of claim 16, wherein diabetes is Type 2 diabetes.

18. The method of claim 14, comprising co-administering the compound and an anti-obesity agent, glucose-lowering agent, or anti-psychotic agent.

19. The method of claim 18, wherein the compound and an anti-obesity agent, glucose-lowering agent, or anti-psychotic agent are administered concomitantly.

20. The method of claim 14, wherein administering results in a reduction of obesity, body weight, body fat content, glucose, insulin resistance or an increase in metabolic rate or insulin sensitivity or any combination thereof.

21. A method of treating diabetes, obesity or metabolic syndrome by administering to a human having diabetes, obesity or metabolic syndrome the compound of claim 1.

22. The method of claim 21, wherein diabetes is Type 2 diabetes.

23. The method of claim 21 wherein treating results in slowed progression and/or amelioration of diabetes, obesity or metabolic syndrome.

24. The method of claim 21, comprising co-administering the compound and an anti-obesity agent.

25. The method of claim 24, wherein the compound and anti-obesity agent, are administered concomitantly.

* * * * *

UNITED STATES PATENT AND TRADEMARK OFFICE
CERTIFICATE OF CORRECTION

PATENT NO. : 8,895,529 B2
APPLICATION NO. : 13/915855
DATED : November 25, 2014
INVENTOR(S) : Sanjay Bhanot et al.

Page 1 of 2

It is certified that error appears in the above-identified patent and that said Letters Patent is hereby corrected as shown below:

ON THE TITLE PAGE

In column 2 (page 1, item 56) at line 39, Under Other Publications, change "dataase" to --database--.

Page 1 (item 74, Attorney) at line 1, Before "Knobbe," insert --Isis Pharmaceuticals, Inc. Patent Dept.;--.

In column 1 (page 2, item 56) at line 12, Under Other Publications, change ""Mas" to --"Mus--.

In column 1 (page 2, item 56) at line 59, Under Other Publications, change "NADPG" to --NADPH--.

In column 2 (page 2, item 56) at line 15, Under Other Publications, change "preadipoctye" to --preadipocyte--.

In column 2 (page 2, item 56) at line 25, Under Other Publications, change "22(31:326-" to --22(3):326- --.

IN THE SPECIFICATION

In column 3 at line 48, Change "131-135)" to --131-135).--.
In column 7 at line 7, Change "SEQ ID NOSEQ ID" to --SEQ ID--.
In column 7 at line 57, Change "Sangvi" to --Sanghvi--.
In column 8 at line 58, Change "know" to --known--.
In column 9 at line 21, Change "give" to --given--.
In column 10 at line 32, Change "nucleobase" to --nucleobase.--.
In column 10 at line 44, Change "furosyl" to --furanosyl--.
In column 11 at line 1, Change "furosyl" to --furanosyl--.
In column 12 at line 13, Change "condition" to --condition.--.

Signed and Sealed this
Twenty-sixth Day of January, 2016

Michelle K. Lee
*Director of the United States Patent and Trademark Office*

CERTIFICATE OF CORRECTION (continued)
U.S. Pat. No. 8,895,529 B2

IN THE SPECIFICATION

In column 16 at line 61, Change "agent" to --agent.--.

In column 17 at line 16, Change "thiazolidenediones);" to --thiazolidinediones);--.

In column 17 at line 18, Change "somatostan," to --somatostatin,--.

In column 20 at line 32 (approx.), Change "(CH2)n" to --$(CH_2)_n$--.

In column 24 at line 7 (approx.), Change "phosphorthioate," to --phosphorothioate,--.

In column 27 at line 62, Change "there" to --their--.

In column 28 at line 41, Change "there" to --their--.

In column 43 at line 48, Change "123" to --123.--.

In column 54 at line 27, Change "NO:" to --NO: 8--.

In column 61 at line 38, Change "111172" to --11172--.

In column 62 at line 32, Change "151" to --151.--.

In column 64 at line 20, Change "155-1626," to --1555-1626,--.

In column 64 at line 13, After "758, 711-776," delete "727-746,".

In column 64 at line 14, After "776," delete "757-776,".

In column 69 at lines 12-13, Change "hydroxymethylcellulosem" to --hydroxyethylcellulose--.

In column 74 at line 27, Change "commerical" to --commercial--.

In column 75 at line 43, Change "(Invetrogen," to --(Invitrogen,--.

In column 75 at line 47 (approx.), Change "(Invetrogen," to --(Invitrogen,--.

In column 82 at line 61 (approx.), Change "regions" to --regions.--.

IN THE CLAIMS

In column 217 at line 27 (approx.), In Claim 1, after "711-776," delete "727-746".

In column 217 at line 28 (approx.), In Claim 1, delete "757-776,".

In column 217 at line 35 (approx.), In Claim 1, change "155-1626," to --1555-1626,--.

SEQUENCE LISTING

<160> NUMBER OF SEQ ID NOS: 173

<210> SEQ ID NO 1
<211> LENGTH: 2418
<212> TYPE: DNA
<213> ORGANISM: H. Sapien

<400> SEQUENCE: 1

```
agtccagctt gggtccctga gagctgtgag aaggagatgc ggctgctgct ggccctgttg      60
ggggtcctgc tgagtgtgcc tgggcctcca gtcttgtccc tggaggcctc tgaggaagtg     120
gagcttgagc cctgcctggc tcccagcctg gagcagcaag agcaggagct gacagtagcc     180
cttgggcagc ctgtgcggct gtgctgtggg cgggctgagc gtggtggcca ctggtacaag     240
gagggcagtc gcctggcacc tgctggccgt gtacgggct ggaggggccg cctagagatt      300
gccagcttcc tacctgagga tgctggccgc tacctctgcc tggcacgagg ctccatgatc     360
gtcctgcaga atctcacctt gattacaggt gactcctcga cctccagcaa cgatgatgag     420
gaccccaagt cccataggga cctctcgaat aggcacagtt accccagca agcaccctac      480
tggacacacc cccagcgcat ggagaagaaa ctgcatgcag tacctgcggg aacaccgtc      540
aagttccgct gtccagctgc aggcaacccc acgccacca tccgctggct taaggatgga     600
caggcctttc atgggggaa ccgcattgga ggcattcggc tgcgccatca gcactggagt      660
ctcgtgatgg agagcgtggt gccctcggac cgcggcacat acacctgcct ggtagagaac     720
gctgtgggca gcatccgtta taactacctg ctagatgtgc tggagcggtc cccgcaccgg     780
cccatcctgc aggccgggct cccggccaac accagccg tggtgggcag cgacgtggag     840
ctgctgtgca aggtgtacag cgatgcccag ccccacatcc agtggctgaa gcacatcgtc     900
atcaacggca gcagcttcgg agccgacggt ttcccctatg tgcaagtcct aaagactgca     960
gacatcaata gctcagaggt ggaggtcctg tacctgcgga acgtgtcagc cgaggacgca    1020
ggcgagtaca cctgcctcgc aggcaattcc atcggcctct cctaccagtc tgcctggctc    1080
acggtgctgc caggtactgg gcgcatcccc cacctcacat gtgacagcct gactccagca    1140
ggcagaacca agtctcccac tttgcagttc tccctggagt caggctcctc cggcaagtca    1200
agctcatccc tggtacgagg cgtgcgtctc tcctccagcg gccccgcctt gctcgccggc    1260
ctcgtgagtc tagatctacc tctcgaccca ctatgggagt tccccggga caggctggtg    1320
cttgggaagc cctaggcga gggctgcttt ggccaggtag tacgtgcaga ggcctttggc    1380
atggaccctg cccggcctga ccaagccagc actgtggccg tcaagatgct caaagacaac    1440
gcctctgaca aggacctggc cgacctggtc tcggagatgg aggtgatgaa gctgatcggc    1500
```

| | |
|---|---|
| cgacacaaga acatcatcaa cctgcttggt gtctgcaccc aggaagggcc cctgtacgtg | 1560 |
| atcgtggagt gcgccgccaa gggaaacctg cgggagttcc tgcgggcccg cgcccccca | 1620 |
| ggccccgacc tcagcccga cggtcctcgg agcagtgagg ggccgctctc cttcccagtc | 1680 |
| ctggtctcct gcgcctacca ggtggcccga ggcatgcagt atctggagtc ccggaagtgt | 1740 |
| atccaccggg acctggctgc ccgcaatgtg ctggtgactg aggacaatgt gatgaagatt | 1800 |
| gctgactttg gctggcccg cggcgtccac cacattgact actataagaa aaccagcaac | 1860 |
| ggccgcctgc ctgtgaagtg gatggcgccc gaggccttgt ttgaccgggt gtacacacac | 1920 |
| cagagtgacg tgtggtcttt tgggatcctg ctatgggaga tcttcaccct cggggggctcc | 1980 |
| ccgtatcctg gcatcccggt ggaggagctg ttctcgctgc tgcgggaggg acatcggatg | 2040 |
| gaccgacccc cacactgccc cccagagctg tacgggctga tgcgtgagtg ctggcacgca | 2100 |
| gcgccctccc agaggcctac cttcaagcag ctggtggagg cgctggacaa ggtcctgctg | 2160 |
| gccgtctctg aggagtacct cgacctccgc ctgaccttcg gaccctattc cccctctggt | 2220 |
| ggggacgcca gcagcacctg ctcctccagc gattctgtct tcagccacga ccccctgcca | 2280 |
| ttgggatcca gctccttccc cttcgggtct ggggtgcaga catgagcaag gctcaaggct | 2340 |
| gtgcaggcac ataggctggt ggccttgggc cttggggctc agccacagcc tgacacagtg | 2400 |
| ctcgaccttg atagcatg | 2418 |

<210> SEQ ID NO 2
<211> LENGTH: 711
<212> TYPE: DNA
<213> ORGANISM: H. Sapien

<400> SEQUENCE: 2

| | |
|---|---|
| aggagatgcg gctgctgctg gccctgttgg gggtcctgct gagtgtgcct gggcctccag | 60 |
| tcttgtccct ggaggcctct gaggaagtgg agcttgagcc ctgcctggct cccagcctgg | 120 |
| agcagcaaga gcaggagctg acagtagccc ttgggcagcc tgtgcgtctg tgctgtgggc | 180 |
| gggctgagcg tggtggccac tggtacaagg agggcagtcg cctggcacct gctggccgtg | 240 |
| tacgggctg gaggggccgc ctagagattg ccagcttcct acctgaggat gctggccgct | 300 |
| acctctgcct ggcacgaggc tccatgatcg tcctgcagaa tctcaccttg attacaggtg | 360 |
| actccttgac ctccagcaac gatgatgagg accccaagtc ccatagggac ctctcgaata | 420 |
| ggcacagtta cccccagcaa ggtcagtagg tctccaagga cttgtgtccc gctgctgctc | 480 |
| atctgatcac tgagaagagg aggcctgtgt gggaacacac ggtcattcta ggggccttcc | 540 |
| cctgccctcc agcaccctac tggacacacc cccagcgcat ggagaagaaa ctgcatgcag | 600 |
| tacctgcggg gaacaccgtc aagttccgct gtccagctgc aggcaacccc acgcccacca | 660 |
| tccgctggct taaggatgga caggcctttc atggggagaa ccgcattgga g | 711 |

<210> SEQ ID NO 3
<211> LENGTH: 662
<212> TYPE: DNA
<213> ORGANISM: H. Sapien

<400> SEQUENCE: 3

| | |
|---|---|
| ggaggagcca ggtgagcagg accctgtgct gggcgcggag tcacgcaggc tcgaggaagg | 60 |
| cagttggtgg gaagtccagc ttgggtccct gagagctgtg agaaggagat gcggctgctg | 120 |
| ctggccctgt tggggtcct gctgagtgtg cctgggcctc cagtcttgtc cctgaggcc | 180 |
| tctgaggaag tggagcttgg tggtaagaga ctctagcagg gagtgaaggg atgcctgggg | 240 |

```
agacagacct gccccctcttg gaccttagat gcttccctct gtccctgatg tagactcctt      300
gactccagca acgatgatga ggaccccaag tcccataggg acctctcgaa taggcacagt      360
tacccccagc aagcaccctα ctggacacac cccagcgca tggagaagaa actgcatgca      420
gtacctgcgg ggaacaccgt caagttccgc tgtccagctg caggcaaccc acgcccacca      480
tccgctggct taaggatgga caggcctttc atggggagaa ccgcattgga ggcattcggc      540
tgcgccatca gcactggagt ctcgtgatgg agagcgtggt gccctcggac gcggcacat      600 acacctgcct ggtagagaac gctgtgggca gcatccgtta taactacctg ctagatgtgc      660
tg                                                                    662
```

<210> SEQ ID NO 4
<211> LENGTH: 1018
<212> TYPE: DNA
<213> ORGANISM: H. Sapien
<220> FEATURE:
<221> NAME/KEY: misc_feature
<222> LOCATION: 729
<223> OTHER INFORMATION: n = A,T,C or G

<400> SEQUENCE: 4

```
tcggggcggg acaggaggtg ggccgctcgc ggccacgccg ccgtcgcggg tacattcctc       60
gctcccggcc gaggagcgct cgggctgtct gcggaccctg ccgcgtgcag gggtcgcggc      120
cggctggagc tgggagtgag gcggcggagg agccaggtga ggaggagcca ggaaggcagt      180
tggtgggaag tccagcttgg gtccctgaga gctgtgagaa ggagatgcgg ctgctgctgg      240
ccctgttggg ggtcctgctg agtgtgcctg ggcctccagt cttgtccctg gaggcctctg      300
aggaagtgga gcttgactcc ttgacctcca gcaacgatga tgaggacccc aagtccccata      360 gggacctctc gaataggcac agttaccccc agcaagcacc ctactggaca cacccccagc      420
gcatggagaa gaaactgcat gcagtacctg cggggaacac cgtcaagttc cgctgtccag      480
ctgcaggcaa ccccacgccc accatccgct ggcttaagga tggacaggcc tttcatgggg      540
agaaccgcat tggaggcatt cggctgcgcc atcagcactg gagtctcgtg atggagagcg      600
tggtgccctc ggaccgcggc acatacacct gcctggtaga gaacgctgtg gcagcatcc      660 gttataacta cctgctagat gtgctggagc ggtccccgca ccgctcatcc tgcaggccgg      720
gctcccggnc aacaccacag tccgtggtgg gcaacgacgt gggacttgct gttgcaggtg      780
tacaccgatt gccagcccca cattcagggg gctgaagcac ttccgcctta acgggaaaca      840
gctttccgga gccgagggtt ttccctctat ggtgccagtt tcttagaaga ctggttgaca      900
tccctctacc ccccaaaggt gggagggacc ctgctaccat gagccgacga ccttcaaccc      960
ctctgctttt gtcaggcccc tccattctta tcttcgcctc cccaacgcc tctccctc      1018
```

<210> SEQ ID NO 5
<211> LENGTH: 3040
<212> TYPE: DNA
<213> ORGANISM: H. Sapien

<400> SEQUENCE: 5

```
ctcgctcccg gccgaggagc gctcgggctg tctgcggacc ctgccgcgtg cagggggtcgc       60 ggccggctgg agctgggagt gaggcggcgg aggagccagg tgaggaggag ccaggaaggc      120
agttggtggg aagtccagct tgggtccctg agagctgtga gaaggagatg cggctgctgc      180
tggccctgtt gggggtcctg ctgagtgtgc ctgggcctcc agtcttgtcc ctggaggcct      240
```

```
ctgaggaagt ggagcttgag ccctgcctgg ctcccagcct ggagcagcaa gagcaggagc    300
tgacagtagc ccttgggcag cctgtgcgtc tgtgctgtgg gcgggctgag cgtggtggcc    360
actggtacaa ggagggcagt cgcctggcac ctgctggccg tgtacggggc tggaggggcc    420
gcctagagat tgccagcttc ctacctgagg atgctggccg ctacctctgc ctggcacgag    480
gctccatgat cgtcctgcag aatctcacct tgattacagg tgactccttg acctccagca    540
acgatgatga ggaccccaag tcccataggg acccctcgaa taggcacagt taccccccagc   600 aagcacccta ctggacacac ccccagcgca tggagaagaa actgcatgca gtacctgcgg    660
ggaacaccgt caagttccgc tgtccagctg caggcaaccc cacgcccacc atccgctggc    720
ttaaggatgg acaggccttt catggggaga accgcattgg aggcattcgg ctgcgccatc    780
agcactggag tctcgtgatg gagagcgtgg tgccctcgga ccgcggcaca tacacctgcc    840
tggtagagaa cgctgtgggc agcatccgct ataactacct gctagatgtg ctggagcggt    900
ccccgcaccg gccatcctg caggccgggc tccggccaa caccacagcc gtggtgggca      960
gcgacgtgga gctgctgtgc aaggtgtaca gcgatgccca gccccacatc cagtggctga   1020
agcacatcgt catcaacggc agcagcttcg gagccgacgg ttttcccctat gtgcaagtcc   1080 taaagactgc agacatcaat agctcagagg tggaggtcct gtacctgcgg aacgtgtcag   1140
ccgaggacgc aggcgagtac acctgcctcg caggcaattc catcggcctc tcctaccagt   1200
ctgcctggct cacggtgctg ccagaggagg accccacatg gaccgcagca gcgcccgagg   1260
ccaggtatac ggacatcatc ctgtacgcgt cgggctccct ggccttggct gtgctcctgc   1320
tgctggccgg gctgtatcga gggcaggcgc tccacgccg gcaccccgc ccgcccgcca     1380 ctgtgcagaa gctctcccgc ttccctctgg cccgacagtt ctccctggag tcaggctctt   1440
ccggcaagtc aagctcatcc ctggtacgag gcgtgcgtct ctcctccagc ggccccgcct   1500
tgctcgccgg cctcgtgagt ctagatctac ctctcgaccc actatgggag ttcccccggg   1560
acaggctggt gcttgggaag ccctaggcg agggctgctt tggccaggta gtacgtgcag    1620
aggcctttgg catggaccct gcccggcctg accaagccag cactgtggcc gtcaagatgc   1680
tcaaagacaa cgcctctgac aaggacctgg ccgacctggt ctcggagatg gaggtgatga   1740
agctgatcgg ccgacacaag aacatcatca acctgcttgg tgtctgcacc caggaagggc   1800
ccctgtacgt gatcgtggag tgcgccgcca agggaaacct gcgggagttc ctgcgggccc   1860 ggcgccccccc aggccccgac ctcagccccg acggtcctcg gagcagtgag gggccgctct  1920
ccttcccagt cctggtctcc tgcgcctacc aggtggcccg aggcatgcag tatctggagt   1980
cccggaagtg tatccaccgg gacctggctg ccgcaatgt gctggtgact gaggacaatg    2040
tgatgaagat tgctgacttt gggctggccc gcggcgtcca ccacattgac tactataaga   2100
aaaccagcaa cggccgcctg cctgtgaagt ggatggcgcc cgaggccttg tttgaccggg   2160
tgtacacaca ccagagtgac gtgtggtctt ttgggatcct gctatgggag atcttcaccc   2220 tcggggctc cccgtatcct ggcatcccgg tggaggagct gttctcgctg ctgcgggagg   2280
gacatcggat ggaccgaccc ccacactgcc cccagagct gtacggctg atgcgtgagt   2340 gctggcacgc agcgccctcc cagaggccta ccttcaagca gctggtggag cgctggacaa   2400
aggtcctgct ggccgtctct gaggagtacc tcgacctccg cctgaccttc ggaccctatt   2460
ccccctctgg tggggacgcc agcagcacct gctcctccag cgattctgtc ttcagccacg   2520 acccctgcc attgggatcc agctcctcc ccttcgggtc tggggtgcag acatgagcaa    2580
ggctcaaggc tgtgcaggca cataggctgg tggccttggg ccttggggct cagccacagc   2640
```

```
ctgacacagt gctcgacctt gatagcatgg ggccoctggc ccagagttgc tgtgccgtgt    2700
ccaagggccg tgcccttgcc cttggagctg ccgtgcctgt gtcctgatgg cccaaatgtc    2760
agggttctgc tcggcttctt ggaccttggc gcttagtccc catcccgggt ttggctgagc    2820
ctggctggag agctgctatg ctaaacctcc tgcctcccaa taccagcagg aggttctggg    2880
cctctgaacc cccttteccc acacctcccc ctgctgctgc tgccccagcg tcttgacggg    2940
agcattggcc cctgagccca gagaagctgg aagcctgccg aaaacaggag caaatggcgt    3000
tttataaatt atttttttga aataaaaaaa aaaaaaaaa                          3040
```

<210> SEQ ID NO 6
<211> LENGTH: 2895
<212> TYPE: DNA
<213> ORGANISM: H. Sapien

<400> SEQUENCE: 6

```
ccgaggagcg ctcgggctgt ctgcggaccc tgccgcgtgc aggggtcgcg gccggctgga      60
gctgggagtg aggcggcgga ggagccaggt gaggaggagc caggaaggca gttggtggga     120
agtccagctt gggtccctga gagctgtgag aaggagatgc ggctgctgct ggccctgttg     180
ggggtcctgc tgagtgtgcc tgggcctcca gtcttgtccc tggaggcctc tgaggaagtg     240
gagcttgagc cctgcctggc tcccagcctg gagcagcaag agcaggagct gacagtagcc     300
cttgggcagc ctgtgcggct gtgctgtggg cgggctgagc gtggtggcca ctggtacaag     360
gagggcagtc gcctggcacc tgctggccgt gtacggggct ggagggggccg cctagagatt    420
gccagcttcc tacctgagga tgctggccgc tacctctgcc tggcacgagg ctccatgatc    480
gtcctgcaga atctcacctt gattacaggt gactccttga cctccagcaa cgatgatgag    540
gaccccaagt cccataggga cctctcgaat aggcacagtt accccccagca agcacccctac    600
tggacacacc cccagcgcat ggagaagaaa ctgcatgcag tacctgcggg aacaccgtc     660
aagttccgct gtccagctgc aggcaacccc acgcccacca tccgctggct taaggatgga    720
caggcctttc atgggagaa ccgcattgga ggcattcggc tgcgccatca gcactggagt     780
ctcgtgatgg agagcgtggt gccctcggac cgcggcacat acacctgcct ggtagagaac    840
gctgtgggca gcatccgcta taactacctg ctagatgtgc tggagcggtc cccgcaccgg    900
cccatcctgc aggccgggct cccggccaac accacagccg tggtgggcag cgacgtggag    960
ctgctgtgca aggtgtacag cgatgcccag ccccacatcc agtggctgaa gcacatcgtc   1020
atcaacggca gcagcttcgg agccgacggt ttccctatg tgcaagtcct aaagactgca   1080
gacatcaata gctcagaggt ggaggtcctg tacctgcgga acgtgtcagc cgaggacgca   1140
ggcgagtaca cctgcctcgc aggcaattcc atcggcctct cctaccagtc tgcctggctc   1200
acggtgctgc caggtactgg gcgcatcccc cacctcacat gtgacagcct gactccagca   1260
ggcagaacca agtctcccac tttgcagttc tccctggagt caggctcttc cggcaagtca   1320
agctcatccc tggtacgagg cgtgcgtctc tcctccagcg gccccgcctt gctcgccggc   1380
ctcgtgagtc tagatctacc tctcgaccca ctatgggagt tccccgggga caggctggtg   1440
cttgggaagc cctaggcga gggctgcttt ggccaggtag tacgtgcaga ggcctttggc    1500
atggaccctg cccggcctga ccaagccagc actgtggccg tcaagatgct caaagacaac   1560
gcctctgaca aggacctggc cgacctggtc tcggagatgg aggtgatgaa gctgatcggc   1620
cgacacaaga acatcatcaa cctgcttggt gtctgcaccc aggaagggcc cctgtacgtg   1680
```

```
atcgtggagt gcgccgccaa gggaaacctg cgggagttcc tgcgggcccg gcgcccccca    1740
ggccccgacc tcagcccga cggtcctcgg agcagtgagg ggccgctctc cttcccagtc    1800
ctggtctcct gcgcctacca ggtggcccga ggcatgcagt atctggagtc ccggaagtgt    1860
atccaccggg acctggctgc ccgcaatgtg ctggtgactg aggacaatgt gatgaagatt    1920
gctgactttg ggctggcccg cggcgtccac cacattgact actataagaa aaccagcaac    1980
ggccgcctgc ctgtgaagtg gatggcgccc gaggccttgt tgaccgggt gtacacacac    2040
cagagtgacg tgtggtcttt tgggatcctg ctatgggaga tcttcaccct cggggctcc    2100
ccgtatcctg gcatcccggt ggaggagctg ttctcgctgc tgcggagggg acatcggatg    2160
gaccgacccc cacactgccc cccagagctg tacgggctga tgcgtgagtg ctggcacgca    2220
gcgccctccc agaggcctac cttcaagcag ctggtggagg cgctggacaa ggtcctgctg    2280
gccgtctctg aggagtacct cgacctccgc ctgaccttcg accctattc ccctctggt    2340
ggggacgcca gcagcacctg ctcctccagc gattctgtct tcagccacga ccccctgcca    2400
ttgggatcca gctccttccc cttcgggtct ggggtgcaga catgagcaag gctcaaggct    2460
gtgcaggcac ataggctggt ggccttgggc cttgggctc agccacagcc tgacacagtg    2520
ctcgaccttg atagcatggg gccctgcc cagagttgct gtgccgtgtc caagggccgt    2580
gcccttgccc ttggagctgc cgtgcctgtg tcctgatggc ccaaatgtca gggttctgct    2640
cggcttcttg gaccatggcg cttagtcccc atcccgggtt tggctgagcc tggctggaga    2700
gctgctatgc taaacctcct gcctcccaat accagcagga ggttctgggc ctctgaaccc    2760
cctttcccca cacctccccc tgctgctgct gccccagcgt cttgacggga gcattggccc    2820
ctgagcccag agaagctgga agcctgccga aaacaggagc aaatggcgtt ttataaatta    2880
tttttttgaa ataaa                                                     2895

<210> SEQ ID NO 7
<211> LENGTH: 12196
<212> TYPE: DNA
<213> ORGANISM: H. Sapiens

<400> SEQUENCE: 7
tgagggagca gaaggaaggg gttctcctat ccgctgcacg gcactgcgca gaagacaggg     60
gagccaggca ttccctgaag ggtgaaaagc aaggagtaga gctgggtagt agactagaat    120
ttaggagcct ggcctggggc ctgggtgggg cgaaagaggc ggagcctgaa tggggtgtgt    180
ataggggggt tgcgtgtagg ggtgtgtgta taggctgggg cggggtcccg ggagtgggct    240
gactgggtcg ggggcggggc tctccaggtg ggcgggatc ttggccaccc ctggccacac    300
ctctctccgg ctcgagctgg tctaggcggg gcgggcccga gggggtgtgg caggaggtgg    360
gcgggcccgg gtggggggg gggggcgtg aaggagggg cgggcccgag caggagggg    420
cgggcccgag gggcggggtg ggacaggagg tgggccgctc gcggccacgc cgccgtcgcg    480
ggtacattcc tcgctcccgg ccgaggagcg ctcgggctgt ctgcgacccc tgccgcgtgc    540
aggggtcgcg gccggctgga gctgggagtg aggcggcgga ggagccaggt gaggaggagc    600
caggtgagca ggaccctgtg ctgggcgcgg agtcacgcag gctcgaggtg agccggaacc    660
cttgtgggcc cgggctgcgc tcccagccgc caggggcga gaggcggcgg ggctacgggg    720
actgccccctc ccggcgcagg ggacctggc gtccgccggg cggcaggggg tggaggggc    780
ggtaaatcag taacccgcag tgcacacagg gcctttttgtc ccgctccgtc caaagagcac    840
cccggccgcg gagctggtta ctcattgccc accgaggcgg gggcaggctg gccctgtgca    900
```

```
gctaccctcg ggacccattg attcgcacct cccccaggc tggcccggca agggtggggg      960
aggacaagcg cgcttgtccc tgcggctgtc ttcgcgccgg cggcagagat gagggacctg     1020
aggccccgaa aagttcagtc acttagtgcc cgggggcctc cagcgcgagt gcggaggct      1080 gaaggagaac ccaggactgt ctgatgccta aggcaggccc tccattccca cgtgggggt     1140 ggtcggtcag cggtcagcag ccatgggtga ctcgactaag gactctgata tcagggcagc    1200
ctggggtagg aataaactcc ccgggcctcc ccacccactc ccagcccaag ctgtgtaccc    1260
aaagagctgc cctccctgcc aagccgagct tggtaggag ttttaccaag gaggatccga     1320
ctggattcga gagttgaggt gggccagaga cagcagtatc tgagtcaggt agagaagagc    1380
aatgaggggc acagagggat gggcaagaga gcacatgtgc ccagttttga aagccaatgg    1440
cttcagcgct cctgaagggg cagacggtgt gaccaaagag ataggcagcg gcagagaggg    1500
agccctagga tgttgagctg atcctgctg gcacaggta gccattaagg gcttgcaagc      1560 tgggggggcat gacatggcag acttgcaggt ttttttgttt gttttttat tttattttat    1620 tttttatt tgttttttt gagacggagt ctcactctgt cgcccaggct ggagtgcagt       1680
ggcgcgatct cggctcactg caagctccgc ctcccgggtt cgcgccattc tcctgcctca    1740
gcctcccgag tagctgggac tacaggcgcc cgccaccgcg cccggctaat ttttgtatt    1800 tttagtagag acggggtttc accgtgttag ccaggatgtt ctcgatctcc tgacctcgtg    1860
atccgcccac ctcggcctcc caaagtgctg ggattacagg tgtgaaccat cgcgcccagc    1920
cgacttgtat tttttaaaa ctctgctgga agatgaaggt tgaagagccg agggagagga    1980
tgtttccaga ggcccatgca agagatggcc atgacctgcc ttgagaaggg gcagggaag    2040 ccagatggac tggaagtgga gtggcagtga ccaaggagga ggaggtgtga taggcttccc    2100
acgcagggta gatccagaga caccagtgcc acccataggc ccctaggact gcagtggtca    2160
ccgattcctt tgtcccagct gagactcagt tctgagtgtt ctattttggg gaacagaggc    2220
gtccttggta gcatttggaa gaggatagcc agctggggtg tgtgtacatc acagcctgac    2280
agtaacagca tccgaaccag aggtgactgg ctaagggcag acccagggca acaggttaac    2340
cgttctaggg ccgggcacag ggaggagaac attccaacac tctgcgtgcc gacgcacgtt    2400 ctctcttta tcctcaaaac agtcctatga ggatagtaag ccagagagag acagagacaa    2460
ggaattacaa gttggtgaga gtcaggattt gaacttggct ctggcagatg gaaaattagg    2520
gtctgtattc tttacaaaac cgtgtgtgcc tcagatggag ttggtgcata caagcagag     2580 gtatccaggg tcgcggtcct gcttgccacg gaaggggccg ccttgtcagt tgtgaccacc    2640
cagccctgga aatgtcagta atgctgtaag gagtggggat cggatcagat gccatccaga    2700
tgctgaagtt tgaccttgtg tcatttttca ctttcttttt tggctcttct gcaatcaatt    2760
catttattta gcaaaaaaga aattatgtgt gccgagagca tgcagaagat atgtctccgt    2820
tctctgcttc cctccaaaaa agaatcccaa aactgctttc tgtgaacgtg tgccagggtc    2880
ccagcaggac tcagggagag caggaagccc agcccagacc ccttgcacaa cctaccgtgg    2940
ggaggcctta ggctctggct actacagagc tggttccagt ctgcactgcc acagcctggc    3000
cagggacttg acacatctg ctggccactt cctgtctcag tttccttatc tgcaaaataa     3060
gggaaaagcc cccacaaagg tgcacgtgta gcaggagctc ttttccctcc ctattttagg    3120
aaggcagttg gtgggaagtc cagcttgggt ccctgagagc tgtgagaagg agatgcggct    3180
gctgctggcc ctgttggggg tcctgctgag tgtgcctggg cctccagtct tgtccctgga    3240
```

```
ggcctctgag gaagtggagc ttggtatggc ttctgaggtg ggagagggtg gcagggtgg    3300
gaagagtggg caccaggagg gggctgctgg gctgagcaaa gctggaaagg atccttgccc   3360
aggccctgag aaggtggcgg cagggcaggg ctcaaccact gagactcagt cagtgcctgg   3420
cttccagcaa gcattcatct atcactgtgt ctgcgagaga ggactggcct tgcagggcgc   3480
agggccctaa gctgggctgc agagctggtg gtgagctcct tacctgggtg tgtgtgcgtg   3540
tgtgtgtgtg ttctgtgcac tgggtgtgtg acctaggagg tccaggcagc atgtgtggta   3600
taagcattat gagggtgata tgccccggtg cagcatgacc ctgtatgtgg caccaacagc   3660
atgtgccttg tgtgtgtgtg tgtccgtatg tgtgtgtgtg tatgcgtgtg tgtgtgtgtg   3720
tgtgtcttgg ccactgtcgt gtgcactaaa tgctgtgtgt gtgacatgcc caagagtgt    3780
ggcatttgcc ctgggtgtgg catccgcagc atgtggctgt gtgggtgtca aggagtggtg   3840
gctccttcag catgcgttgc aaagtgcttg tgccctgcat gtgcggtgtg ttctttgtac   3900
acaggaggct gcctcagatg gggctgcggg gtctgctgac ctctgccctc tgcccacaga   3960
gccctgcctg gctcccagcc tggagcagca agagcaggag ctgacagtag cccttgggca   4020
gcctgtgcgt ctgtgctgtg ggcgggctga gcgtggtggc cactggtaca aggagggcag   4080
tcgcctggca cctgctggcc gtgtacgggg ctggaggggc cgcctagaga ttgccagctt   4140
cctacctgag gatgctggcc gctacctctg cctggcacga ggctccatga tcgtcctgca   4200
gaatctcacc ttgattacag gtggtaagag actctagcag ggagtgaagg gatgcctggg   4260
gagacagacc tgcccctctt ggaccttaga tgcttccctc tgtccctgat gtagactcct   4320
tgacctccag caacgatgat gaggaccccca agtcccatag ggacccctcg aataggcaca   4380
gttaccccca gcaaggtcag taggtctcca aggacttgtg tccccgctgc tgctcatctg   4440
atcactgaga agaggaggcc tgtgtgggaa cacacggtca ttctaggggc ttcccctgc    4500
cctccagcac cctactggac acaccccag cgcatggaga agaaactgca tgcagtacct    4560
gcggggaaca ccgtcaagtt ccgctgtcca gctgcaggca accccacgcc caccatccgc   4620
tggcttaagg atggacaggc ctttcatggg gagaaccgca ttggaggcat tcgggtgagt   4680
ctctgggttc caagaccgtc tgctccccca ttttcattcc ttcatcagtc ccctcatacc   4740
tacaagcata cctataaatc aatcgaatga gtgaagcgat tgcggggccc cggaaggagc   4800
cctggactgt ggacctgggc agctctggtt cccttctgc tactctctgg caagtgactt     4860
aacctctcag cctcagcaac tccatttgta aagggagaag aatcactgac tggttggtct   4920
gcataagcct tagcatctca tcgtcttgat gagaccctgc agggtcggct ccatgctgtc   4980
atgaggcaac tgagtctcag agaaggcaag ggttggctca agtagcaca gctagggaga    5040
gggagagcta aaattccaaa ggctcaaacc caaggctcaa gcgccctggg gagcctactc   5100
ctttgtgcca tagtccttgg cctgggcctg atgttctcag ggcctagaga gcttgacaag   5160
agccctgtgg gcaggatgag gatctagcct cctggtcctc tggcccccctt ggtggacatg  5220
gtccggtggt cccggacact ctctctgcct gcagctgcgc catcagcact ggagtctcgt   5280
gatggagagc gtggtgccct cggaccgcgg cacatacacc tgcctggtag agaacgctgt   5340
gggcagcatc cgctataact acctgctaga tgtgctgggt gagcgcgggg ctgggaacag   5400
gggaggcctg acccattttg ggctcagttg tgccctcttg gtggggtcta gtctggcagg   5460
caggatggac tcagatgagt caggcagctt ggtgagcagg tgggtcaggg gaaagcacag   5520
gggttagtgt ggggctggag gagcagaggt ctgccaagag gaaaacaag aaggacatcc     5580
aggcagaggg cgcagcccga gcggagggcc tgagtataac aaacgccctg cacttgcagg   5640
```

```
ccagcatatt cgtagggcgt ggcgtttata tggggagcca ggtggtggag ggttttgaat    5700
gctaggctga gatgttgtcc ttgacccgaa gcaataggga gccagggaag gtttaagcag    5760
ggtaagcagg agacagacaa gaagctgcag aaaggtccct cccttgaact tgaggaaggc    5820
tggagggagg caaacagggt gcttctatgg gtgccggtgg tcagggttga ctgtctcgcc    5880
cggtccccag agcggtcccc gcaccggccc atcctgcagg ccgggctccc ggccaacacc    5940
acagccgtgt gggcagcga cgtggagctg ctgtgcaagg tgtacagcga tgcccagccc    6000
cacatccagt ggctgaagca catcgtcatc aacggcagca gcttcggagc cgacggtttc    6060
ccctatgtgc aagtcctaaa ggtaaaaggt gcaccctgct gcagcctggg ccccattctt    6120
ctcccacctt gggttggggg gctccccagc ttccctgttg ccacagtgt ggccccaggc    6180
cctgctgtga ccccagagca tgtccccac cccagactgc agacatcaat agctcagagg    6240
tggaggtcct gtacctgcgg aacgtgtcag ccgaggacgc aggcgagtac acctgcctcg    6300
caggcaattc catcggcctc tcctaccagt ctgcctggct cacggtgctg ccaggtgagc    6360
acctgaaggg ccaggagatg ctgcgagatg cccctctggg ccagcagtgg gggctgtggc    6420
ctgttgggtg gtcagtctct gttggcctgt ggggtctggc ctgggggca gtgtgtggat    6480
ttgtgggttt gagctgtatg acagcccctc tgtgcctctc cacacgtggc cgtccatgtg    6540
accgtctgct gaggtgtggg tgcctggac tgggcataac tacagcttcc tccgtgtgtg    6600
tccccacata tgttgggagc tgggagggac tgagttaggg tgcacggggc ggccagtctc    6660
accactgacc agtttgtctg tctgtgtgtg tccatgtgcg agggcagagg aggaccccac    6720
atggaccgca gcagcgcccg aggccaggta tacggacatc atcctgtacg cgtcgggctc    6780
cctggccttg gctgtgctcc tgctgctggc cgggctgtat cgagggcagg cgctccacgg    6840
ccggcaccc cgcccgcccg ccactgtgca gaagctctcc cgcttccctc tggcccgaca    6900
ggtactgggc gcatccccca cctcacatgt gacagcctga ctccagcagg cagaaccaag    6960
tctcccactt tgcagttctc cctggagtca ggctcttccg gcaagtcaag ctcatccctg    7020
gtacgaggcg tgcgtctctc ctccagcggc cccgccttgc tcgccggcct cgtgagtcta    7080
gatctacctc tcgacccact atgggagttc ccccgggaca ggtgcgctga gctgtgtggg    7140
ggcaggacg cgggcgccgg gttgcagccc gccctccgca ggagtgactc ggaggtctga    7200
ggctggactt tctccatctc caggctggtg cttgggaagc ccctaggcga gggctgcttt    7260
ggccaggtag tacgtgcaga ggcctttggc atggaccctg cccggcctga ccaagccagc    7320
actgtggccg tcaagatgct caaaggtgag tgtggcccgg tgtggtggct cacacctgta    7380
acgccagcac tttaggaggc tgagggtggg aggatcgctt gaatccagga attcgaggcc    7440
agcctgggca acatggcaag acttcatctc tacaaaaaaa aaataagaaa attagttggg    7500
tgtggtggtg tgtgccttta gtctcagtta ctagggaggc tgaggcagga ggatcccttg    7560
aatccaggag ttgaggttg cagggagcca tgatcacgcc actgtattcc agcctgggca    7620
acacagtgag accctatctg aaaaaataaa taaataaata aaaataaaag gtgaacgtgg    7680
cagcctggag gaggtgctat ggcattggga ctaatagaag gggctcacgg tgccaccagg    7740
tgagccctgg agctgggaga ggctgtggga tcccacccctt aaacctgcaa ttcacctctg    7800
ctcctgaccc tggcaagtga cttctgagcc tcagttttcc cttgtgtcat atgggtagaa    7860
taacagtccc tactcccagc ccaaggattg tggaaagtgc ctggctcata gtcagggctc    7920
aataaatctt caccactggg gtgatgatga tgagaagaat ttggtgtgac aggcttgata    7980
```

```
tcctgtgtca gcattagtct gtgtcagctt tgacttcaca tctccttgtc agcctcacag      8040
gccctctacc tccttcctta tggttccccc cagacacacc ctcagcctcc cttggaccct      8100
ccctaggtct gccccccacg tccactgctg taggaggaca gcccttctgc ttgcacccag      8160
gcccagcccc ggggtgctct tgctgggcac tcctgcaccc cacccatcag ggcctctcct      8220
tgcagttccc cagcccctc tgcaagaatg gcctccactg ctcttctgct cctccctcc        8280 tctctacaca gctggggcca cctggtgctc cctggggaggc agggattgag aaatgcacat     8340
tgtgtcattg gcccagggcc acaggtcagc cccagggggct cagccagaga agccaaagca    8400
gccttcttcc caagctcccc ggctgcaccc ggcctgccgc cagctccctg aattcccagg      8460
ccagttggaa gccaggccct ggtcaaacag accccagggc gccagcctgc tttccgcacc      8520
cagaagctct gacccccatgc ggggactacc gctgaccccct ccagcggcag cttccttcct   8580
tccttcctgc tccgagctct tcccctctct cctgtgtcct gggcctgccc gctggaaggc     8640
ctgcctctta gatccttgat acagttgcat ccttgcaact gctgtgacag gcagggtgtg     8700
acccactgct ctgtttccca caagacgaac ctgaggttca gagacgctag gagactttt      8760 caaggccaca cagcctagca aggattcagc cctagaccta cgtagccctg gtccagtgct     8820
gcttgtcctg cacctgcctc tgcatgctcc ctcgtgcagt tggagggcag cctcttcacc    8880
ccgtctgctg cccttacaga caacgcctct gacaaggacc tggccgacct ggtctcggag     8940
atggaggtga tgaagctgat cggccgacac aagaacatca tcaacctgct tggtgtctgc    9000
acccaggaag gtggggccga ggcggggctg gctgcacggg ccgttagggt gcagagccaa    9060
agctttggca gcctctccac gctccctcca ctccctctgc agggcccctg tacgtgatcg    9120
tggagtgcgc cgccaaggga aacctgcggg agttcctgcg ggcccggcgc ccccaggcc     9180 ccgacctcag ccccgacggt cctcggagca gtgaggggcc gctctccttc ccagtcctgg    9240
tctcctgcgc ctaccaggtg gcccgaggca tgcagtatct ggagtcccgg aaggtacagg    9300
cgctagggct ctgagcccct ctcagtctct ccagctccac tctcaggcct gtggcattca    9360
atgtcccgac ttctccctct ctgctctttt tcatgacccc acctcagtgt ccccaggcat    9420
tcacgctttc ctgcattccc cactcgttcc tcacccttcc ccagaggggga gggggacgc    9480 aggagaaggc actccccgtt tctaaacctt gacctcctcc tctgtaaagt gggtggaggg    9540
cccctgcccc cgggcctgct gggggtggt gtgtgctcaa ctccaggcca ggtgtcctga     9600
ggcacccaag cccccgctcc ctgcagtgta tccaccggga cctggctgcc cgcaatgtgc    9660
tggtgactga ggacaatgtg atgaagattg ctgactttgg gctggcccgc ggcgtccacc    9720
acattgacta ctataagaaa accagcaacg tgagggagat ggggcagaac tggatggggg    9780
tggaggggca ctgggcccgg ggtggcaggc acgaggacct gtgggactct gcactgaggc    9840
cctctctccc ctccagggcc gcctgcctgt gaagtggatg gcgcccgagg ccttgtttga    9900
ccgggtgtac acacaccaga gtgacgtgtg agtcctgccg gcggtcactg tcctacccca   9960 caaaagggc aaggcactgc ccaaagtcac gtggccccag gagtcatgcg ctcgagggct    10020
ccttcagatt tggtctggga cccgagtggg cccagactcc aggaggagcc cattccccaa    10080
cagctgtggt gggtcatgtc tgtggggtcc ccgtcctag ccccggtcgt cgggagggcg     10140
ctgagccaca ctgagccctg gccctacctc caggtggtct tttgggatcc tgctatggga   10200
gatcttcacc ctcgggggct cccgtatcc tggcatcccg gtggaggagc tgttctcgct    10260
gctgcgggag ggacatcgga tggaccgacc cccacactgc cccccagagc tgtgaggcct    10320
caccctgccc tcgaccccac tttccagtcc tcctcctcct ctgccctgac catggcctca   10380
```

| | | | | | |
|---|---|---|---|---|---|
|gggtgtgtcc|cggccagaag|gacaacacta|acaacaactc|ctcgtcctcc|tcctcctctt|10440|
|cctcttcctc|ctcctcctct|tcctcctcct|cctcttcctc|ctcctcttcc|tcctcctcct|10500|
|cttcctcctc|ctcctcttcc|tccttctcct|cctgctcctc|ttcctcctcc|ttctcttcct|10560|
|cctcctcctc|ttcctcctcc|tcctcttcct|cctcctcctc|ttcctccttc|tcctcctgct|10620|
|cctcttcctc|ctccttctct|tcctcctcct|tctcttcctc|ctcctcctcc|tgctcctctt|10680|
|cctcctcctc|ctcttcctcc|tcctcagcct|agtggagtgt|cctggcctgg|cttctactga|10740|
|tgaccctcct|atccctcatc|aaactcccca|ccaaactcct|ccccacccag|agaaccccg|10800|
|gtcctcccct|tcctcctgaa|ggcctgaggc|tccctgtgac|cctccgcccc|acctctcgca|10860|
|ggtacgggct|gatgcgtgag|tgctggcacg|cagcgccctc|ccagaggcct|accttcaagc|10920|
|agctggtgga|ggcgctggac|aaggtcctgc|tggccgtctc|tgaggaggta|cagcccctcc|10980|
|cacccaccac|ctccctctgc|ctgctcccct|ccaggcctca|tctggcctga|ccgcgtggac|11040|
|atgcgccccg|tccatcccg|ggcgctgcag|aggctgacca|gctccgttcc|ccacagtacc|11100|
|tcgacctccg|cctgaccttc|ggaccctatt|cccctctgg|tggggacgcc|agcagcacct|11160|
|gctcctccag|cgattctgtc|ttcagccacg|accccctgcc|attgggatcc|agctccttcc|11220|
|ccttcgggtc|tggggtgcag|acatgagcaa|ggctcaaggc|tgtgcaggca|cataggctgg|11280|
|tggccttggg|ccttggggct|cagccacagc|ctgacacagt|gctcgacctt|gatagcatgg|11340|
|ggcccctggc|ccagagttgc|tgtgccgtgt|ccaagggccg|tgcccttgcc|cttggagctg|11400|
|ccgtgcctgt|gtcctgatgg|cccaaatgtc|agggttctgc|tcggcttctt|ggaccttggc|11460|
|gcttagtccc|catcccgggt|ttggctgagc|ctggctggag|agctgctatg|ctaaacctcc|11520|
|tgcctcccaa|taccagcagg|aggttctggg|cctctgaacc|ccctttcccc|acacctcccc|11580|
|ctgctgctgc|tgccccagcg|tcttgacggg|agcattggcc|cctgagccca|gagaagctgg|11640|
|aagcctgccg|aaaacaggag|caaatggcgt|tttataaatt|attttttga|aataaagctc|11700|
|tgtgtgcctg|ggtcttccct|gagcaacatg|gagtggggtg|aggtggaggg|atccctccag|11760|
|cagagttctg|cctacaggac|acggactgag|ggcactggac|caggccatgg|gctccgccac|11820|
|ctccactgcc|ccaggagcca|gtgtgtgcct|atctgggtcc|gcctgtccca|ccagccccat|11880|
|cttgtgtctg|cgacagtgtg|aatgagtatt|aatgggctga|gtccgcattg|cactatacac|11940|
|ggtgggactc|ctgtaccctc|tgcacatgtg|tgtgtgtgca|tgtgtgccct|gcagctgtcc|12000|
|ccaagggagc|tggcagcccc|cctcccccat|ctgctcagca|ttaaccaagc|tgaccgttaa|12060|
|cacagcatga|aaatctgaga|gccagcctta|ggccgcggcc|cgctcccacg|ctctgccggc|12120|
|tcaggctggg|ggcttgtgga|ggccatgccc|gccccgccct|ggccagtctc|ccgggcagca|12180|
|gctggttgcc|gcccgc| | | | |12196|

<210> SEQ ID NO 8
<211> LENGTH: 12041
<212> TYPE: DNA
<213> ORGANISM: H. Sapeins

<400> SEQUENCE: 8

| | | | | | |
|---|---|---|---|---|---|
|caggggagcc|aggcattccc|tgaagggtga|aaagcaagga|gtagagctgg|gtagtagact|60|
|agaatttagg|agcctggcct|ggggcctggg|tggggcgaaa|gaggcggagc|ctgaatgggg|120|
|tgtgtatagg|ggggttgcgt|gtagggtgt|gtgtataggc|tggggcgggg|tcccgggagt|180|
|gggctgactg|ggtcggggggc|ggggctctcc|aggtgggcgg|ggatcttggc|cacccctggc|240|

```
cacacctctc tccggctcga gctggtctag gcggggcggg cccgaggggg tgtggcagga    300
ggtgggcggg cccgggtggg ggggggggg  gcgtggaagg agggcgggc  ccgagcagga    360
ggggcgggc  ccgaggggcg gggtgggaca ggaggtgggc cgctcgcggc cacgccgccg    420
tcgcgggtac attcctcgct cccggccgag gagcgctcgg gctgtctgcg gaccctgccg    480
cgtgcagggg tcgcggccgg ctggagctgg gagtgaggcg gcggaggagc caggtgagga    540
ggagccaggt gagcaggacc ctgtgctggg cgcggagtca cgcaggctcg aggtgagccg    600
gaaccttgt  gggcccgggc tgcgctccca gccgccaggg ggcgagaggc ggcggggcta    660
cggggactgc ccctcccggc gcaggggacc tgggcgtccg ccgggcggca ggggtggag     720
ggggcggtaa atcagtaacc cgcagtgcac acagggcctt ttgtcccgct ccgtccaaag    780
agcaccccgg ccgcggagct ggttactcat tgcccaccga ggcgggggca ggctggccct    840
gtgcagctac cctcgggacc cattgattcg cacctccccc caggctggcc cggcaagggt    900
ggggaggac  aagcgcgctt gtccctgcgg ctgtcttcgc gccggcggca gagatgaggg    960
acctgaggcc ccgaaaagtt cagtcactta gtgcccgggg gcctccagcg cgagtgcggg   1020
aggctgaagg agaacccagg actgtctgat gcctaaggca ggccctccat tcccacgtgg   1080
ggggtggtcg gtcagcggtc agcagccatg ggtgactcga ctaaggactc tgatatcagg   1140
gcagcctggg gtaggaataa actccccggg cctccccacc cactcccagc ccaagctgtg   1200
tacccaaaga gctgccctcc ctgccaagcc gagcttggta gggagtttta ccaaggagga   1260
tccgactgga ttcgagagtt gaggtgggcc agagacagca gtatctgagt caggtagaga   1320
agagcaatga ggggcacaga gggatgggca agagagcaca tgtgcccagt tttgaaagcc   1380
aatggcttca gcgctcctga agggcagac  ggtgtgacca agagatagg  cagcggcaga   1440
gagggagccc taggatgttg agctggatcc tgctgggcac aggtagccat taagggcttg   1500
caagctgggg ggcatgacat ggcagacttg caggttttt  tgtttgtttt tttatttat    1560
tttattttt  tattttgttt ttttgagac  ggagtctcac tctgtcgccc aggctggagt   1620
gcagtggcgc gatctcggct cactgcaagc tccgcctccc gggttcgcgc cattctcctg   1680
cctcagcctc ccgagtagct gggactacag gcgcccgcca ccgcgccgg  ctaatttttt   1740
gtatttttag tagagacggg gtttcaccgt gttagccagg atgttctcga tctcctgacc   1800
tcgtgatccg cccacctcgg cctcccaaag tgctgggatt acaggtgtga accatcgcgc   1860
ccagccgact tgtagttttt taaaactctg ctggaagatg aaggttgaag agccgaggga   1920
gaggatgttt ccagaggccc atgcaagaga tggccatgac ctgccttgag aaggggcagg   1980
ggaagccaga tggactggaa gtggagtggc agtgaccaag gaggaggagg tgtgataggc   2040
ttcccacgca gggtagatcc agagacacca gtgccaccca taggccccta ggactgcagt   2100
ggtcaccgat tcctttgtcc cagctgagac tcagttctga gtgttctatt ttggggaaca   2160
gaggcgtcct tggtagcatt tggaagagga tagccagctg gggtgtgtgt acatcacagc   2220
ctgacagtaa cagcatccga accagaggtg actggctaag gcagaccca  gggcaacagg   2280
ttaaccgttc tagggccggg cacagggagg agaacattcc aacactctgc gtgccgacgc   2340
acgttctctc ttttatcctc aaaacagtcc tatgaggata gtaagccaga gagagacaga   2400
gacaaggaat tacaagttgg tgagagtcag gatttgaact tggctctggc agatggaaaa   2460
ttagggtctg tattctttac aaaaccgtgt gtgcctcaga tggagttggt gcataacaag   2520
cagaggtatc cagggtcgcg gtcctgcttg ccacggaagg ggccgccttg tcagttgtga   2580
ccacccagcc ctggaaatgt cagtaatgct gtaaggagtg gggatcggat cagatgccat   2640
```

-continued

```
ccagatgctg aagtttgacc ttgtgtcatt tttcactttc ttttttggct cttctgcaat    2700
caattcattt atttagcaaa aaagaaatta tgtgtgccga gagcatgcag aagatatgtc    2760
tccgttctct gcttccctcc aaaaaagaat cccaaaactg ctttctgtga acgtgtgcca    2820
gggtcccagc aggactcagg gagagcagga agcccagccc agaccccttg cacaacctac    2880
cgtggggagg ccttaggctc tggctactac agagctggtt ccagtctgca ctgccacagc    2940
ctggccaggg acttggacac atctgctggc cacttcctgt ctcagtttcc ttatctgcaa    3000
aataagggaa aagccccac aaaggtgcac gtgtagcagg agctctttc cctccctatt     3060 ttaggaaggc agttggtggg aagtccagct tgggtccctg agagctgtga aaggagatg     3120 cggctgctgc tggcccctgtt gggggtcctg ctgagtgtgc ctgggcctcc agtcttgtcc   3180
ctggaggcct ctgaggaagt ggagcttggt atggcttctg aggtgggaga gggtggcagg   3240
ggtgggaaga gtgggcacca ggaggggct gctgggctga gcaaagctgg aaaggatcct    3300
tgcccaggcc ctgagaaggt ggcggcaggg cagggctcaa ccactgagac tcagtcagtg   3360
cctggcttcc agcaagcatt catctatcac tgtgtctgcg agagaggact ggccttgcag   3420
ggcgcagggc cctaagctgg gctgcagagc tggtggtgag ctccttacct gggtgtgtgt   3480
gcgtgtgtgt gtgtgttctg tgcactgggt gtgtgaccta ggaggtccag gcagcatgtg   3540
tggtataagc attatgaggg tgatatgccc cggtgcagca tgaccctgta tgtggcacca   3600
acagcatgtg ccttgtgtgt gtgtgtgtcc gtatgtgtgt gtgtgtatgc gtgtgtgtgt   3660
gtgtgtgtgt cttggccact gtcgtgtgca ctaaatgctg tgtgtgtgac atgccccaag   3720
agtgtggcat ttgccctggg tgtggcatcc gcagcatgtg gctgtgtggg tgtcaaggag   3780
tggtggctcc ttcagcatgc gttgcaaagt gcttgtgccc tgcatgtgcg gtgtgttctt   3840
tgtacacagg aggctgcctc agatgggct gcggggtctg ctgacctctg ccctctgccc    3900
acagagccct gcctggctcc cagcctggag cagcaagagc aggagctgac agtagccctt   3960
gggcagcctg tgcgtctgtg ctgtgggcgg gctgagcgtg gtggccactg gtacaaggag   4020
ggcagtcgcc tggcacctgc tggccgtgta cggggctgga ggggccgcct agagattgcc   4080
agcttcctac ctgaggatgc tggccgctac ctctgcctgg cacgaggctc catgatcgtc   4140
ctgcagaatc tcaccttgat tacaggtggt aagagactct agcagggagt gaagggatgc   4200
ctggggagac agacctgccc ctcttggacc ttagatgctt ccctctgtcc ctgatgtaga   4260
ctccttgacc tccagcaacg atgatgagga ccccaagtcc catagggacc cctcgaatag   4320
gcacagttac ccccagcaag gtcagtaggt ctccaaggac ttgtgtcccc gctgctgctc   4380
atctgatcac tgagaagagg aggcctgtgt gggaacacac ggtcattcta ggggccttcc   4440
cctgccctcc agcaccctac tggacacacc ccagcgcat ggagaagaaa ctgcatgcag    4500
tacctgcggg gaacaccgtc aagttccgct gtccagctgc aggcaacccc acgcccacca   4560
tccgctggct taaggatgga caggcctttc atggggagaa ccgcattgga ggcattcggg   4620
tgagtctctg ggttccaaga ccgtctgctc ccccatttc attccttcat cagtcccctc    4680
atacctacaa gcatacctat aaatcaatcg aatgagtgaa gcgattgcgg ggccccggaa   4740
ggagccctgg actgtggacc tgggcagctc tggttcccct tctgctactc tctgcaagt    4800 gacttaacct ctcagcctca gcaactccat ttgtaaaggg agaagaatca ctgactggtt   4860
ggtctgcata agccttagca tctcatcgtc ttgatgagac cctgcagggt cggctccatg   4920
ctgtcatgag gcaactgagt ctcagagaag gcaagggttg gctcaaagta gcacagctag   4980
```

```
ggagagggag agctaaaatt ccaaaggctc aaacccaagg ctcaagcgcc ctggggagcc    5040
tactcctttg tgccatagtc cttggcctgg gcctgatgtt ctcagggcct agagagcttg    5100
acaagagccc tgtgggcagg atgaggatct agcctcctgg tcctctggcc cccttggtgg    5160
acatggtccg gtggtcccgg acactctctc tgcctgcagc tgcgccatca gcactggagt    5220
ctcgtgatgg agagcgtggt gccctcggac cgcggcacat acacctgcct ggtagagaac    5280
gctgtgggca gcatccgcta taactacctg ctagatgtgc tgggtgagcg cggggctggg    5340
aacaggggag gcctgaccca ttttgggctc agttgtgccc tcttggtggg gtctagtctg    5400
gcaggcagga tggactcaga tgagtcaggc agcttggtga gcaggtgggt caggggaaag    5460
cacaggggtt agtgtggggc tggaggagca gaggtctgcc aagaggaaaa acaagaagga    5520
catccaggca gagggcgcag cccgagcgga gggcctgagt ataacaaacg ccctgcactt    5580
gcaggccagc atattcgtag ggcgtggcgt ttatatgggg agccaggtgg tggagggttt    5640
tgaatgctag gctgagatgt tgtccttgac ccgaagcaat agggagccag gaaaggttta    5700
agcagggtaa gcaggagaca gacaagaagc tgcagaaagg tccctcccTt gaacttgagg    5760
aaggctggag ggaggcaaac agggtgcttc tatgggtgcc ggtggtcagg gttgactgtc    5820
tcgcccggtc cccagagcgg tccccgcacc ggcccatcct gcaggccggg ctcccggcca    5880
acaccacagc cgtggtgggc agcgacgtgg agctgctgtg caaggtgtac agcgatgccc    5940
agccccacat ccagtggctg aagcacatcg tcatcaacgg cagcagcttc ggagccgacg    6000
gtttccccta tgtgcaagtc ctaaaggtaa aaggtgcacc ctgctgcagc ctgggcccca    6060
ttcttctccc accttgggtt gggggggctcc ccagcttccc tgttggccac agtgtggccc    6120
caggccctgc tgtgacccca gagcatgtcc cccacccccag actgcagaca tcaatagctc    6180
agaggtggag gtcctgtacc tgcggaacgt gtcagccgag gacgcaggcg agtacacctg    6240
cctcgcaggc aattccatcg gcctctccta ccagtctgcc tggctcacgg tgctgccagg    6300
tgagcacctg aagggccagg agatgctgcg agatgcccct ctgggccagc agtgggggct    6360
gtggcctgtt gggtggtcag tctctgttgg cctgtggggt ctggcctggg gggcagtgtg    6420
tggatttgtg ggtttgagct gtatgacagc ccctctgtgc ctctccacac gtggccgtcc    6480
atgtgaccgt ctgctgaggt gtgggtgcct gggactgggc ataactacag cttcctccgt    6540
gtgtgtcccc acatatgttg ggagctggga gggactgagt tagggtgcac ggggcggcca    6600
gtctcaccac tgaccagttt gtctgtctgt gtgtgtccat gtgcgagggc agaggaggac    6660
cccacatgga ccgcagcagc gcccgaggcc aggtatacgg acatcatcct gtacgcgtcg    6720
ggctccctgg ccttggctgt gctcctgctg ctggccgggc tgtatcgagg gcaggcgctc    6780 cacgccggc acccccgccc gcccgccact gtgcagaagc tctcccgctt ccctctggcc    6840
cgacaggtac tgggcgcatc ccccacctca catgtgacag cctgactcca gcaggcagaa    6900
ccaagtctcc cactttgcag ttctccctgg agtcaggctc ttccggcaag tcaagctcat    6960
ccctggtacg aggcgtgcgt ctctcctcca gcggccccgc cttgctcgcc ggcctcgtga    7020
gtctagatct acctctcgac ccactatggg agttcccccg gacaggtgc gctgagctgt    7080 gtggggggcag gacgcgggc gccgggttgc agcccgccct ccgcaggagt gactcggagg    7140
tctgaggctg gactttctcc atctccaggc tggtgcttgg gaagccccta ggcgagggct    7200
gctttggcca ggtagtacgt gcagaggcct ttggcatgga ccctgcccgg cctgaccaag    7260
ccagcactgt ggccgtcaag atgctcaaag gtgagtgtgg cccggtgtgg tggctcacac    7320
ctgtaacgcc agcactttag gaggctgagg gtgggaggat cgcttgaatc caggaattcg    7380
```

```
aggccagcct gggcaacatg gcaagacttc atctctacaa aaaaaaaata agaaaattag   7440
ttgggtgtgg tggtgtgtgc ctttagtctc agttactagg gaggctgagg caggaggatc   7500
ccttgaatcc aggagttgga ggttgcaggg agccatgatc acgccactgt attccagcct   7560
gggcaacaca gtgagaccct atctgaaaaa ataaataaat aaataaaaat aaaaggtgaa   7620
cgtggcagcc tggaggaggt gctatggcat tgggactaat agaaggggct cacggtgcca   7680
ccaggtgagc cctggagctg ggagaggctg tgggatccca cccttaaacc tgcaattcac   7740
ctctgctcct gaccctggca agtgacttct gagcctcagt tttcccttgt gtcatatggg   7800
gtagataaca gtccctactc ccagcccaag gattgtggaa agtgcctggc tcatagtcag   7860
ggctcaataa atcttcacca ctggggtgat gatgatgaga agaatttggt gtgacaggct   7920
tgatatcctg tgtcagcatt agtctgtgtc agctttgact tcacatctcc ttgtcagcct   7980
cacaggccct ctacctcctt ccttatggtt ccccccagac acaccctcag cctcccttgg   8040
accctcccta ggtctgcccc ccacgtccac tgctgtagga ggacagccct tctgcttgca   8100
cccaggccca gccccggggt gctcttgctg ggcactcctg caccccaccc atcagggcct   8160
ctccttgcag ttccccagcc ccctctgcaa gaatggcctc cactgctctt ctgctcctcc   8220
cctcctctct acacagctgg ggccacctgg tgctccctgg gaggcaggga ttgagaaatg   8280
cacattgtgt cattggccca gggccacagg tcagccccag gggctcagcc agagaagcca   8340
aagcagcctt cttcccaagc tccccggctg caccccggcct gccgccagct ccctgaattc   8400
ccaggccagt tggaagccag gccctggtca aacagacccc agggcgccag cctgcttcc    8460 gcacccagaa gctctgaccc catgcgggga ctaccgctga cccctccagc ggcagcttcc   8520
ttccttcctt cctgctccga gctcttcccc tctctcctgt gtcctgggcc tgcccgctgg   8580
aaggcctgcc tcttagatcc ttgatacagt tgcatccttg caactgctgt gacaggcagg   8640
gtgtgaccca ctgctctgtt tcccacaaga cgaacctgag gttcagagac gctaggagac   8700
tttttcaagg ccacacagcc tagcaaggat tcagccctag acctacgtag ccctggtcca   8760
gtgctgcttg tcctgcacct gcctctgcat gctccctcgt gcagttggag ggcagcctct   8820
tcaccccgtc tgctgcccTT acagacaacg cctctgacaa ggacctggcc gacctggtct   8880
cggagatgga ggtgatgaag ctgatcggcc gacacaagaa catcatcaac ctgcttggtg   8940
tctgcaccca ggaaggtggg gccgaggcgg ggctggctgc acgggccgtt agggtgcaga   9000
gccaaagctt tggcagcctc tccacgctcc ctccactccc tctgcagggc ccctgtacgt   9060
gatcgtggag tgcgccgcca agggaaacct gcgggagttc ctgcgggccc ggcgcccccc   9120
aggccccgac ctcagccccg acggtcctcg gagcagtgag gggccgctct ccttcccagt   9180
cctggtctcc tgcgcctacc agtgtggccg aggcatgcag tatctggagt cccggaaggt   9240
acaggcgcta gggctctgag cccctctcag tctctccagc tccactctca ggcctgtggc   9300
attcaatgtc ccgacttctc cctctctgct cttttttcatg accccacctc agtgtccca   9360 ggcattcacg ctttcctgca ttccccactc gttcctcacc cttccccaga ggggagaggg   9420
gacgcaggag aaggcactcc ccgtttctaa accttgacct cctcctctgt aaagtgggtg   9480
gagggcccct gccccgggc ctgctggggg gtggtgtgtg ctcaactcca ggccaggtgt   9540
cctgaggcac ccaagccccc gctccctgca gtgtatccac cgggacctgg ctgcccgcaa   9600
tgtgctggtg actgaggaca atgtgatgaa gattgctgac tttgggctgg cccgcggcgt   9660
ccaccacatt gactactata agaaaaccag caacgtgagg gagatggggc agaactggat   9720
```

```
gggggtggag gggcactggg cccggggtgg caggcacgag gacctgtggg actctgcact    9780
gaggccctct ctcccctcca gggccgcctg cctgtgaagt ggatggcgcc cgaggccttg    9840
tttgaccggg tgtacacaca ccagagtgac gtgtgagtcc tgccggcggt cactgtccta    9900
ccccacaaaa agggcaaggc actgcccaaa gtcacgtggc cccaggagtc atgcgctcga    9960
gggctccttc agatttggtc tgggacccga gtgggcccag actccaggag gagcccattc   10020
cccaacagct gtggtgggtc atgtctgtgg ggtcccccgt cctagccccg gtcgtcggga   10080
gggcgctgag ccacactgag ccctggccct acctccaggt ggtcttttgg gatcctgcta   10140
tgggagatct tcaccctcgg gggctccccg tatcctggca tcccggtgga ggagctgttc   10200
tcgctgctgc gggagggaca tcggatggac cgaccccccac actgcccccc agagctgtga   10260
ggcctcaccc tgccctcgac cccactttcc agtcctcctc ctcctctgcc ctgaccatgg   10320
cctcagggtg tgtcccggcc agaaggacaa cactaacaac aactcctcgt cctcctcctc   10380
ctcttcctct tcctcctcct cctcttcctc ctccctcctct tcctcctcct cttcctcctc   10440
ctcctcttcc tcctcctcct cttcctcctt ctcctcctgc tcctcttcct cctccttctc   10500
ttcctcctcc tcctcttcct cctcctcctc ttcctcctcc tcctcttcct cctttctcctc   10560
ctgctcctct tcctcctcct tctcttcctc ctccttctct tcctcctcct cctcctgctc   10620
ctcttcctcc tcctcctctt cctcctcctc agcctagtgg agtgtcctgg cctggcttct   10680
actgatgacc ctcctatccc tcatcaaact ccccaccaaa ctcctcccca cccagagaac   10740
ccccggtcct cccccttcctc ctgaaggcct gaggctccct gtgaccctcc gccccacctc   10800
tcgcaggtac gggctgatgc gtgagtgctg gcacgcagcg ccctcccaga ggcctacctt   10860
caagcagctg gtggaggcgc tggacaaggt cctgctggcc gtctctgagg aggtacagcc   10920
cctcccaccc accacctccc tctgcctgct ccccctccagg cctcatctgg cctgaccgcg   10980
tggacatgcg ccccgtccca tcccgggcgc tgcagaggct gaccagctcc gttccccaca   11040
gtacctcgac ctccgcctga ccttcggacc ctattccccc tctggtgggg acgccagcag   11100
cacctgctcc tccagcgatt ctgtcttcag ccacgacccc ctgccattgg gatccagctc   11160
cttccccttc gggtctgggg tgcagacatg agcaaggctc aaggctgtgc aggcacatag   11220
gctggtggcc ttgggccttg gggctcagcc acagcctgac acagtgctcg accttgatag   11280
catggggccc ctgccccaga gttgctgtgc cgtgtccaag ggccgtgccc ttgcccttgg   11340
agctgccgtg cctgtgtcct gatggcccaa atgtcagggt tctgctcggc ttcttggacc   11400
ttggcgctta gtccccatcc cgggtttggc tgagcctggc tggagagctg ctatgctaaa   11460
cctcctgcct cccaatacca gcaggaggtt ctgggcctct gaaccccctt tccccacacc   11520
tccccctgct gctgctgccc cagcgtcttg acgggagcat tggcccctga gcccagagaa   11580
gctggaagcc tgccgaaaac aggagcaaat ggcgtttat aaattatttt tttgaaataa   11640
agctctgtgt gcctgggtct tccctgagca acatggagtg gggtgaggtg gagggatccc   11700
tccagcagag ttctgcctac aggacacgga ctgagggcac tggaccaggc catgggctcc   11760
gccacctcca ctgccccagg agccagtgtg tgcctatctg ggtccgcctg tcccaccagc   11820
cccatcttgt gtctgcgaca gtgtgaatga gtattaatgg gctgagtccg cattgcacta   11880
tacacggtgg gactcctgta ccctctgcac atgtgtgtgt gtgcatgtgt gccctgcagc   11940
tgtccccaag ggagctggca gccccctcc cccatctgct cagcattaac caagctgacc   12000
gttaacacag catgaaaatc tgagagccag ccttaggccg c                       12041
```

<210> SEQ ID NO 9
<211> LENGTH: 2844
<212> TYPE: DNA
<213> ORGANISM: Mus musculus

<400> SEQUENCE: 9

| | | | | | |
|---|---|---|---|---|---|
| gtggtcagtg | ggaagtctgg | ccctgatcct | gagatcagct | ggaaggaaat | gtggctgctc | 60 |
| ttggccctgt | tgagcatctt | tcaggggaca | ccagctttgt | cccttgaggc | ctctgaggaa | 120 |
| atggagcagg | agccctgcct | agccccaatc | ctggagcagc | aagagcaggt | gttgacggtg | 180 |
| gccctgggc | agcctgtgag | gctgtgctgt | gggcgcaccg | agcgtggtcg | tcactggtac | 240 |
| aaagagggca | gccgcctagc | atctgctggg | cgagtacggg | gttggagagg | ccgcctggag | 300 |
| atcgccagct | tccttcctga | ggatgctggc | cgatacctct | gcctggcccg | tggctccatg | 360 |
| accgtcgtac | acaatcttac | gttgcttatg | gatgactcct | taacctccat | cagtaatgat | 420 |
| gaagacccca | agacactcag | cagctcctcg | agtggtcatg | tctacccaca | gcaagcaccc | 480 |
| tactggacac | accccaacg | catggagaag | aaactgcatg | cagtgcctgc | cgggaatact | 540 |
| gtcaaattcc | gctgtccagc | tgcagggaac | cccatgccta | ccatccactg | gctcaaggat | 600 |
| ggacaggcct | tccacgggga | gaatcgtatt | ggaggcattc | ggctgcgcca | ccaacactgg | 660 |
| agcctggtga | tggaaagtgt | ggtaccctcg | gaccgtggca | catacacatg | ccttgtggag | 720 |
| aactctctgg | gtagcattcg | ctacagctat | ctcctggatg | tgctgagcg | gtccccgcac | 780 |
| cggcccatcc | tgcaggcggg | gctcccagcc | aacaccacag | ctgtggttgg | cagcgatgtg | 840 |
| gagctactct | gcaaggtgta | cagcgacgcc | cagccccaca | tacagtggct | gaaacacgtc | 900 |
| gtcatcaacg | gcagcagctt | cggcgccgac | ggtttcccct | acgtacaagt | cctgaagaca | 960 |
| acagacatca | atagctcgga | ggtagaggtc | ttgtatctga | ggaacgtgtc | cgctgaggat | 1020 |
| gcaggagagt | atacctgtct | ggcgggcaac | tccatcggcc | tttcctacca | gtcagcgtgg | 1080 |
| ctcacggtgc | tgccagagga | agacctcacg | tggacaacag | caaccctga | ggccagatac | 1140 |
| acagatatca | tcctgtatgt | atcaggctca | ctggttctgc | ttgtgctcct | gctgctggcc | 1200 |
| ggggtgtatc | atcggcaagt | catccgtggc | cactactctc | gccagcctgt | cactatacaa | 1260 |
| aagctgtccc | gtttccctt | ggcccgacag | ttctctttgg | agtcgaggtc | ctctggcaag | 1320 |
| tcaagtttgt | ccctggtgcg | aggtgtccgt | ctctcctcca | gcggcccgcc | cttgctcacg | 1380 |
| ggccttgtga | atctagacct | gcctctcgat | ccgctttggg | aattccccg | ggacaggttg | 1440 |
| gtgctcggaa | agcccctggg | tgagggctgc | tttgggcaag | tggttcgtgc | agaggccttt | 1500 |
| ggtatggatc | cctcccggcc | cgaccaaacc | agcaccgtgg | ctgtgaagat | gctgaaagac | 1560 |
| aatgcctccg | acaaggattt | ggcagacctg | gtctccgaga | tggaggtgat | gaagctaatc | 1620 |
| ggaagacaca | agaacatcat | caacctgctg | ggtgtctgca | ctcaggaagg | gcccctgtac | 1680 |
| gtgattgtgg | aatgtgccgc | caagggaaac | cttcgggaat | tcctccgtgc | ccggcgcccc | 1740 |
| ccaggccctg | atctcagccc | tgatggacct | cggagcagcg | aaggaccact | ctccttcccg | 1800 |
| gccctagtct | cctgtgccta | ccaggtggcc | cgaggcatgc | agtatctgga | gtctcggaag | 1860 |
| tgcatccacc | gggacctggc | tgcccgaaat | gtgctggtga | ccgaggatga | tgtgatgaag | 1920 |
| atcgctgact | ttgggctggc | acgtggtgtc | caccacattg | actactacaa | gaaaaccagc | 1980 |
| aacggccgcc | tgccagtcaa | atggatggct | ccagaggcat | tgttcgaccg | cgtgtacaca | 2040 |
| caccagagtg | acgtgtatgg | gctaatgagg | gagtgctggc | acgcagcccc | atctcagagg | 2100 |
| cctacttta | agcagctggt | ggaagctctg | gacaaggtcc | tgctggctgt | ctctgaagag | 2160 |

| | | | | |
|---|---|---|---|---|
| taccttgacc | tccgcctgac | ctttggaccc | ttttctccct | ccaatgggga tgccagcagc | 2220 |
| acctgctcct | ccagtgactc | ggttttcagc | cacgacccct | tgcccctcga gccaagcccc | 2280 |
| ttcccttct | ctgactcgca | gacgacatga | gccggggagc | agcaatgttg tatgggctac | 2340 |
| gcggcccatg | gccgtgggtc | tcctcgctga | gctgcaacct | gatgcatcga catttaatgt | 2400 |
| tggcagtgtc | aggcctctga | cttgagacta | ctgctgtcgc | agatcctctc tctggccctg | 2460 |
| ttttggggag | ggccattctt | ggtcctaagg | ttcatagttg | aggccttctg ttccagcctt | 2520 |
| atgcccccat | ctcagagttc | aactctcatc | tcaagatcat | ggccttgccc ttggactcat | 2580 |
| cctcagagaa | gttaagcatt | aaggcttggc | acgagcctcc | gtctccgggg ctctccggga | 2640 |
| ctagctgcaa | aacttatgct | ctaaacattt | ctagttcccc | caaacaacct agaggccttg | 2700 |
| ggacttcaca | tcccccagca | cacaagcctc | accacccct | gccatccccc ctccattgct | 2760 |
| tgttccagca | tcttggtgaa | aggggcatca | gctctggtgt | ccctgagaga cgagaagcct | 2820 |
| gtgggaacga | cagaagacat | ggca | | | 2844 |

<210> SEQ ID NO 10
<211> LENGTH: 3323
<212> TYPE: DNA
<213> ORGANISM: Mus musculus

<400> SEQUENCE: 10

| | | | | |
|---|---|---|---|---|
| cccacgcgtc | cggaacgact | gagactgggc | gatccagtcc | caacggggag ctcccgcact | 60 |
| agggtaccgg | gctgacattt | gccgggtctc | ggaccacgcc | tctcagatca gaagtggtcc | 120 |
| aggaggggcg | gagtccgagg | tgggcggggc | aggagggggc | agcccccgc cacgctgcag | 180 |
| ttgcagggac | attcctggct | cttcggcccg | gggcggagga | gctccgggcg ggtgagtgtg | 240 |
| ccagccctgc | cgggatcgtg | acccgcgcgc | gcggagccg | gcggcggag gagccaggaa | 300 |
| ggtggtcagt | gggaagtctg | gccctgatcc | tgagatcagc | tggaaggaaa tgtggctgct | 360 |
| cttggccctg | ttgagcatct | ttcagggac | accagctttg | tcccttgagg cctctgagga | 420 |
| aatggagcag | gagccctgcc | tagccccaat | cctggagcag | caagagcagg tgttgacggt | 480 |
| ggccctgggg | cagcctgtga | ggctgtgctg | tgggcgcacc | gagcgtggtc gtcactggta | 540 |
| caaagagggc | agccgcctag | catctgctgg | gcgagtacgg | ggttggagag gccgcctgga | 600 |
| gatcgccagc | ttccttcctg | aggatgctgg | ccgataccc | tgcctggccc gtggctccat | 660 |
| gaccgtcgta | cacaatctta | cgttgcttat | ggatgactcc | ttaacctcca tcagtaatga | 720 |
| tgaagacccc | aagacactca | gcagctcctc | gagtggtcat | gtctacccac agcaagcacc | 780 |
| ctactggaca | cacccccaac | gcatggagaa | gaaactgcat | gcagtgcctg ccgggaatac | 840 |
| tgtcaaattc | cgctgtccag | ctgcaggaa | ccccatgcct | accatccact ggctcaagga | 900 |
| tggacaggcc | ttccacgggg | agaatcgtat | tggaggcatt | cggctgcgcc accaacactg | 960 |
| gagcctggtg | atggaaagtg | tggtacccctc | ggaccgtggc | acatacacat gccttgtgga | 1020 |
| gaactctctg | ggtagcattc | gctacagcta | tctcctggat | gtgctggagc ggtccccgca | 1080 |
| ccggcccatc | ctgcaggcgg | ggctcccagc | caacaccaca | gctgtggttg gcagcgatgt | 1140 |
| ggagctactc | tgcaaggtgt | acagcgacgc | ccagccccac | atacagtggc tgaaacacgt | 1200 |
| cgtcatcaac | ggcagcagct | tcggcgccga | cggttttccc | tacgtacaag tcctgaagac | 1260 |
| aacagacatc | aatagctcgg | aggtagaggt | cttgtatctg | aggaacgtgt ccgctgagga | 1320 |
| tgcaggagag | tatacctgtc | tggcgggcaa | ctccatcggc | cttttcctacc agtcagcgtg | 1380 |
| gctcacggtg | ctgccagagg | aagacctcac | gtggacaaca | gcaacccctg aggccagata | 1440 |

| | |
|---|---|
| cacagatatc atcctgtatg tatcaggctc actggttctg cttgtgctcc tgctgctggc | 1500 |
| cggggtgtat catcggcaag tcatccgtgg ccactactct cgccagcctg tcactataca | 1560 |
| aaagctgtcc cgtttccctt tggcccgaca gttctctttg gagtcgaggt cctctggcaa | 1620 |
| gtcaagtttg tccctggtgc gaggtgtccg tctctcctcc agcggcccgc ccttgctcac | 1680 |
| gggccttgtg aatctagacc tgcctctcga tccgctttgg gaattccccc gggacaggtt | 1740 |
| ggtgctcgga aagcccctgg gtgagggctg ctttgggcaa gtggttcgtg cagaggcctt | 1800 |
| tggtatggat ccctcccggc ccgaccaaac cagcaccgtg gctgtgaaga tgctgaaaga | 1860 |
| caatgcctcc gacaaggatt tggcagacct ggtctccgag atggaggtga tgaagctaat | 1920 |
| cggaagacac aagaacatca tcaacctgct gggtgtctgc actcaggaag gccccctgta | 1980 |
| cgtgattgtg aatgtgccg ccaagggaaa tcttcgggaa ttcctccgtg cccggcgccc | 2040 |
| cccaggccct gatctcagcc ctgatggacc tcggagcagc gaaggaccac tctccttccc | 2100 |
| ggccctagtc tcctgtgcct accaggtggc ccgaggcatg cagtatctgg agtctcggaa | 2160 |
| gtgcatccac cgggacctgg ctgcccgaaa tgtgctggtg accgaggatg atgtgatgaa | 2220 |
| gatcgctgac tttgggctgg cacgtggtgt ccaccacatt gactactata agaaaaccag | 2280 |
| caacggccgc ctgccagtca atggatggc tccagaggcg ttgttcgacc gtgtgtacac | 2340 |
| acaccagagt gacgtgtggt ctttcgggat cctgctgtgg gaaatcttca ccctcggggg | 2400 |
| ctccccatac cctggcattc cggtggagga gctcttctca ctgctgcgag aggggcacag | 2460 |
| gatggagcgg cccccaaact gcccctcaga gctgtatggg ctaatgaggg agtgctggca | 2520 |
| cgcagtccca tctcagaggc ctacttttaa gcagctggtg aagctctgg acaaggtcct | 2580 |
| gctggctgtc tctgaagagt accttgacct ccgcctgacc tttggaccct tttctccctc | 2640 |
| caatgggat gccagcagca cctgctcctc cagtgactcg gttttcagcc acgaccctt | 2700 |
| gccccctcgag ccaagcccct tccctttctc tgactcgcag acgacatgag ccggggagca | 2760 |
| gcaattttgt atgggctacg cggcccatgg ccgtgggtct cctcgctgag ctgcaacctg | 2820 |
| atgcatcgac atttaatgtt ggcagtgtca ggcctctgac ttgagactac tgctgtcgca | 2880 |
| gatcctctct ctggccctgt tttggggagg gccattcttg gtcctaaggt tcatagttga | 2940 |
| ggccttctgt tccagcctta tgctcccatc tcagagttca actctcatct caagatcatg | 3000 |
| gccttgccct tggactcatc ctcagagaag ttaagcatta aggccttggc acgcagcctc | 3060 |
| cgtctccggg gctctccggg cctagctgca aaacttatgc tctaaacatt tctagttccc | 3120 |
| ccaaacaacc tagaggcctt gggacttcac atccccagc acacaagcct caccacccc | 3180 |
| tgccatcccc cctccattgc ttgttccagc atcttggtga aggggcatc agctctggtg | 3240 |
| tccctgagag acgggaagcc tgtgggaacg acagaagaac atggcatttt tataaattat | 3300 |
| tttttttgaaa aaaaaaaaaa aaa | 3323 |

<210> SEQ ID NO 11
<211> LENGTH: 591
<212> TYPE: DNA
<213> ORGANISM: Mus musculus

<400> SEQUENCE: 11

| | |
|---|---|
| gcaggattgt tgtgtcccgt gtgtgtagca tgttctctgt gtgcggggtg ggggtgggggg | 60 |
| gcactagcct ccgatggagc tatgggtatc aatgactcct gccatctgcc ctcagagccc | 120 |
| tgcctagccc caatcctgga gcagcaagag caggtgttga cggtgccct ggggcagcct | 180 |

| | |
|---|---|
| gtgaggctgt gctgtgggcg caccgagcgt ggtcgtcact ggtacaaaga gggcagccgc | 240 |
| ctagcatctg ctgggcgagt acggggttgg agaggccgcc tggagatcgc cagcttcctt | 300 |
| cctgaggatg ctggccgata cctctgcctg gcccgtggct ccatgaccgt cgtacacaat | 360 |
| cttacgttgc ttatggatga ctccttaacc tccatcagta atgatgaaga ccccaagaca | 420 |
| ctcagcagct cctcgagtgg tcatgtctac ccacagcaag caccctactg gacacacccc | 480 |
| caacgcatgg agaagaaact gcatgcagtg cctgccggga atactgtcaa attccgctgt | 540 |
| ccagctgcag gaaccccat gcctaccatc cactggctca aggatggaca g | 591 |

<210> SEQ ID NO 12
<211> LENGTH: 3098
<212> TYPE: DNA
<213> ORGANISM: Mus musculus

<400> SEQUENCE: 12

| | |
|---|---|
| ccctgccggg atcgtgaccc gcgcgcgcgg gagccgggcg gcggaggagc caggaaggtg | 60 |
| gtcagtggga agtctggccc tgatcctaga tcagctggaa ggaaatgtgg ctgctcttgg | 120 |
| ccctgttgag catcttttcag gggacaccag cttttgtccct tgaggcctct gaggaaatgg | 180 |
| agcaggagcc ctgcctagcc ccaatcctgg agcagcaaga gcaggtgttg acggtggccc | 240 |
| tggggcagcc tgtgaggctg tgctgtgggc gcaccgagcg tggtcgtcac tggtacaaag | 300 |
| agggcagccg cctagcatct gctgggcgag tacggggttg gagaggccgc ctggagatcg | 360 |
| ccagcttcct tcctgaggat gctggccgat acctctgcct ggcccgtggc tccatgaccg | 420 |
| tcgtacacaa tcttacgttg cttatggatg actccttaac ctccatcagt aatgatgaag | 480 |
| accccaagac actcagcagc tcctcgagtg gtcatgtcta cccacagcaa gcaccctact | 540 |
| ggacacaccc caacgcatg gagaagaaac tgcatgcagt gcctgccggg aatactgtca | 600 |
| aattccgctg tccagcctgc aggaaccca tgcctaccat ccactggctc aaggatggac | 660 |
| aggccttcca cggggagaat cgtattgag gcattcggct gcgccaccaa cactggagcc | 720 |
| tggtgatgga aagtgtggta ccctcggacc gcggcacata cacatgcctt gtggagaact | 780 |
| ctctgggtag cattcgctac agctatctcc tggatgtgct ggagcggtcc ccgcaccggc | 840 |
| ccatcctgca ggcggggctc ccagccaaca ccacagctgt ggttggcagc gatgtggagc | 900 |
| tactctgcaa ggtgtacagc gacgcccagc cccacataca gtggctgaaa cacgtcgtca | 960 |
| tcaacggcag cagcttcggc gccgacggtt tcccctacgt acaagtcctg aagacaacag | 1020 |
| acatcaatat ctcggaggta caggtcttgt atctgaggaa cgtgtccgct gaggatgcag | 1080 |
| gagagtatac ctgtctggcg ggcaactcca tcggcctttc ctaccagtca gcgtggctca | 1140 |
| cggtgctgcc agaggaagac ctcacgtgga acaacagcaac ccctgaggcc agatacacag | 1200 |
| atatcatcct gtatgtatca ggctcactgg ttctgcttgt gctcctgctg ctggccgggg | 1260 |
| tgtatcatcg gcaagtcatc cgtggccact actctcgcca gcctgtcact atacaaaagc | 1320 |
| tgtcccgttt cccttttggcc cgacagttct cttttggagtc gaggtcctct ggcaagtcaa | 1380 |
| gtttgtccct ggtgcgaggt gtccgtctct cctccagcgg cccgcccttg ctcacgggcc | 1440 |
| ttgtgaatct agacctgcct ctcgatccgc tttgggaatt cccccgggac aggttggtgc | 1500 |
| tcggaaagcc cctgggtgag ggctgctttg gcaagtggt tcgtgcagag gcctttgggc | 1560 |
| aagtggttcg tgcagaggcc tttggtatgg atccctcccg gcccgaccaa accagcaccg | 1620 |
| tggctgtgaa gatgctgaaa gacaatgcct ccgacaagga tttggcagac ctggtctccg | 1680 |
| agatggaggt gatgaagcta atcggaagac acaagaacat catcaacctg ctgggtgtct | 1740 |

```
gcactcagga agggcccctg tacgtgattg tggaatgtgc cgccaaggga aaccttcggg    1800
aattcctccg tgcccggcgc cccccaggcc ctgatctcag ccctgatgga cctcggagca    1860
gcgaaggacc actctccttc ccggccctag tctcctgtgc ctaccaggtg gcccgaggca    1920
tgcagtatct ggagtctcgg aagtgcatcc accgggacct ggctgcccga aatgtgctgg    1980
tgaccgagga tgatgtgatg aagatcgctg actttgggct ggcacgtggt gtccaccaca    2040
ttgactacta taagaaaacc agcaacggcc gcctgccagt caaatggatg gctccagagg    2100
cattgttcga ccgcgtgtac acacaccaga gtgacgtgtg gtctttcgag atcctgctgt    2160
gggaaatctt caccctcggg ggctccccat accctggcat tccggtggag gagctcttct    2220
cactgctgcg agaggggcac aggatggagc ggccccaaa ctgcccctca gagctgtatg    2280
ggctaatgag ggagtgctgg cacgcagccc catctcagag gcctactttt aagcagctgg    2340
tggaagctct ggacaaggtc ctgctggctg tctctgaaga gtaccttgac ctccgcctga    2400
cctttggacc cttttctccc tccaatgggg atgccagcag cacctgctcc tccagtgact    2460
cggttttcag ccacgaccct tgcccctcg agccaagccc cttcccttc tctgactcgc    2520 agacgacatg agccggggag cagcaatgtt gtatgggcta cgcggcccat ggcgtgggtc    2580
tcctcgctga gctgcaacct gatgcatcga catttaatgt tggcagcgtc aggcctctga    2640
cttgagacta ctgctgtcgc agatcctctc tctggccctg ttttggggag ggccattctt    2700
ggtcctaagg ttcatagttg aggccttctg ttccagcctt atgccccat ctcagagttc    2760 aactctcatc tcaagatcat ggccttgccc ttggactcat cctcagagaa gttaagcatt    2820
aaggcttggc acgagcctcc gtctccgggg ctctccggga ctagctgcaa aacttatgct    2880
ctaaacattt ctagttcccc caaacaacct agaggcttg ggacttcaca tcccccagca    2940
cacaagcctc accaccccct gccatccccc ctccattgct tgttccagca tcttggtgaa    3000
aggggcatca gctctggtgt ccctgagaga cgagaagcct gtgggaacga cagaagacat    3060 ggcatttta taaattattt ttttgaaata aaaaaaaa                              3098

<210> SEQ ID NO 13
<211> LENGTH: 9816
<212> TYPE: DNA
<213> ORGANISM: Mus musculus

<400> SEQUENCE: 13
gttctagaac tcactctgta gaccaggctg gcctcgaact cagaaaccca cctgcctctg      60
cctccccagt gcgccgccgc caccccgacc gaccgagata tattttaaat atcctctgaa     120
ggtcgctcag gccaaggaga ggtcaggtct ctctgatgtt ctgtgatttc acggaaaacc     180
agagagcctg tgagtgcca aattgaggaa gagcaaagga tagagcaagg tagcaagtta     240
gaccttgcag gttggacgtg ggccccggga acgactgaga ctgggcgatc cagtcccaac     300
ggggagctcc cgcactaggg taccgggctg acatttgccg gtctcggac cacgcctctc     360 agatcagaag tggtccagga ggggcggagt ccgaggtggg cggggcagga gggggcagcc     420
ccccgccacg ctgcagttgc agggacattc ctggctcttc ggcccggggc ggaggagctc     480
cgggcgggtg agtgtgccag ccctgccggg atcgtgaccc gcgcgcgcgg gagccgggcg     540
gcggaggagc caggtgagcc gggccccctgc gccgggagcg gagccctcta gctctgggcc     600
agttgggcca cacaccgtac tcccggccgc cgtggggaca gcggccgtgg agctcccgag     660
ctgccccctc tgtcccgggg accttggcgc ccgcgcggcg ggagtggttg ggtggagggg     720
```

```
gcggtaaatc agtaacccgc agcgcacaca gggccttttg tcccctccg ttcaaagagc       780 accctggtca ccgctctggt tacttattgc ccaccggggc gggggcgatg ggccagctgt       840
ctatgcaact ccgcacgggg accgctgacg tgcacctccc tccaagagcg acggggtggg       900
ggcattaaag taagagcact gtcgcccctg gcaaaaaaaa aaaaagtaat gctcgcagtc       960
gcttgcacag agtacctcat cgcgtgagtg caggagggtg aacaacttag cgctctctga      1020
tgacagtccc aagtgctagc gatcctaagg ggccagcctt ggtgaccaga ctaagaattc      1080
tgtggttgtg agttcagggt aacctgtgag tgggaataaa acctccccgg acctgtccgc      1140
cccaacccaa gctggagatg aagcatggcc ctctctgctt tgcagggtgt ggtaggagtc      1200 tttttgcagat gggccgagca aactaggggg tagggggacag atcaaggttt taaggcaata      1260
gaggaacacg gaggtacagg caagggagca aacatgtcgg cgtttagaat ttactgaagg      1320
gacagactgt gggagttaca aggttgacac tggcatttaa aatgaagcgt agaaaagctg      1380
ggcccagcac atgggccttg atgggtagta ctagccaggc tgaggcagga gcctcaccat      1440
ttgtagacct gcttggtttg cagagtgagt ttcaatgcca gtcttcctgg tcaactttag      1500
tgagaacttg tctcaaaata atagaaaaag aaacaggagg gtcctgcagt taacccttag      1560
gggcttgtaa tctgggtgac agggagaaaa aacaaaatca aaacaaaaaa actagtgggc      1620
agtgaagaac caaggtttgc caagatacca agcgagaaat gaccatgacc tagtctctgt      1680
ggggcagggg agctgagaga cattgaggtc agtagactga ttaggcctga gtcttcctca      1740
gcagtgggct gagaaaaacc ctcggcaggg ttcccagttt ggtaaagtat ggaatgcatc      1800
ttctaagaat catgctgttt tcttcaactg tcactcacta acattggcct gatacggaga      1860
ttagcatggc ccctgtgcaa agatggcgcg cacactcaca agagcagggc cccaaagaaa      1920
aagaacactg atccaaagat gctggtgaca cctggctgtt atccaggact aggtaacagc      1980
ctgtgcgtcc ctgggactcc actggttccc tggtcaagtt aaggcttagg tctgagtctt      2040
ccttttgtga aacagatgct ccactacagc atgtggacaa gtctgtgtat cagacttaaa      2100
ctccatatca gaagcagaga ctgagtcatg tcagacaaac ggtgccggtg cacactcagt      2160
atggggactg ggagaatgtc tcaccgatgc cctgtgtgtg ccatccctcc atatatggtc      2220 ccttttgtc cctgaagcaa ccctatgatg ataacaattc agaaagggac aaaggtaggt      2280
aggtcttggc aggaatcagg atttgaattt gtcgctacca gacatgtaaa acctgtgcca      2340
attacagagc cagctagaca ggaagctcaa tggcagaggc tttgcttagc atgcaaggag      2400
gtcctgggtt caacccacaa ctctgaaaaa caataaacaa agccaaacaa gctcctacgc      2460
tgtctaagat gaagctgtga gggaacaaac caccagaagt gtcctcagga tgcttgtccg      2520
gctcggaacg aggaagaatg tccttgattt ggactgcgcc tcgtgacagc acacaccgct      2580
ggaagcgtcc caaactgggc atggaagtgt tggtgacgct aacgagtgag gtcccgttag      2640
acggtgtcca gatgccccca gatgccgaag gctggccttg ttttgggtt gcccttctct      2700 tctttgagcc ttcagcaatg aattcattta ttcagcagaa aaataaatga tgtgcaaagg      2760
ataagtcacc atctctgctt ccttccaaga aaagaatcct gaaacttctc tctctgtgaa      2820
ggcatgccag gtcacagtag gatccaaggc agcaggaagt ccgcacatgc cctgcagaac      2880
ctccttaagg gaggctgtgg ctctgcccag cagtgttggc ttcagcttct gccttgtgga      2940
gtttggatga gcctgctgac tgcttcctgt ctctgggtct tcatctgcaa aacaaagaat      3000
gggacctgca catgaccatg accggagctc ttctcccccc cccccaatct ccctctgttt      3060
taggaaggtg gtcagtggga agtctggccc tgatcctgag atcagctgga aggaaatgtg      3120
```

```
gctgctcttg gccctgttga gcatctttca ggggacacca gctttgtccc ttgaggcctc   3180
tgaggaaatg gagcagggta tggcctctaa ggtgggagag ggtggcaggg atgtcaggga   3240
atggcaccag aagctggaga ggatcctggc ccttggcccc aagaaggagg cagcggggca   3300
gggcgatgcg attcactgtt tccctctcgg caagcacaca cctatctgta tgtctacaag   3360
agaggattag ccttacaggg cacagagcct gggctaggct gcagagccag tggtgagccc   3420
cttggctgtg tatgtatgtg tgtggttcta tgcactgggt gtgttggttg ggaggggcaa   3480
gcagcatgtg tgatgtatga accaagtata gtgggcctca gaggtgtggc atgtgtcctg   3540
tatgtggcac ctgtagcatg tgccttgtgt gtatatgtgt gtatatcttg ggtaatggca   3600
tgtctagcat gtgtgccaag tgtgtgtgtg gtgtgtgtgt gtgtgtgtgt gtgtgtgtga   3660
caactcccag gaaaaatgtg acactggccc tgtgcaaaac atttgtagca tgtggttaca   3720
tttgggggaa cagcatgtat cacaggattg ttgtgtcccg tgtgtgtagc atgttctctg   3780 tgtgcgggt ggggtgggg ggcactagcc tccgatggag ctatgggtat caatgactcc    3840
tgccatctgc cctcagagcc ctgcctagcc ccaatcctgg agcagcaaga gcaggtgttg   3900
acggtggccc tggggcagcc tgtgaggctg tgctgtgggc gcaccgagcg tggtcgtcac   3960
tggtacaaag agggcagccg cctagcatct gctgggcgag tacggggttg gagaggccgc   4020
ctggagatcg ccagcttcct tcctgaggat gctggccgat acctctgcct ggcccgtggc   4080
tccatgaccg tcgtacacaa tcttacgttg cttatggatg gtaagagggt ctgggcaggg   4140 cttttaagggt cccttgggag agaaaccct cttctcttgg atttcagatg ccttcctttg    4200
tccctgaata gactccttaa cctccatcag taatgatgaa gaccccaaga cactcagcag   4260
ctcctcgagt ggtcatgtct acccacagca aggtcggtgc ctcctcccaa ggactcttct   4320
ccacctggtc actgaggaga gacttgtgtg ggagccgagc tcaccttagg gtcctaattg   4380
ctctttcttt cctctctagc accctactgg acacacccc aacgcatgga gaagaaactg    4440
catgcagtgc ctgccgggaa tactgtcaaa ttccgctgtc cagctgcagg gaaccccatg   4500
cctaccatcc actggctcaa ggatggacag gccttccacg gggagaatcg tattggaggc   4560
attcgggtga gtctggacta cccaagtcca tcttctccac cattttcatt tttccccaca   4620
tagcccctca cataggtgga tagatgacga ggaatgtaat tccagagccc cagagcatgg   4680
acatctctgg ctcaagttct tcttacaaag tgcaacttcc cagcctcagc agaaactaac   4740
tcctgttatg ttctggtagg ggttttcatt gttggcaatg aacgtttatg cccaggggc    4800 actaaaggat tattttaatt atttttattt atgtgtaagt accatacaca tgtgtgcatc   4860
tgatccccag gagctagaat tacataggca gttgtgagtt gcctgatgtg ggagctggga   4920
accaagctca ggtcctctag aagagcagcg agcgctctta accactgagc atctctccag   4980
ccctgatgat ggggatcctc tctctatgta accctgatgg tcctggaact cactatgtag   5040
acttggctgg ccttgaactc acaaggaact aacctgcctc cactctgact tccaagtgct   5100
tggactaagg gcatctgggg tgatgattat ttttattttt taagatagat atatagatag   5160
atatagatat agatgtagat gtagatgtag atgtagatgt agatgtagat gtagatgtag   5220
atgtagatat agatatagat atagatatag atatagatat agataatata gatatagata   5280
tagatataga tatagatata gatatagata tagatgccgg gcagtggtga cacacacctt   5340
taatcccagc acttaggagg cagaggcagg tggatttctg agttcaaggc tagcctggtc   5400
tacagagtga gttccaggac agccagggct tgaaaacaaa caaacaaaca aacaaacaaa   5460
```

```
caacaacaac aaatatatat atatatatat atatatatat atatatacac      5520
atatatatat accataactg tcttcagaca caccagaaga gggcatcaga tcccattaca   5580
gatggttgtg aggtaactgc tgggaattga actcggaacc tctgatgctc ttaaccgctg   5640
agccatctct ccagccccca tgatgctggt ttctgacaca ggatcagagt acaggctatc   5700
tccaacccca acctcctggg tagcatctcc tttaaggtga ggagaaacac tgagctacta   5760
gggtttagct tgctgtcagg aggaaactga gactcagagc cagtaaagac tacataggga   5820
gcagtcctgg gtagggata gctgaacttg aaagactcaa tccagggctt agacgttgtt    5880
tttggtttgt tttttgtttt ttttttgggg ggggggttg tggtgtttgt tttgcttgtt    5940
cttttgaccc aggatctcat tgtgtagtct tgagtggttt gaaactccat ctgtagacca    6000
agctggcctt gaattcatgt cctcttgcct ttggctggct tccaagtgtt gtgattaaga    6060
tgtacaccac catgcctggt cttcaaacat caccaccact accaccacca ccaccaccac    6120
ctccaccacc tcctcctcct cctcctcctc ctcctcctcc tcctcctcct cctcctcctc    6180
cttcttcttc ttcttcttct tcttcttctt cttcttcttt ttcttcttct tcttcttctt    6240
ctcctcctcc tcctcctctc cttcctcctc ttcctccttc ttttccctct ttttactact    6300
actactactt ccacttatta ttattttta agatttgttt attttatgtg tgtgaatatt     6360
ttgtctgcat gtatatatgt gtgctgtgca catgctcagt gcctgcagag gccagaagag    6420
agtgtcagat tccctaggaa ctggagtcac acctggttgt gagccactac catgtatttg    6480
ctgggaatca aatctggggc ctctggaaga gcgtcagtct tcttaactcc taaacaatgc    6540
ctccagccca acagagacac ttcttacagc ctctttctct gttcaggagt ctctggcttt    6600
ggcctaatcc tctcagggc taggaagatt gggaagagcc ccatagacag attctgacct     6660
ctccttgtcc tggcttact gggtcccta tgaacatttc ctctactcct gcctgcttcc       6720
agctgcgcca ccaacactgg agcctggtga tggaaagtgt ggtaccctcg gaccgtggca    6780
catacacatg ccttgtggag aactctctgg gtagcattcg ctacagctat ctcctggatg    6840
tgctgggtga gtggatgggc tgggcaggta ggacaaagaa tttggcttat cttcagctcg    6900
gtcagtcctg caagggtggg tatcttgtgt tggaaactag acgaagtcag tttcagatga    6960
gcaaaataag cccaagggtc agcaggaagc aacggggtgg gggtgggctg aaggagcaga    7020
agtctgccat agggaacggg agaaggggt ccaggcagat ggcaaaggct gaattcagct     7080
ctttagaatg tagtgcaggg gctggtgaga tggctcagtg gttaagagca ctgactgctc    7140
ttccgaaggc cctgagttca atcccagca accacatggt ggctcacaac cacctgtaat     7200
gagatctgac gcactttct ggtgtgtctg aagacagcta cagtgtgctt acatataaca     7260
ataaataaac cttttataaa aaaagaat gtagtgcatt tgtgggcagt atatgccatg       7320
ggtgcaacat ttgtggggct aggggacagg gtgtggacat tctgaagtga atcctagccc    7380
aaagacagta aagccataaa accttaaagg aaggtaaaca gaagatagac aagatctgag    7440
ctgtgtgttc agaagtcctt cccctgatct aggagcgggg ctgggggcag gtaaactggg    7500
tgatttcgtg ggtgccactg gtcagggttg acggcctggc ccggcccca gagcggtccc      7560 cgcaccggcc catcctgcag gcggggctcc cagccaacac cacagctgtg gttggcagcg     7620
atgtggagct actctgcaag gtgtacagcg acgcccagcc ccacatacag tggctgaaac    7680
acgtcgtcat caacggcagc agcttcggcg ccgacggttt cccctacgta caagtcctga   7740
aggtgagctt cctgctagcg cccaggcccc gggggggggg ggcatccttt cccattaggg    7800
tgggatagta cccaactacc ctcccagctg tagtgtggcc cagagtctcc cgtgacctag    7860
```

| | |
|---|---|
| tgtgtccgct gcttcagaca acagacatca atagctcgga ggtagaggtc ttgtatctga | 7920 |
| ggaacgtgtc cgctgaggat gcaggagagt atacctgtct ggcgggcaac tccatcggcc | 7980 |
| tttcctacca gtcagcgtgg ctcacggtgc tgccaggtga gggccctgct gaggaagagg | 8040 |
| gggtcgggga gggggggaggt cctgggcgag actacaggac tcctctctgg tccattgagg | 8100 |
| cctgtaaggt aggcagtttc cttggccagt ggggtataca gtttgtcctt tggcactgtg | 8160 |
| aatgctctca ctgaattcag cagggatatg tatttaattt aacgagactg tccatgtgac | 8220 |
| ccgtgggaat ataagactat atatataact gcgattttc ttttttaaag atttatttat | 8280 |
| tttatgtatg tgagtacatg tactgtagct gtacagatgg ttgtgagcct tcatgtggtt | 8340 |
| gttgggaatt gagtttagga cctctgctct ctctggtcaa ccccactcgc tcaggtgggt | 8400 |
| cccactgact ccagcacaga aatttattta tttattagta ttatatataa gtacactgta | 8460 |
| gctgtcttta gacgccctag aagagggcat cagatctcat tacagatggt tgtgagccac | 8520 |
| catgtggttt ctgggatttg aactcaggac cttcagaaga acagtcagtg ctcttacccc | 8580 |
| tgagccatct ctccagcccg taactgtgac ttttttcagtg tgtgtcctta tatgtgttag | 8640 |
| taactatggg gacctaggct gggggcgggg ggaaggggag ggctggtcaa tctgaccacc | 8700 |
| gactgactgc tcgttttctc tgtctatgtt catctaacga gcagaggaag acctcacgtg | 8760 |
| gacaacagca acccctgagg ccagatacac agatatcatc ctgtatgtat caggctcact | 8820 |
| ggttctgctt gtgctcctgc tgctggccgg ggtgtatcat cggcaagtca tccgtggcca | 8880 |
| ctactctcgc cagcctgtca ctatacaaaa gctgtcccgt ttcccttttgg cccgacaggt | 8940 |
| actgtgcctg ttccccagcc cccacccact gtacggctct cagcctgacc ccagcaggca | 9000 |
| gaacgaatct ctcactttgc agttctcttt ggagtcgagg tcctctggca agtcaagttt | 9060 |
| gtccctggtg cgaggtgtcc gtctctcctc cagcggcccg cccttgctca cgggccttgt | 9120 |
| gaatctagac ctgcctctcg atccgctttg ggaattcccc cgggacaggt acactgagga | 9180 |
| ggctaggact gagggtgcca gctcaggagt ggtacccaca gtctgaggca cgggtcttct | 9240 |
| tggcctctag gttggtgctc ggaaagcccc tgggtgaggg ctgctttggg caagtggttc | 9300 |
| gtgcagaggc ctttggtatg gatccctccc ggcccgacca aaccagcacc gtggctgtga | 9360 |
| agatgctgaa aggtacacat ggcaacctgg gcaaggtgtg ctgggccac gcaaggggtt | 9420 |
| tacacggact gcccgtgctg gggccacgca gtgggctata gggatagccg gtgctagggc | 9480 |
| cacacaaggg gctacacaga ctgcccatgc tgggaccaca caaggggcta cacggactac | 9540 |
| atgtgctagg ccacgcagc aggctgtagg gatagcccat gctggggcca cgcaagaggc | 9600 |
| tatacatgag aaaggcccca ggttttccac ccttgggcct gaagcccaac cctgttgctg | 9660 |
| gccctggcga gtgacttcca agcctcagtt tcctgttggg cctccgtggg gatgactaaa | 9720 |
| gaccccttac ttcttagggt cgaagtttat agatgtttct gataaaccgt ggcttagtaa | 9780 |
| atttttggtg tagggtttga aactggcttt cttttc | 9816 |

<210> SEQ ID NO 14
<211> LENGTH: 19001
<212> TYPE: DNA
<213> ORGANISM: Mus musculus

<400> SEQUENCE: 14

| | |
|---|---|
| gttcctggct tccgggagct tagtggtcgg tccccagctg attacatgaa taacaactat | 60 |
| gcagttacag cctgccaagt gcgaagaaga aagaatggct gttagtgctc acaggtcaga | 120 |

```
tatgaacatg tgaattctcc ttccagcaag tctcttcagc agcctactat catttactga    180
tttgctgagg agcaaacaaa gacagagaca aggctgatag acagtactga gattcagggc    240
tcattctttt ctccatccta acaaagggga cttggcaaat ccccagggat gtcctgggc     300 cttgaacgga gaccaaagtg ccagaccaat agagagcagg ttagactagg aacaggggat    360
gggtgagcaa agacccaggg ataggatggg gagcaacaca ggaggaggag gtctgtacat    420
gtggaccaga ccaccatgtc atcacaacac tatctatgta aaaccagag gaagtattct     480 tttaaagcat tatttatttt atgtatgtga gtccactgta gctgctctca gacacagcag    540
aagaaggcat cggatcccat tacagatggt tgtgagccac catgtggttg ctgggaattg    600
aactcaggac ctctggaaga gcagtcaggg cggggcagtg gtggcacacg cctttaatcc    660
cagcacttgg gaagcagagg caggcaaact tctgagttta aggccagcct ggtctacaaa    720
gtgagttcca ggacagccag ggctatacag agaaaccctg tcttgaaaaa acaaaaacaa    780
aaacaaaaac cccaaacaaa caaaagaaa caacaaaaaa actttttaga gtgaaattt      840 aaacttttaa aaataaaagc acaacttttt acaaattaaa gtttaaagtt ttttcctctc    900 tctcttctc tctctctctc tcccctccc tccccccccc ctcttttccg agactgtgtt      960
tctctgtata gctctggctg ttctagaact cactctgtag accaggctgg cctcgaactc    1020
agaaacccac ctgcctctgc ctccccagtg cgccgccgcc accccgaccg accgagatat    1080
attttaaata tcctctgaag gtcgctcagg ccaaggagag gtcaggtctc tctgatgttc    1140
tgtgatttca cggaaaacca gagagcctgg tgagtgccaa attgaggaag agcaaaggat    1200
agagcaaggt agcaagttag accttgcagg ttggacgtgg ggccccggaa cgactgagac    1260
tgggcgatcc agtcccaacg gggagctccc gcactagggt accgggctga catttgccgg    1320
gtctcggacc acgcctctca gatcagaagt ggtccaggag gggcggagtc cgaggtgggc    1380
ggggcaggag ggggcagccc cccgccacgc tgcagttgca gggacattcc tggctcttcg    1440
gcccggggcg gaggagctcc gggcgggtga gtgtgccagc cctgccggga tcgtgacccg    1500
cgcgcgcggg agccgggcgg cggaggagcc aggtgagccg ggcccctgcg ccgggagcgg    1560
agccctctag ctctgggcca gttgggccac acaccgtact cccggccgcc gtggggacag    1620
cggccgtgga gctcccgagc tgccccctct gtcccgggga ccttggcgcc cgcgcggcgg    1680
gagtggttgg gtggagggg cggtaaatca gtaacccgca gcgcacacag ggccttttgt     1740
ccccctccgt tcaaagagca ccctggtcac cgctctggtt acttattgcc caccggggcg    1800
ggggcgatgg gccagctgtc tatgcaactc cgcacgggga ccgctgacgt gcacctccct    1860
ccaagagcga cggggtgggg gcattaaagt aagagcactg tcgcccctgg caaaaaaaaa    1920
aaaagtaatg ctcgcagtcg cttgcacaga gtacctcatc gcgtgagtgc aggagggtga    1980
acaacttagc gctctctgat gacagtccca agtgctagcg atcctaaggg gccagccttg    2040
gtgaccagac taagaattct gtggttgtga gttcaggta acctgtgagt gggaataaaa     2100
cctccccgga cctgtccgcc ccaacccaag ctggagatga agcatggccc tctctgcttt    2160
gcagggtgtg gtaggagtct tttgcagatg ggccgagcaa actaggggggt aggggacaga   2220 tcaaggtttt aaggcaatag aggaacacgg aggtacaggc aagggagcaa acatgtcggc    2280
gtttagaatt tactgaaggg acagactgtg ggagttacaa ggttgacact ggcatttaaa    2340
atgaagcgta gaaagctgg gcccagcaca tgggccttga tgggtagtac tagccaggct     2400
gaggcaggag cctcaccatt tgtagacctg cttggtttgc agagtgagtt tcaatgccag    2460
tcttcctggt caactttagt gagaacttgt ctcaaaataa tagaaaaaga aacaggaggg    2520
```

```
tcctgcagtt aacccttagg ggcttgtaat ctgggtgaca gggagaaaaa acaaaatcaa    2580
aacaaaaaaa ctagtgggca gtgaagaacc aaggtttgcc aagataccaa gcgagaaatg    2640
accatgacct agtctctgtg gggcagggga gctgagagac attgaggtca gtagactgat    2700
taggcctgag tcttcctcag cagtgggctg agaaaaaccc tcggcagggt tcccagtttg    2760
gtaaagtatg gaatgcatct tctaagaatc atgctgtttt cttcaactgt cactcactaa    2820
cattggcctg atacggagat tagcatggcc cctgtgcaaa gatggcgcgc acactcacaa    2880
gagcagggcc ccaaagaaaa agaacactga tccaaagatg ctggtgacac ctggctgtta    2940
tccaggacta ggtaacagcc tgtgcgtccc tgggactcca ctggttccct ggtcaagtta    3000
aggcttaggt ctgagtcttc cttttgtgaa acagatgctc cactacagca tgtggacaag    3060
tctgtgtatc agacttaaac tccatatcag aagcagagac tgagtcatgt cagacaaacg    3120
gtgccggtgc acactcagta tggggactgg gagaatgtct caccgatgcc ctgtgtgtgc    3180
catccctcca tatatggtcc cttttttgtcc ctgaagcaac cctatgatga taacaattca    3240
gaaagggaca aaggtaggta ggtcttggca ggaatcagga tttgaatttg tcgctaccag    3300
acatgtaaaa cctgtgccaa ttacagagcc agctagacag gaagctcaat ggcagaggct    3360
ttgcttagca tgcaaggagg tcctgggttc aacccacaac tctgaaaaac aataaacaaa    3420
gccaaacaag ctcctacgct gtctaagatg aagctgtgag ggaacaaacc accagaagtg    3480
tcctcaggat gcttgtccgg ctcggaacga ggaagaatgt ccttgatttg gactgcgcct    3540
cgtgacagca cacaccgctg gaagcgtccc aaactgggca tggaagtgtt ggtgacgcta    3600
acgagtgagg tcccgttaga cggtgtccag atgcccccag atgccgaagg ctggccttgt    3660
ttttgggttg ccccttctctt ctttgagcct tcagcaatga attcatttat tcagcagaaa    3720
aataaatgat gtgcaaagga taagtcacca tctctgcttc cttccaagaa aagaatcctg    3780
aaacttctct ctctgtgaag gcatgccagg tcacagtagg atccaaggca gcaggaagtc    3840
cgcacatgcc ctgcagaacc tccttaaggg aggctgtggc tctgcccagc agtgttggct    3900
tcagcttctg ccttgtggag tttgatgag cctgctgact gcttcctgtc tctgggtctt    3960
catctgcaaa acaaagaatg ggacctgcac atgaccatga ccggagctct tctccccccc    4020
ccccaatctc cctctgtttt aggaaggtgg tcagtgggaa gtctggccct gatcctgaga    4080
tcagctggaa ggaaatgtgg ctgctcttgg ccctgttgag catctttcag gggacaccag    4140
ctttgtccct tgaggcctct gaggaaatgg agcagggtat ggcctctaag gtgggagagg    4200
gtggcaggga tgtcagggaa tggcaccaga agctggagag gatcctggcc cttgccccca    4260
agaaggaggc agcggggcag ggcgatgcga ttcactgttt ccctctcggc aagcacacac    4320
ctatctgtat gtctacaaga gaggattagc cttacagggc acagagcctg ggctaggctg    4380
cagagccagt ggtgagcccc ttggctgtgt atgtatgtgt gtggttctat gcactgggtg    4440
tgttggttgg gaggggcaag cagcatgtgt gatgtatgaa ccaagtatag tgggcctcag    4500
aggtgtggca tgtgtcctgt atgtggcacc tgtagcatgt gccttgtgtg tatatgtgtg    4560
tatatcttgg gtaatggcat gtctagcatg tgtgccaagt gtgtgtgtgg tgtgtgtgtg    4620
tgtgtgtgtg tgtgtgtgac aactcccagg aaaaatgtga cactgccct gtgcaaaaca    4680 tttgtagcat gtggttacat ttgggggaac agcatgtatc acaggattgt tgtgtcccgt    4740
gtgtgtagca tgttctctgt gtgcggggtg ggggtggggg gcactagcct ccgatggagc    4800
tatgggtatc aatgactcct gccatctgcc ctcagagccc tgcctagccc caatcctgga    4860
```

```
gcagcaagag caggtgttga cggtggccct ggggcagcct gtgaggctgt gctgtgggcg    4920
caccgagcgt ggtcgtcact ggtacaaaga gggcagccgc ctagcatctg ctgggcgagt    4980
acggggttgg agaggccgcc tggagatcgc cagcttcctt cctgaggatg ctggccgata    5040
cctctgcctg gcccgtggct ccatgaccgt cgtacacaat cttacgttgc ttatggatgg    5100
taagagggtc tgggcagggc tttaagggtc ccttgggaga gaaacccctc ttctcttgga    5160
tttcagatgc cttcctttgt ccctgaatag actccttaac ctccatcagt aatgatgaag    5220
accccaagac actcagcagc cctcgagtg gtcatgtcta cccacagcaa ggtcggtgcc    5280
tcctcccaag gactcttctc cacctggtca ctgaggagag acttgtgtgg gagccgagct    5340
caccttaggg tcctaattgc tcttttcttc ctctctagca ccctactgga cacacccca    5400 acgcatggag aagaaactgc atgcagtgcc tgccgggaat actgtcaaat tccgctgtcc    5460
agctgcaggg aaccccatgc ctaccatcca ctggctcaag gatggacagg ccttccacgg    5520
ggagaatcgt attggaggca ttcgggtgag tctggactac ccaagtccat cttctccacc    5580
attttcattt ttccccacat agcccctcac ataggtggga agatgacgag gaatgtaatt    5640
ccagagcccc agagcatgga catctctggc tcaagttctt cttacaaagt gcaacttccc    5700
agcctcagca gaaactaact cctgttatgt tctggtaggg gttttcattg ttggcaatga    5760
acgtttatgg cccaggggca ctaaaggatt attttaatta tttttattta tgtgtaagta    5820
ccatacacat gtgtgcatct gatccccagg agctagaatt acataggcag ttgtgagttg    5880
cctgatgtgg gagctgggaa ccaagctcag gtcctctaga agagcagcga gcgctcttaa    5940
ccactgagca tctctccagc cctgatgatg gggatcctct ctctatgtaa ccctgatggt    6000
cctggaactc actatgtaga cttggctggc cttgaactca aaggaacta acctgcctcc    6060 actctgactt ccaagtgctt ggactaaggg catctggggt gatgattatt tttatttttt    6120
aagatagata tatagataga tatagatata gatgtagatg tagatgtaga tgtagatgta    6180
gatgtagatg tagatgtaga tgtagatata gatatagata tagatataga tatagatata    6240
gatatagata tagatataga tatagatata gatatagata tagatataga tgccgggcag    6300
tggtgacaca caccttaat cccagcactt aggaggcaga ggcaggtgga tttctgagtt    6360
caaggctagc ctggtctaca gagtgagttc caggacagcc agggcttgaa acaaacaaa    6420 caaacaaaca aacaaacaac aacaacaaat atatatat atatatatat atatatatat    6480
atatatatat atacacatat atatatacca taactgtctt cagacacacc agaagagggc    6540
atcagatccc attacagatg gttgtgaggt aactgctggg aattgaactc ggaacctctg    6600
atgctcttaa ccgctgagcc atctctccag cccccatgat gctggtttct gacacaggat    6660
cagagtacag gctatctcca accccaacct cctgggtagc atctccttta aggtgaggag    6720
aaacactgag ctactagggt ttagcttgct gtcaggagga aactgagact cagagccagt    6780
aaagactaca tagggagcag tcctgggtag gggatagctg aacttgaaag actcaatcca    6840
gggcttagac gttgtttttg gtttgttttt tgttttttt tttgggggg gggttgtggt    6900 gtttgttttg cttgttcttt tgacccagga tctcattgtg tagtcttgag tggtttgaaa    6960
ctccatctgt agaccaagct ggccttgaat tcatgtcctc ttgcctttgg ctggcttcca    7020
agtgttgtga ttaagatgta caccaccatg cctggtcttc aaacatcacc accactacca    7080
ccaccaccac caccacctcc accacctcct cctcctcctc ctcctcctcc tcctcctcct    7140
cctcctcctc ctcctcctc ttcttcttct ttcttcttc ttcttttct    7200 tcttcttctt cttcttctcc tcctcctcct cctctcctc ctctcttcc tccttctttt    7260
```

```
ccctctttt  actactacta  ctacttccac  ttattattat  tttttaagat  ttgtttattt   7320
tatgtgtgtg  aatattttgt  ctgcatgtat  atatgtgtgc  tgtgcacatg  ctcagtgcct   7380
gcagaggcca  gaagagagtg  tcagattccc  taggaactgg  agtcacacct  ggttgtgagc   7440
cactaccatg  tatttgctgg  gaatcaaatc  tggggcctct  ggaagagcgt  cagtcttctt   7500
aactcctaaa  caatgcctcc  agcccaacag  agacacttct  tacagcctct  ttctctgttc   7560
aggagtctct  ggctttggcc  taatcctctc  aggggctagg  aagattggga  agagccccat   7620
agacagattc  tgacctctcc  ttgtcctggc  tttactgggt  cccctatgaa  catttcctct   7680
actcctgcct  gcttccagct  gcgccaccaa  cactggagcc  tggtgatgga  aagtgtggta   7740
ccctcggacc  gtggcacata  cacatgcctt  gtggagaact  ctctgggtag  cattcgctac   7800
agctatctcc  tggatgtgct  gggtgagtgg  atgggctggg  caggtaggac  aaagaatttg   7860
gcttatcttc  agctcggtca  gtcctgcaag  ggtgggtatc  ttgtgttgga  aactagacga   7920
agtcagtttc  agatgagcaa  aataagccca  agggtcagca  ggaagcaacg  gggtgggggt   7980
gggctgaagg  agcagaagtc  tgccatagg  aacgggagaa  gggggtccag  gcagatggca   8040
aaggctgaat  tcagctcttt  agaatgtagt  gcagggctg  gtgagatggc  tcagtggtta   8100
agagcactga  ctgctcttcc  gaaggccctg  agttcaaatc  ccagcaacca  catggtggct   8160
cacaaccacc  tgtaatgaga  tctgacgcac  ttttctggtg  tgtctgaaga  cagctacagt   8220
gtgcttacat  ataacaataa  ataaaccttt  tataaaaaaa  aagaatgtag  tgcatttgtg   8280
ggcagtatat  gccatgggtg  caacatttgt  ggggctaggg  gacagggtgt  ggacattctg   8340
aagtgaatcc  tagcccaaag  acagtaaagc  cataaaacct  taaggaagg  taaacagaag   8400 atagacaaga  tctgagctgt  gtgttcagaa  gtccttcccc  tgatctagga  gcggggctgg   8460
gggcaggtaa  actgggtgat  ttcgtgggtg  ccactggtca  gggttgacgg  cctggcccgg   8520
cccccagagc  ggtccccgca  ccggcccatc  ctgcaggcgg  ggctcccagc  caacaccaca   8580
gctgtggttg  gcagcgatgt  ggagctactc  tgcaaggtgt  acagcgacgc  ccagcccac   8640 atacagtggc  tgaaacacgt  cgtcatcaac  ggcagcagct  tcggcgccga  cggtttcccc   8700
tacgtacaag  tcctgaaggt  gagcttcctg  ctagcgccca  ggccccgggg  ggggggggca   8760
tcctttccca  ttagggtggg  atagtaccca  actaccctcc  cagctgtagt  gtggcccaga   8820
gtctcccgtg  acctagtgtg  tccgctgctt  cagacaacag  acatcaatag  ctcggaggta   8880
gaggtcttgt  atctgaggaa  cgtgtccgct  gaggatgcag  gagagtatac  ctgtctggcg   8940
ggcaactcca  tcggcctttc  ctaccagtca  gcgtggctca  cggtgctgcc  aggtgagggc   9000
cctgctgagg  aagagggggt  cggggagggg  ggaggtcctg  ggcgagacta  caggactcct   9060
ctctggtcca  ttgaggcctg  taaggtaggc  agtttccttg  gccagtgggg  tatacagttt   9120
gtcctttggc  actgtgaatg  ctctcactga  attcagcagg  gatatgtatt  taatttaacg   9180
agactgtcca  tgtgacccgt  gggaatataa  gactatatat  ataactgcga  ttttctttt   9240 ttaaagattt  atttatttta  tgtatgtgag  tacatgtact  gtagctgtac  agatggttgt   9300
gagccttcat  gtggttgttg  ggaattgagt  ttaggacctc  tgctctctct  ggtcaacccc   9360
actcgctcag  gtgggtccca  ctgactccag  cacagaaatt  tatttattta  ttagtattat   9420
atataagtac  actgtagctg  tctttagacg  ccctagaaga  gggcatcaga  tctcattaca   9480
gatggttgtg  agccaccatg  tggtttctgg  gatttgaact  caggaccttc  agaagaacag   9540
tcagtgctct  taccctgag  ccatctctcc  agcccgtaac  tgtgactttt  tcagtgtgtg   9600
```

```
tccttatatg tgttagtaac tatggggacc taggctgggg gcggggggaa ggggagggct    9660
ggtcaatctg accaccgact gactgctcgt tttctctgtc tatgttcatc taacgagcag    9720
aggaagacct cacgtggaca acagcaaccc ctgaggccag atacacagat atcatcctgt    9780
atgtatcagg ctcactggtt ctgcttgtgc tcctgctgct ggccggggtg tatcatcggc    9840
aagtcatccg tggccactac tctcgccagc ctgtcactat acaaaagctg tcccgtttcc    9900
ctttggcccg acaggtactg tgcctgttcc ccagccccca cccactgtac ggctctcagc    9960
ctgaccccag caggcagaac gaatctctca ctttgcagtt ctctttggag tcgaggtcct   10020
ctggcaagtc aagtttgtcc ctggtgcgag gtgtccgtct ctcctccagc ggcccgccct   10080
tgctcacggg ccttgtgaat ctagacctgc ctctcgatcc gctttgggaa ttcccccggg   10140
acaggtacac tgaggaggct aggactgagg gtgccagctc aggagtggta cccacagtct   10200
gaggcacggg tcttcttggc ctctaggttg gtgctcggaa agccctggg tgagggctgc    10260 tttgggcaag tggttcgtgc agaggccttt ggtatggatc cctcccggcc cgaccaaacc   10320
agcaccgtgg ctgtgaagat gctgaaaggt acacatggca acctgggcaa ggtgtgctgg   10380
ggccacgcaa ggggtttaca cggactgccc gtgctggggc cacgcagtgg gctataggga   10440
tagccggtgc tagggccaca caaggggcta cacagactgc ccatgctggg accacacaag   10500
gggctacacg gactacatgt gctagggcca cgcagcaggc tgtagggata gcccatgctg   10560
gggccacgca agaggctata catgagaaag gccccaggtt ttccaccctt gggcctgaag   10620
cccaaccctg ttgctggccc tggcgagtga cttccaagcc tcagtttcct gttgggcctc   10680
cgtggggatg actaaagacc ccttacttct tagggtcgaa gtttatagat gtttctgata   10740
aaccgtggct tagtaaattt ttggtgtagg gtttgaaact ggctttcttt tctttcattc   10800
tttctttttt gtttggaatt ttacttttgt ttgtttgttt gtttgtttgt ttttgttttt   10860 gttttgttt ttgttttgag acaagagttt ctctgactgt cctagaactc actctgtaga   10920
tcagaccagc ctctgcttcc caagtgctga gattaaaggc atgccccacc atgcccggat   10980
gggaccgttt tgttctgttt tgaggctgac ctagaggtca ctctgtaatc tagccctgcc   11040
tggaactcac agcgattctc ctacaccagc ctctcgagta ctggaattac acctgactgg   11100
ctcagtaaag tttagccact gggtgatgat ccctatgaga tttgtggtga tcgcagctta   11160
atatccctcc cctgttagct ctccgcattt atcaccttat catcctccac attgagtgcc   11220 tcaccccat caaatccact aaacaataca ccttcaacac acattcctcc cagtccttag    11280
tagagaacag tcccagtctc agggctggag agatggctta gccaatgaga gtgctccatg   11340
ctcttgcagc ggactcaagt tcaattccca gcaccaacat ctgacaactc aaaaccacct   11400
gtaactccag ctccagagat tctgatatcc tcttctggct tctgaaggca ctatacacac   11460
acacacacac acacatacac acacacacac acacacacat acgagagaga gagagagaga   11520
gagagagaga gagagagaga gagagagaga gagagagaaa tacaaaaata   11580
aatcttaaaa ataaaaagtc ccaggttcaa gctgggtctg gtggcacagc ctgtaatctt   11640
gggtgaagtt acagatagag ctcaagtgct gactggacaa cttagtaaaa cccttcccca   11700
atatatgaag aggcctggct gagtagtaga acacttgtcc aacatgtgcg agaaccactg   11760
tgtgatcccc aagaataatg gagaggataa ggaaacccag acctcaggcg atgtccccaa   11820
agtgtcctgc aggtgcttgg tgtgtgctct ggaacttct tttatatttg tcttttttt     11880 tttttaagtt tattacattt tcagacatgg ccacacgata cagtcctggc tggcctgaa    11940 cttctagacc agactggact tgaatctgca gggatccact tgcctctgcc tcccaagtgc   12000
```

```
tgggatttag ggtgattatt gtgttgtgtg tgtaagtgtg agcacacatc atagcttgtg   12060
catagagcgg tcagagaaca acttatggag taaatttcag gggtcagtct tgtcatcagg   12120
cttgtgcacc acgccatctt gctcgctcct ttatgtcttc ttctattgtt tattatctgt   12180
cgttttgttc tgtgtaaata atatcatcat atcatgctta ctcaatacct tgatgtttaa   12240
cagcataccc ttgggtccta gctgtcttgc cggccccct tagaatctgt tgctgccgtc    12300
cctagcattc ttcccttcct cactccctcc actctgcaca gctggagcca gctggcactt   12360
tctgtgaggc agcgattgtg aaataggctt tccatattg atgtacgcct aggataagag    12420
ttatgtcttt gtcccaaggt cacaggtcag ccctagtccc tggtccttag cccactcttt   12480
cctagagaag tcacagaagt atcctctaat gcataacaaa acctcaggac acttcttgcc   12540
cctagggact gttacccagg gaccagttag cacagcttcc ttcctgtcta gagcttctac   12600
ctctctcctg tccctggac ctgcttatgg gaagatcagt tctttgagag tcttcatgtt    12660
ttgtccttgc aacttttgtg ggaggtgttc tgctgcgtat aagacgagtc tgagattcga   12720
gaggttgaga gaccatgagt atgaatgcca ggtgtatgtg tgtgtggata taggcatagg   12780
tgtatgtgca tgtataggta taggtatatg tgcacatata ggtgtaggtg tatgtgatat   12840
ataggtatag gcatatgtgc atgacaggtg taggtgtata tgcatgtata ggtaggtgta   12900
tgtgcatgta taggtatagg tatatgtgca catataggtg taggtgtatg tgatatatag   12960
gtataggcat atgtgcatga caggtgtagg tgtatatgca tgtataggta ggtgtatgtg   13020
catgtatagg tataggtata tgtgcacata taggtatagg tatatgtgca catataggta   13080
taggtatatg tgcacatata ggtgtaggtg taggtgtagg tgtaggtgta taggtatatg   13140
tgcacatata ggtgtaggtg tatgtgcctg tataggtgta tgtgcgtgtg gacataggca   13200
taagtgtgca acatcagatg cctcctctat cactcaccag cttggttttt tgagacaatc   13260
tcttgctgaa cctgggactt gctgtttcag ctacactagc tcaccatcta gctacccccc   13320
tcctccaacc tgtgtgtgcc ctgtgttagg gccacagccg ctgcactgct ccacccaatt   13380
ttttcatgca tgccggggat ccgaactcag atcctcgtgc ttgtgctgcg ggcactccat   13440
tcactgaaca tctccccatc aaagccagga ggctgaggca ggcagatctc tgagttcaag   13500
gccagcctgg actacagagc tagttctgga acagccaagg ctacacagag aaacacgatc   13560
ttaaataagt tttgtttgtt tgtttgtttg tttttagtta gggtctctat agtcttcctg   13620
gatggtctca aactcatgga agactaatgg tgtgctccac tactcttggc ctggaatgat   13680
ttttttgttg tttttttgttt tgggggggct ttttgttttt caagacaggg tttctctgtg   13740
tggccctggc tgtcctggaa ctcactctgt agaccaggct ggccttgaac tcagaaatcc   13800
gcctgcctct gcctcccgag tgctgggatt aaaggcgtgt gccaccactg cccagctgga   13860 atgattttt tttttttttt tttttgaga cagggtttct ctgtgcagcc ctggctgtcc    13920
tggaactcac tctgtagacc aggctggcct cgaactcaga atccgcctg cctctgcctc    13980 ccaagtgctg ggattaaagg tgtgcgccac cacgcccggc ttggaatgat ttttttaaag   14040
catctacttt tttgagagtt tcatacatga gtacgtattt acaacatttc caccccattc   14100
tctcttcctc caaatccttc tatgcttcct gatccctctt taaacacaca cacacacaca   14160
cacacacaca cacacacaca cactgttttg agtttgtttg ttggttggtt tgttttgtc    14220 tcctgtagcc caggctggct tcatattcac caagtgctaa gattagacgt gggctctatc   14280
ctgcccagtt ttatactgtg atgaggatag accacagact tcatgctagg caagcactct   14340
```

```
acaaactgaa ctacatccct agcccgaaag gcttcttctg agacacacag cccagcaggg    14400
tttcacccca gacttccttg gcaccctcac cctctcccgt gatgctcttg tggagttgga    14460
gggcaacttc ctcagcccag ctgttgcttt gcagacaatg cctccgacaa ggatttggca    14520
gacctggtct ccgagatgga ggtgatgaag ctaatcggaa gacacaagaa catcatcaac    14580
ctgctgggtg tctgcactca ggaaggtgtg gcaggagcag ggaatcagat gcgcagttgg    14640
gatgcaaagg accactcttg ccagacttcc catcccctgg tccatggctt ccctctgtag    14700
ggcccctgta cgtgattgtg gaatgtgccg ccaagggaaa ccttcgggaa ttcctccgtg    14760
cccggcgccc cccaggccct gatctcagcc ctgatggacc tcggagcagc gaaggaccac    14820
tctccttccc ggccctagtc tcctgtgcct accaggtggc ccgaggcatg cagtatctgg    14880
agtctcggaa ggtgtggaca aaggacagtt gtgctggggt ctccacacct tcttgctggg    14940
ggcactgaat gtcctcagca gcccccttgt ttccagctca caggtctatc ctttaaccat    15000
cattcccata catttgcagc taaccctgca gatccccatc tgtaacccg cgggtcccca    15060 ttctctccac ccattctttt acccgagggc aagcatggct caggcgtggg ctctgaacaa    15120
atgtgcttct ttcttttct ctttctggtt ctggggattc agcccaggcc tttgcccatt    15180
ccatttctct ttttgttttt cttttgtttt ttcgagacag ggtttctctg tatagccctg    15240
gctgtcctgg aactcacttt gtagaccagg ctggcctcga actcagaaat ccgcctgcct    15300
ctgcctccca agggctggga ttaaaggcat gcgccaccac gcccggctcc attccatttc    15360
tcatctgttc cggggctgag ggactggccc ctgggcttgc tgtgaaatga tcaactccca    15420
gacctgtgtc ttgatactcc taaactccct acctgtcctc agtgcatcca ccgggacctg    15480
gctgcccgaa atgtgctggt gaccgaggat gatgtgatga agatcgctga ctttgggctg    15540
gcacgtggtg tccaccacat tgactactat aagaaaacca gcaacgtgag gggcacctcg    15600
gagatacacg ggagcgaggc ggggactaga cctggtctga aagggatagg tcctatacta    15660
ctcacaccac tgtccccgcc tccttcctcc agggccgcct gccagtcaaa tggatggctc    15720
cagaggcatt gttcgaccgc gtgtacacac accagagtga cgtgtgagtc tgggaaatgg    15780
gttctaagat ggctgctgcc tgtcttcaag tcgtcatccc ctctaaaagg caaggcgct    15840 tgccaaagtc acgagatctt aggagttctt ctgacactcc aaaagaaagg agtgcccctc    15900
cctatcccca agggtggatc ttgaccgcaa tagcctttac tacagcttca aggagaaagg    15960
aaggaaggaa gctgggccct gctgagccac agttctgcct ccaggtggtc tttcgggatc    16020
ctgctgtggg aaatcttcac cctcgggggc tccccatacc ctggcattcc ggtggaggag    16080
ctcttctcac tgctgcgaga ggggcacagg atggagcggc cccaaactg cccctcagag    16140 ctgtaagctc acccctcctg ccccagtggt cagacctcat ctgcggtcct gactttgacg    16200
tcagcttttg gccctggccg tcccactcac ggtccctcct cttcttctcc actcacggtg    16260
gcctggtctt gttcctactc tcccactaaa ctgccctgcg cagccccacc ccaccccatc    16320
cccagccacg accccacac cccaaccccta gggagcgcac agtcctcact ttgcgggccc    16380
tacacacaaa cctctttgac ctgttcccag gtatgggcta atgagggagt gctggcacgc    16440
agccccatct cagaggccta cttttaagca gctggtggaa gctctggaca aggtcctgct    16500
ggctgtctct gaagaggtac tgcccattcc cacctcgtgc cctctctctg cccgctccca    16560
tgacctaggg atatgaacac gaagcatcct gtccccaagg ctggaagctg accagctctg    16620
ttccttgcag taccttgacc tccgcctgac cttggaccc ttttctccct ccaatgggga    16680
tgccagcagc acctgctcct ccagtgactc ggttttcagc cacgacccctt tgcccctcga    16740
```

```
gccaagcccc ttccctttct ctgactcgca gacgacatga gccggggagc agcaatgttg    16800
tatgggctac gcggcccatg gccgtgggtc tcctcgctga gctgcaacct gatgcatcga    16860
catttaatgt tggcagtgtc aggcctctga cttgagacta ctgctgtcgc agatcctctc    16920
tctggccctg ttttggggag ggccattctt ggtcctaagg ttcatagttg aggccttctg    16980
ttccagcctt atgctcccat ctcagagttc aactctcatc tcaagatcat ggccttgccc    17040
ttggactcat cctcagagaa gttaagcatt aaggccttgg cacgcagcct ccgtctccgg    17100
ggctctccgg gactagctgc aaaacttatg ctctaaacat ttctagttcc cccaaacaac    17160
ctagaggcct tgggacttca catccccag cacacaagcc tcaccacccc ctgccatccc     17220
ccctccattg cttgttccag catcttggtg aaaggggcat cagctctggt gtccctgaga    17280
gacgagaagc ctgtgggaac gacagaagaa catggcattt ttataaatta ttttttttgaa   17340 ataaatctct gtgtgcctgg tggcttccct gtgtggcagg gtgtagggtg ggaagatttt    17400
ccacgttggg agtttggtct gggtggcaca gacgactgag gaggtgggtg ccaggccttc    17460
agctggcttc tgcctccagc tgtgctatag cagactcaga agcagataag cgcacccttg    17520
cctttgtctg tctgtccgtc cgtcctacag aactatcctt gtatatgcca cggttggtga    17580
gtgagtgctc gagggcagat gagcccacac tacaccatct gtaaggcagg ccctgtatcc    17640
tctgcacacg catccatgtt tggcccaaga cttgtcccca agggagctgg cgtcccctcc    17700
cccatctgct cagcattaac caaactgacc gttaacacag cacgaaggaa acgtgaaatc    17760
aagcctccag ccgcagcctg ctcccacggt ctggatctgc ccgctcaggc tcagggcttg    17820 tggggccgt gccgccctg cctggccctg gcctgtctcc caggcagcag ctggttaccg       17880
cctggctgag ctgcagctgt ccccacttgc atgatcctcc ctggaggctg tcacaaccct    17940
gttctcagcc cccaccccag agagatcagc ttcccagagc tctgagcctg gaaatgtact    18000
ggactccatt ctgacagttt cagctgctcc ctaaccctga acattagggt gggcagggag    18060
aggccgaaag tggttccaga cttctgctc cctggttcct acaagctctc tgggagtgag     18120
gactgcaaat gtatttaggc ttccagagac tcatgtacaa atttaagggt agctctaaag    18180
agatggctca ttgcttaaga gcacctgtaa ctttccccag ggacctggtt ttgattccca    18240
gcacctacta ctactaccat gtgtgacccc agttcctagg caatcaacat cctcttctga    18300
tttccatggg taccggacac acagacatat acatgcaggc aaaaagttca catatgtaaa    18360
aagaacacaa aagtaattag atatagatat aaagatagat agataggtag atagatagac    18420
agttggctcc ctgtatacat accatacata ataaccaaat attctgatgg cctagtcggt    18480
catcagtggg aggagaggcc ctaggtgctg tgaaggttct atgccccagt atagggaat     18540 gccaggactg ggaatgggag tgggttggtt ggggagcaag ggaagggag aggataggag      18600 attttcagag gggaaactag gaaagggat aacatttaa acgtaaataa agaaaatatc       18660
caataaaaaa acattcttt tttttttttt ctagacaggg tttctctgta tagttctggc      18720
tgtcctggaa ctcactttgt agaccaggct ggtctcgaac tcagaaatct gcctacctct    18780
gcctccccag cgctgggatt aaaggcgtgc accaccacgc caggccaaaa ccaaacattc    18840
ttattgagac ccgcttccaa actcagtttc ccgttagaga ttactagtca gtgactgagt    18900
cctgtcacca ctccaggtgt ccgtcttgag gcggagtact tgggtttgcc tgggtcagga    18960
aatgattggg aggttgggat gaggtaaaca aacagaccaa g                        19001
```

<210> SEQ ID NO 15

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
gggctggcac actcacccgc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gatcccggca gggctggcac                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ggtcacgatc ccggcagggc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
gccacatttc cttccagctg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
ccaagagcag ccacatttcc                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
tcaacagggc caagagcagc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
```
ttcctcagag gcctcaaggg                                      20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
aggaaggaag ctggcgatct                                      20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
cagcatcctc aggaaggaag                                      20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
ccacgggcca ggcagaggta                                      20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
gtcatggagc cacgggccag                                      20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
aggagtcatc cataagcaac                                      20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
ggttaaggag tcatccataa                                      20

<210> SEQ ID NO 28
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 28
tgatggaggt taaggagtca                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
tgtgtccagt agggtgcttg                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
ccagtggatg gtaggcatgg                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
ttgagccagt ggatggtagg                                                   20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
aaggcatgtg tatgtgccac                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tccacaaggc atgtgtatgt                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
aatgctaccc agagagttct                                                   20
```

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ccagcacatc caggagatag                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
gctgctgccg ttgatgacga                                            20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tgttgtcttc aggacttgta                                            20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
agccacgctg actggtagga                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ctctggcagc accgtgagcc                                            20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tgatacatac aggatgatat                                            20

<210> SEQ ID NO 41
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 41
acaagcagaa ccagtgagcc                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ggagcacaag cagaaccagt                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tacaccccgg ccagcagcag                                          20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
gacttgccag aggacctcga                                          20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
gggacaaact tgacttgcca                                          20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
cctcgcacca gggacaaact                                          20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
acaaggcccg tgagcaaggg                                          20

```
<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
caaagcagcc ctcacccagg                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
tctgcacgaa ccacttgccc                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
gagggatcca taccaaaggc                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
gaggcattgt ctttcagcat                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
ggtctgccaa atccttgtcg                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
tgtcttccga ttagcttcat                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 54
agacacccag caggttgatg                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
gagtgcagac acccagcagg                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
gggcccttcc tgagtgcaga                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
ccatcagggc tgagatcagg                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
ccagatactg catgcctcgg                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
tggatgcact tccgagactc                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
ccccgagggt gaagatttcc                                              20

<210> SEQ ID NO 61
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 61
tgtgcccctc tcgcagcagt                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
cctcattagc ccatacagct                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
ttgtccagag cttccaccag                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gccagcagga ccttgtccag                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
ctcttcagag acagccagca                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
gtcaggcgga ggtcaaggta                                                    20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
```
agaaaagggt ccaaaggtca                                                    20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
cccattggag ggagaaaagg                                                    20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
tggcatcccc attggaggga                                                    20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
tgctgctggc atccccattg                                                    20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
cagggccaga gagaggatct                                                    20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tggaacagaa ggcctcaact                                                    20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
ccaagggcaa ggccatgatc                                                    20

<210> SEQ ID NO 74
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 74
atgagtccaa gggcaaggcc                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
tgaggatgag tccaagggca                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
tagagcataa gttttgcagc                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
atgtttagag cataagtttt                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
tagaaatgtt tagagcataa                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
aggcctctag gttgtttggg                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
tttataaaaa tgccatgttc                                              20
```

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
ttccatgccc agtttgggac                                           20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
ggagtcattg atacccatag                                           20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gtcagagtgg aggcaggtta                                           20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
ttgattccca gcaaatacat                                           20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
acccagcaca tccaggagat                                           20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
ccccacaaat gttgcaccca                                           20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
gcccaggttg ccatgtgtac                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
ggttttgtta tgcattagag                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
gatcaggaag catagaagga                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
gacagtggtg tgagtagtat                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
gaacaggtca aagaggtttg                                              20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
cagcgggaca caagtccttg                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
aactgccttc ctcgagcctg                                              20

<210> SEQ ID NO 94

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
gtcaaggagt caagctccac                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
ggtagaggga tgtcaaccag                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
ggcagggtcc gcagacagcc                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
cagcagccgc atctccttct                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
ggcacactca gcaggacccc                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
caagactgga ggcccaggca                                              20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
```
gagccaggca gggctcaagc                                           20

```
<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
```
cctgctcttg ctgctccagg                                           20

```
<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
```
tactgtcagc tcctgctctt                                           20

```
<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
```
aggctgccca agggctactg                                           20

```
<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
```
tccttgtacc agtggccacc                                           20

```
<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
```
ggccagcagg tgccaggcga                                           20

```
<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
```
aatctctagg cggcccctcc                                           20

```
<210> SEQ ID NO 107
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 107
gacgatcatg gagcctcgtg                                             20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
ttctgcagga cgatcatgga                                             20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
atcatcgttg ctggaggtca                                             20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
gtccagtagg gtgcttgctg                                             20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
ggtgtgtcca gtagggtgct                                             20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
tgcagtttct tctccatgcg                                             20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
ccatccttaa gccagcggat                                             20
```

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
cccatgaaag gcctgtccat                                           20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
aatgcggttc tccccatgaa                                           20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
gcgcagccga atgcctccaa                                           20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
tctccatcac gagactccag                                           20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
cgttctctac caggcaggtg                                           20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
cttgcacagc agctccacgt                                           20

<210> SEQ ID NO 120
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 120
tacaccttgc acagcagctc                                        20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
ccgaagctgc tgccgttgat                                        20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
tgtctgcagt ctttaggact                                        20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
ctctgagcta ttgatgtctg                                        20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
tccacctctg agctattgat                                        20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
ctgacacgtt ccgcaggtac                                        20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
actggtagga gaggccgatg                                        20

```
<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
gcgctgctgc ggtccatgtg                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
tgccctcgat acagcccggc                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
ttgccggaag agcctgactc                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
taccagggat gagcttgact                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
cctcgtacca gggatgagct                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
aagcaccagc ctgtcccggg                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 133
aggcctctgc acgtactacc                                           20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
ttgacggcca cagtgctggc                                           20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
cttgtgtcgg ccgatcagct                                           20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
gggtgcagac accaagcagg                                           20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
agaccaggac tgggaaggag                                           20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
ttccgggact ccagatactg                                           20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
ggtggataca cttccgggac                                           20

<210> SEQ ID NO 140
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 140
cgatgtccct cccgcagcag                                                   20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
atcagcccgt acagctctgg                                                   20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
gtcgaggtac tcctcagaga                                                   20

<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
ctggaggagc aggtgctgct                                                   20

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
gctgaagaca gaatcgctgg                                                   20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 145
gtcgtggctg aagacagaat                                                   20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
```
tcatgtctgc accccagacc                                           20

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
agccttgctc atgtctgcac                                           20

<210> SEQ ID NO 148
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 148
tgtgtcaggc tgtggctgag                                           20

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
aagggcacgg cccttggaca                                           20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 150
atttgggcca tcaggacaca                                           20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 151
agcagaaccc tgacatttgg                                           20

<210> SEQ ID NO 152
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 152
cctgctggta ttgggaggca                                           20

<210> SEQ ID NO 153
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 153
acagcacagc cgcacaggct                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 154
cgcccagtac ctggcagcac                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 155
ggagcgagga atgtacccgc                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 156
tccggctcac ctcgagcctg                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 157
ggaaacatcc tctccctcgg                                              20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 158
gaagccatac caagctccac                                              20

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 159
ttcactccct gctagagtct                                              20
```

```
<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 160
gtcaaggagt ctacatcagg                                          20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
agtcaggctg tcacatgtga                                          20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 162
gtgagcccct tctattagtc                                          20

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 163
aatgtgcatt tctcaatccc                                          20

<210> SEQ ID NO 164
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 164
aacggcccgt gcagccagcc                                          20

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 165
caggactcac acgtcactct                                          20
```

```
<210> SEQ ID NO 166
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 166
cagcccgtac ctgcgagagg                                                 20

<210> SEQ ID NO 167
<211> LENGTH: 19
<212> TYPE: DNA
<213> ORGANISM: Artificial Sequence
<220> FEATURE:
<223> OTHER INFORMATION: Primer

<400> SEQUENCE: 167
ccttatgccc ccatctcag                                                  19

<210> SEQ ID NO 168
<211> LENGTH: 19
<212> TYPE: DNA
<213> ORGANISM: Artificial Sequence
<220> FEATURE:
<223> OTHER INFORMATION: Primer

<400> SEQUENCE: 168
tcccaaggcc tctaggttg                                                  19

<210> SEQ ID NO 169
<211> LENGTH: 50
<212> TYPE: DNA
<213> ORGANISM: Artificial Sequence
<220> FEATURE:
<223> OTHER INFORMATION: Probe

<400> SEQUENCE: 169
ctctccggga ctagctgcaa aacttatgct ctaaacattt ctagttcccc                50

<210> SEQ ID NO 170
<211> LENGTH: 19
<212> TYPE: DNA
<213> ORGANISM: Artificial Sequence
<220> FEATURE:
<223> OTHER INFORMATION: Primer

<400> SEQUENCE: 170
gttctgctcg gcttcttgg                                                  19

<210> SEQ ID NO 171
<211> LENGTH: 19
<212> TYPE: DNA
<213> ORGANISM: Artificial Sequence
<220> FEATURE:
<223> OTHER INFORMATION: Primer

<400> SEQUENCE: 171
aggcttccag cttctctgg                                                  19

<210> SEQ ID NO 172
<211> LENGTH: 50
<212> TYPE: DNA
<213> ORGANISM: Artificial Sequence
<220> FEATURE:
<223> OTHER INFORMATION: Probe
```

```
<400> SEQUENCE: 172
ggctgagcct ggctggagag ctgctatgct aaacctcctg cctcccaata              50

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 173
ccttccctga aggttcctcc                                               20
```